(12) United States Patent
Hecker et al.

(10) Patent No.: US 10,570,159 B2
(45) Date of Patent: *Feb. 25, 2020

(54) BORONIC ACID DERIVATIVES AND THERAPEUTIC USES THEREOF

(71) Applicant: Qpex Biopharma, Inc., San Diego, CA (US)

(72) Inventors: Scott J. Hecker, Del Mar, CA (US); Raja K. Reddy, San Diego, CA (US); Tomasz Glinka, Cupertino, CA (US); Olga Rodny, Mill Valley, CA (US)

(73) Assignee: Qpex Biopharma, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/378,323

(22) Filed: Apr. 8, 2019

(65) Prior Publication Data

US 2019/0233443 A1 Aug. 1, 2019

Related U.S. Application Data

(63) Continuation of application No. 15/636,424, filed on Jun. 28, 2017, now Pat. No. 10,294,249.

(60) Provisional application No. 62/357,165, filed on Jun. 30, 2016.

(51) Int. Cl.
| | |
|---|---|
| C07F 5/02 | (2006.01) |
| C07F 5/04 | (2006.01) |
| A61K 31/69 | (2006.01) |
| A61P 31/00 | (2006.01) |
| C07F 5/05 | (2006.01) |
| A61P 31/04 | (2006.01) |
| A61K 45/06 | (2006.01) |
| A61K 31/407 | (2006.01) |
| A61K 31/4196 | (2006.01) |
| A61K 31/426 | (2006.01) |

(52) U.S. Cl.
CPC .............. *C07F 5/05* (2013.01); *A61K 31/407* (2013.01); *A61K 31/4196* (2013.01); *A61K 31/426* (2013.01); *A61K 31/69* (2013.01); *A61K 45/06* (2013.01); *A61P 31/00* (2018.01); *A61P 31/04* (2018.01); *C07F 5/025* (2013.01); *Y02A 50/471* (2018.01)

(58) Field of Classification Search
CPC ... C07F 5/02; C07F 5/04; A61K 53/69; A61K 31/69; A61P 33/00; A61P 31/00
USPC ................................... 558/286, 288; 514/64
See application file for complete search history.

(56) References Cited

U.S. PATENT DOCUMENTS

| | | | |
|---|---|---|---|
| 3,686,398 A | 8/1972 | Kohn et al. | |
| 4,194,047 A | 3/1980 | Christensen et al. | |
| 4,260,543 A | 4/1981 | Miller | |
| 4,353,807 A | 10/1982 | Braid | |
| 4,409,214 A | 10/1983 | Takaya et al. | |
| 4,822,786 A | 4/1989 | Zama et al. | |
| 5,442,100 A | 8/1995 | Bjorkquiest et al. | |
| 5,888,998 A | 3/1999 | Maiti et al. | |
| 6,184,363 B1 | 2/2001 | Shoichet et al. | |
| 6,586,615 B1 | 7/2003 | Kettner et al. | |
| 7,271,186 B1 | 9/2007 | Shoichet et al. | |
| 7,439,253 B2 | 10/2008 | Lampilas et al. | |
| 7,582,621 B2 | 9/2009 | Baker et al. | |
| 7,612,087 B2 | 11/2009 | Aszodi et al. | |
| 7,674,913 B2 | 3/2010 | Campbell | |
| 7,825,139 B2 | 11/2010 | Campbell et al. | |
| 8,680,136 B2 | 3/2014 | Hirst et al. | |
| 9,012,491 B2 | 4/2015 | Reddy et al. | |
| 9,101,638 B2 | 8/2015 | Reddy et al. | |
| 9,132,140 B2 | 9/2015 | Reddy et al. | |
| 9,156,858 B2 | 10/2015 | Reddy et al. | |
| 9,241,947 B2 | 1/2016 | Reddy et al. | |
| 9,296,763 B2 | 3/2016 | Hirst et al. | |
| 9,511,142 B2 | 12/2016 | Burns et al. | |
| 9,642,869 B2 | 5/2017 | Reddy et al. | |
| 9,687,497 B1 | 6/2017 | Bis et al. | |
| 9,694,025 B2 | 7/2017 | Hirst et al. | |
| 10,004,758 B2 | 6/2018 | Hirst et al. | |
| 10,206,937 B2 | 2/2019 | Reddy et al. | |
| 10,294,249 B2 * | 5/2019 | Hecker ................... | C07F 5/025 |
| 2004/0019203 A1 | 1/2004 | Micetich et al. | |
| 2004/0157826 A1 | 8/2004 | Lampilas et al. | |
| 2005/0020572 A1 | 1/2005 | Aszodi et al. | |
| 2005/0070719 A1 | 3/2005 | Belyakov et al. | |
| 2006/0019116 A1 | 1/2006 | Conley et al. | |

(Continued)

FOREIGN PATENT DOCUMENTS

| | | | |
|---|---|---|---|
| EP | 1550657 A1 | 7/2005 | |
| EP | 2508506 A1 | 10/2012 | |

(Continued)

OTHER PUBLICATIONS

Abdel-Magid et al., "Reductive Amination of Aldehydes and Ketones with Sodium Triacetoxyborohydride: Studies on Direct and Indirect Reductive Amination Procedures", J Org Chem. (1996) 61(11):3849-3862.

Adediran et al., "A 'cephalosporin-like' cyclic depsipeptide: Synthesis and reaction with beta-lactam-recognizing enzymes", Bioorg Med Chem Lett. (1999) 9(3):341-346.

Aizpurua et al., "Synthesis of benzyl halides from aldehydes promoted by halosilanes and 1,1,3,3-tetramethyldisiloxane (TMDS)", Tetrahedron Lett. (1984) 25(10):1103-1104.

Akiyama et al., "N-Hydroxy Amides. Part 6. Synthesis and Spectroscopic Properties of 1-Hydroxypiperazine-2,5-diones", J Chem Soc., Perkin Trans I, (1989) 2:235-239.

(Continued)

*Primary Examiner* — Venkataraman Balasubramanian
(74) *Attorney, Agent, or Firm* — Knobbe, Martens, Olson & Bear, LLP

(57) ABSTRACT

Disclosed herein are antimicrobial compounds compositions, pharmaceutical compositions, the method of use and preparation thereof. Some embodiments relate to boronic acid derivatives and their use as therapeutic agents, for example, β-lactamase inhibitors (BLIs).

26 Claims, No Drawings

(56) References Cited

U.S. PATENT DOCUMENTS

| | | |
|---|---|---|
| 2006/0178357 A1 | 8/2006 | Buynak et al. |
| 2006/0210883 A1 | 9/2006 | Chen et al. |
| 2010/0056478 A1 | 3/2010 | Desarbre et al. |
| 2010/0120715 A1 | 5/2010 | Burns et al. |
| 2010/0256092 A1 | 10/2010 | Xia et al. |
| 2010/0292185 A1 | 11/2010 | Burns et al. |
| 2011/0288063 A1 | 11/2011 | Maiti et al. |
| 2012/0040932 A1 | 2/2012 | Hirst et al. |
| 2013/0316978 A1 | 11/2013 | Reddy et al. |
| 2013/0331355 A1 | 12/2013 | Griffith et al. |
| 2013/0345172 A1 | 12/2013 | Hirst et al. |
| 2014/0194381 A1 | 7/2014 | Reddy et al. |
| 2014/0194382 A1 | 7/2014 | Reddy et al. |
| 2014/0194384 A1 | 7/2014 | Reddy et al. |
| 2014/0194385 A1 | 7/2014 | Reddy et al. |
| 2014/0194386 A1 | 7/2014 | Burns et al. |
| 2014/0206648 A1 | 7/2014 | Reddy et al. |
| 2014/0274954 A1 | 9/2014 | Chellappan et al. |
| 2015/0119363 A1 | 4/2015 | Dudley et al. |
| 2016/0220591 A1 | 8/2016 | Hirst et al. |
| 2016/0339045 A1 | 11/2016 | Griffith et al. |
| 2017/0057979 A1 | 3/2017 | Hecker et al. |
| 2017/0088561 A1 | 3/2017 | Reddy et al. |
| 2017/0136047 A1 | 5/2017 | Reddy et al. |
| 2017/0173055 A1 | 6/2017 | Bis et al. |
| 2018/0051041 A1 | 2/2018 | Hecker et al. |
| 2018/0071325 A1 | 3/2018 | Hirst et al. |
| 2018/0207183 A1 | 7/2018 | Hirst et al. |
| 2018/0214465 A1 | 8/2018 | Hirst et al. |
| 2019/0084999 A1 | 3/2019 | Hecker et al. |
| 2019/0211037 A1 | 7/2019 | Hecker et al. |

FOREIGN PATENT DOCUMENTS

| | | |
|---|---|---|
| FR | 2573070 A1 | 5/1986 |
| JP | 2003-229277 | 8/2003 |
| JP | 2004-291253 | 10/2004 |
| WO | WO 1987/05297 | 9/1987 |
| WO | WO 1989/10961 | 11/1989 |
| WO | WO 1998/56392 A1 | 12/1998 |
| WO | WO 2000/035904 A1 | 6/2000 |
| WO | WO 2000/035905 A1 | 6/2000 |
| WO | WO 2001/023374 A1 | 4/2001 |
| WO | WO 2001/030149 | 5/2001 |
| WO | WO 2002/022137 A1 | 3/2002 |
| WO | WO 2002/083884 | 10/2002 |
| WO | WO 2003/070714 | 8/2003 |
| WO | WO 2004/039859 | 5/2004 |
| WO | WO 2004/058679 A2 | 7/2004 |
| WO | WO 2004/064755 A2 | 8/2004 |
| WO | WO 2005/033090 | 4/2005 |
| WO | WO 2005/035532 A1 | 4/2005 |
| WO | WO 2005/087700 | 9/2005 |
| WO | WO 2006/052733 A1 | 5/2006 |
| WO | WO 2006/091771 | 8/2006 |
| WO | WO 2007/058602 A2 | 5/2007 |
| WO | WO 2007/065288 A2 | 6/2007 |
| WO | WO 2007/095638 | 8/2007 |
| WO | WO 2008/039420 A2 | 4/2008 |
| WO | WO 2008/116813 A1 | 10/2008 |
| WO | WO 2009/046098 A1 | 4/2009 |
| WO | WO 2009/064413 A1 | 5/2009 |
| WO | WO 2009/064414 A1 | 5/2009 |
| WO | WO 2009/091856 A1 | 7/2009 |
| WO | WO 2009/117540 A1 | 9/2009 |
| WO | WO 2009/139834 A1 | 11/2009 |
| WO | WO 2009/140309 A2 | 11/2009 |
| WO | WO 2010/056827 A1 | 5/2010 |
| WO | WO 2010/075286 A1 | 7/2010 |
| WO | WO 2010/097675 A1 | 9/2010 |
| WO | WO 2010/130708 A1 | 11/2010 |
| WO | WO 2010/144338 A1 | 12/2010 |
| WO | WO 2011/017125 A1 | 2/2011 |
| WO | WO 2011/103686 A1 | 9/2011 |
| WO | WO 2011/123502 A1 | 10/2011 |
| WO | WO 2011/154953 | 12/2011 |
| WO | WO 2012/021455 A1 | 2/2012 |
| WO | WO 2012/058065 A1 | 5/2012 |
| WO | WO 2012/067664 A1 | 5/2012 |
| WO | WO 2012/106995 A1 | 8/2012 |
| WO | WO 2012/136383 A1 | 10/2012 |
| WO | WO 2013/033461 A1 | 3/2013 |
| WO | WO 2013/053372 A1 | 4/2013 |
| WO | WO 2013/056163 A1 | 4/2013 |
| WO | WO 2013/092979 A1 | 6/2013 |
| WO | WO 2013/104774 A1 | 7/2013 |
| WO | WO 2013/104897 A1 | 7/2013 |
| WO | WO 2013/122888 A2 | 8/2013 |
| WO | WO 2013/184845 A1 | 12/2013 |
| WO | WO 2014/089365 A1 | 6/2014 |
| WO | WO 2014/107535 A1 | 7/2014 |
| WO | WO 2014/107536 A1 | 7/2014 |
| WO | WO 2014/110442 A1 | 7/2014 |
| WO | WO 2014/144380 A1 | 9/2014 |
| WO | WO 2014/151958 A1 | 9/2014 |
| WO | WO 2015/171398 A1 | 11/2015 |
| WO | WO 2015/171430 A1 | 11/2015 |
| WO | WO 2015/179308 A1 | 11/2015 |
| WO | WO 2015/191907 A1 | 12/2015 |
| WO | WO 2016/003929 A1 | 1/2016 |
| WO | WO 2016/065282 A1 | 4/2016 |
| WO | WO 2016/149393 | 9/2016 |

OTHER PUBLICATIONS

Allen et al., "Ansel's Pharmaceutical Dosage Forms and Drug Delivery Systems", 8th Edition (2004) TOC only.

Ambrose et al., Pharmacokinetics-pharmacodynamics of antimicrobial therapy: it's not just for mice anymore. Clin Infect Dis. (2007) 44: 79-86.

Ambrose et al., "Pharmacokinetics-pharmacodynamics of CB-618 in combination with cefepime, ceftazidime, ceftolozane and meropenem: the pharmacological basis for a stand-alone beta-lactamase inhibitor", Antimicrob Agents Chemother. (Nov. 2017) 61(12): e00630-17; 7 pages.

American Chemical Society. STN Chemical Database Registry RN: 1226917; Jun. 2010; 2 pages.

Arya et al., "Advances in asymmetric enolate methodology", Tetrahedron (2000) 56:917-947.

Austad et al. "Development of a multi kilogram-scale, tandem cyclopropanation ring-expansion reaction en route to hedgehog antagonist IPI-926", Org Process Res Dev., (2016) 20(4):786-798; Supporting Information, 70 pages.

Babic et al., "What's new in antibiotic resistance? Focus on beta-lactamases", Drug Res Updates (2006) 9:142-156.

Banker G.S. et al. [Eds.], Modern Pharmaceutics, 4th Edition; Marcel Dekker, Inc. (2002); Chapters 9 and 10, 98 pages.

Bassetti et al., "New antibiotics for bad bugs: where are we?", Ann Clin Microbiol Antimicrob. (2013) 12:22-36.

Becker, Daniel E., "Antimicrobial Drugs", Anesth Prog (2013) 60:111-123.

Beenen et al., "Asymmetric copper-catalyzed synthesis of alpha-amino boronate esters from N-tert-butanesulfinyl aldimines", J Am Chem Soc. (2008) 130(22):6910-6911.

Berkhout et al., "Pharmacodynamics of Ceftazidime and Avibactam in Neutropenic Mice with Thigh or Lung Infection", Antimicrob Agents Chemother. (2015) 60 (1): 368-375.

Bhavani et al., Pharmacokinetic-Pharmacodynamic (PK_PD) basis for CLSI carbapenem (CARB) susceptibility breakpoint changes. abstr Abstracts of Papers, 50th Interscience Conference on Antimicrobial Agents and Chemotherapy, Sep. 12-15, 2010; #A1-1382, Boston, MA; 3 pages.

Biedrzycki et al., "Derivatives of tetrahedral boronic acids", J. Organomet. Chem. (1992) 431 :255-270.

Bilello et al., "Effect of 2',3'-8 didehydro-3'-deoxythymidine in an in vitro hollow-fiber pharmacodynamic model system correlates with results of dose-ranging clinical studies", Antimicrob Agents Chemother. (1994) 38(6): 1386-1391.

Bou et al., "Cloning, nucleotide sequencing, and analysis of the gene encoding an AmpC beta-lactamase in Acinetobacter baumannii", Antimicrob Agents Chemother (2000) 44(2):428-432.

(56) References Cited

OTHER PUBLICATIONS

Bou et al., "OXA-24, a novel class D beta-lactamase with carbapenemase activity in an Acinetobacter baumannii clinical strain", Antimicrob Agents Chemother (2000) 44(6):1556-1561 and Erratum: Antimicrob Agents Chemother. (2006) 50(6) 2280.
Bowker et al., Comparative pharmacodynamics of meropenem using an in-vitro model to simulate once, twice and three times daily dosing in humans. J Antimicrob Chemother (1998) 42: 461-467.
Brabez et al., "Design,synthesis, and biological studies of efficient multivalent melanotropin ligands: tools toward melanoma diagnosis and treatment", J Med Chem. (2011) 54(20):7375-7384.
Braisted et al., "Discovery of a potent small molecule IL-2 inhibitor through fragment assembly", J Am Chem Soc., (2003) 125(13): 3714-3715; Supporting Information, 42 pages.
Brosz et al., "Resolution of alpha-aminoboronic esters by diastereoselective crystallization with pinanediols. Confirmation by x-ray analysis", Tetrahedron: Asymmetry (1997) 8(9):1435-1440.
Buesking et al., "Asymmetric Synthesis of Protected alpha-Amino Boronic Acid Derivatives with an Air- and Moisture-stable Cu(II) Catalyst", J Org Chem. (Mar. 2014) 79(8): 3671-3677.
Bulik et al., "Comparison of the activity of a human simulated, high-dose, prolonged infusion of meropenem against *Klebsiella pneumoniae* producing the KPC carbapenemase versus that against *Pseudomonas aeruginosa* in an in vitro pharmacodynamic model", Antimicrob Agents Chemother (2010) 54(2): 804-810.
Bundgaard H. [Ed.], "Design of Prodrugs", Elsevier (1985); TOC, 2 pages.
Bush et al., "Minireview: Updated Functional Classification of beta-Lactamases," Antimicrob Agents Chemo. (2010) 54(3):969-976.
CAS Registry No. 105892-95-3 Boronic acid [1-(phenylsulfonyl)heptyl]-, dimethyl ester (2015); 2 pages.
CAS Registry No. 2005:329437 CAPLUS; "Product subclass 28: Vinylboranes", Vaultier et al., (2004); XP-002764965; 1 page.
CAS Registry No. 831209-98-4 6H-Dibenz[c,e][1,2]oxaborin, 6a,10a-dihydro-6-hydroxy; Entered STN: Feb. 15, 2005; 1 page.
CAS Registry No. 831210-03-8 6H-Dibenz[c,e][1,2]oxaborin, 2,4-dibromo-6a, 10a-dihydro-6-hydroxy; Feb. 15, 2005; 1 page.
CAS Registry Nos. 69190-59/60 (2-(bis(phenylthio)methyl)-4,4,5,5-tetramethyl-1,3,2-dioxaborolane) and 69190-60-9 (2-(bis(phenylthio)methyl)-1,3,2-dioxaborinane) Scheme 18 (2015); 2 pages.
Chandrasekhar et al., "The first Corey-Chaykovsky epoxidation and cyclopropanation in ionic liquids", Tetrahedron Letts. (2003) 44:3629-3630.
Charette et al., "Palladium-catalyzed Suzuki-type cross-couplings of iodocyclopropanes with boronic acids: Synthesis of trans-1,2-dicyclopropyl alkenes", J Org Chem. (1996) 61(25): 8718-8719; Supporting Information, 52 pages.
Chemicalland21.com. "Meglumine", Jun. 7, 2011. Downloaded from </www.chemicalland21.com/lifescience/phar/N-METHYL-D-GLUCAMINE.htm>; 2 pages.
Cheng et al., "Synthesis of Aryl Thioethers through the N-Chlorosuccinimide-Promoted Cross-Coupling Reaction of Thiols with Grignard Reagents", J Org Chem. (2012) 77(22):10369-10374.
Chinchilla et al., "Recent advances in Sonogashira reactions", Chem Soc Rev., (2011) 40: 5084-5121.
Clark et al., "Concise synthesis of the C-1-C-12 fragment of amphidinolides T1-T5", Org Biomol Chem. (2011) 9(13): 4823-4830.
Clinical and Laboratory Standards Institute (formerly NCCLS, National Committee for Clinical Laboratory Standards). "Methods for Dilution of Antimicrobial Susceptibility Tests for Bacteria That Grow Aerobically; Approved Standard—9th Edition", CLSI (Jan. 2012) M07-A9 32(2): 88 pages.
Clinical and Laboratory Standards Institute (formerly NCCLS, National Committee for Clinical Laboratory Standards). "Methods for Dilution of Antimicrobial Susceptibility Tests for Bacteria That Grow Aerobically", CLSI (Jan. 2006) M7-A7 26(2), 64 pages.

Clinical and Laboratory Standards Institute (formerly NCCLS, National Committee for Clinical Laboratory Standards). "Methods for Dilution of Antimicrobial Susceptibility Tests for Bacteria That Grow Aerobically", CLSI (Jan. 2009) M07-A8 29(2), 88 pages.
Clinical Trial NCT02168946, "A Phase 3, Multi-Center, Randomized, Open-Label Study of Carbavance (Meropenem/RPX7009) Versus Best Available Therapy in Subjects with Selected Serious Infecations Due to Carbapenem-Resistant Enterobacteriaceae", Oct. 6, 2014; retrieved online from URL:https://clinicaltrials.gov/archive/NCT02168946/20140_10_06.
Conte et al., "Intrapulmonary pharmacokinetics and pharmacodynamics of meropenem", Int J Antimicrob Agents (Dec. 2005) 26(6):449-456.
Coppa et al., "A Facile, Convenient and Selective Homolytic Carbamolylation of Heteroaromatic Bases", Heterocycles (1993) 36(12):2687-2696.
Coutts et al., "Two Efficient Methods for the Cleavage of Pinanediol Boronate Esters Yielding the Free Boronic Acids", Tetrahedron Lett. (1994) 35(29):5109-5112.
Craig WA., "Pharmacokinetic/pharmacodynamic parameters: rationale for antibacterial dosing of mice and men", Clin Infect Dis. (1998) 26(1): 1-10.
Cunha, "Meropenem in elderly and renally impaired patients", Int'l J Antimicro Agents (1998) 10: 107-117.
Danziger et al., "Automated Site-directed Drug Design: A General Algorithm for Knowledge Acquisition about Hydrogen-bonding Regions at Protein Surfaces", Proc. Royal Soc London, Series B, Biol. Sciences (1989) 236(1283):101-113.
Darses et al., "Potassium Organotrifluoroborates: New Perspectives in organic Synthesis", Chem Rev. (2008) 108:288-325.
Davoli et al., "Enantioselective total synthesis of (−)-microcarpalide", Tetrahedron (2005) 61:4427-4436.
de Meijere A. [Ed], Science of Synthesis—vol. 24; "Three Carbon-Heteroatom Bonds: Ketene Acetals and Yne-X Compounds", TOC 46 pages.
Di Gioia et al., "Optically Pure N-Hydroxy-O-triisopropylsilyl-alpha-L-amino Acid Methyl Esters from AlCl3-Assisted Ring Opening of Chiral Oxaziridines by Nitrogen Containing Nucleophiles", J Org Chem. (2005) 70(25):10494-10501.
Dörwald F.Z., *Side Reactions in Organic Synthesis—A guide to Successful Synthesis Design*, Wiley-VCH Verlag GmbH & Co. KGaA, Weinheim, Germany (2005); Preface in 4 pages.
Drawz et al., "Three Decades of beta-Lactamase Inhibitors", Clin Microbiol Reviews (Jan. 2010) 23(1):160-201.
Drusano et al., Meropenem: clinical response in relation to in vitro susceptibility. Clin Microbiol Infect. (2000) 6: 185-194.
Dunetz et al., "Large-scale applications of amide coupling reagents for the synthesis of pharmaceuticals", Org Process Res Develop. (2016) 20(2): 140-177.
Eggen et al., "Total synthesis of cryptophycin-24 (Arenastatin A) amenable to structural modifications in the C16 side chain", J Org Chem. (2000) 65(23): 7792-7799; and Supporting documents, 22 pages.
Eidam et al., "Design, synthesis, crystal structures and antimicrobial activity of sulfonamide boronic acids as beta-lactamase inhibitors", J Med Chem. (2010) 53(21):7852-7863.
Eissenstat et al., "Aminoalkylindoles: Structure-Activity Relationships of Novel Cannabinoid Mimetics", J Med Chem. (1995) 38(16):3094-3105.
El Nezhawy et al., "Synthesis and antioxidant activity of some thiazolidin-4-one derivatives", Springer; Chemical Monthly/Monatshefte für Chemie (2009) 140(5):531-539.
Endo et al., "Chemoselective Suzuki coupling of diborylmethane for facile synthesis of benzylboronates", Org Lett. (2011) 13(13):3368-3371.
Fan, et al. (2009): STN International HCAPLUS database, Columbus (OH), accession No. 2009: 425839; 6 pages.
Farquhar et al., "Intensely potent doxorubicin analogues: structure-activity relationship", J. Med. Chem. (1998) 41(6):965-972.
Ghosh et al., "Enantioselective total synthesis of (+)-largazole, a potent inhibitor of histone deacetylase", Org Lett. (2008) 10(17):3907-3909.

(56) References Cited

OTHER PUBLICATIONS

Giroux, A., "Synthesis of benzylic boronates via palladium-catalyzed cross-coupling reaction of bis(pinacolato)diboron with benzylic halides", Tetrahedron Lett. (2003) 44:233-235.
Goodman et al., [Eds.], "The Pharmacological Basis of Therapeutics", 8th. Edition, Pergamon Press (1990); TOC, 8 pages.
Gorovoy et al., "Boron-Containing Peptidomimetics—A Novel Class of Selective Anti-tubercular Drugs", Chem Biol Drug Des. (Jan. 2013) 81(3):408-413.
Gossinger et al., "Towards EPC-syntheses of the structural class of cochleamycins and macquarimicins. Part 3: EPC-syntheses of the beta-keto lactone subunits and first attempts towards the syntheses of the pentacyclic antibiotics of this group", Tetrahedron (2007) 63:8336-8350.
Graham et al., "D is for Drugs", Chemistry & Industry, Mar. 19, 2013, pp. 28-30, Downloaded from http://www.concertpharma.com/wp-content/uploads/2014/12/ChemistryIndustry-0313.pdf; 3 pages.
Greene, et al., "Greene's Protective Groups in Organic Synthesis", 4th Edition, (2007); pp. 774, 785 & 787.
Gunanathan et al., "Ruthenium catalyzed hydroboration of terminal alkynes to Z vinylboronates", J Am Chem Soc. (2012) 134(35): 14349-14352; Supporting Information, 32 pages.
Hall D.G., [Ed], Boronic Acids [vol. 2]: Preparations and applications in Organic Synthesis, Medicine and Materials, Wiley-VCH, Weinheim, $2^{nd}$ Edition (2011); TOC.
Hama et al., "Palladium-Catalyzed alpha-Arylation of Zinc Enolates of Esters: Reaction Conditions and Substrate Scope", J Org Chem. (2013) 78(17):8250-8266.
Hartung et al., "Highly Z-selective and Enantioselective Ring Opening/Cross Metathesis Catalyzed by Resolved Stereogenic-At-Ru Complex", J Am Chem Soc. (Jul. 2013) 135(28): 10183-10185.
He et al., "Ligand-promoted borylation of C(sp3)—H bonds with palladium(II) catalysts", Angew Chem Int Ed., (2016) 55(2): 785-789.
Hecker et al., "Discovery of a Cyclic Boronic Acid beta-Lactamase Inhibitor (RPX7009) with Utility vs Class A Serine Carbapenemases", J Med Chem. (Mar. 2015) 58:3682-3692.
Higuchi et al., [Eds.] "Pro-drugs as Novel Drug Delivery Systems", ACS Symposium Series 14 (1975); TOC, 3 pages.
Hoveyda A., "Evolution of catalytic stereoselective olefin metathesis: From ancillary transformation to purveyor of stereochemical identity", J Org Chem. (Jun. 2014) 79(11): 4763-4792.
Hu et al., "Ag(I)-catalyzed C—H borylation of terminal alkynes", Tetrahedron (2014) 70: 5815-5819.
Imanishi et al., "Discovery of a Novel Series of Biphenyl Benzoic Acid Derivatives as Potent and Selective Human beta3-Adrenergic Receptor Agonists with Good Oral Bioavailability. Part I", J Med Chem. (2008) 51(6):1925-1944.
Inglis et al., "Observations on the Deprotection of Pinanediol and Pinacol Boronate Esters via Fluorinated Intermediates", J Org Chem. (2010) 75(2):468-471.
International Search Report and Written Opinion dated Oct. 12, 2017 for International Application No. PCT/US2017/039787, filed Jun. 28, 2017.
Ishii et al, "In vitro potentiation of carbapenems with ME1071, a Novel metallo-β-lactamase inhibitor, against metallo-β-lactamase producing pseudomonas aeruginosa clinical isolates." Antimicrob. Agents Chemother. doi:10.1128/AAC.01397-09 (2010) 54(9):3625-3629.
Ishiyama et al., "Palladium(0)-catalyzed cross-coupling reaction of alkoxydiboron with haloarenes: A direct procedure for arylboronic esters", J Org Chem. (1995) 60(23): 7508-7510; Supporting Information, 35 pages.
Ito et al., "An efficient constructive method for a tricyclic system: an important intermediate for the synthesis of tricycloclavulone", Tetrahedron Lett. (2003) 44:1259-1261.
Jadhav et al., "Direct synthesis of [alpha-[(tert-Butoxycarbonyl)amino]alkyl]-boronates from (alpha-Haloalkyl)boronates", Org Chem. (1996) 61(22):7951-7954.

Jagannathan et al., "Synthesis of Boronic Acid Analogues of alpha-Amino Acids by Introducing Side Chains as Electrophiles", J Org Chem. (2001) 66(19):6375-6380.
Jang et al., Copper-catalyzed trans-hydroboration of terminal aryl alkynes: Stereodivergent synthesis of alkenylboron compounds. Org Letts. (2016) 18(6): 1390-1393; Supporting Information, Supporting Information, 37 pages.
Jiang et al., "A Practical Synthesis of Cefcapene Pivoxil", Synthesis (2012) 44:207-214.
Johnson et al., "A drug targeting motif for glycosidase inhibitors: An iminosugar-boronate shows unexpectedly selective beta-galactosidase inhibition", Tetrahed Lttrs. (2002) 43(49):8905-8908.
Jordan V.C., "Tamoxifen: A most unlikely pioneering medicine", Drug Discovery (2003) 2:205-213.
Kabalka et al., "Synthesis of a series of bornonated unnatural cyclic amino acids as potential boron neutron capture therapy agents", Appl Organomet Chem. (2008) 22(9):516-522.
Kanai et al., "Synthesis of ortho-Acylbenzylboronates via Cross-Coupling Reaction of (Dialkoxyboryl)methylzinc Reagents with Haloarenes. A Stable ortho-Quinodimethane Precursor", Chem Letts. (1993) 22(5):845-848.
Kawamorita et al., "Synthesis of Primary and Secondary Alkylboronates through Site-Selective C(sp3)—H Activation with Silica-supported Monophosphine-Ir Catalysts", J Am Chem Soc. (2013) 135(8):2947-2950.
Kikuchi et al., "Comparison of the Pharmacodynamics of Biapenem in Bronchial Epithelial Lining Fluid in Healthy Volunteers Given Half-Hour and Three-Hour Intravenous Infusions", Antimicrob Agents Chemother. (Jul. 2009) 53(7):2799-2803.
Kint et al., "New-found fundamentals of bacterial persistence", Trends Microbiol. (2012) 20(12):577-585.
Kose et al., "Synthesis of photochromic 2,3-bis(5-methyl-2-phenyl-4-thiazolyl)-1,4-naphthoquinone derivatives", J Photochem Photobiol. A: Chemistry. (2011) 219(1):58-61.
Kotha et al., "Recent applications of the suzuki-miyaura cross-coupling reaction in organic synthesis", Tetrahedron (2002) 58:9633-9695.
Kuang et al., "Convenient and stereoselctive synthesis of (Z)-1-bromo-1-alkenes by microwave-induced reaction", Tetrahedron Letts. (2001) 42(23): 3893-3896.
Kumar et al., "Development of Practical Methodologies for the Synthesis of Functionalized Benzoboroxoles", Tetrahedron Lett. (Aug. 25, 2010) 51(34):4482-4485.
Kumar et al., "Synthesis of intermediates for the lactone moiety of mevinic acids via tellurium chemistry", J. Org. Chem., (1994) 59(17):4760-4764.
Kusakabe et al., "Preparation of Optically Acitve 2-Furylcarbinols by Kinetic Resolution Using the Sharpless Reagent and Their Application in Organic Synthesis", J org Chem (1989) 54(9):2085-2091.
Kuti et al., "Use of Monte Carlo simulation to design an optimized pharmacodynamic dosing strategy for meropenem", J Clin Pharmacol. (Oct. 2003) 43(10:1116-1123.
Laitar et al., "Catalytic diboration of aldehydes via insertion into the copper-boron bond", J Am Chem Soc. (2006) 128(34):11036-11037.
Lapuebla et al., "Activity of Meropenem Combined with RPX7009, a Novel beta-Lactamase Inhibitor, against Gram-Negative Clinical Isolates in New York City", Antimicrob Agents Chemother. (Aug. 2015) 59(8):4856-4860.
Larock R. [Ed.] *Comprehensive Organic Transformations*, VCH Publishers 1989; TOC, 11 pages.
Lebel et al., "Boc-protected amines via a mild and efficient one-pot Curtius rearrangement", Org Letts. (2005) 7(19): 4107-4110.
Lee et al., "Comparison of 30-min and 3-h infusion regimens for imipenem/cilastatin and for meropenem evaluated by Monte Carlo simulation", Diagn Microbiol Infect Dis. (2010) 68: 251-258.
Lee et al., "Vicinal Diboronates in High Enantiomeric Purity through Tandem Site-Selective NHC—Cu-Catalyzed Boron-Copper Additions to Terminal Alkynes", J Am Chem Soc. (Dec. 2009) 131(51):18234-18235.

(56) References Cited

OTHER PUBLICATIONS

Li et al, "Novel macrocyclic HCV NS3 protease inhibitors derived from α-amino cyclic boronates", Bioorganic Med Chem Lett. (2010) 20:5695-5700.
Li et al., "Population Pharmacokinetic Analysis and Dosing Regimen Optimization of Meropenem in Adult Patients", J Clin Pharmacol. (2006) 46(10): 1171-1178.
Li et al., "Stereoselective total synthesis of etnangien and etnangien methyl ester", J Org Chem. (2010) 75(8):2429-2444.
Li et al., "Synthesis and evaluation of novel alpha-amino cyclic boronates as inhibitors of HCV NS3 protease", Bioorg Med Chem Lett. (2010) 20:3550-3556.
Liang et al., "The Efficient Copper(I) (Hexabenzyl)tren Catalyst and Dendritic Analogues for Green "Click" Reactions between Azides and Alkynes in Organic Solvent and in Water: Positive Dendritic Effects and Monometallic Mechanism", Advance Syn Catal. (2011) 353(18): 3434-3450.
Lima et al., "Bioisosterism: A Useful Strategy for Molecular Modification and Drug Design", Curr Med Chem. (2005) 12:23-49.
Lin et al., "Enantioselective syn and anti homocrotylation of aldehydes: Application to the formal synthesis of spongidepsin", J Am Chem Soc. (2015) 137(40): 13176-13182; Supporting Information, 177 pages.
Liu et al., "Application of Stereoselective Ether Transfer to the Synthesis of Isotactic Polyethers", J Org Chem. (2010) 75(12):3953-3957.
Liu et al., "Selective Protein tyrosine phosphatase 1B inhibitors: Targeting the second phosphotyrosine binding site with non-carboxylic acid-containing ligands", J Med Chem. (2003) 46(16):3437-3440.
Livermore et al., "Activities of NXL104 combinations with Ceftazidime and Aztreonam against Carbapenemase-producing Enterobacteriaceae", Antimicr Agents Chemother. (2011) 55(1):390-394.
Livermore et al., "Activity of biapenem (RPX2003) combined with the boronate beta-lactamase inhibitor RPX7009 against carbapenem-resistant Enterobacteriaceae", J Antimicrob Chemother. (Aug. 2013) 68(8):1825-1831.
Lodise et al., "Penetration of meropenem into epithelial lining fluid of patients with ventilator-associated pneumonia", Antimicrob Agents Chemother. (Apr. 2011) 55(4):1606-1610.
Louie et al., Impact of meropenem in combination with tobramycin in a murine model of Pseudomonas aeruginosa pneumonia. Antimicrob Agents Chemother (2013) 57: 2788-2792.
Luithle et al., "Synthesis of enantiomerically pure cis-cyclopropylboronic esters", Eur J Org Chem. (2000) 14: 2557-2562.
MacVane et al., Characterizing in vivo pharmacodynamics of carbapenems against *Acinetobacter baumannii* in a Murine thigh infection model to support breakpoint determinations. Antimicrob Agents Chemother (2014) 58: 599-601.
Maguire, B.A., "Inhibition of Bacterial Ribosome Assembly: a Suitable Drug Target?", Microbiology and Molecular Biology Reviews, Mar. 2009, p. 22-35.
Malfertheiner et al., "Current concepts in the management of Helicobacter pylori infection: the Maastricht III Consensus Report", Gut (2007) 56(6):772-781.
Matteson et al., "(Alkoxyalkyl)boronic Ester Intermediates for Asymmetric Synthesis", Organometallics (1996) 15:152-163.
Matteson et al., "A Directed Chiral Synthesis of Amino Acids from Boronic Esters", Tetrahedron Lett. (1987) 28(39):4499-4502.
Matteson et al., "Cesium Alkyltrifluoroborates from Asymmetric Boronic Esters", Synlett (Jul. 2006) 20:3501-3503.
Matteson et al., "Glass-Catalyzed Conversion of Boronic Esters of Asymmetric Diols to Diol Sulfites and Amine Complexes of Boron Halides", Oranometallics (2001) 20(13):2920-2923 & supporting Information (9 pages).
Matteson et al., "Iodomethaneboronic Esters and Aminomethaneboronic Esters", J Organomet. Chem. (1979) 170:259-264.
Matteson et al., "Synthesis of a (Beta-acetamido-alpha-acetoxyethyl) boronic ester via azido boronic esters", J Organomet Chem. (2008) 693:2258-2262.

Matteson et al., "A stereospecific convergent coupling of nucleophilic and electrophilic chiral carbons", J. Am. Chem. Soc. (1989) 111:4399-4402.
Matteson et al., "Synthesis of asymmetrically deuterated glycerol and dibenzylglyceraldehyde via boronic esters", J. Am. Chem. Soc. (1990) 112:3964-3969.
Matteson, "Alpha-Halo Baronic Esters in Asymmetric Synthesis", Tetrahedron (1998) 54(36):10555-10607.
Matteson, "Boronic Esters in Asymmetric Synthesis", J Org Chem. (Oct. 2013) 78(20): 10009-10023.
Matteson, "Boronic esters in stereodirected synthesis", Tetrahedron (1989) 45(7):1859-1885.
Matteson, D.S., "Asymmetric Synthesis with Boronic Esters", Acc Chem Res. (1988) 21(8):294-300.
McOmie J.R.W. [Ed], *Protective Groups in Organic Chemistry*, Plenum Press, London & New York (1973); TOC, 3 pages.
McSharry et al., "Prediction of the pharmacodynamically linked variable of oseltamivir carboxylate for influenza A virus using an in vitro hollow-fiber infection model system", Antimicrob Agents Chemother (2009) 53(6): 2375-2381.
Meanwell, "Synopsis of some recent tactical application of bioisosteres in drug design", J. Med. Chem. (2011) 54:2529-2591.
Mendoza et al., "Bis(phenylthio)methaneboronic Esters as Sources of Carbanions and Ketene Thioacetals", J Org Chem. (1979) 44(8):1352-1354.
Micalizio et al., "A Boronic Ester Annulation Strategy for Diversity-Oriented Organic Synthesis", Angew Chem Int Ed Engl. (2002) 41(1):152-154.
Mkhalid et al., "C—H activation for the construction of C—B bonds", Chem Rev. (2010) 110(2): 890-931.
Molander et al., "Highly stereoselective synthesis of cis-alkenyl pinacolboronates and potassium cis-alkenyltrifluoroborates via a hydroboration/protodeboronation approach", J Org Chem. (2008) 73(17): 6841-6844.
Montalbetti et al., "Amide bond formation and peptide coupling", Tetrahedron (2005) 61:10827-10852.
Montefour et al., "Acinetobacter baumannii: an emerging multidrug-resistant pathogen in critical care", Crit Care Nurse (2008) 28(1):15-25.
Morandi et al., "Structure-based optimization of cephalothin-analogue boronic acids as beta-lactamase inhibitors", Bioorg Med Chem. (2008) 16(3):1195-205. Epub Nov. 7, 2007.
Mori et al., "Synthesis of 1,3-dienes from alkynes and ethylene: Acetic acid 2-methylene-3-phenethylbut-3-enyl ester", Org Synth. (2005) 81: 1-13.
Morrill et al., "Treatment Options for Carbapenem-Resistant *Enterobacteriaceae* Infections", Open Forum Infectious Diseases [OFID] Apr. 2015; 15 pages.
Munar et al., "Drug Dosing Adjustments in Patients with Chronic Kidney Disease", Am Fam Physician (May 2007) 75(1): 1487-1496.
Nema et al., "Excipients and Their Role in Approved Injectable Products: Current Usage and Future Directions", PDA J Pharm Sci Technol. (2011) 65(3):287-332.
Ness et al., "Structure-based design guides the improved efficacy of deacylation transition state analogue inhibitors of TEM-1 beta-Lactamase", Biochemistry (2000) 39(18):5312-5321.
Nicasio et al., "Pharmacokinetics-Pharmacodynamics of Tazobactam in Combination with Piperacillin in an In Vitro Infection Model", Antimicrob Agents Chemother. (2016) 60: 2075-2080. doi: 10.1128/AAC.02747-15.
Nicolau DP., "Pharmacokinetic and pharmacodynamic properties of meropenem", Clin Infect Dis. (2008) 47 Suppl 1: S32-S40.
Noguchi et al., "Boron-masking strategy for the selective synthesis of oligoarenes via iterative Suzuki-Miyaura coupling", J Am Chem Soc. (2007) 129(4): 758-759; Supporting Information, 46 pages.
Nordmann et al., How to Detect NDM-1 Producers, J. Clin. Micro. (2011) 49:718-721.
Overman et al., "Organic Synthesis—Working with Hazardous Chemicals", Org Synth. (1990) 68: 182; 5 pages.
Panek et al., "Diastereoselectivity in the borane methyl sulfide promoted hydroboration of .alpha.-alkoxy-.beta, gamma.-unsaturated esters. Documentation of an alkoxy-directed hydroboration reaction", J. Org. Chem. (1992) 57(20):5288-5290.

(56) References Cited

OTHER PUBLICATIONS

Paquette L.A. [Ed.] *Encyclopedia of Reagents for Organic Synthesis*, vol. 1; J. Wiley & Sons (1995); Cover Only.
Patani et al., "Bioisosterism: A Rational Approach in Drug Design", Chem Rev. (1996) 96:3147-3176.
Paterson et al., "Extended-Spectrum beta-Lactamases: a Clinical Update", Clin Microbiol Rev. (2005) 18(4):657-686.
Pellissier, H., "Recent developments in asymmetric cyclopropanation", Tetrahedron (2008) 64(30-31): 7041-7095.
Perez et al., "Why are we afraid of Acinetobacter baumannii?", Expert Rev Anti Infect Ther. (2008) 6(3):269-71.
Pietruszka et al., "Enantiomerically pure cyclopropylamines from cyclopropylboronic esters", Eur J Org Chem. (2009) 34: 5998-6008.
Pine et al., "Resonance vs. Tautomerism" in *Organic Chemistry*; McGraw-Hill, New York 4th Ed. (1980), pp. 218-219.
Pintaric et al., "An Opportunity for Mg-Catalyzed Grignard-Type Reactions: Direct Coupling of Benzylic Halides with Pinacolborane with 10 mol % of Magnesium", J Am Chem Soc. (2010) 132(34): 11825-11827.
Powell et al., "Compendium of excipients for parenteral formulations", PDA J Pharm Sci Technol. (1998) 52(5):238-311.
Rehm et al., *Staphylococcus aureus*: Methicillin-Susceptible *S. aureus* to Methicillin-Resistant *S. aureus* and Vancomycin-Resistant *S. aureus*", Clinical Infectious Diseases 2010; 51(S2):S176-S182.
Reissig et al.,"High diastereoselection in the alkylation of siloxy-substituted methyl cyclopropanecarboxylates: consequence of a pyramidal ester enolate anion?", J. Am. Chem. Soc. (1982) 104:1735-1737.
Robak et al., "Synthesis and applications of tert-butanesulfinamide", Chem Rev. (2010) 110(6):3600-3740.
Roche, E.B. (Ed.)., Bioreversible Carriers in Drug Design: Theory and Application. New York: Pergamon Press (1987); pp. 14-21.
Rodriguez-Martinez et al., "VIM-19, a Metallo-beta-lactamase with increased Carbapenemase Activity from *Escherichia coli* and Klebsiella pneumoniae", Antimicro Agents Chemother. (2010) 54(1):471-476.
Rubino et al., "Phase 1 Study of the Safety, Tolerability, and Pharmacokinetics of Vaborbactam and Meropenem Alone and in Combination following Single and Multiple Doses in Healthy Adult Subjects", Antimicrob Agents Chemother. (Apr. 2018) 62(4): E02228-17; 12 pages.
Sabet et al., "Activity of Meropenem-Vaborbactam in Mouse Models of Infection Due to KPC-Producing Carbapenem-Resistant Enterobacteriaceae", Antimicrob Agents Chemother. (2017) 62:1 10 e01446-379 17.
Sabet et al., "Activity of Simulated Human Dosage Regimens of Meropenem and Vaborbactam against Carbapenem-Resistant Enterobacteriaceae in an In Vitro Hollow-Fiber Model", Antimicrob Agents Chemother (2017) 62. pii: e01969-17. doi: 10.1128/AAC.01969-17.
Sabet et al., "In Vivo Efficacy of Carbavance (Meropenem/RPX7009) Against KPC-producing Enterobacteriaceae", Abstracts of the 54th Interscience Conference on Antimicrobial Agents and Chemotherapy (Sep. 5-9, 2014) F-958; 3 pages.
Sawant et al., "Synthesis of the C1-C13 Fragment of Biselyngbyaside", Synlett (2011) 20: 3002-3004.
Sawyer et al., "Physical properties and synthetic utility of a-alkoxyorganolithium species as studied through ligand selectivity in tin-lithium exchange", J. Am. Chem. Soc. (1988) 110:842-853.
Scriven et al., "Azides: Their preparation and synthetic uses", Chem Rev. (1988) 88(2): 297-368.
Selander et al., "Palladium-catalyzed allylic C—OH functionalization for efficient synthesis of functionalized allylsilanes", J Am Chem Soc. (2011) 133(3):409-411.
Shaffer, Robyn Kroop, "The Challenge of Antibiotic-Resistant *Staphylococcus*: Lessons from Hospital Nurseries in the mid-20th Century", Yale J Biol Med. (2013) 86:261-270.
Shao et al., "Asymmetric hydrogenation of 3,5-Dioxoesters catalyzed by Ru-binap complex: A short step asymmetric synthesis of 6-substituted 5,6-dehydro-2-pyrones", Tetrahedron (1993) 49(10):1997-2010.
Singer et al., "Catalytic, enantioselective acetate aldol additions to alpha-, beta-ynals: Preparation of optically active propargylic alcohols", Tetrahedron (1998) 54(25): 7025-7032.
Singh et al., "Asymmetric Homologation of Boronic Esters Bearing Azido and Silyloxy Substituents", J Org Chem. (2000) 65(20):6650-6653 and Erratum: J Org Chem. (2001) 66(22):7560.
Sliwka et al., "Synthetic Sulfur Carotenoids II: Optically Active Carotenoid Thiols", Tetrahedron: Asymmetry (1993) 4(3):361-368.
Solladié et al., "First Stereocontrolled Synthesis of the (3S,5R,7R,10R,11 R)-C1-C13 Fragment of Nystatin A(1)", J Org Chem. (1999) 64(15):5447-5452.
Souto et al., "Synthesis and biological characterization of the histone deacetylase inhibitor largazole and c7-modified analogues", J. Med. Chem. (2010) 53(12):4654-4667.
Spiegel et al., "CP-263,114 synthetic studies. Construction of an isotwistane ring system via rhodium carbenoid C—H insertion", Tetrahedron (2002) 58:6545-6554.
Sumida et al., "Boron-selective biaryl coupling approach to versatile dibenzoxaborins and application to concise synthesis of defucogilvocarcin M", Org Ltt. (Dec. 2014) 16(23):6240-6243.
Sun et al., "Programmed Synthesis of a Contiguous Stereotriad Motif by Triple Stereospecific Reagent-controlled Homologation", Org Lttr. (Jul. 2013) 15(17):4500-4503.
Sun et al., "A method for the deprotection of alkylpinacolyl boronate esters", J Org Chem. (2011) 76(9): 3571-3575; Supporting Information, 8 pages.
Tam et al., "Optimization of meropenem minimum concentration/MIC ratio to suppress in vitro resistance of *Pseudomonas aeruginosa*", Antimicrob Agents Chemother. (2005) 49(12): 4920-4927.
Teo et al., "Efficient and highly aldehyde selective Wacker oxidation", Org Lett. (2012) 14(13):3237-3239.
Theuretzbacher et al., "Update on antibacterial and antifungal drugs—can we master the resistance crisis?", Curr Opin Pharmacol. (2011) 11:429-432.
U.S. Department of Health and Human Resources, "Antibiotic Resistance Threats in the United States, 2013"; 114 pages.
Valters et al., "Ring-Chain Tautomerism", Plenum Press, New York and London, Softcover reprint of the hardcover 1st Ed. 1985, Chapter 1, 23 pages.
VanScoy et al., "Pharmacokinetics-pharmacodynamics of tazobactam in 386 combination with ceftolozane in an in vitro infection model", Antimicrob Agents Chemother. (2013) 57: 2809-2814. doi: 10.1128/AAC.02513-12.
Vasil'Ev et al., (1977): STN International HCAPLUS database, Columbus (OH), accession No. 1977: 72730; 1 page.
Vitor et al., "Rhenium(I)- and technetium(I) tricarbonyl complexes anchored by bifunctional pyrazole-diamine and pyrazole-dithioether chelators", J Organometal Chem (2004) 689(25):4764-4774.
Voituriez et al., "Preparation of a storable zinc carbenoid species and its application in cyclopropanation, chain extension, and [2,3]-sigmatropic rearrangement reactions", J Org Chem. (2010) 75(4): 1244-1250; Supporting Information, 20 pages.
Waley, Stephen G., "A quick method for the determination of inhibition constants", Biochem J. (1982) 205(3):631-633.
Walker et al., "Pharmacodynamic activities of meropenem in an animal infection model", (1994), Abstracts of Papers #A91, 34th Interscience Conference on Antimicrobial Agents and Chemotherapy, Orlando , FL., 5 pages.
Walsh et al., "Metallo-beta-Lactamases: the Quiet before the Storm?", Clin Microbiol Rev. (2005) 18(2):306-325.
Wang et al., "Recognition and resistance in TEM beta-lactamase", Biochemistry (2003) 42(28):8434-8444.
Webb et al., "Metal catalysed hydroboration of vinyl sulfides, sulfoxides, sulfones, and sulfonates", J Mol Cat A: Chem. (2007) 275:91-100.
Wilson, D.N., "The A-Z of bacterial translation inhibitors", Critical Reviews in Biochemistry and Molecular Biology, 2009; 44(6): 393-433.
Wohlrab et al., "Total synthesis of plusbacin A3: a depsipeptide antibiotic active against vancomycin-resistant bacteria", J. Am. Chem. Soc. (2007) 129:4175-4177.

(56) References Cited

OTHER PUBLICATIONS

Wong et al., "A chemoselective Reformatsky-Negishi approach to α-haloaryl esters", Tetrahedron (2014) 70(7): 1508-1515.
Xia et al., "Synthesis and SAR of novel benzoxaboroles as a new class of beta-lactamase inhibitors", Bioorg Med Chem Lett. (2011) 21:2533-2536.
Xie et al., "Group-assisted purification (GAP) chemistry for the synthesis of Velcade via asymmetric borylation of N-phosphinylimines", Beilstein J Org Chem (Mar. 2014) 10:746-751.
Yamamoto et al., "Iridium-catalyzed hydroboration of alkenes with pinacolborane", Tetrahedron (2004) 60:10695-10700.
Yanagisawa et al., "Nonpeptide angiotensin II receptor antagonists: synthesis, biological activities, and structure-activity relationships of imidazole-5-carboxylic acids bearing alkyl, alkenyl, and hydroxyalkyl substituents at the 4-position and their related compounds", J Med Chem. (1996) 39(1):323-338.
Yuen et al., "Deprotection of pinacolyl boronate esters via hydrolysis of intermediate potassium trifluoroborates", Tetrahed Lttr. (2005)46(46):7899-7903.
Zhu et al., "Design, preparation, x-ray crystal structure, and reactivity of o-alkoxyphenyliodonium bis(methoxycarbonyl)methanide, a highly soluble carbene precursor", Org Lett. (2012) 14(12): 3170-3173; Supporting Information, 76 pages.
CAS Registry No. 2114651-20-4; "7-Benzofurancarboxylic acid", Aurora Fine Chemicals; Aug. 16, 2017; 1 page.
CAS Registry No. 1780853-40-8; "7-Benzofurancarboxylic acid", Aurora Fine Chemicals; Jun. 15, 2015; 1 page.
CAS Registry No. 1427326-65-5; "7-Benzofurancarboxylic acid", Ellanova Laboratories; Apr. 5, 2013; 1 page.
CAS Registry No. 1344904-36-4; "7-Benzofurancarboxylic acid", Asiba Pharmatech, Inc.; Nov. 13, 2011; 1 page.
CAS Registry No. 1890373-92-8; "Benzoic acid", Aurora Fine Chemicals; Apr. 15, 2016; 1 page.
Cheng et al., "Inhibitors of hepatitis C virus polymerase: Synthesis and characterization of novel 2-oxy-6-fluoro-N-((S)-1-hydroxy-3-phenylpropan-2-yl)-benzamides", Bioorg Med Chem Ltts. (2010) 20:2119-2124.
Miriagou et al., "Acquired carbapenemases in Gram-negative bacterial pathogens: detection and surveillance issues", Clin Microbiol Infect. (Feb. 2010) 16(2):112-122.
Queenan et al., "Carbapenemases: the Versatile β-Lactamases", Clin Microbiol Rev. (Jun. 2007) 20(3): 440-458.
International Preliminary Report on Patentability dated May 23, 2018 for International Application No. PCT/US2017/039787, filed Jun. 28, 2017.

* cited by examiner

BORONIC ACID DERIVATIVES AND THERAPEUTIC USES THEREOF

INCORPORATION BY REFERENCE TO ANY PRIORITY APPLICATIONS

The present application is a continuation of U.S. application Ser. No. 15/636,424, filed Jun. 28, 2017, which claims the benefit of priority to U.S. Provisional Appl. No. 62/357,165, filed Jun. 30, 2016, both of which are incorporated by references in their entireties.

BACKGROUND

Field

The present application relates to the fields of chemistry and medicine. More particularly, the present application relates to boronic acid antimicrobial compounds, compositions, their preparation, and their use as therapeutic agents.

Description of the Related Art

Antibiotics have been effective tools in the treatment of infectious diseases during the last half-century. From the development of antibiotic therapy to the late 1980s there was almost complete control over bacterial infections in developed countries. However, in response to the pressure of antibiotic usage, multiple resistance mechanisms have become widespread and are threatening the clinical utility of anti-bacterial therapy. The increase in antibiotic resistant strains has been particularly common in major hospitals and care centers. The consequences of the increase in resistant strains include higher morbidity and mortality, longer patient hospitalization, and an increase in treatment costs.

Various bacteria have evolved β-lactam deactivating enzymes, namely, β-lactamases, that counter the efficacy of the various β-lactam antibiotics. β-lactamases can be grouped into 4 classes based on their amino acid sequences, namely, Ambler classes A, B, C, and D. Enzymes in classes A, C, and D include active-site serine β-lactamases, and class B enzymes, which are encountered less frequently, are Zn-dependent. These enzymes catalyze the chemical degradation of β-lactam antibiotics, rendering them inactive. Some β-lactamases can be transferred within and between various bacterial strains and species. The rapid spread of bacterial resistance and the evolution of multi-resistant strains severely limits β-lactam treatment options available.

The increase of class D β-lactamase-expressing bacterium strains such as *Acinetobacter baumannii* has become an emerging multidrug-resistant threat. *A. baumannii* strains express A, C, and D class β-lactamases. The class D β-lactamases such as the OXA families are particularly effective at destroying carbapenem type β-lactam antibiotics, e.g., imipenem, the active carbapenems component of Merck's Primaxin® (Montefour, K. et al., Crit. Care Nurse 2008, 28, 15; Perez, F. et al., Expert Rev. Anti Infect. Ther. 2008, 6, 269; Bou, G.; Martinez-Beltran, J., Antimicrob. Agents Chemother. 2000, 40, 428. 2006, 50, 2280; Bou, G. et al., J. Antimicrob. Agents Chemother. 2000, 44, 1556). This has imposed a pressing threat to the effective use of drugs in that category to treat and prevent bacterial infections. Indeed the number of catalogued serine-based β-lactamases has exploded from less than ten in the 1970s to over 300 variants. These issues fostered the development of five "generations" of cephalosporins. When initially released into clinical practice, extended-spectrum cephalosporins resisted hydrolysis by the prevalent class A β-lactamases, TEM-1 and SHV-1. However, the development of resistant strains by the evolution of single amino acid substitutions in TEM-1 and SHV-1 resulted in the emergence of the extended-spectrum β-lactamase (ESBL) phenotype.

New β-lactamases have recently evolved that hydrolyze the carbapenem class of antimicrobials, including imipenem, biapenem, doripenem, meropenem, and ertapenem, as well as other β-lactam antibiotics. These carbapenemases belong to molecular classes A, B, and D. Class A carbapenemases of the KPC-type predominantly in *Klebsiella pneumoniae* but now also reported in other Enterobacteriaceae, *Pseudomonas aeruginosa* and *Acinetobacter baumannii*. The KPC carbapenemase was first described in 1996 in North Carolina, but since then has disseminated widely in the US. It has been particularly problematic in the New York City area, where several reports of spread within major hospitals and patient morbidity have been reported. These enzymes have also been recently reported in France, Greece, Sweden, United Kingdom, and an outbreak in Germany has recently been reported. Treatment of resistant strains with carbapenems can be associated with poor outcomes.

The zinc-dependent class B metallo-β-lactamases are represented mainly by the VIM, IMP, and NDM types. IMP and VIM-producing *K. pneumonia* were first observed in 1990s in Japan and 2001 in Southern Europe, respectively. IMP-positive strains remain frequent in Japan and have also caused hospital outbreaks in China and Australia. However, dissemination of IMP-producing Enterobacteriaceae in the rest of the word appears to be somewhat limited. VIM-producing enterobacteria can be frequently isolated in Mediterranean countries, reaching epidemic proportions in Greece. Isolation of VIM-producing strains remains low in Northern Europe and in the United States. In stark contrast, a characteristic of NDM-producing *K. pneumonia* isolates has been their rapid dissemination from their epicenter, the Indian subcontinent, to Western Europe, North America, Australia and Far East. Moreover, NDM genes have spread rapidly to various species other than *K. pneumonia*.

The plasmid-expressed class D carbapenemases belong to OXA-48 type. OXA-48 producing *K. pneumonia* was first detected in Turkey, in 2001. The Middle East and North Africa remain the main centers of infection. However, recent isolation of OXA-48-type producing organisms in India, Senegal and Argentina suggest the possibility of a global expansion. Isolation of OXA-48 in bacteria other than *K. pneumonia* underlines the spreading potential of OXA-48.

Treatment of strains producing any of these carbapenemases with carbapenems can be associated with poor outcomes.

Another mechanism of β-lactamase mediated resistance to carbapenems involves combination of permeability or efflux mechanisms combined with hyper production of beta-lactamases. One example is the loss of a porin combined in hyperproduction of ampC beta-lactamase results in resistance to imipenem in *Pseudomonas aeruginosa*. Efflux pump over expression combined with hyperproduction of the ampC β-lactamase can also result in resistance to a carbapenem such as meropenem.

Thus, there is a need for improved β-lactamase inhibitors (BLIs).

SUMMARY

Some embodiments described herein relate to compounds having the structure of the Formula I or II, or pharmaceutically acceptable salts thereof:

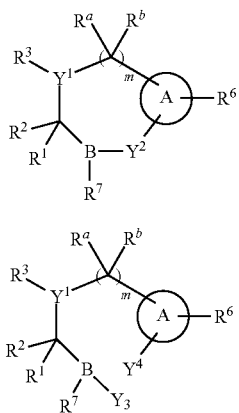

wherein
Y$^1$ is N or CR$^4$;
m is an integer of 0 or 1;

(a)
R$^2$ and R$^3$ together with the atoms to which they are attached form a fused ring or ring system selected from the group consisting of C$_{3-7}$carbocyclyl, 3-10 membered heterocyclyl, C$_{6-10}$ aryl, and 5-10 membered heteroaryl, each optionally substituted with one or more R$^5$, and each of R$^1$, R$^4$, R$^a$, and R$^b$ is independently selected from the group consisting of H, amino, halogen, cyano, hydroxy, optionally substituted C$_{1-6}$ alkyl, optionally substituted C$_{1-6}$ haloalkyl, optionally substituted C$_{1-6}$ alkoxy, optionally substituted C$_{1-6}$ haloalkoxy, optionally substituted (C$_{1-6}$ alkoxy)C$_{1-6}$ alkyl, optionally substituted C$_{2-10}$ alkenyl, optionally substituted C$_{2-10}$alkynyl, optionally substituted C$_{3-7}$ carbocyclyl, optionally substituted 3-10 membered heterocyclyl, optionally substituted C$_{6-10}$aryl, optionally substituted 5-10 membered heteroaryl, optionally substituted (C$_{3-7}$carbocyclyl)C$_{1-6}$alkyl, optionally substituted (3-10 membered heterocyclyl)C$_{1-6}$alkyl, optionally substituted (C$_{6-10}$ aryl)C$_{1-6}$alkyl, (C$_{6-10}$aryl)C$_{1-6}$alkoxy, optionally substituted (5-10 membered heteroaryl)C$_{1-6}$alkyl, acyl, C-carboxy, O-carboxy, C-amido, N-amido, S-sulfonamido, N-sulfonamido, —SR$^c$, —C(O)(CH$_2$)$_{0-3}$SR$^c$, —C(O)(CH$_2$)$_{1-3}$R$^d$, —NR$^f$C(O)NR$^f$R$^g$, —NR$^f$S(O)$_2$NR$^f$R$^g$, —C(=NR$^e$)R$^c$, —C(=NR$^e$)NR$^f$R$^g$, —NR$^f$CR$^c$(=NR$^e$), —NR$^f$C(=NR$^e$)NR$^f$R$^g$, —S(O)(CH$_2$)$_{1-3}$R$^c$, and —NR$^f$S(O)$_2$NR$^f$OR$^d$; or (b)
R$^3$ and R$^4$ together with the atoms to which they are attached form a spirocyclic ring or ring system selected from the group consisting of C$_{3-7}$carbocyclyl and 3-10 membered heterocyclyl, each optionally substituted with one or more R$^5$, and each of R$^1$, R$^2$, R$^a$, and R$^b$ is independently selected from the group consisting of H, amino, halogen, cyano, hydroxy, optionally substituted C$_{1-6}$ alkyl, optionally substituted C$_{1-6}$ haloalkyl, optionally substituted C$_{1-6}$ alkoxy, optionally substituted C$_{1-6}$ haloalkoxy, optionally substituted (C$_{1-6}$ alkoxy)C$_{1-6}$ alkyl, optionally substituted C$_{2-10}$alkenyl, optionally substituted C$_{2-10}$alkynyl, optionally substituted C$_{3-7}$ carbocyclyl, optionally substituted 3-10 membered heterocyclyl, optionally substituted C$_{6-10}$aryl, optionally substituted 5-10 membered heteroaryl, optionally substituted (C$_{3-7}$carbocyclyl)C$_{1-6}$alkyl, optionally substituted (3-10 membered heterocyclyl)C$_{1-6}$alkyl, optionally substituted (C$_{6-10}$ aryl)C$_{1-6}$alkyl, (C$_{6-10}$aryl)C$_{1-6}$alkoxy, optionally substituted (5-10 membered heteroaryl)C$_{1-6}$alkyl, acyl, C-carboxy, O-carboxy, C-amido, N-amido, S-sulfonamido, N-sulfonamido, —SR$^c$, —C(O)(CH$_2$)$_{0-3}$SR$^c$, —C(O)(CH$_2$)$_{1-3}$R$^d$, —NR$^f$C(O)NR$^f$R$^g$, —NR$^f$S(O)$_2$NR$^f$R$^g$, —C(=NR$^e$)R$^c$, —C(=NR$^e$)NR$^f$R$^g$, —NR$^f$CR$^c$(=NR$^e$), —NR$^f$C(=NR$^e$)NR$^f$R$^g$, —S(O)(CH$_2$)$_{1-3}$R$^c$, and —NR$^f$S(O)$_2$NR$^f$OR$^d$; or (c)
R$^1$ and R$^2$ together with the atoms to which they are attached form a spirocyclic ring or ring system selected from the group consisting of C$_{3-7}$carbocyclyl and 3-10 membered heterocyclyl, each optionally substituted with one or more R$^5$, and each of R$^3$, R$^4$, R$^a$, and R$^b$ is independently selected from the group consisting of H, amino, halogen, cyano, hydroxy, optionally substituted C$_{1-6}$ alkyl, optionally substituted C$_{1-6}$ haloalkyl, optionally substituted C$_{1-6}$ alkoxy, optionally substituted C$_{1-6}$ haloalkoxy, optionally substituted (C$_{1-6}$ alkoxy)C$_{1-6}$ alkyl, optionally substituted C$_{2-10}$alkenyl, optionally substituted C$_{2-10}$alkynyl, optionally substituted C$_{3-7}$ carbocyclyl, optionally substituted 3-10 membered heterocyclyl, optionally substituted C$_{6-10}$aryl, optionally substituted 5-10 membered heteroaryl, optionally substituted (C$_{3-7}$carbocyclyl)C$_{1-6}$alkyl, optionally substituted (3-10 membered heterocyclyl)C$_{1-6}$alkyl, optionally substituted (C$_{6-10}$ aryl)C$_{1-6}$alkyl, (C$_{6-10}$aryl)C$_{1-6}$alkoxy, optionally substituted (5-10 membered heteroaryl)C$_{1-6}$alkyl, acyl, C-carboxy, O-carboxy, C-amido, N-amido, S-sulfonamido, N-sulfonamido, —SR$^c$, —C(O)(CH$_2$)$_{0-3}$SR$^c$, —C(O)(CH$_2$)$_{1-3}$R$^d$, —NR$^f$C(O)NR$^f$R$^g$, —NR$^f$S(O)$_2$NR$^f$R$^g$, —C(=NR$^e$)R$^c$, —C(=NR$^e$)NR$^f$R$^g$, —NR$^f$CR$^c$(=NR$^e$), —NR$^f$C(=NR$^e$)NR$^f$R$^g$, —S(O)(CH$_2$)$_{1-3}$R$^c$, and —NR$^f$S(O)$_2$NR$^f$OR$^d$; or (d)
R$^a$ and R$^b$ together with the atoms to which they are attached form a spirocyclic ring or ring system selected from the group consisting of C$_{3-7}$ carbocyclyl and 3-10 membered heterocyclyl, each optionally substituted with one or more R$^5$, and each of R$^1$, R$^2$, R$^3$, and R$^4$ is independently selected from the group consisting of H, amino, halogen, cyano, hydroxy, optionally substituted C$_{1-6}$ alkyl, optionally substituted C$_{1-6}$ haloalkyl, optionally substituted C$_{1-6}$ alkoxy, optionally substituted C$_{1-6}$ haloalkoxy, optionally substituted (C$_{1-6}$ alkoxy)C$_{1-6}$ alkyl, optionally substituted C$_{2-10}$alkenyl, optionally substituted C$_{2-10}$alkynyl, optionally substituted C$_{3-7}$ carbocyclyl, optionally substituted 3-10 membered heterocyclyl, optionally substituted C$_{6-10}$aryl, optionally substituted 5-10 membered heteroaryl, optionally substituted (C$_{3-7}$carbocyclyl)C$_{1-6}$alkyl, optionally substituted (3-10 membered heterocyclyl)C$_{1-6}$alkyl, optionally substituted (C$_{6-10}$ aryl)C$_{1-6}$alkyl, (C$_{6-10}$aryl)C$_{1-6}$alkoxy, optionally substituted (5-10 membered heteroaryl)C$_{1-6}$alkyl, acyl, C-carboxy, O-carboxy, C-amido, N-amido, S-sulfonamido, N-sulfonamido, —SR$^c$, —C(O)(CH$_2$)$_{0-3}$SR$^c$, —C(O)(CH$_2$)$_{1-3}$R$^d$, —NR$^f$C(O)NR$^f$R$^g$, —NR$^f$S(O)$_2$NR$^f$R$^g$, —C(=NR$^e$)R$^c$, —C(=NR$^e$)NR$^f$R$^g$, —NR$^f$CR$^c$(=NR$^e$), —NR$^f$C(=NR$^e$)NR$^f$R$^g$, —S(O)(CH$_2$)$_{1-3}$R$^c$, and —NR$^f$S(O)$_2$NR$^f$OR$^d$; or (e)
R$^a$ and R$^4$ together with the atoms to which they are attached form a fused ring or ring system selected from the group consisting of $C_{3-7}$ carbocyclyl, 3-10 membered heterocyclyl, $C_{6-10}$ aryl, and 5-10 membered heteroaryl, each optionally substituted with one or more $R^5$ and each of $R^1$, $R^2$, $R^3$, and $R^b$ is independently selected from the group consisting of H, amino, halogen, cyano, hydroxy, optionally substituted $C_{1-6}$ alkyl, optionally substituted $C_{1-6}$ haloalkyl, optionally substituted $C_{1-6}$ alkoxy, optionally substituted $C_{1-6}$ haloalkoxy, optionally substituted ($C_{1-6}$ alkoxy)$C_{1-6}$ alkyl, optionally substituted $C_{2-10}$alkenyl, optionally substituted $C_{2-10}$alkynyl, optionally substituted $C_{3-7}$ carbocyclyl, optionally substituted 3-10 membered heterocyclyl, optionally substituted $C_{6-10}$aryl, optionally substituted 5-10 membered heteroaryl, optionally substituted ($C_{3-7}$carbocyclyl)$C_{1-6}$alkyl, optionally substituted (3-10 membered heterocyclyl)$C_{1-6}$alkyl, optionally substituted ($C_{6-10}$ aryl)$C_{1-6}$alkyl, ($C_{6-10}$aryl)$C_{1-6}$alkoxy, optionally substituted (5-10 membered heteroaryl)$C_{1-6}$alkyl, acyl, C-carboxy, O-carboxy, C-amido, N-amido, S-sulfonamido, N-sulfonamido, $-SR^c$, $-C(O)(CH_2)_{0-4}SR^c$, $-C(O)(CH_2)_{1-3}R^d$, $-NR^fC(O)NR^fR^g$, $-NR^fS(O)_2NR^fR^g$, $-C(=NR^e)R^c$, $-C(=NR^e)NR^fR^g$, $-NR^fCR^c(=NR^e)$, $-NR^fC(=NR^e)NR^fR^g$, $-S(O)(CH_2)_{1-3}R^c$, and $-NR^fS(O)_2NR^fOR^d$;

$R^5$ is $-Y^5-(CH_2)_t-G$;
t is an integer of 0 or 1;
G is selected from the group consisting of H, amino, halogen, cyano, hydroxy, optionally substituted $C_{1-6}$ alkyl, optionally substituted $C_{1-6}$ haloalkyl, optionally substituted $C_{1-6}$ alkoxy, optionally substituted $C_{1-6}$ haloalkoxy, optionally substituted ($C_{1-6}$ alkoxy)$C_{1-6}$ alkyl, optionally substituted $C_{2-10}$alkenyl, optionally substituted $C_{2-10}$alkynyl, optionally substituted $C_{3-7}$ carbocyclyl, optionally substituted 3-10 membered heterocyclyl, optionally substituted $C_{6-10}$aryl, optionally substituted 5-10 membered heteroaryl, optionally substituted ($C_{3-7}$carbocyclyl)$C_{1-6}$alkyl, optionally substituted (3-10 membered heterocyclyl)$C_{1-6}$alkyl, optionally substituted ($C_{6-10}$aryl)$C_{1-6}$alkyl, ($C_{6-10}$aryl)$C_{1-6}$ alkoxy, optionally substituted (5-10 membered heteroaryl)$C_{1-6}$alkyl, acyl, C-carboxy, O-carboxy, C-amido, N-amido, S-sulfonamido, N-sulfonamido, $-SR^c$, $-C(O)(CH_2)_{0-3}SR^c$, $-C(O)(CH_2)_{1-3}R^d$, $-NR^fC(O)NR^fR^g$, $-NR^fS(O)_2NR^fR^g$, $-C(=NR^e)R^c$, $-C(=NR^e)NR^fR^g$, $-NR^fCR^c(=NR^e)$, $-NR^fC(=NR^e)NR^fR^g$, $-S(O)(CH_2)_{1-3}R^c$, and $-NR^fS(O)_2NR^fOR^d$;

A is selected from the group consisting of $C_{3-7}$ carbocyclyl, 3-10 membered heterocyclyl, $C_{6-10}$aryl, and 5-10 membered heteroaryl, each optionally substituted by one or more $R^{12}$;

$R^6$ is selected from the group consisting of H, halogen, optionally substituted $C_{1-6}$alkyl, OH, $-C(O)OR$, optionally substituted $C_{1-6}$ alkoxy, amino, $-N(OR^8)R^9$, optionally substituted $C_{1-6}$ alkylthiol, C-amido, S-sulfonamido, CN, sulfinyl, sulfonyl, and a carboxylic acid isostere;

R is selected from the group consisting of H, $C_{1-9}$ alkyl, $-CR^{10}R^{11}OC(O)C_{1-9}$alkyl, $-CR^{10}R^{11}OC(O)C_{3-7}$carbocyclyl, $-CR^{10}R^{11}OC(O)$(3 to 7 membered heterocyclyl), $-CR^{10}R^{11}OC(O)C_{2-8}$alkoxyalkyl, $-CR^{10}R^{11}OC(O)OC_{1-9}$alkyl, $-CR^{10}R^{11}OC(O)OC_{3-7}$carbocyclyl, $-CR^{10}R^{11}OC(O)O$(3 to 7 membered heterocyclyl), $-CR^{10}R^{11}OC(O)OC_{2-8}$alkoxyalkyl, $-CR^{10}R^{11}OC(O)C_{6-10}$aryl, $-CR^{10}R^{11}OC(O)OC_{6-10}$ aryl, $-CR^{10}R^{11}C(O)NR^{13}R^{14}$, $-CR^{10}R^{11}OC(O)O(CH_2)_{1-3}C(O)NR^{13}R^{14}$, $-CR^{10}R^{11}OC(O)O(CH_2)_{2-3}OC(O)C_{1-4}$ alkyl, $-CR^{10}R^{11}OC(O)O(CH_2)_{1-3}C(O)OC_{1-4}$ alkyl, $-CR^{10}R^{11}OC(O)(CH_2)_{1-3}OC(O)C_{1-4}$ alkyl, and

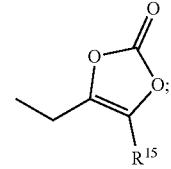

$R^7$ is selected from the group consisting of —OH, optionally substituted $C_{1-6}$ alkoxy, amino, and $-N(OR^8)R^9$;

each $R^8$ and $R^9$ is independently selected from the group consisting of H, halogen, optionally substituted $C_{1-4}$alkyl, optionally substituted $C_{3-7}$ carbocyclyl, optionally substituted 3-10 membered heterocyclyl, optionally substituted $C_{6-10}$aryl, and optionally substituted 5-10 membered heteroaryl;

each $R^{10}$ and $R^{11}$ is independently selected from the group consisting of H, optionally substituted $C_{1-4}$alkyl, optionally substituted $C_{3-7}$ carbocyclyl, optionally substituted 3-10 membered heterocyclyl, optionally substituted $C_{6-10}$aryl, and optionally substituted 5-10 membered heteroaryl;

$R^{12}$ is selected from the group consisting of hydrogen, amino, halogen, cyano, hydroxy, optionally substituted $C_{1-6}$ alkyl, optionally substituted $C_{1-6}$ haloalkyl, optionally substituted $C_{1-6}$ alkoxy, optionally substituted $C_{1-6}$ haloalkoxy, optionally substituted ($C_{1-6}$ alkoxy)$C_{1-6}$ alkyl, optionally substituted $C_{2-10}$alkenyl, optionally substituted $C_{2-10}$alkynyl, optionally substituted $C_{3-7}$ carbocyclyl, optionally substituted 3-10 membered heterocyclyl, optionally substituted $C_{6-10}$aryl, optionally substituted 5-10 membered heteroaryl, optionally substituted ($C_{3-7}$carbocyclyl)$C_{1-6}$ alkyl, optionally substituted (3-10 membered heterocyclyl)$C_{1-6}$alkyl, optionally substituted ($C_{6-10}$aryl)$C_{1-6}$alkyl, ($C_{6-10}$-aryl)$C_{1-6}$alkoxy, optionally substituted (5-10 membered heteroaryl)$C_{1-6}$alkyl, acyl, C-carboxy, O-carboxy, C-amido, N-amido, S-sulfonamido, N-sulfonamido, sulfhydryl, $-C(O)(CH_2)_{0-3}SR^c$, $-C(O)(CH_2)_{1-3}R^d$, $-NR^fC(O)NR^fR^g$, $-NR^fS(O)_2NR^fR^g$, $-C(=NR^e)R^c$, $-C(=NR^e)NR^fR^g$, $-NR^fCR^c(=NR^e)$, $-NR^fC(=NR^e)NR^fR^g$, $-S(O)(CH_2)_{1-3}R^c$, $-NR^fS(O)_2NR^fOR^d$, and $-(CH_2)_p-Y^6-(CH_2)_qK$;

each $R^{13}$ and $R^{14}$ is independently selected from the group consisting of H, optionally substituted $C_{1-6}$alkyl, optionally substituted $C_{3-7}$ carbocyclyl, optionally substituted 3-10 membered heterocyclyl, optionally substituted $C_{6-10}$aryl, and optionally substituted 5-10 membered heteroaryl;

$R^{15}$ is optionally substituted $C_{1-6}$ alkyl;

$Y^2$ is selected from the group consisting of —O—, —S—, and $-NR^9-$;

$Y^3$ is selected from the group consisting of —OH, —SH, and $-NHR^9$;

$Y^4$ is selected from the group consisting of —OH, optionally substituted $C_{1-6}$ alkoxy, amino, and $-N(OR^8)R^9$; and $Y^5$ is selected from the group consisting of —S—, $-S(O)-$, $-S(O)_2-$, —O—, $-CR^fR^g-$, and $-NR^g-$, or $Y^5$ is absent;

$Y^6$ is selected from the group consisting of —S—, —S(O)—, —S(O)$_2$—, —O—, —CR$^f$R$^g$—, and —NR$^f$—;

K is selected from the group consisting of C-amido; N-amido; S-sulfonamido; N-sulfonamido; —NR$^f$C(O)NR$^f$R$^g$; —NR$^f$S(O)$_2$NR$^f$R$^g$; —C(=NR$^e$)R$^c$; —C(=NR$^e$)NR$^f$R$^g$; —NR$^f$CR$^c$(=NR$^e$); —NR$^f$C(=NR$^e$)NR$^f$R$^g$; C$_{1-4}$ alkyl optionally substituted with 0-2 substituents selected from the group consisting of C$_{1-4}$ alkoxy, amino, halogen, C-amido, and N-amido; C$_{6-10}$ aryl optionally substituted with 0-2 substituents selected from the group consisting of C$_{1-4}$ alkyl, C$_{1-4}$ alkoxy, amino, halogen, C-amido, and N-amido; C$_{3-7}$ carbocyclyl optionally substituted with 0-2 substituents selected from the group consisting of C$_{1-4}$ alkyl, C$_{1-4}$ alkoxy, amino, halogen, C-amido, and N-amido; 5-10 membered heteroaryl optionally substituted with 0-2 substituents selected from the group consisting of C$_{1-4}$ alkyl, C$_{1-4}$ alkoxy, amino, halogen, C-amido, and N-amido; and 3-10 membered heterocyclyl optionally substituted with 0-2 substituents selected from the group consisting of C$_{1-4}$ alkyl, C$_{1-4}$ alkoxy, amino, halogen, C-amido, and N-amido;

each R$^c$, R$^d$, R$^e$, R$^f$, and R$^g$ are independently selected from the group consisting of H, halogen, optionally substituted C$_{1-4}$alkyl, optionally substituted C$_{3-7}$ carbocyclyl, optionally substituted 3-10 membered heterocyclyl, optionally substituted C$_{6-10}$aryl, and optionally substituted 5-10 membered heteroaryl; and each p and q is independently 0 or 1.

Some embodiments described herein relate to compounds having the structure of the Formula III or IV, or pharmaceutically acceptable salts thereof:

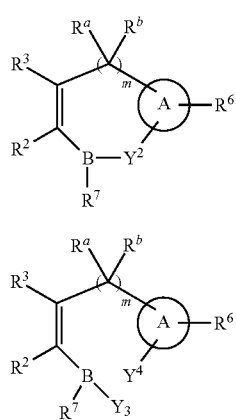

III

IV wherein
(a)
each of R$^2$ and R$^3$ is independently selected from the group consisting of H, amino, halogen, cyano, hydroxy, optionally substituted C$_{1-6}$ alkyl, optionally substituted C$_{1-6}$ haloalkyl, optionally substituted C$_{1-6}$ alkoxy, optionally substituted C$_{1-6}$ haloalkoxy, optionally substituted (C$_{1-6}$ alkoxy)C$_{1-6}$ alkyl, optionally substituted C$_{2-10}$alkenyl, optionally substituted C$_{2-10}$alkynyl, optionally substituted C$_{3-7}$ carbocyclyl, optionally substituted 3-10 membered heterocyclyl, optionally substituted C$_{6-10}$aryl, optionally substituted 5-10 membered heteroaryl, optionally substituted (C$_{3-7}$ carbocyclyl)C$_{1-6}$alkyl, optionally substituted (3-10 membered heterocyclyl)C$_{1-6}$alkyl, optionally substituted (C$_{6-10}$aryl)C$_{1-6}$alkyl, (C$_{6-10}$aryl)C$_{1-6}$alkoxy, optionally substituted (5-10 membered heteroaryl)C$_{1-6}$ alkyl, acyl, C-carboxy, O-carboxy, C-amido, N-amido, S-sulfonamido, N-sulfonamido, —SR$^c$, —C(O)(CH$_2$)$_{0-4}$SR$^c$, —C(O)(CH$_2$)$_{1-3}$R$^d$, —NR$^f$C(O)NR$^f$R$^g$, —NR$^f$S(O)$_2$NR$^f$R$^g$, —C(=NR$^e$)R$^c$, —C(=NR$^e$)NR$^f$R$^g$, —NR$^f$CR$^c$(=NR$^e$), —NR$^f$C(=NR$^e$)NR$^f$R$^g$, —S(O)(CH$_2$)$_{1-3}$R$^c$, and —NR$^f$S(O)$_2$NR$^f$OR$^d$, or R$^2$ and R$^3$ together with the atoms to which they are attached form a fused ring or ring system selected from the group consisting of C$_{3-7}$carbocyclyl, 3-10 membered heterocyclyl, C$_{6-10}$ aryl, and 5-10 membered heteroaryl, each optionally substituted with one or more R$^5$;

m is an integer of 0 or 1; and each R$^a$ and R$^b$ is independently selected from the group consisting of H, amino, halogen, cyano, hydroxy, optionally substituted C$_{1-6}$ alkyl, optionally substituted C$_{1-6}$ haloalkyl, optionally substituted C$_{1-6}$ alkoxy, optionally substituted C$_{1-6}$ haloalkoxy, optionally substituted (C$_{1-6}$ alkoxy)C$_{1-6}$ alkyl, optionally substituted C$_{2-10}$alkenyl, optionally substituted C$_{2-10}$alkynyl, optionally substituted C$_{3-7}$ carbocyclyl, optionally substituted 3-10 membered heterocyclyl, optionally substituted C$_{6-10}$aryl, optionally substituted 5-10 membered heteroaryl, optionally substituted (C$_{3-7}$ carbocyclyl)C$_{1-6}$alkyl, optionally substituted (3-10 membered heterocyclyl)C$_{1-6}$alkyl, optionally substituted (C$_{6-10}$aryl)C$_{1-6}$alkyl, (C$_{6-10}$aryl)C$_{1-6}$alkoxy, optionally substituted (5-10 membered heteroaryl)C$_{1-6}$ alkyl, acyl, C-carboxy, O-carboxy, C-amido, N-amido, S-sulfonamido, N-sulfonamido, —SR$^c$, —C(O)(CH$_2$)$_{0-4}$SR$^c$, —C(O)(CH$_2$)$_{1-3}$R$^d$, —NR$^f$C(O)NR$^f$R$^g$, —NR$^f$S(O)$_2$NR$^f$R$^g$, —C(=NR$^e$)R$^c$, —C(=NR$^e$)NR$^f$R$^g$, —NR$^f$CR$^c$(=NR$^e$), —NR$^f$C(=NR$^e$)NR$^f$R$^g$, —S(O)(CH$_2$)$_{1-3}$R$^c$, and —NR$^f$S(O)$_2$NR$^f$OR$^d$, or R$^a$ and R$^b$ together with the atoms to which they are attached form a spiro ring or ring system selected from the group consisting of C$_{3-7}$carbocyclyl and 3-10 membered heterocyclyl, each optionally substituted with one or more R$^5$; or (b)
m is 1;
R$^a$ and R$^3$ together with the atoms to which they are attached form a fused ring or ring system selected from the group consisting of C$_{3-7}$carbocyclyl and 3-10 membered heterocyclyl, each optionally substituted with one or more R$^5$; and each R$^2$ and R$^b$ is independently selected from the group consisting of H, amino, halogen, cyano, hydroxy, optionally substituted C$_{1-6}$ alkyl, optionally substituted C$_{1-6}$ haloalkyl, optionally substituted C$_{1-6}$ alkoxy, optionally substituted C$_{1-6}$ haloalkoxy, optionally substituted (C$_{1-6}$ alkoxy)C$_{1-6}$ alkyl, optionally substituted C$_{2-10}$alkenyl, optionally substituted C$_{2-10}$alkynyl, optionally substituted C$_{3-7}$ carbocyclyl, optionally substituted 3-10 membered heterocyclyl, optionally substituted C$_{6-10}$aryl, optionally substituted 5-10 membered heteroaryl, optionally substituted (C$_{3-7}$ carbocyclyl)C$_{1-6}$alkyl, optionally substituted (3-10 membered heterocyclyl)C$_{1-6}$alkyl, optionally substituted (C$_{6-10}$aryl)C$_{1-6}$alkyl, (C$_{6-10}$aryl)C$_{1-6}$alkoxy, optionally substituted (5-10 membered heteroaryl)C$_{1-6}$ alkyl, acyl, C-carboxy, O-carboxy, C-amido, N-amido, S-sulfonamido, N-sulfonamido, —SR$^c$, —C(O)(CH$_2$)$_{0-4}$SR$^c$, —C(O)(CH$_2$)$_{1-3}$R$^d$, —NR$^f$C(O)

NR$^f$R$^g$, —NR$^f$S(O)$_2$NR$^f$R$^g$, —C(=NR$^e$)R$^c$, —C(=NR$^e$)NR$^f$R$^g$, —NR$^f$CR$^c$(=NR$^e$), —NR$^f$C(=NR$^e$)NR$^f$R$^g$, —S(O)(CH$_2$)$_{1-3}$R$^c$, and —NR$^f$S(O)$_2$NR$^f$OR$^d$;

R$^5$ is —Y$^5$—(CH$_2$)$_t$-G;

t is an integer of 0 or 1;

G is selected from the group consisting of H, amino, halogen, cyano, hydroxy, optionally substituted C$_{1-6}$ alkyl, optionally substituted C$_{1-6}$ haloalkyl, optionally substituted C$_{1-6}$ alkoxy, optionally substituted C$_{1-6}$ haloalkoxy, optionally substituted (C$_{1-6}$ alkoxy)C$_{1-6}$ alkyl, optionally substituted C$_{2-10}$alkenyl, optionally substituted C$_{2-10}$alkynyl, optionally substituted C$_{3-7}$ carbocyclyl, optionally substituted 3-10 membered heterocyclyl, optionally substituted C$_{6-10}$aryl, optionally substituted 5-10 membered heteroaryl, optionally substituted (C$_{3-7}$carbocyclyl)C$_{1-6}$alkyl, optionally substituted (3-10 membered heterocyclyl)C$_{1-6}$alkyl, optionally substituted (C$_{6-10}$aryl)C$_{1-6}$alkyl, (C$_{6-10}$aryl)C$_{1-6}$ alkoxy, optionally substituted (5-10 membered heteroaryl)C$_{1-6}$alkyl, acyl, C-carboxy, O-carboxy, C-amido, N-amido, S-sulfonamido, N-sulfonamido, —SR$^c$, —C(O)(CH$_2$)$_{0-3}$SR$^c$, —C(O)(CH$_2$)$_{1-3}$R$^d$, —NR$^f$C(O)NR$^f$R$^g$, —NR$^f$S(O)$_2$NR$^f$R$^g$, —C(=NR$^e$) R$^c$, —C(=NR$^e$)NR$^f$R$^g$, —NR$^f$CR$^c$(=NR$^e$), —NR$^f$C (=NR$^e$)NR$^f$R$^g$, —S(O)(CH$_2$)$_{1-3}$R$^c$, and —NR$^f$S(O)$_2$ NR$^f$OR$^d$;

A is a ring system selected from the group consisting of C$_{3-7}$ carbocyclyl, 3-10 membered heterocyclyl, C$_{6-10}$aryl, and 5-10 membered heteroaryl, each optionally substituted with one or more R$^{12}$;

R$^6$ is selected from the group consisting of H, halogen, optionally substituted C$_{1-6}$alkyl, OH, —C(O)OR, optionally substituted C$_{1-6}$ alkoxy, amino, —N(OR$^8$) R$^9$, optionally substituted C$_{1-6}$ alkylthiol, C-amido, S-sulfonamido, CN, sulfinyl, sulfonyl, and a carboxylic acid isostere;

R is selected from the group consisting of H, C$_{1-9}$ alkyl, —CR$^{10}$R$^{11}$OC(O)C$_{1-9}$alkyl, —CR$^{10}$R$^{11}$OC(O)C$_{3-7}$carbocyclyl, —CR$^{10}$R$^{11}$OC(O)(3 to 7 membered heterocyclyl), —CR$^{10}$R$^{11}$C(O)C$_{2-8}$alkoxyalkyl, —CR$^{10}$R$^{11}$OC(O)OC$_{1-9}$alkyl, —CR$^{10}$R$^{11}$OC(O)OC$_{3-7}$ carbocyclyl, —CR$^{10}$R$^{11}$OC(O)O (3 to 7 membered heterocyclyl), —CR$^{10}$R$^{11}$OC(O)OC$_{2-8}$alkoxyalkyl, —CR$^{10}$R$^{11}$OC(O)C$_{6-10}$aryl, —CR$^{10}$R$^{11}$OC(O)OC$_{6-10}$ aryl, —CR$^{10}$R$^{11}$C(O)NR$^{13}$R$^{14}$, —CR$^{10}$R$^{11}$OC(O)O (CH$_2$)$_{1-3}$C(O)NR$^{13}$R$^{14}$, —CR$^{10}$R$^{11}$OC(O)O(CH$_2$)$_{2-3}$ OC(O)C$_{1-4}$ alkyl, —CR$^{10}$R$^{11}$OC(O)O(CH$_2$)$_{1-3}$C(O) OC$_{1-4}$ alkyl, —CR$^{10}$R$^{11}$OC(O)(CH$_2$)$_{1-3}$OC(O)C$_{1-4}$ alkyl, and

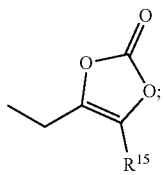

R$^7$ is selected from the group consisting of —OH, optionally substituted C$_{1-6}$ alkoxy, amino, and —N(OR$^8$)R$^9$;

each R$^8$ and R$^9$ is independently selected from the group consisting of H, halogen, optionally substituted C$_{1-4}$alkyl, optionally substituted C$_{3-7}$ carbocyclyl, optionally substituted 3-10 membered heterocyclyl, optionally substituted C$_{6-10}$aryl, and optionally substituted 5-10 membered heteroaryl;

each R$^{10}$ and R$^{11}$ is independently selected from the group consisting of H, optionally substituted C$_{1-4}$alkyl, optionally substituted C$_{3-7}$ carbocyclyl, optionally substituted 3-10 membered heterocyclyl, optionally substituted C$_{6-10}$aryl, and optionally substituted 5-10 membered heteroaryl;

R$^{12}$ is selected from the group consisting of hydrogen, amino, halogen, cyano, hydroxy, optionally substituted C$_{1-6}$ alkyl, optionally substituted C$_{1-6}$ haloalkyl, optionally substituted C$_{1-6}$ alkoxy, optionally substituted C$_{1-6}$ haloalkoxy, optionally substituted C$_{1-6}$alkylthiol, optionally substituted (C$_{1-6}$ alkoxy)C$_{1-6}$ alkyl, optionally substituted C$_{2-10}$alkenyl, optionally substituted C$_{2-10}$alkynyl, optionally substituted C$_{3-7}$ carbocyclyl, optionally substituted 3-10 membered heterocyclyl, optionally substituted C$_{6-10}$aryl, optionally substituted 5-10 membered heteroaryl, optionally substituted (C$_{3-7}$carbocyclyl)C$_{1-6}$alkyl, optionally substituted (3-10 membered heterocyclyl)C$_{1-6}$alkyl, optionally substituted (C$_{6-10}$aryl)C$_{1-6}$alkyl, (C$_{6-10}$aryl)C$_{1-6}$ alkoxy, optionally substituted (5-10 membered heteroaryl)C$_{1-6}$alkyl, acyl, C-carboxy, O-carboxy, C-amido, N-amido, S-sulfonamido, N-sulfonamido, sulfhydryl, —C(O)(CH$_2$)$_{0-3}$SR$^c$, —C(O)(CH$_2$)$_{1-3}$R$^d$, —NR$^f$C(O)NR$^f$R$^g$, —NR'S(O)$_2$NR$^f$R$^g$, —C(=NR$^e$) R$^c$, —C(=NR$^e$)NR$^f$R$^g$, —NR$^f$CR$^c$(=NR$^e$), —NR$^f$C (=NR$^e$)NR$^f$R$^g$, —S(O)(CH$_2$)$_{1-3}$R$^c$, —NR$^f$S(O)$_2$ NR$^f$OR$^d$, and —(CH$_2$)$_p$—Y$^6$—(CH$_2$)$_q$K;

each R$^{13}$ and R$^{14}$ is independently selected from the group consisting of H, optionally substituted C$_{1-6}$alkyl, optionally substituted C$_{3-7}$ carbocyclyl, optionally substituted 3-10 membered heterocyclyl, optionally substituted C$_{6-10}$aryl, and optionally substituted 5-10 membered heteroaryl;

R$^{15}$ is optionally substituted C$_{1-6}$ alkyl;

Y$^2$ is selected from the group consisting of —O—, —S—, and —NR$^9$—;

Y$^3$ is selected from the group consisting of —OH, —SH, and —NHR$^9$;

Y$^4$ is selected from the group consisting of —OH, optionally substituted C$_{1-6}$ alkoxy, amino, and —N(OR$^8$)R$^9$;

Y$^5$ is selected from the group consisting of —S—, —S(O)—, —S(O)$_2$—, —O—, —CR$^f$R$^g$—, and —NR$^g$—, or Y$^5$ is absent;

Y$^6$ is selected from the group consisting of —S—, —S(O)—, —S(O)$_2$—, —O—, —CR$^f$R$^g$—, and —NR$^f$—;

K is selected from the group consisting of C-amido; N-amido; S-sulfonamido; N-sulfonamido; —NR$^f$C(O) NR$^f$R$^g$; —NR$^f$S(O)$_2$NR$^f$R$^g$; —C(=NR$^e$)R$^c$; —C(=NR$^e$)NR$^f$R$^g$; —NR$^f$CR$^c$(=NR$^e$); —NR$^f$C (=NR$^e$)NR$^f$R$^g$; C$_{1-4}$ alkyl optionally substituted with 0-2 substituents selected from the group consisting of C$_{1-4}$ alkoxy, amino, halogen, C-amido, and N-amido; C$_{6-10}$ aryl optionally substituted with 0-2 substituents selected from the group consisting of C$_{1-4}$ alkyl, C$_{1-4}$ alkoxy, amino, halogen, C-amido, and N-amido; C$_{3-7}$ carbocyclyl optionally substituted with 0-2 substituents selected from the group consisting of C$_{1-4}$ alkyl, C$_{1-4}$ alkoxy, amino, halogen, C-amido, and N-amido; 5-10 membered heteroaryl optionally substituted with 0-2 substituents selected from the group consisting of C$_{1-4}$ alkyl, C$_{1-4}$ alkoxy, amino, halogen, C-amido, and N-amido; and 3-10 membered heterocyclyl optionally substituted with 0-2 substituents selected from the group consisting of $C_{1-4}$ alkyl, $C_{1-4}$ alkoxy, amino, halogen, C-amido, and N-amido;

each $R^c$, $R^d$, $R^e$, $R^f$, and $R^g$ are independently selected from the group consisting of H, halogen, optionally substituted $C_{1-4}$alkyl, optionally substituted $C_{3-7}$ carbocyclyl, optionally substituted 3-10 membered heterocyclyl, optionally substituted $C_{6-10}$aryl, and optionally substituted 5-10 membered heteroaryl; and each p and q is independently 0 or 1.

Some further embodiments described herein relate to compounds having the structure of the Formula V, or pharmaceutically acceptable salts thereof

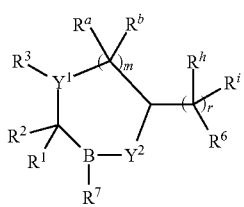

V wherein
Y is N or $CR^4$;
m is an integer of 0 or 1;
r is an integer of 0 or 1;

(a)
$R^2$ and $R^3$ together with the atoms to which they are attached form a fused ring or ring system selected from the group consisting of $C_{3-7}$carbocyclyl, 3-10 membered heterocyclyl, $C_{6-10}$ aryl, and 5-10 membered heteroaryl, each optionally substituted with one or more $R^5$, and each of $R^1$, $R^4$, $R^a$, and $R^b$ is independently selected from the group consisting of H, amino, halogen, cyano, hydroxy, optionally substituted $C_{1-6}$ alkyl, optionally substituted $C_{1-6}$ haloalkyl, optionally substituted $C_{1-6}$ alkoxy, optionally substituted $C_{1-6}$ haloalkoxy, optionally substituted $(C_{1-6}$ alkoxy$)C_{1-6}$ alkyl, optionally substituted $C_{2-10}$alkenyl, optionally substituted $C_{2-10}$alkynyl, optionally substituted $C_{3-7}$ carbocyclyl, optionally substituted 3-10 membered heterocyclyl, optionally substituted $C_{6-10}$aryl, optionally substituted 5-10 membered heteroaryl, optionally substituted $(C_{3-7}$carbocyclyl$)C_{1-6}$alkyl, optionally substituted (3-10 membered heterocyclyl$)C_{1-6}$alkyl, optionally substituted $(C_{6-10}$ aryl$)C_{1-6}$alkyl, $(C_{6-10}$aryl$)C_{1-6}$alkoxy, optionally substituted (5-10 membered heteroaryl$)C_{1-6}$alkyl, acyl, C-carboxy, O-carboxy, C-amido, N-amido, S-sulfonamido, N-sulfonamido, —$SR^c$, —$C(O)(CH_2)_{0-3}SR^c$, —$C(O)(CH_2)_{1-3}R^d$, —$NR^fC(O)NR^fR^g$, —$NR^fS(O)_2NR^fR^g$, —$C(=NR^e)R^c$, —$C(=NR^e)NR^fR^g$, —$NR^fCR^c(=NR^e)$, —$NR^fC(=NR^e)NR^fR^g$, —$S(O)(CH_2)_{1-3}R^c$, and —$NR^fS(O)_2NR^fOR^d$; or (b)
$R^3$ and $R^4$ together with the atoms to which they are attached form a spirocyclic ring or ring system selected from the group consisting of $C_{3-7}$carbocyclyl and 3-10 membered heterocyclyl, each optionally substituted with one or more $R^5$, and each of $R^1$, $R^2$, $R^a$, and $R^b$ is independently selected from the group consisting of H, amino, halogen, cyano, hydroxy, optionally substituted $C_{1-6}$ alkyl, optionally substituted $C_{1-6}$ haloalkyl, optionally substituted $C_{1-6}$ alkoxy, optionally substituted $C_{1-6}$ haloalkoxy, optionally substituted $(C_{1-6}$ alkoxy$)C_{1-6}$ alkyl, optionally substituted $C_{2-10}$alkenyl, optionally substituted $C_{2-10}$alkynyl, optionally substituted $C_{3-7}$ carbocyclyl, optionally substituted 3-10 membered heterocyclyl, optionally substituted $C_{6-10}$aryl, optionally substituted 5-10 membered heteroaryl, optionally substituted $(C_{3-7}$carbocyclyl$)C_{1-6}$alkyl, optionally substituted (3-10 membered heterocyclyl$)C_{1-6}$alkyl, optionally substituted $(C_{6-10}$ aryl$)C_{1-6}$alkyl, $(C_{6-10}$aryl$)C_{1-6}$alkoxy, optionally substituted (5-10 membered heteroaryl$)C_{1-6}$alkyl, acyl, C-carboxy, O-carboxy, C-amido, N-amido, S-sulfonamido, N-sulfonamido, —$SR^c$, —$C(O)(CH_2)_{0-3}SR^c$, —$C(O)(CH_2)_{1-3}R^d$, —$NR^fC(O)NR^fR^g$, —$NR^fS(O)_2NR^fR^g$, —$C(=NR^e)R^c$, —$C(=NR^e)NR^fR^g$, —$NR^fCR^c(=NR^e)$, —$NR^fC(=NR^e)NR^fR^g$, —$S(O)(CH_2)_{1-3}R^c$, and —$NR^fS(O)_2NR^fOR^d$; or (c)
$R^1$ and $R^2$ together with the atoms to which they are attached form a spirocyclic ring or ring system selected from the group consisting of $C_{3-7}$carbocyclyl and 3-10 membered heterocyclyl, each optionally substituted with one or more $R^5$, and each of $R^3$, $R^4$, $R^a$, and $R^b$ is independently selected from the group consisting of H, amino, halogen, cyano, hydroxy, optionally substituted $C_{1-6}$ alkyl, optionally substituted $C_{1-6}$ haloalkyl, optionally substituted $C_{1-6}$ alkoxy, optionally substituted $C_{1-6}$ haloalkoxy, optionally substituted $(C_{1-6}$ alkoxy$)C_{1-6}$ alkyl, optionally substituted $C_{2-10}$alkenyl, optionally substituted $C_{2-10}$alkynyl, optionally substituted $C_{3-7}$ carbocyclyl, optionally substituted 3-10 membered heterocyclyl, optionally substituted $C_{6-10}$aryl, optionally substituted 5-10 membered heteroaryl, optionally substituted $(C_{3-7}$carbocyclyl$)C_{1-6}$alkyl, optionally substituted (3-10 membered heterocyclyl$)C_{1-6}$alkyl, optionally substituted $(C_{6-10}$ aryl$)C_{1-6}$alkyl, $(C_{6-10}$aryl$)C_{1-6}$alkoxy, optionally substituted (5-10 membered heteroaryl$)C_{1-6}$alkyl, acyl, C-carboxy, O-carboxy, C-amido, N-amido, S-sulfonamido, N-sulfonamido, —$SR^c$, —$C(O)(CH_2)_{0-3}SR^c$, —$C(O)(CH_2)_{1-3}R^d$, —$NR^fC(O)NR^fR^g$, —$NR^fS(O)_2NR^fR^g$, —$C(=NR^e)R^c$, —$C(=NR^e)NR^fR^g$, —$NR^fCR^c(=NR^e)$, —$NR^fC(=NR^e)NR^fR^g$, —$S(O)(CH_2)_{1-3}R^c$, and —$NR^fS(O)_2NR^fOR^d$; or (d)
$R^a$ and $R^b$ together with the atoms to which they are attached form a spirocyclic ring or ring system selected from the group consisting of $C_{3-7}$ carbocyclyl and 3-10 membered heterocyclyl, each optionally substituted with one or more $R^5$, and each of $R^1$, $R^2$, $R^3$, and $R^4$ is independently selected from the group consisting of H, amino, halogen, cyano, hydroxy, optionally substituted $C_{1-6}$ alkyl, optionally substituted $C_{1-6}$ haloalkyl, optionally substituted $C_{1-6}$ alkoxy, optionally substituted $C_{1-6}$ haloalkoxy, optionally substituted $(C_{1-6}$ alkoxy$)C_{1-6}$ alkyl, optionally substituted $C_{2-10}$alkenyl, optionally substituted $C_{2-10}$alkynyl, optionally substituted $C_{3-7}$ carbocyclyl, optionally substituted 3-10 membered heterocyclyl, optionally substituted $C_{6-10}$aryl, optionally substituted 5-10 membered heteroaryl, optionally substituted $(C_{3-7}$carbocyclyl$)C_{1-6}$alkyl, optionally substituted (3-10 membered heterocyclyl$)C_{1-6}$alkyl, optionally substituted $(C_{6-10}$ aryl$)C_{1-6}$alkyl, $(C_{6-10}$aryl$)C_{1-6}$alkoxy, optionally substituted (5-10 membered heteroaryl$)C_{1-6}$alkyl, acyl, C-carboxy, O-carboxy, C-amido, N-amido, S-sulfonamido, N-sulfonamido, —$SR^c$, —$C(O)(CH_2)_{0-3}SR^c$, —$C(O)(CH_2)_{1-3}R^d$, —$NR^fC(O)NR^fR^g$, —NR$^f$S(O)$_2$NR$^f$R$^g$, —C(=NR$^e$)R$^c$, —C(=NR$^e$)NR$^f$R$^g$, —NR$^f$CR$^c$(=NR$^e$), —NR$^f$C(=NR$^e$)NR$^f$R$^g$, —S(O)(CH$_2$)$_{1-3}$R$^c$, and —NR$^f$S(O)$_2$NR$^f$OR$^d$; or (e) R$^a$ and R$^4$ together with the atoms to which they are attached form a fused ring or ring system selected from the group consisting of C$_{3-7}$ carbocyclyl, 3-10 membered heterocyclyl, C$_{6-10}$ aryl, and 5-10 membered heteroaryl, each optionally substituted with one or more R$^5$, and each of R$^1$, R$^2$, R$^3$, and R$^b$ is independently selected from the group consisting of H, amino, halogen, cyano, hydroxy, optionally substituted C$_{1-6}$ alkyl, optionally substituted C$_{1-6}$ haloalkyl, optionally substituted C$_{1-6}$ alkoxy, optionally substituted C$_{1-6}$ haloalkoxy, optionally substituted (C$_{1-6}$ alkoxy)C$_{1-6}$ alkyl, optionally substituted C$_{2-10}$alkenyl, optionally substituted C$_{2-10}$alkynyl, optionally substituted C$_{3-7}$ carbocyclyl, optionally substituted 3-10 membered heterocyclyl, optionally substituted C$_{6-10}$aryl, optionally substituted 5-10 membered heteroaryl, optionally substituted (C$_{3-7}$carbocyclyl)C$_{1-6}$alkyl, optionally substituted (3-10 membered heterocyclyl)C$_{1-6}$alkyl, optionally substituted (C$_{6-10}$ aryl)C$_{1-6}$alkyl, (C$_{6-10}$aryl)C$_{1-6}$alkoxy, optionally substituted (5-10 membered heteroaryl)C$_{1-6}$alkyl, acyl, C-carboxy, O-carboxy, C-amido, N-amido, S-sulfonamido, N-sulfonamido, —SR$^c$, —C(O)(CH$_2$)$_{0-3}$SR$^c$, —C(O)(CH$_2$)$_{1-3}$R$^d$, —NR$^f$C(O)NR$^f$R$^g$, —NR$^f$S(O)$_2$NR$^f$R$^g$, —C(=NR$^e$)R$^c$, —C(=NR$^e$)NR$^f$R$^g$, —NR$^f$CR$^c$(=NR$^e$), —NR$^f$C(=NR$^e$)NR$^f$R$^g$, —S(O)(CH$_2$)$_{1-3}$R$^c$, and —NR$^f$S(O)$_2$NR$^f$OR$^d$;

R$^5$ is —Y$^5$—(CH$_2$)$_t$-G;

t is an integer of 0 or 1;

G is selected from the group consisting of H, amino, halogen, cyano, hydroxy, optionally substituted C$_{1-6}$ alkyl, optionally substituted C$_{1-6}$ haloalkyl, optionally substituted C$_{1-6}$ alkoxy, optionally substituted C$_{1-6}$ haloalkoxy, optionally substituted (C$_{1-6}$ alkoxy)C$_{1-6}$ alkyl, optionally substituted C$_{2-10}$alkenyl, optionally substituted C$_{2-10}$alkynyl, optionally substituted C$_{3-7}$ carbocyclyl, optionally substituted 3-10 membered heterocyclyl, optionally substituted C$_{6-10}$aryl, optionally substituted 5-10 membered heteroaryl, optionally substituted (C$_{3-7}$carbocyclyl)C$_{1-6}$alkyl, optionally substituted (3-10 membered heterocyclyl)C$_{1-6}$alkyl, optionally substituted (C$_{6-10}$aryl)C$_{1-6}$alkyl, (C$_{6-10}$aryl)C$_{1-6}$alkoxy, optionally substituted (5-10 membered heteroaryl)C$_{1-6}$alkyl, acyl, C-carboxy, O-carboxy, C-amido, N-amido, S-sulfonamido, N-sulfonamido, —SR$^c$, —C(O)(CH$_2$)$_{0-3}$SR$^c$, —C(O)(CH$_2$)$_{1-3}$R$^d$, —NR$^f$C(O)NR$^f$R$^g$, —NR$^f$S(O)$_2$NR$^f$R$^g$, —C(=NR$^e$)R$^c$, —C(=NR$^e$)NR$^f$R$^g$, —NR$^f$CR$^c$(=NR$^e$), —NR$^f$C(=NR$^e$)NR$^f$R$^g$, —S(O)(CH$_2$)$_{1-3}$R$^c$, and —NR$^f$S(O)$_2$NR$^f$OR$^d$;

R$^6$ is selected from the group consisting of optionally substituted —(CH$_2$)nC(O)OR and a carboxylic acid isostere;

n is an integer selected from 0 to 6;

R is selected from the group consisting of H, C$_{1-9}$ alkyl, —CR$^{10}$R$^{11}$OC(O)C$_{1-9}$alkyl, —CR$^{10}$R$^{11}$OC(O)C$_{3-7}$carbocyclyl, —CR$^{10}$R$^{11}$OC(O)(3 to 7 membered heterocyclyl), —CR$^{10}$R$^{11}$OC(O)C$_{2-8}$alkoxyalkyl, —CR$^{10}$R$^{11}$OC(O)OC$_{1-9}$alkyl, —CR$^{10}$R$^{11}$OC(O)OC$_{3-7}$ carbocyclyl, —CR$^{10}$R$^{11}$OC(O)O (3 to 7 membered heterocyclyl), —CR$^{10}$R$^{11}$OC(O)OC$_{2-8}$alkoxyalkyl, —CR$^{10}$R$^{11}$OC(O)C$_{6-10}$aryl, —CR$^{10}$R$^{11}$OC(O)OC$_{6-10}$ aryl, —CR$^{10}$R$^{11}$C(O)NR$^{13}$R$^{14}$, —CR$^{10}$R$^{11}$OC(O)O (CH$_2$)$_{1-3}$C(O)NR$^{13}$R$^{14}$, —CR$^{10}$R$^{11}$OC(O)O(CH$_2$)$_{2-3}$ OC(O)C$_{1-4}$ alkyl, —CR$^{10}$R$^{11}$OC(O)O(CH$_2$)$_{1-3}$C(O) OC$_{1-4}$ alkyl, —CR$^{10}$R$^{11}$OC(O)(CH$_2$)$_{1-3}$OC(O)C$_{1-4}$ alkyl, and

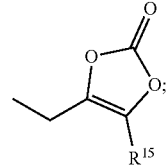

R$^7$ is selected from the group consisting of —OH, optionally substituted C$_{1-6}$ alkoxy, amino, and —N(OR$^8$)R$^9$;

each R$^8$ and R$^9$ is independently selected from the group consisting of H, halogen, optionally substituted C$_{1-4}$alkyl, optionally substituted C$_{3-7}$ carbocyclyl, optionally substituted 3-10 membered heterocyclyl, optionally substituted C$_{6-10}$aryl, and optionally substituted 5-10 membered heteroaryl;

each R$^{10}$ and R$^{11}$ is independently selected from the group consisting of H, optionally substituted C$_{1-4}$alkyl, optionally substituted C$_{3-7}$ carbocyclyl, optionally substituted 3-10 membered heterocyclyl, optionally substituted C$_{6-10}$aryl, and optionally substituted 5-10 membered heteroaryl;

each R$^{13}$ and R$^{14}$ is independently selected from the group consisting of H, optionally substituted C$_{1-6}$alkyl, optionally substituted C$_{3-7}$ carbocyclyl, optionally substituted 3-10 membered heterocyclyl, optionally substituted C$_{6-10}$aryl, and optionally substituted 5-10 membered heteroaryl;

R$^{15}$ is optionally substituted C$_{1-6}$ alkyl;

Y$^2$ is selected from the group consisting of —O—, —S—, and —NR$^9$—;

Y$^5$ is selected from the group consisting of —S—, —S(O)—, —S(O)$_2$—, —O—, —CR$^f$R$^g$—, and —NR$^g$—, or Y$^5$ is absent;

each R$^c$, R$^d$, R$^e$, R$^f$, and R$^g$ are independently selected from the group consisting of H, halogen, optionally substituted C$_{1-4}$alkyl, optionally substituted C$_{3-7}$ carbocyclyl, optionally substituted 3-10 membered heterocyclyl, optionally substituted C$_{6-10}$aryl, and optionally substituted 5-10 membered heteroaryl; and each R$^h$ and R$^i$ is independently selected from the group consisting of H, halogen, cyano, amino, C-amido, N-amido, optionally substituted C$_{1-4}$alkyl, optionally substituted C$_{3-7}$ carbocyclyl, optionally substituted 3-10 membered heterocyclyl, optionally substituted C$_{6-10}$aryl, and optionally substituted 5-10 membered heteroaryl; or R$^h$ and R$^i$ together with the atoms to which they are attached form a spirocyclic ring or ring system selected from the group consisting of C$_{3-7}$ carbocyclyl, 3-10 membered heterocyclyl, C$_{6-10}$ aryl, and 5-10 membered heteroaryl, each optionally substituted with one or more R$^5$.

Some embodiments described herein relate to compounds having the structure of Formula VI, or pharmaceutically acceptable salts thereof:

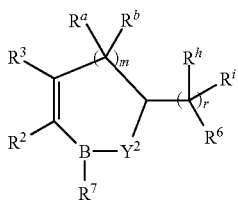

VI wherein r is an integer of 0 or 1;

(a)

each of $R^2$ and $R^3$ is independently selected from the group consisting of H, amino, halogen, cyano, hydroxy, optionally substituted $C_{1-6}$ alkyl, optionally substituted $C_{1-6}$ haloalkyl, optionally substituted $C_{1-6}$ alkoxy, optionally substituted $C_{1-6}$ haloalkoxy, optionally substituted $(C_{1-6}$ alkoxy$)C_{1-6}$ alkyl, optionally substituted $C_{2-10}$alkenyl, optionally substituted $C_{2-10}$alkynyl, optionally substituted $C_{3-7}$ carbocyclyl, optionally substituted 3-10 membered heterocyclyl, optionally substituted $C_{6-10}$aryl, optionally substituted 5-10 membered heteroaryl, optionally substituted $(C_{3-7}$ carbocyclyl$)C_{1-6}$alkyl, optionally substituted (3-10 membered heterocyclyl$)C_{1-6}$alkyl, optionally substituted $(C_{6-10}$-aryl$)C_{1-6}$alkyl, $(C_{6-10}$aryl$)C_{1-6}$alkoxy, optionally substituted (5-10 membered heteroaryl$)C_{1-6}$ alkyl, acyl, C-carboxy, O-carboxy, C-amido, N-amido, S-sulfonamido, N-sulfonamido, $-SR^c$, $-C(O)(CH_2)_{0-3}SR^c$, $-C(O)(CH_2)_{1-3}R^d$, $-NR^fC(O)NR^fR^g$, $-NR^fS(O)_2NR^fR^g$, $-C(=NR^e)R^c$, $-C(=NR^e)NR^fR^g$, $-NR^fCR^c(=NR^e)$, $-NR^fC(=NR^e)NR^fR^g$, $-S(O)(CH_2)_{1-3}R^c$, and $-NR^fS(O)_2NR^fOR^d$, or $R^2$ and $R^3$ together with the atoms to which they are attached form a fused ring or ring system selected from the group consisting of $C_{3-7}$carbocyclyl and 3-10 membered heterocyclyl, each optionally substituted with one or more $R^5$;

m is an integer of 0 or 1;

each $R^a$ and $R^b$ is independently selected from the group consisting of H, amino, halogen, cyano, hydroxy, optionally substituted $C_{1-6}$ alkyl, optionally substituted $C_{1-6}$ haloalkyl, optionally substituted $C_{1-6}$ alkoxy, optionally substituted $C_{1-6}$ haloalkoxy, optionally substituted $(C_{1-6}$ alkoxy$)C_{1-6}$ alkyl, optionally substituted $C_{2-10}$alkenyl, optionally substituted $C_{2-10}$alkynyl, optionally substituted $C_{3-7}$ carbocyclyl, optionally substituted 3-10 membered heterocyclyl, optionally substituted $C_{6-10}$aryl, optionally substituted 5-10 membered heteroaryl, optionally substituted $(C_{3-7}$ carbocyclyl$)C_{1-6}$alkyl, optionally substituted (3-10 membered heterocyclyl$)C_{1-6}$alkyl, optionally substituted $(C_{6-10}$aryl$)C_{1-6}$alkyl, $(C_{6-10}$aryl$)C_{1-6}$alkoxy, optionally substituted (5-10 membered heteroaryl$)C_{1-6}$ alkyl, acyl, C-carboxy, O-carboxy, C-amido, N-amido, S-sulfonamido, N-sulfonamido, $-SR^c$, $-C(O)(CH_2)_{0-3}SR^c$, $-C(O)(CH_2)_{1-3}R^d$, $-NR^fC(O)NR^fR^g$, $-NR^fS(O)_2NR^fR^g$, $-C(=NR^e)R^c$, $-C(=NR^e)NR^fR^g$, $-NR^fCR^c(=NR^e)$, $-NR^fC(=NR^e)NR^fR^g$, $-S(O)(CH_2)_{1-3}R^c$, and $-NR^fS(O)_2NR^fOR^d$, or $R^a$ and $R^b$ together with the atoms to which they are attached form a ring or ring system selected from the group consisting of $C_{3-7}$carbocyclyl, and 3-10 membered heterocyclyl, each optionally substituted with one or more $R^5$; or (b)

m is 1;

$R^a$ and $R^3$ together with the atoms to which they are attached form a ring or ring system selected from the group consisting of $C_{3-7}$carbocyclyl, and 3-10 membered heterocyclyl, each optionally substituted with one or more $R^5$; and each $R^2$ and $R^b$ is independently selected from the group consisting of H, amino, halogen, cyano, hydroxy, optionally substituted $C_{1-6}$ alkyl, optionally substituted $C_{1-6}$ haloalkyl, optionally substituted $C_{1-6}$ alkoxy, optionally substituted $C_{1-6}$ haloalkoxy, optionally substituted $(C_{1-6}$ alkoxy$)C_{1-6}$ alkyl, optionally substituted $C_{2-10}$alkenyl, optionally substituted $C_{2-10}$alkynyl, optionally substituted $C_{3-7}$ carbocyclyl, optionally substituted 3-10 membered heterocyclyl, optionally substituted $C_{6-10}$aryl, optionally substituted 5-10 membered heteroaryl, optionally substituted $(C_{3-7}$ carbocyclyl$)C_{1-6}$alkyl, optionally substituted (3-10 membered heterocyclyl$)C_{1-6}$alkyl, optionally substituted $(C_{6-10}$-aryl$)C_{1-6}$alkyl, $(C_{6-10}$aryl$)C_{1-6}$alkoxy, optionally substituted (5-10 membered heteroaryl$)C_{1-6}$ alkyl, acyl, C-carboxy, O-carboxy, C-amido, N-amido, S-sulfonamido, N-sulfonamido, $-SR^c$, $-C(O)(CH_2)_{0-3}SR^c$, $-C(O)(CH_2)_{1-3}R^d$, $-NR^fC(O)NR^fR^g$, $-NR^fS(O)_2NR^fR^g$, $-C(=NR^e)R^c$, $-C(=NR^e)NR^fR^g$, $-NR^fCR^c(=NR^e)$, $-NR^fC(=NR^e)NR^fR^g$, $-S(O)(CH_2)_{1-3}R^c$, and $-NR^fS(O)_2NR^fOR^d$;

$R^5$ is $-Y^5-(CH_2)_t-G$;

t is an integer of 0 or 1;

G is selected from the group consisting of H, amino, halogen, cyano, hydroxy, optionally substituted $C_{1-6}$ alkyl, optionally substituted $C_{1-6}$ haloalkyl, optionally substituted $C_{1-6}$ alkoxy, optionally substituted $C_{1-6}$ haloalkoxy, optionally substituted $(C_{1-6}$ alkoxy$)C_{1-6}$ alkyl, optionally substituted $C_{2-10}$alkenyl, optionally substituted $C_{2-10}$alkynyl, optionally substituted $C_{3-7}$ carbocyclyl, optionally substituted 3-10 membered heterocyclyl, optionally substituted $C_{6-10}$aryl, optionally substituted 5-10 membered heteroaryl, optionally substituted $(C_{3-7}$carbocyclyl$)C_{1-6}$alkyl, optionally substituted (3-10 membered heterocyclyl$)C_{1-6}$alkyl, optionally substituted $(C_{6-10}$aryl$)C_{1-6}$alkyl, $(C_{6-10}$aryl$)C_{1-6}$alkoxy, optionally substituted (5-10 membered heteroaryl$)C_{1-6}$alkyl, acyl, C-carboxy, O-carboxy, C-amido, N-amido, S-sulfonamido, N-sulfonamido, $-SR^c$, $-C(O)(CH_2)_{0-3}SR^c$, $-C(O)(CH_2)_{1-3}R^d$, $-NR^fC(O)NR^fR^g$, $-NR^fS(O)_2NR^fR^g$, $-C(=NR^e)R^c$, $-C(=NR^e)NR^fR^g$, $-NR^fCR^c(=NR^e)$, $-NR^fC(=NR^e)NR^fR^g$, $-S(O)(CH_2)_{1-3}R^c$, and $-NR^fS(O)_2NR^fOR^d$;

$R^6$ is selected from the group consisting of optionally substituted $-(CH_2)nC(O)OR$ and a carboxylic acid isostere;

n is an integer selected from 0 to 6;

R is selected from the group consisting of H, $C_{1-9}$ alkyl, $-CR^{10}R^{11}OC(O)C_{1-9}$alkyl, $-CR^{10}R^{11}OC(O)C_{3-7}$carbocyclyl, $-CR^{10}R^{11}OC(O)(3$ to 7 membered heterocyclyl), $-CR^{10}R^{11}OC(O)C_{2-8}$alkoxyalkyl, $-CR^{10}R^{11}OC(O)OC_{1-9}$alkyl, $-CR^{10}R^{11}OC(O)OC_{3-7}$carbocyclyl, $-CR^{10}R^{11}OC(O)O$ (3 to 7 membered heterocyclyl), $-CR^{10}R^{11}OC(O)OC_{2-8}$alkoxyalkyl, $-CR^{10}R^{11}OC(O)C_{6-10}$aryl, $-CR^{10}R^{11}OC(O)OC_{6-10}$aryl, $-CR^{10}R^{11}C(O)NR^{13}R^{14}$, $-CR^{10}R^{11}OC(O)O(CH_2)_{1-3}C(O)NR^{13}R^{14}$, $-CR^{10}R^{11}OC(O)O(CH_2)_{2-3}OC(O)C_{1-4}$ alkyl, —CR$^{10}$R$^{11}$OC(O)O(CH$_2$)$_{1-3}$C(O)OC$_{1-4}$ alkyl, —CR$^{10}$R$^{11}$OC(O)(CH$_2$)$_{1-3}$OC(O)C$_{1-4}$ alkyl, and

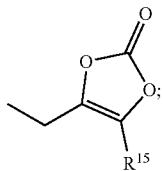

R$^7$ is selected from the group consisting of —OH, optionally substituted C$_{1-6}$ alkoxy, amino, and —N(OR$^8$)R$^9$;

each R$^8$ and R$^9$ is independently selected from the group consisting of H, halogen, optionally substituted C$_{1-4}$alkyl, optionally substituted C$_{3-7}$ carbocyclyl, optionally substituted 3-10 membered heterocyclyl, optionally substituted C$_{6-10}$aryl, and optionally substituted 5-10 membered heteroaryl;

each R$^{10}$ and R$^{11}$ is independently selected from the group consisting of H, optionally substituted C$_{1-4}$alkyl, optionally substituted C$_{3-7}$ carbocyclyl, optionally substituted 3-10 membered heterocyclyl, optionally substituted C$_{6-10}$aryl, and optionally substituted 5-10 membered heteroaryl;

each R$^{13}$ and R$^{14}$ is independently selected from the group consisting of H, optionally substituted C$_{1-6}$alkyl, optionally substituted C$_{3-7}$ carbocyclyl, optionally substituted 3-10 membered heterocyclyl, optionally substituted C$_{6-10}$aryl, and optionally substituted 5-10 membered heteroaryl;

R$^{15}$ is optionally substituted C$_{1-6}$ alkyl;

Y$^2$ is selected from the group consisting of —O—, —S—, and —NR$^9$—;

Y$^5$ is selected from the group consisting of —S—, —S(O)—, —S(O)$_2$—, —O—, —CR$^f$R$^g$—, and —NR$^g$—, or Y$^5$ is absent;

each R$^c$, R$^d$, R$^e$, R$^f$, and R$^g$ are independently selected from the group consisting of H, halogen, optionally substituted C$_{1-4}$alkyl, optionally substituted C$_{3-7}$ carbocyclyl, optionally substituted 3-10 membered heterocyclyl, optionally substituted C$_{6-10}$aryl, and optionally substituted 5-10 membered heteroaryl; and each R$^h$ and R$^i$ is independently selected from the group consisting of H, halogen, cyano, amino, C-amido, N-amido, optionally substituted C$_{1-4}$alkyl, optionally substituted C$_{3-7}$carbocyclyl, optionally substituted 3-10 membered heterocyclyl, optionally substituted C$_{6-10}$aryl, and optionally substituted 5-10 membered heteroaryl; or R$^h$ and R$^i$ together with the atoms to which they are attached form a spirocyclic ring or ring system selected from the group consisting of C$_{3-7}$ carbocyclyl, 3-10 membered heterocyclyl, C$_{6-10}$ aryl, and 5-10 membered heteroaryl, each optionally substituted with one or more R$^5$.

Some further embodiments described herein relate to pharmaceutical compositions comprising a therapeutically effective amount of a compound having the structure of Formula I, II, III, IV, V or VI, as described herein, or pharmaceutically acceptable salts thereof, and a pharmaceutically acceptable excipient. In some embodiments, the pharmaceutical composition may further comprise an additional medicament.

Some additional embodiments described herein relate to methods of treating a bacterial infection comprising administering a compound having the structure of Formula I, II, III, IV, V or VI as described herein, or pharmaceutically acceptable salts thereof to a subject in need thereof. In some embodiments, the method further comprises administering to the subject an additional medicament, for example, the additional medicament may be selected from an antibacterial agent, an antifungal agent, an antiviral agent, an anti-inflammatory agent, or an antiallergic agent.

DETAILED DESCRIPTION OF EMBODIMENTS

Compounds of Formula I or II

In some embodiments, compounds that contain a boronic acid moiety are provided that act as antimicrobial agents and/or as potentiators of antimicrobial agents. Various embodiments of these compounds include compounds having the structures of Formula I or II as described above or pharmaceutically acceptable salts thereof. In some embodiments of the compounds of Formula I or II, R is selected from H, C$_{1-9}$ alkyl, —CR$^{10}$R$^{11}$OC(O)C$_{1-9}$alkyl, —CR$^{10}$R$^{11}$OC(O)OC$_{1-9}$alkyl, —CR$^{10}$R$^{11}$OC(O)C$_{6-10}$aryl, —CR$^{10}$R$^{11}$OC(O)OC$_{6-10}$aryl and

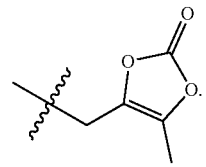 [SMILES: *Cc1oc(=O)oc1C]

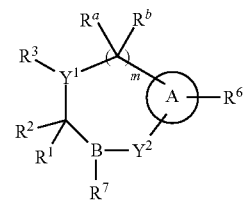

I

II

In some embodiments, the compounds of Formula I or II are also represented by the structure of Formula Ia or IIa, or pharmaceutically acceptable salts thereof:

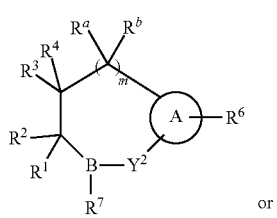

Ia or

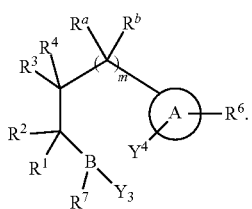

IIa

In some embodiments, the compounds of Formula Ia or IIa are also represented by the structure of Formula Ib or IIb, or pharmaceutically acceptable salts thereof:

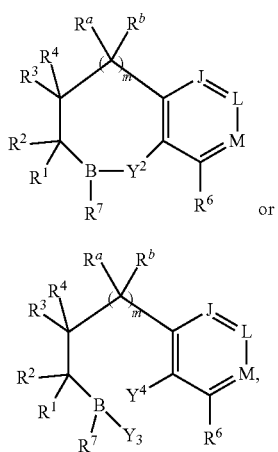

Ib or

IIb wherein each J, L, M is independently selected from $CR^{12}$ or N (nitrogen).

In some embodiments, m is 0 and the compounds of Formula Ib or IIb are also represented by the structure of Formula Ic or IIc, or pharmaceutically acceptable salts thereof:

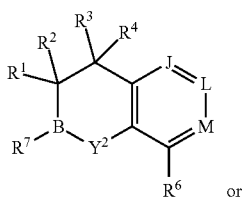

Ic or

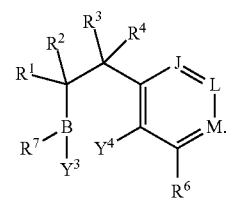

IIc

In some embodiments, the compounds of Formula Ic or IIc are in various stereoisomeric form, including those represented by the structure of Formula Ic-1, Ic-2, IIc-1 or IIc-2, or pharmaceutically acceptable salts thereof:

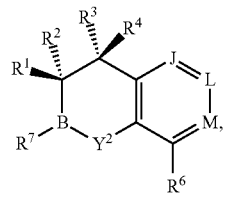

Ic-1

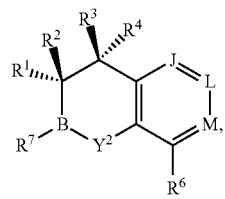

Ic-2

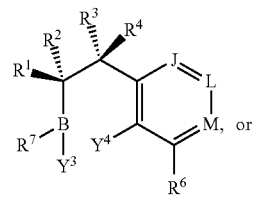

IIc-1 or

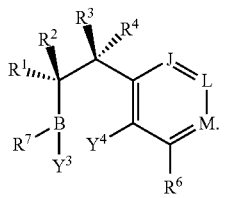

IIc-2

In some embodiments of the compounds of Formula I, Ia, Ib, Ic, II, IIa, IIb, or IIc, $R^2$ and $R^3$ together with the atoms to which they are attached form a ring or ring system selected from the group consisting of $C_{3-7}$carbocyclyl, 3-10 membered heterocyclyl, $C_{6-10}$ aryl, and 5-10 membered heteroaryl, each optionally substituted with one or more $R^5$. In some such embodiments, $R^2$ and $R^3$ together with the atoms to which they are attached form $C_{3-7}$carbocyclyl optionally substituted with one or more $R^5$. In some further embodiments, wherein $R^2$ and $R^3$ together with the atoms to which they are attached form cyclopropyl, bicyclo[2.2.1]heptyl, bicyclo[2.2.1]heptenyl, tetrahydrofuranyl, or dihydrofuranyl, each optionally substituted with one or more $R^5$. In some particular embodiments, the compound of Formula Ic or IIc is also represented by the structure of Formula Id or IId, or pharmaceutically acceptable salts thereof:

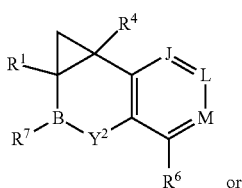

Id or

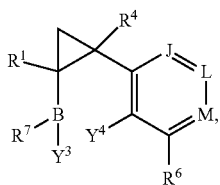

wherein the cyclopropyl moiety

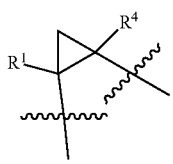

is optionally substituted with one or more $R^5$. In one embodiment,

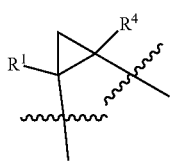

is substituted with one $R^5$. In another embodiment,

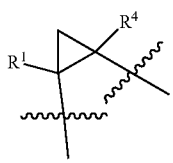

is substituted with two $R^5$.

In some embodiments, the compounds of Formula Id or IId are in various stereoisomeric forms, including those represented by the structure of Formula Id-1, Id-2, IId-1 or IId-2, or pharmaceutically acceptable salts thereof:

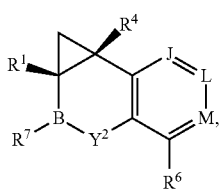

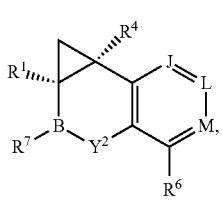

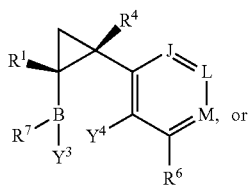

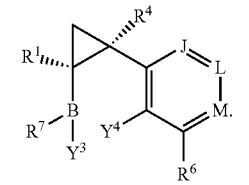

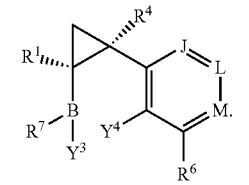

In some embodiments of the compounds of Formula I, Ia, Ib, Ic, Id, II, IIa, IIb, IIc or IId as described herein, $R^1$ is hydrogen. In another embodiment, $R^1$ is an optionally substituted $C_{1-6}$ alkyl, for example, $C_{1-6}$ hydroxyalkyl.

In some embodiments of the compounds of Formula I, Ia, Ib, Ic, Id, II, IIa, IIb, IIc or IId as described herein, $R^4$ is hydrogen.

In some other embodiments of the compounds of Formula I, Ia, Ib, Ic, II, IIa, IIb, or IIc, $R^3$ and $R^4$ together with the atoms to which they are attached form a spiro ring or ring system selected from the group consisting of $C_{3-7}$carbocyclyl, and 3-10 membered heterocyclyl, each optionally substituted with one or more $R^5$. In some such embodiments, $R^3$ and $R^4$ together with the atoms to which they are attached form $C_{3-7}$carbocyclyl optionally substituted with one or more $R^5$. In one embodiment, $R^3$ and $R^4$ together with the atoms to which they are attached form cyclopropyl optionally substituted with one or more $R^5$. In some other embodiments, $R^3$ and $R^4$ together with the atoms to which they are attached form 3-10 membered heterocyclyl optionally substituted with one or more $R^5$, for example, 3, 4, 5, 6, or 7 membered heterocyclyl comprising one, two or three heteroatoms selected from the group consisting of oxygen, nitrogen or sulfur. In some such embodiments, $R^1$ is hydrogen. In some such embodiments, $R^2$ is hydrogen.

In some embodiments of the compounds of Formula I, Ia, Ib, Ic, Id, II, IIa, IIb, IIc or IId as described herein, $R^6$ is —C(O)OR. In some such embodiments, R is H or $C_{1-9}$ alkyl. In some other embodiments, R is —$CR^{10}R^{11}OC(O)C_{1-9}$ alkyl, —$CR^{10}R^{11}OC(O)C_{3-7}$carbocyclyl, —$CR^{10}R^{11}OC(O)$(3 to 7 membered heterocyclyl), or —$CR^{10}R^{11}OC(O)C_{2-8}$alkoxyalkyl. In some such embodiments, the 3 to 7 membered heterocyclyl is

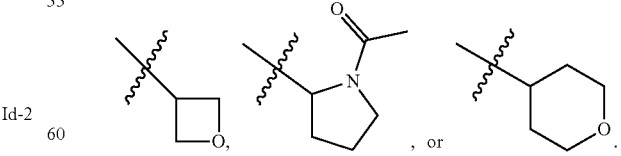

In some further embodiments, R is —$CR^{10}R^{11}OC(O)OC_{1-9}$ alkyl, —$CR^{10}R^{11}OC(O)OC_{3-7}$carbocyclyl, —$CR^{10}R^{11}OC(O)O$ (3 to 7 membered heterocyclyl), or —$CR^{10}R^{11}OC(O)OC_{2-8}$alkoxyalkyl. In some such embodiments, the 3 to 7 membered heterocyclyl is

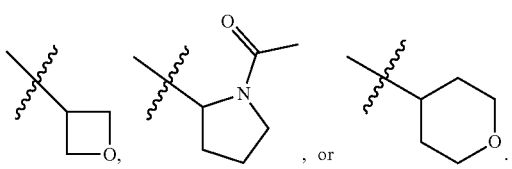

In still some further embodiments, R is $CR^{10}R^{11}C(O)NR^{13}R^{14}$. In some such embodiments, each of $R^{13}$ and $R^{14}$ is independently H or $C_{1-6}$ alkyl. In still some further embodiments, R is $-CR^{10}R^{11}OC(O)O(CH_2)_{1-3}C(O)NR^{13}R^{14}$, $-CR^{10}R^{11}OC(O)O(CH_2)_{2-3}OC(O)C_{1-4}$alkyl, $-CR^{10}R^{11}OC(O)(CH_2)_{1-3}OC(O)C_{1-4}$ alkyl, or $-CR^{10}R^{11}OC(O)O(CH_2)_{1-3}C(O)OC_{1-4}$ alkyl. In some embodiments, each $R^{10}$ and $R^{11}$ is independently hydrogen or $C_{1-6}$ alkyl.

In some embodiments of the compounds of Formula I, Ia, Ib, Ic, Id, II, IIa, IIb, IIc or IId as described herein, $R^7$ is —OH.

In some embodiments of the compounds of Formula I, Ia, Ib, Ic, or Id as described herein, $Y^2$ is —O—.

In some embodiments of the compounds of Formula II, IIa, IIb, IIc or IId as described herein, $Y^3$ is —OH. In some embodiments, $Y^4$ is —OH.

In some embodiments of the compounds of Formula I, Ia, Ib, Ic, Id, II, IIa, IIb, IIc or IId as described herein, $Y^5$ is absent and t is 0, and $R^5$ is selected from the group consisting of amino, halogen, cyano, hydroxy, optionally substituted $C_{1-6}$ alkoxy, acyl, C-carboxy, C-amido, N-amido, N-sulfonamido, $-SR^c$, $-C(O)(CH_2)_{0-3}SR^c$, $-C(O)(CH_2)_{1-3}R^d$, $-NR^fC(O)NR^fR^g$, $-NR^fS(O)_2NR^fR^g$, $-C(=NR^e)R^c$, $-C(=NR^e)NR^fR^g$, $-NR^fCR^c(=NR^e)$, $-NR^fC(=NR^e)NR^fR^g$, $-S(O)(CH_2)_{1-3}R^c$, and $-NR^fS(O)_2NR^fOR^d$. In one embodiment, $R^5$ is halogen.

In some embodiments of the compounds of Formula Ib, Ic, Id, IIb, IIc, or IId as described herein, each J, L and M is $CR^{12}$. In some such embodiments, $R^{12}$ is hydrogen, halogen, $C_{1-6}$ alkoxy, or $C_{1-6}$ haloalkoxy. In some other embodiments, at least one of J, L and M of Formula Ib, Ic, Id, IIb, IIc, or IId is N (nitrogen). In one such embodiment, M is nitrogen.

In some embodiments, the compounds of Formula I or II as described herein are selected from the group consisting of

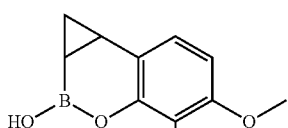

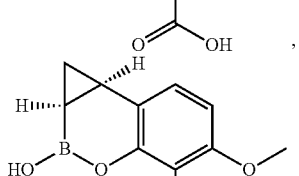

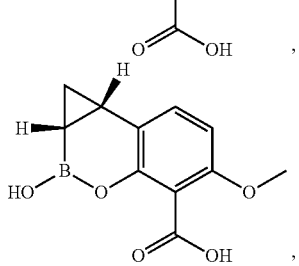

-continued

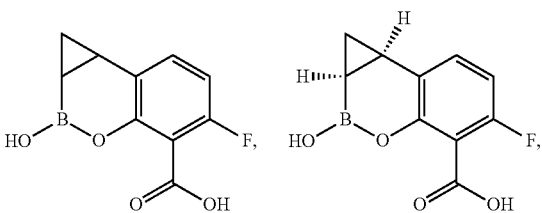

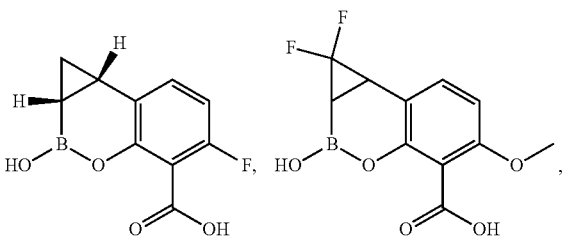

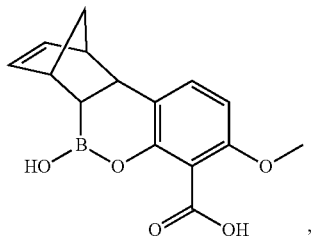

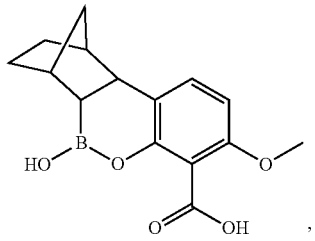

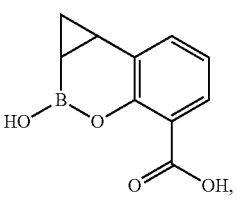
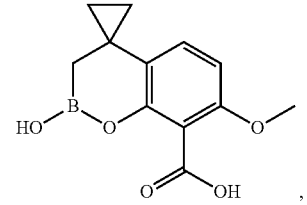

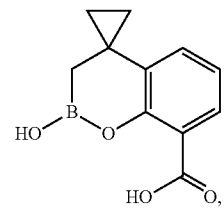
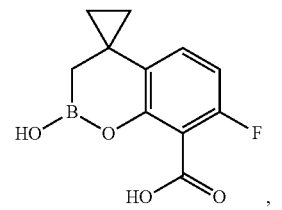

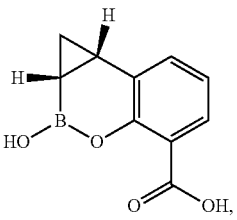
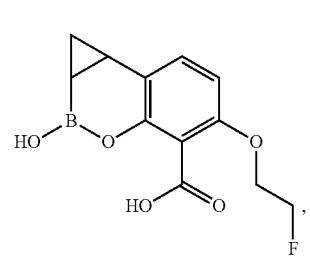

-continued
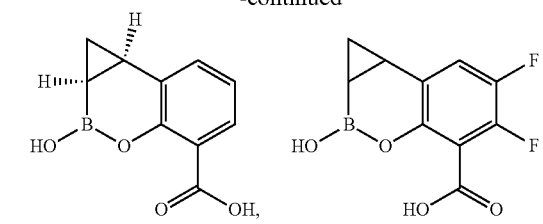
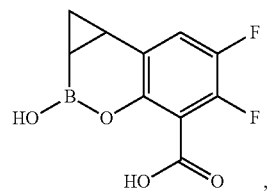
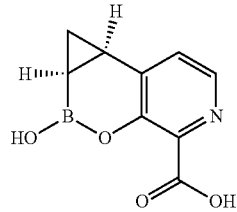
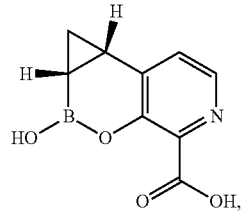
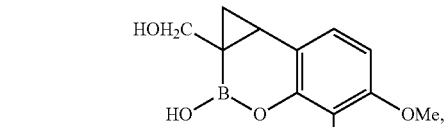
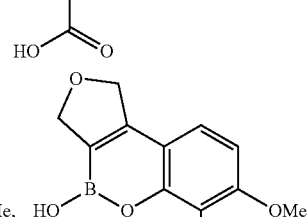
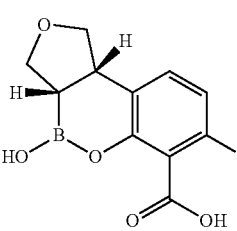
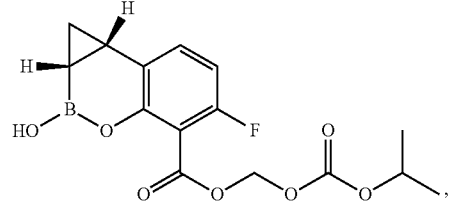
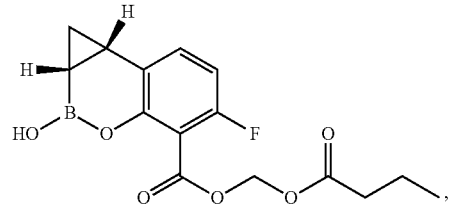
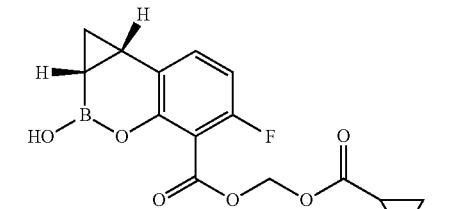
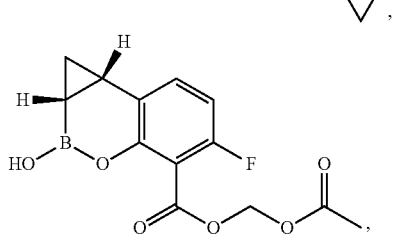
-continued
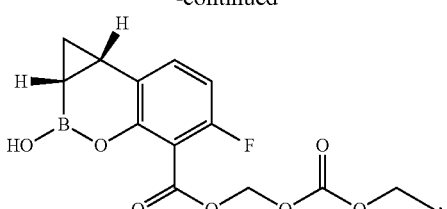
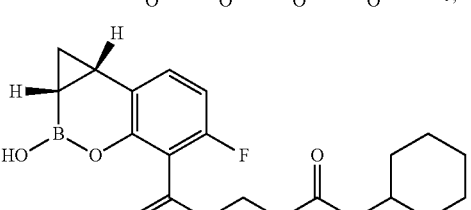
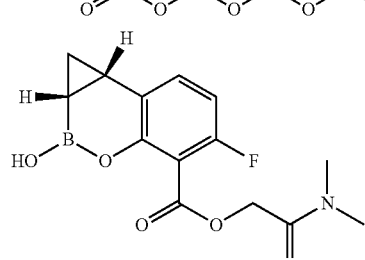
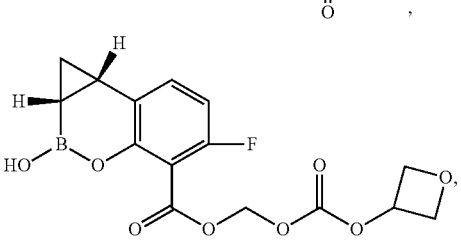
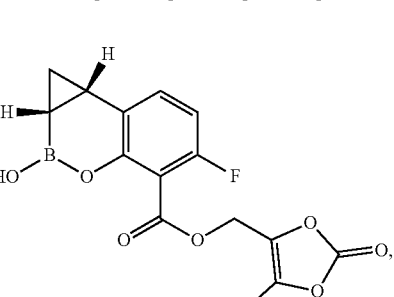
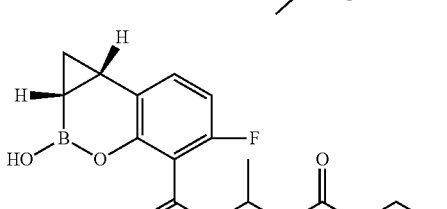
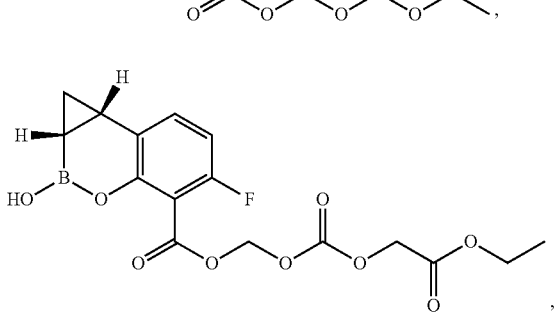

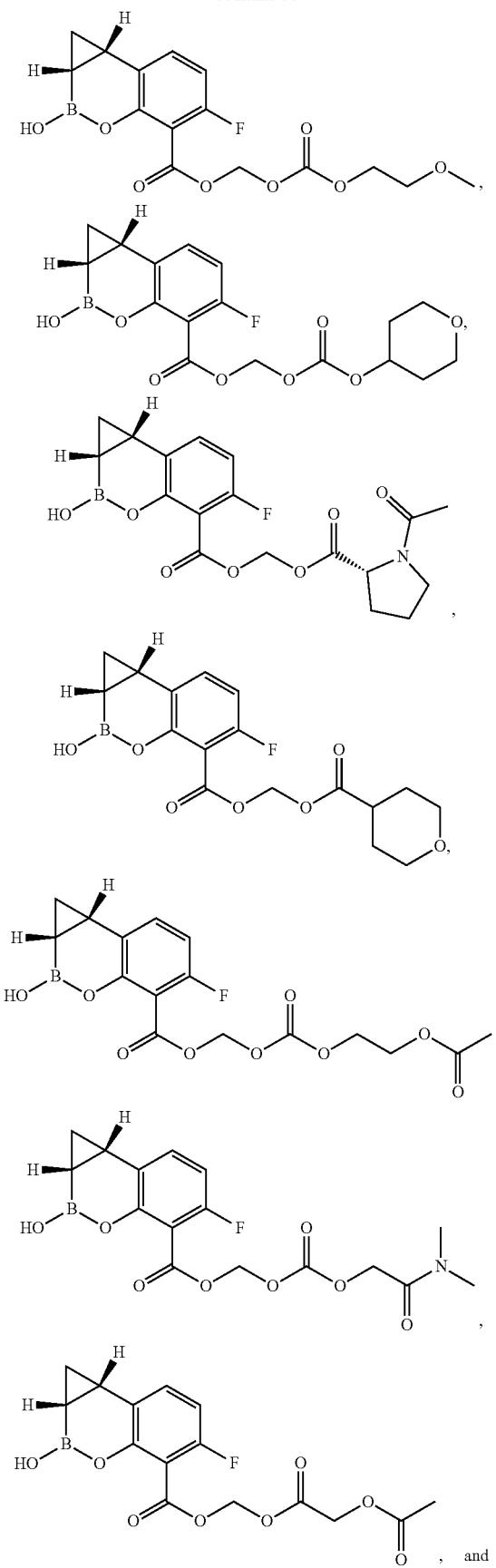
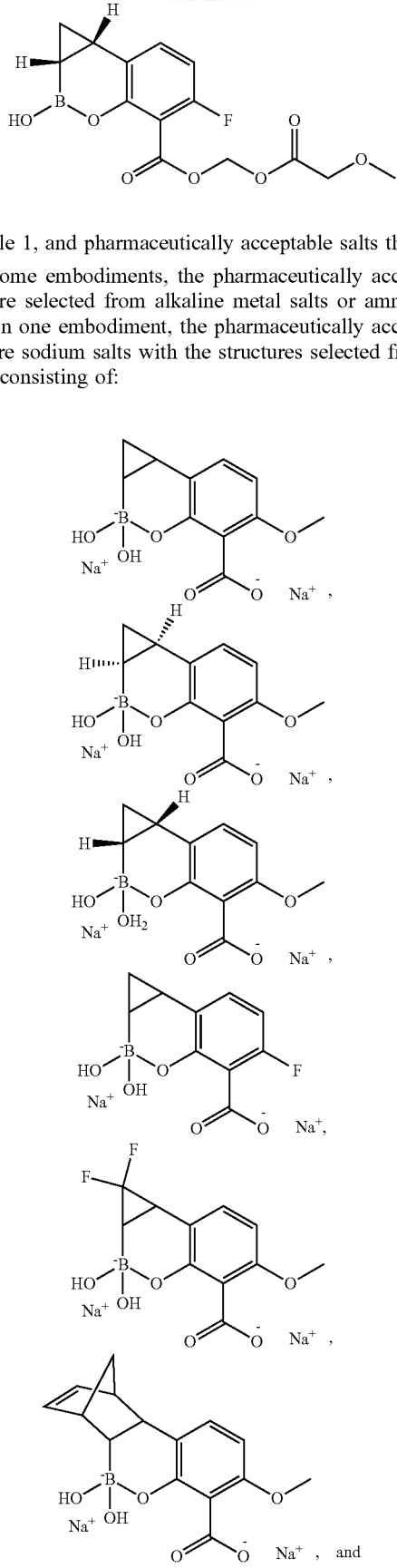
of Table 1, and pharmaceutically acceptable salts thereof.
In some embodiments, the pharmaceutically acceptable salts are selected from alkaline metal salts or ammonium salts. In one embodiment, the pharmaceutically acceptable salts are sodium salts with the structures selected from the group consisting of:

-continued

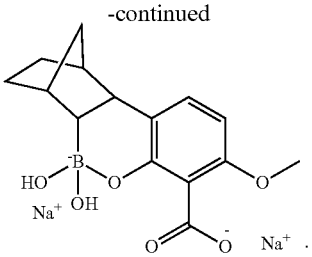

Compounds of Formula III or IV

In some embodiments, compounds that contain a boronic acid moiety are provided that act as antimicrobial agents and/or as potentiators of antimicrobial agents. Various embodiments of these compounds include compounds having the structures of Formula III or IV as described above or pharmaceutically acceptable salts thereof. In some embodiments of the compounds of Formula III or IV, R is selected from H, $C_{1-9}$ alkyl, —$CR^{10}R^{11}OC(O)C_{1-9}$alkyl, —$CR^{10}R^{11}OC(O)OC_{1-9}$alkyl, —$CR^{10}R^{11}OC(O)C_{6-10}$aryl, —$CR^{10}R^{11}OC(O)OC_{6-10}$aryl and

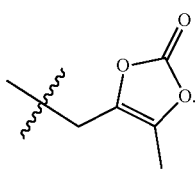 [SMILES: *Cc1oc(=O)oc1C]

III

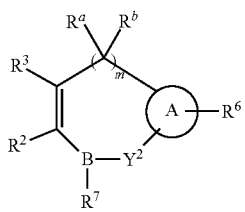

IV

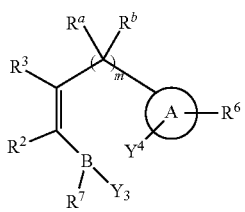

In some embodiments, the compounds of Formula III or IV are also represented by the structure of Formula IIIa or IVa, or pharmaceutically acceptable salts thereof:

IIIa

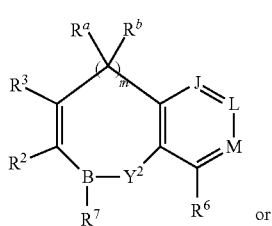

or

IVa

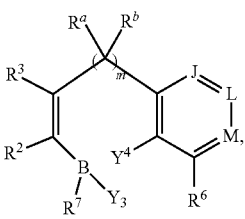

wherein each J, L, M is independently selected from $CR^{12}$ or N (nitrogen).

In some embodiments, m is 0 and the compounds of Formula IIIa or IVa are also represented by the structure of Formula IIIb or IVb, or pharmaceutically acceptable salts thereof:

IIIb

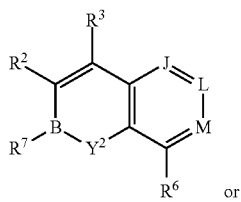

or

IVb

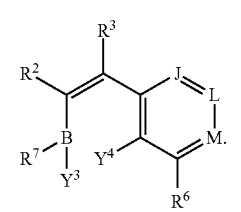

In some embodiments of the compounds of Formula III, IIIa, IIIb, IV, IVa, or IVb as described herein, $R^2$ is selected from H, halogen, or $C_{1-6}$ alkyl.

In some embodiments of the compounds of Formula III, IIIa, IIIb, IV, IVa, or IVb as described herein, $R^3$ is hydrogen.

In some other embodiments of the compounds of Formula III, IIIa, IIIb, IV, IVa, or IVb as described herein, $R^2$ and $R^3$ together with the atoms to which they are attached form a fused ring or ring system selected from the group consisting of $C_{3-7}$carbocyclyl, 3-10 membered heterocyclyl, $C_{6-10}$ aryl, and 5-10 membered heteroaryl, each optionally substituted with one or more $R^5$. In some such embodiments, $R^2$ and $R^3$ together with the atoms to which they are attached form $C_{3-7}$carbocyclyl optionally substituted with one or more $R^5$. In one embodiment, $R^2$ and $R^3$ together with the atoms to which they are attached form cyclopropyl optionally substituted with one or more $R^5$.

In some embodiments of the compounds of Formula III, IIIa, IIIb, IV, IVa, or IVb as described herein, $R^6$ is —C(O)OR. In some such embodiments, R is H or $C_{1-9}$ alkyl. In some other embodiments, R is —$CR^{10}R^{11}OC(O)C_{1-9}$alkyl, —$CR^{10}R^{11}OC(O)C_{3-7}$carbocyclyl, —$CR^{10}R^{11}OC(O)$(3 to 7 membered heterocyclyl), or —$CR^{10}R^{11}OC(O)C_{2-8}$alkoxyalkyl. In some such embodiments, the 3 to 7 membered heterocyclyl is

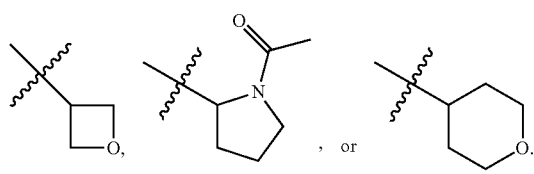

In some further embodiments, R is —CR$^{10}$R$^{11}$OC(O)OC$_{1-9}$ alkyl, —CR$^{10}$R$^{11}$OC(O)OC$_{3-7}$carbocyclyl, —CR$^{10}$R$^{11}$OC(O)O (3 to 7 membered heterocyclyl), or —CR$^{10}$R$^{11}$OC(O) OC$_{2-8}$alkoxyalkyl. In some such embodiments, the 3 to 7 membered heterocyclyl is

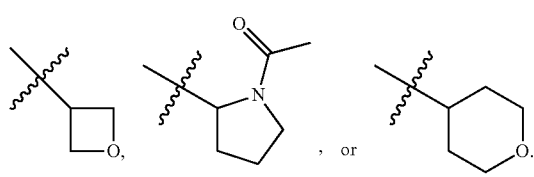

In still some further embodiments, R is CR$^{10}$R$^{11}$C(O) NR$^{13}$R$^{14}$. In some such embodiments, each of R$^{13}$ and R$^{14}$ is independently H or C$_{1-6}$alkyl. In still some further embodiments, R is —CR$^{10}$R$^{11}$OC(O)O(CH$_2$)$_{1-3}$C(O) NR$^{13}$R$^{14}$, —CR$^{10}$R$^{11}$OC(O)O(CH$_2$)$_{2-3}$OC(O)C$_{1-4}$ alkyl, —CR$^{10}$R$^{11}$OC(O)(CH$_2$)$_{1-3}$OC(O)C$_{1-4}$ alkyl, or —CR$^{10}$R$^{11}$OC(O)O(CH$_2$)$_{1-3}$C(O)OC$_{1-4}$ alkyl. In some embodiments, each R$^{10}$ and R$^{11}$ is independently hydrogen or C$_{1-6}$ alkyl.

In some embodiments of the compounds of Formula III, IIIa, IIIb, IV, IVa, or IVb as described herein, R$^7$ is —OH.

In some embodiments of the compounds of Formula III, IIIa, or IIIb as described herein, Y$^2$ is —O—.

In some embodiments of the compounds of Formula IV, IVa, or IVb as described herein, Y$^3$ is —OH. In some embodiments, Y$^4$ is —OH.

In some embodiments of the compounds of Formula IIIa, IIIb, IVa, or IVb as described herein, each J, L and M is CR$^{12}$. In some such embodiments, R$^{12}$ is selected from hydrogen, halogen or C$_{1-6}$ alkoxy. In some other embodiments, at least one of J, L and M is N (nitrogen). In one embodiment, M is N.

In some embodiments, the compounds of Formula III or IV are selected from the group consisting of

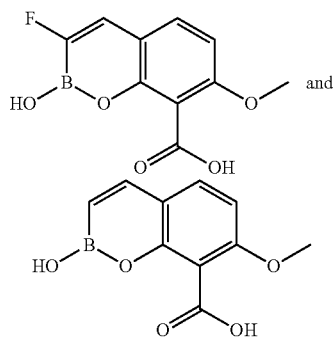

of Table 1, or pharmaceutically acceptable salts thereof.

In some embodiments, the pharmaceutically acceptable salts are selected from alkaline metal salts or ammonium salts. In one embodiment, the pharmaceutically acceptable salts are sodium salts.

Compounds of Formula V

In some embodiments, compounds that contain a boronic acid moiety are provided that act as antimicrobial agents and/or as potentiators of antimicrobial agents. Various embodiments of these compounds include compounds having the structures of Formula V as described above or pharmaceutically acceptable salts thereof. In some embodiments of the compounds of Formula V, R is selected from H, C$_{1-9}$ alkyl, —CR$^{10}$R$^{11}$OC(O)C$_{1-9}$alkyl, —CR$^{10}$R$^{11}$OC(O) OC$_{1-9}$alkyl, —CR$^{10}$R$^{11}$OC(O)C$_{6-10}$aryl, —CR$^{10}$R$^{11}$C(O) OC$_{6-10}$aryl and

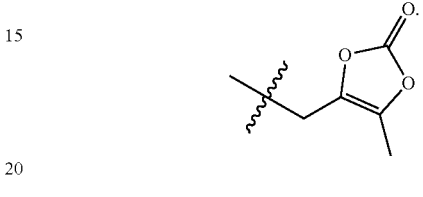

V

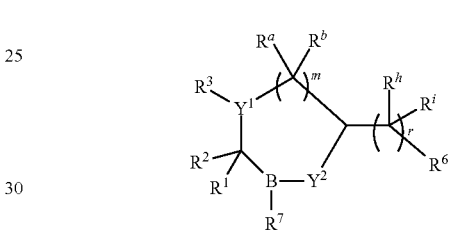

In some embodiments, the compounds of Formula V are also represented by the structure of Formula Va, or pharmaceutically acceptable salts thereof:

Va

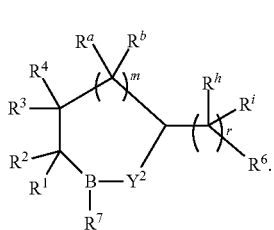

In some embodiments, m is 1 and the compounds of Formula Va are also represented by the structure of Formula Vb, or pharmaceutically acceptable salts thereof:

Vb

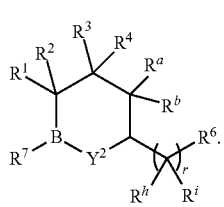

In some embodiments of the compounds of the Formula V, Va or Vb, both R$^a$ and R$^b$ are H.

In some embodiments of the compounds of the Formula V, Va or Vb as described herein, R$^2$ and R$^3$ together with the atoms to which they are attached form a fused ring or ring system selected from the group consisting of $C_{3-7}$ carbocyclyl, 3-10 membered heterocyclyl, $C_{6-10}$ aryl, and 5-10 membered heteroaryl, each optionally substituted with one or more $R^5$. In some such embodiments, $R^2$ and $R^3$ together with the atoms to which they are attached form $C_{3-7}$carbocyclyl optionally substituted with one or more $R^5$. In one embodiment, $R^2$ and $R^3$ together with the atoms to which they are attached form cyclopropyl optionally substituted with one or more $R^5$.

In some embodiments of the compounds of the Formula V, Va or Vb as described herein, r is 1, and both $R^h$ and $R^i$ are H.

In some embodiments of the compounds of the Formula V, Va or Vb as described herein, $R^6$ is —$(CH_2)nC(O)OR$ and n is 0. In some such embodiment, the compound is also represented by the structure of Formula Vc or pharmaceutically acceptable salts thereof:

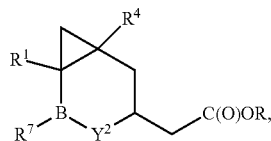

Vc wherein the cyclopropyl moiety

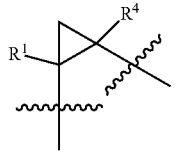

is optionally substituted with one or more $R^5$. In one example,

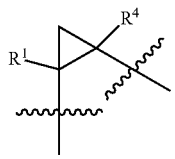

is substituted with one $R^5$ and the compound is also represented by the structure of Formula Vd:

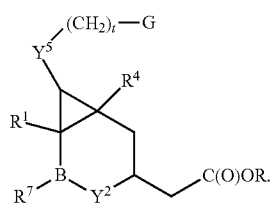

Vd

In some embodiments, the compounds of Formula Vc are in various stereoisomeric forms, including those represented by the structure of Formula Vc-1 or Vc-2, or pharmaceutically acceptable salts thereof:

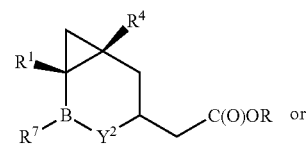

Vc-1

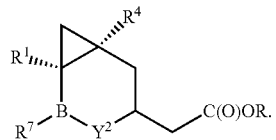

Vc-2

In some embodiments of the compounds of Formula V, Va, Vb or Vc as described herein, $R^7$ is —OH.

In some embodiments of the compounds of Formula V, Va, Vb or Vc as described herein, $Y^2$ is —O—.

Compounds of Formula VI

In some embodiments, compounds that contain a boronic acid moiety are provided that act as antimicrobial agents and/or as potentiators of antimicrobial agents. Various embodiments of these compounds include compounds having the structures of Formula VI as described above or pharmaceutically acceptable salts thereof. In some embodiments of the compounds of Formula VI, R is selected from H, $C_{1-9}$ alkyl, —$CR^{10}R^{11}OC(O)C_{1-9}$alkyl, —$CR^{10}R^{11}OC(O)OC_{1-9}$alkyl, —$CR^{10}R^{11}OC(O)C_{6-10}$aryl, —$CR^{10}R^{11}OC(O)OC_{6-10}$aryl and

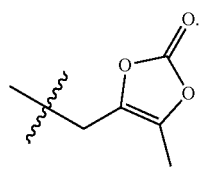 [SMILES: *Cc1oc(=O)oc1C]

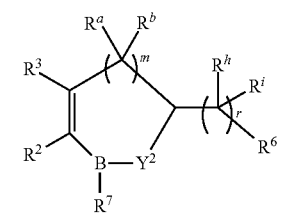

VI

In some embodiments, m is 1 and the compounds of Formula VI are also represented by the structure of Formula VIa, or pharmaceutically acceptable salts thereof:

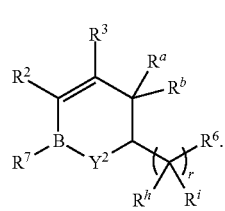

VIa

In some embodiments of the compounds of Formula VI or VIa, both $R^a$ and $R^b$ are H.

In some embodiments of the compounds of Formula VI or VIa, r is 1, and both $R^h$ and $R^i$ are H.

In some embodiments of the compounds of the Formula VI or VIa as described herein, $R^6$ is —(CH$_2$)nC(O)OR and n is 0. In some such embodiment, the compound is also represented by the structure of Formula VIb or pharmaceutically acceptable salts thereof:

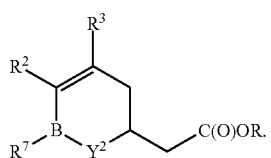

VIb

In some embodiments of the compounds of Formula VI, VIa, or VIb as described herein, $R^7$ is —OH.

In some embodiments of the compounds of Formula VI, VIa, or VIb as described herein, $Y^2$ is —O—.

Exemplary compounds described herein are illustrated in Table 1 below.

TABLE 1-continued

| Compd# | Structure |
|---|---|
| 12 | (structure) |
| 13 | (structure) |
| 14 | (structure) |
| 15 | (structure) |
| 16 | (structure) |
| 17 | (structure) |
| 18 | (structure) |
| 19 | (structure) |
| 20 | (structure) |
| 21 | (structure) |
| 22 | (structure) |
| 23 | (structure) |
| 24 | (structure) |
| 25 | (structure) |

TABLE 1-continued

| Compd# | Structure |
|---|---|
| 26 | (structure) |
| 27 | (structure) |
| 28 | (structure) |
| 29 | (structure) |
| 30 | (structure) |
| 31 | (structure) |
| 32 | (structure) |
| 33 | (structure) |
| 34 | (structure) |
| 35 | (structure) |
| 36 | (structure) |
| 37 | (structure) |
| 38 | (structure) |

TABLE 1-continued

| Compd# | Structure |
|---|---|
| 39 | 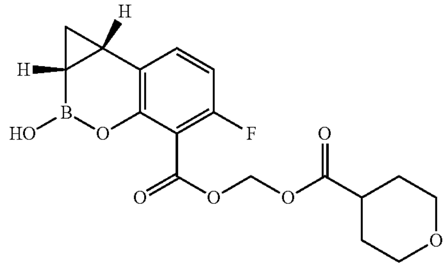 |
| 40 | 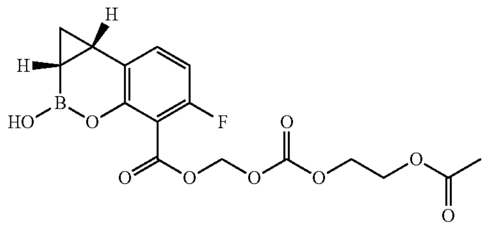 |
| 41 | 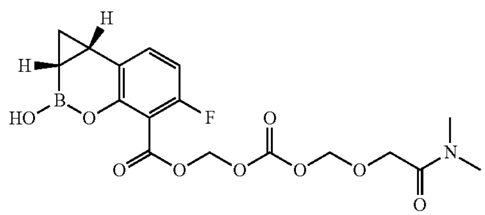 |
| 42 | 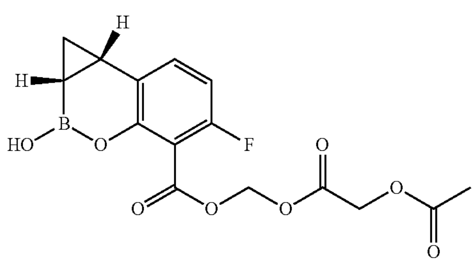 |
| 43 | 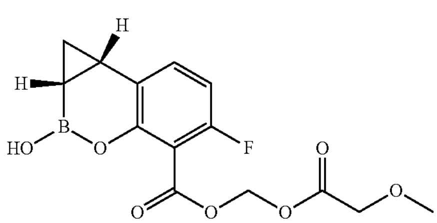 |

In some embodiments, the pharmaceutically acceptable salts are selected from alkaline metal salts or ammonium salts. In one embodiment, the pharmaceutically acceptable salts are sodium salts, including disodium salts.

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

In some embodiments, due to the facile exchange of boron esters, the compounds described herein may convert to or exist in equilibrium with alternate forms. Accordingly, in some embodiments, the compounds described herein may exist in combination with one or more of these forms. For example, as shown below, the compounds disclosed herein may exist in cyclic boronate monoesters with the structure of Formulae I, Ia, Ib, Ic, and Id or in acyclic form as boronic acids with the structure of Formulae II, IIa, IIb, IIc, IId, or may exist as a mixture of the two forms depending on the medium. In some embodiments, the compounds disclosed herein may exist in cyclic form as cyclic boronate monoesters with the structure of Formulae III, IIIa, and IIIb or in acyclic form as boronic acids with the structure of Formulae IV, IVa and IVb, or may exist as a mixture of the two forms depending on the medium. Exemplary equilibrium equation between the cyclic boronate monoesters and the acyclic form boronic acids are demonstrated below:

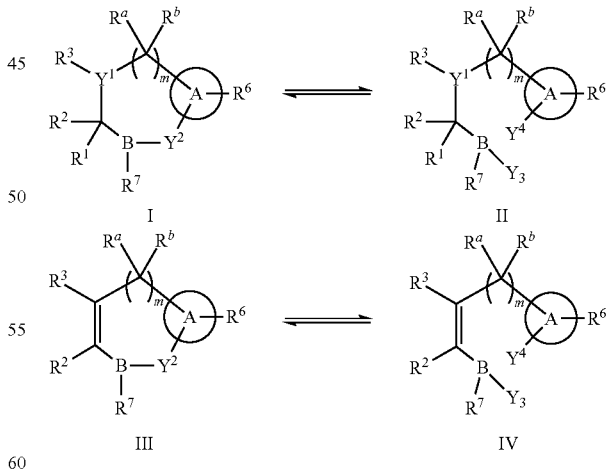

In some embodiments, the compounds described herein may exist in cyclic dimeric form, trimeric form or tetrameric form. For example, the compound of Formula II may exist in dimeric form (II-A), trimeric form (II-B), or tetrameric form (II-C):

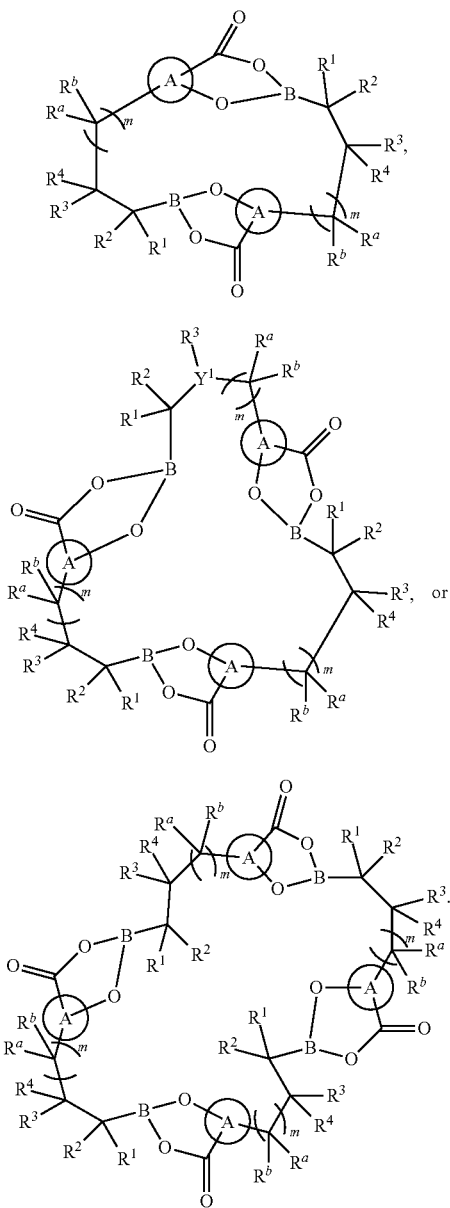

II-A

II-B

II-C

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. The use of "or" or "and" means "and/or" unless stated otherwise. Furthermore, use of the term "including" as well as other forms, such as "include", "includes," and "included," is not limiting. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

The section headings used herein are for organizational purposes only and are not to be construed as limiting the subject matter described.

As used herein, common organic abbreviations are defined as follows:

Ac Acetyl
aq. Aqueous
Bn Benzyl
Bz Benzoyl
BOC or Boc tert-Butoxycarbonyl
° C. Temperature in degrees Centigrade
DCM Dichloromethane
DMF N,N-dimethylformamide
EA Ethyl acetate
ESBL Extended-spectrum β-lactamase
Et Ethyl
g Gram(s)
h or hr Hour(s)
HATU 2-(7-aza-1H-benzotriazole-1-yl)-1,1,3,3-tetramethyluronium hexafluorophosphate
iPr Isopropyl
m or min Minute(s)
MECN Acetonitrile
mL Milliliter(s)
NMR Nuclear magnetic resonance
PE Petroleum ether
PG Protecting group
Ph Phenyl
rt Room temperature
TBDMSCl tert-Butyldimethylsilyl chloride
TBS tert-Butyldimethylsilyl
Tert, t tertiary
TFA Trifluoroacetic acid
THF Tetrahydrofuran
TLC Thin-layer chromatography
μL Microliter(s)

As used herein, "Ca to Cb" or "Ca-b" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range;

e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkylthio" refers to the formula —SR wherein R is an alkyl as is defined above, such as "$C_{1-9}$ alkylthio" and the like, including but not limited to methylmercapto, ethylmercapto, n-propylmercapto, 1-methylethylmercapto (isopropylmercapto), n-butylmercapto, iso-butylmercapto, sec-butylmercapto, tert-butylmercapto, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "$C_{2-4}$ alkynyl" or similar designations. By way of example only, "$C_{2-4}$ alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

As used herein, "heteroalkyl" refers to a straight or branched hydrocarbon chain containing one or more heteroatoms, that is, an element other than carbon, including but not limited to, nitrogen, oxygen and sulfur, in the chain backbone. The heteroalkyl group may have 1 to 20 carbon atom, although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 4 carbon atoms. The heteroalkyl group may be designated as "$C_{1-4}$ heteroalkyl" or similar designations. The heteroalkyl group may contain one or more heteroatoms. By way of example only, "$C_{1-4}$ heteroalkyl" indicates that there are one to four carbon atoms in the heteroalkyl chain and additionally one or more heteroatoms in the backbone of the chain.

As used herein, "alkylene" means a branched, or straight chain fully saturated di-radical chemical group containing only carbon and hydrogen that is attached to the rest of the molecule via two points of attachment (i.e., an alkanediyl). The alkylene group may have 1 to 20 carbon atoms, although the present definition also covers the occurrence of the term alkylene where no numerical range is designated. The alkylene group may also be a medium size alkylene having 1 to 9 carbon atoms. The alkylene group could also be a lower alkylene having 1 to 4 carbon atoms. The alkylene group may be designated as "$C_{1-4}$ alkylene" or similar designations. By way of example only, "$C_{1-4}$ alkylene" indicates that there are one to four carbon atoms in the alkylene chain, i.e., the alkylene chain is selected from the group consisting of methylene, ethylene, ethan-1,1-diyl, propylene, propan-1,1-diyl, propan-2,2-diyl, 1-methyl-ethylene, butylene, butan-1,1-diyl, butan-2,2-diyl, 2-methyl-propan-1,1-diyl, 1-methyl-propylene, 2-methyl-propylene, 1,1-dimethyl-ethylene, 1,2-dimethyl-ethylene, and 1-ethyl-ethylene.

As used herein, "alkenylene" means a straight or branched chain di-radical chemical group containing only carbon and hydrogen and containing at least one carbon-carbon double bond that is attached to the rest of the molecule via two points of attachment. The alkenylene group may have 2 to 20 carbon atoms, although the present definition also covers the occurrence of the term alkenylene where no numerical range is designated. The alkenylene group may also be a medium size alkenylene having 2 to 9 carbon atoms. The alkenylene group could also be a lower alkenylene having 2 to 4 carbon atoms. The alkenylene group may be designated as "$C_{2-4}$ alkenylene" or similar designations. By way of example only, "$C_{2-4}$ alkenylene" indicates that there are two to four carbon atoms in the alkenylene chain, i.e., the alkenylene chain is selected from the group consisting of ethenylene, ethen-1,1-diyl, propenylene, propen-1,1-diyl, prop-2-en-1,1-diyl, 1-methyl-ethenylene, but-1-enylene, but-2-enylene, but-1,3-dienylene, buten-1,1-diyl, but-1,3-dien-1,1-diyl, but-2-en-1,1-diyl, but-3-en-1,1-diyl, 1-methyl-prop-2-en-1,1-diyl, 2-methyl-prop-2-en-1,1-diyl, 1-ethyl-ethenylene, 1,2-dimethyl-ethenylene, 1-methyl-propenylene, 2-methyl-propenylene, 3-methyl-propenylene, 2-methyl-propen-1,1-diyl, and 2,2-dimethyl-ethen-1,1-diyl.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "aryloxy" and "arylthio" refers to RO— and RS—, in which R is an aryl as is defined above, such as "$C_{6-10}$ aryloxy" or "$C_{6-10}$ arylthio" and the like, including but not limited to phenyloxy.

An "aralkyl" or "arylalkyl" is an aryl group connected, as a substituent, via an alkylene group, such as "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-4}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-4}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

A "(carbocyclyl)alkyl" is a carbocyclyl group connected, as a substituent, via an alkylene group, such as "$C_{4-10}$ (carbocyclyl)alkyl" and the like, including but not limited to, cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

As used herein, "cycloalkyl" means a fully saturated carbocyclyl ring or ring system. Examples include cyclopropyl, cyclobutyl, cyclopentyl, and cyclohexyl.

As used herein, "cycloalkenyl" means a carbocyclyl ring or ring system having at least one double bond, wherein no ring in the ring system is aromatic. An example is cyclohexenyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

A "(heterocyclyl)alkyl" is a heterocyclyl group connected, as a substituent, via an alkylene group. Examples include, but are not limited to, imidazolinylmethyl and indolinylethyl.

As used herein, "acyl" refers to —C(=O)R, wherein R is selected from hydrogen, optionally substituted $C_{1-6}$ alkyl, halogen, optionally substituted $C_{2-6}$ alkenyl, optionally substituted $C_{2-6}$ alkynyl, optionally substituted $C_{3-7}$ carbocyclyl, optionally substituted $C_{6-10}$ aryl, optionally substituted 5-10 membered heteroaryl, and optionally substituted 3-10 membered heterocyclyl, as defined herein. Non-limiting examples include formyl, acetyl, propanoyl, benzoyl, and acryl.

An "O-carboxy" group refers to a "—OC(=O)R" group in which R is selected from hydrogen, optionally substituted $C_{1-6}$ alkyl, halogen, optionally substituted $C_{2-6}$ alkenyl, optionally substituted $C_{2-6}$ alkynyl, optionally substituted $C_{3-7}$ carbocyclyl, optionally substituted $C_{6-10}$ aryl, optionally substituted 5-10 membered heteroaryl, and optionally substituted 3-10 membered heterocyclyl, as defined herein.

A "C-carboxy" group refers to a "—C(=O)OR" group in which R is selected from hydrogen, halogen, optionally substituted $C_{1-6}$ alkyl, optionally substituted $C_{2-6}$ alkenyl, optionally substituted $C_{2-6}$ alkynyl, optionally substituted $C_{3-7}$ carbocyclyl, optionally substituted $C_{6-10}$ aryl, optionally substituted 5-10 membered heteroaryl, and optionally substituted 3-10 membered heterocyclyl, as defined herein. A non-limiting example includes carboxyl (i.e., —C(=O)OH).

A "cyano" group refers to a "—CN" group.

A "cyanato" group refers to an "—OCN" group.

An "isocyanato" group refers to a "—NCO" group.

A "thiocyanato" group refers to a "—SCN" group.

An "isothiocyanato" group refers to an "—NCS" group.

A "sulfinyl" group refers to an "—S(=O)R" group in which R is selected from hydrogen, optionally substituted $C_{1-6}$ alkyl, optionally substituted $C_{2-6}$ alkenyl, optionally substituted $C_{2-6}$ alkynyl, optionally substituted $C_{3-7}$ carbocyclyl, optionally substituted $C_{6-10}$ aryl, optionally substituted 5-10 membered heteroaryl, and optionally substituted 3-10 membered heterocyclyl, as defined herein.

A "sulfonyl" group refers to an "—SO$_2$R" group in which R is selected from hydrogen, optionally substituted $C_{1-6}$ alkyl, optionally substituted $C_{2-6}$ alkenyl, optionally substituted $C_{2-6}$ alkynyl, optionally substituted $C_{3-7}$ carbocyclyl, optionally substituted $C_{6-10}$ aryl, optionally substituted 5-10 membered heteroaryl, and optionally substituted 3-10 membered heterocyclyl, as defined herein.

An "S-sulfonamido" group refers to a "—SO$_2$NR$_A$R$_B$" group in which R$_A$ and R$_B$ are each independently selected from hydrogen, halogen, optionally substituted $C_{1-6}$ alkyl, optionally substituted $C_{1-6}$ alkoxy, optionally substituted $C_{2-6}$ alkenyl, optionally substituted $C_{2-6}$ alkynyl, optionally substituted $C_{3-7}$ carbocyclyl, optionally substituted $C_{6-10}$ aryl, optionally substituted 5-10 membered heteroaryl, and optionally substituted 3-10 membered heterocyclyl, as defined herein.

An "N-sulfonamido" group refers to a "—N(R$_A$)SO$_2$R$_B$" group in which R$_A$ and R$_B$ are each independently selected from hydrogen, halogen, optionally substituted $C_{1-6}$ alkyl, optionally substituted $C_{2-6}$ alkenyl, optionally substituted $C_{2-6}$ alkynyl, optionally substituted $C_{3-7}$ carbocyclyl, optionally substituted $C_{6-10}$ aryl, optionally substituted 5-10 membered heteroaryl, and optionally substituted 3-10 membered heterocyclyl, as defined herein.

A "C-amido" group refers to a "—C(=O)NR$_A$R$_B$" group in which R$_A$ and R$_B$ are each independently selected from hydrogen, halogen, optionally substituted $C_{1-6}$ alkyl, optionally substituted $C_{1-6}$ alkoxy, optionally substituted $C_{2-6}$ alkenyl, optionally substituted $C_{2-6}$ alkynyl, optionally substituted $C_{3-7}$ carbocyclyl, optionally substituted $C_{6-10}$ aryl, optionally substituted 5-10 membered heteroaryl, and optionally substituted 3-10 membered heterocyclyl, as defined herein.

An "N-amido" group refers to a "—N(R$_A$)C(=O)R$_B$" group in which R$_A$ and R$_B$ are each independently selected from hydrogen, halogen, optionally substituted $C_{1-6}$ alkyl, optionally substituted $C_{1-6}$ alkoxy, optionally substituted $C_{2-6}$ alkenyl, optionally substituted $C_{2-6}$ alkynyl, optionally substituted $C_{3-7}$ carbocyclyl, optionally substituted $C_{6-10}$ aryl, optionally substituted 5-10 membered heteroaryl, and optionally substituted 3-10 membered heterocyclyl, as defined herein.

An "O-carbamyl" group refers to a "—OC(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-carbamyl" group refers to an "—N(R$_A$)OC(=O)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-thiocarbamyl" group refers to a "—OC(=S)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, aC$_{6-10}$ ryl, 5-10 membered heteroaryl, and 5-10 membered heterocyclyl, as defined herein.

An "N-thiocarbamyl" group refers to an "—N(R$_A$)OC(=S)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "amino" group refers to a "—NR$_A$R$_B$" group in which R$_A$ and R$_B$ are each independently selected from hydrogen, halogen, optionally substituted $C_{1-6}$ alkyl, optionally substituted $C_{2-6}$ alkenyl, optionally substituted $C_{2-6}$ alkynyl, optionally substituted $C_{3-7}$ carbocyclyl, optionally substituted $C_{6-10}$ aryl, optionally substituted 5-10 membered heteroaryl, and optionally substituted 3-10 membered heterocyclyl as defined herein. A non-limiting example includes free amino (i.e., —NH$_2$).

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$)alkyl (e.g., —CF$_3$), halo($C_1$-$C_6$)alkoxy (e.g., —OCF$_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (═O). Wherever a group is described as "optionally substituted" that group can be substituted with the above substituents.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —CH$_2$—, —CH$_2$CH$_2$—, —CH$_2$CH(CH$_3$)CH$_2$—, and the like. Other radical naming conventions clearly indicate that the radical is a di-radical such as "alkylene" or "alkenylene."

When two R groups are said to form a ring (e.g., a carbocyclyl, heterocyclyl, aryl, or heteroaryl ring) "together with the atom to which they are attached," it is meant that the collective unit of the atom and the two R groups are the recited ring. The ring is not otherwise limited by the definition of each R group when taken individually. For example, when the following substructure is present:

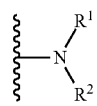

and R$^1$ and R$^2$ are defined as selected from the group consisting of hydrogen and alkyl, or R$^1$ and R$^2$ together with the nitrogen to which they are attached form a heterocyclyl, it is meant that R$^1$ and R$^2$ can be selected from hydrogen or alkyl, or alternatively, the substructure has structure:

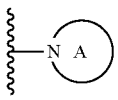

where ring A is a heteroaryl ring containing the depicted nitrogen.

Similarly, when two "adjacent" R groups are said to form a ring "together with the atom to which they are attached," it is meant that the collective unit of the atoms, intervening bonds, and the two R groups are the recited ring. For example, when the following substructure is present:

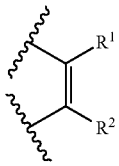

and R$^1$ and R$^2$ are defined as selected from the group consisting of hydrogen and alkyl, or R$^1$ and R$^2$ together with the atoms to which they are attached form an aryl or carbocylyl, it is meant that R$^1$ and R$^2$ can be selected from hydrogen or alkyl, or alternatively, the substructure has structure:

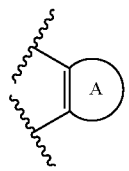

where A is an aryl ring or a carbocylyl containing the depicted double bond.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

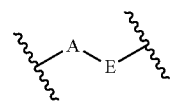

includes the substituent being oriented such that the A is attached at the leftmost attachment point of the molecule as well as the case in which A is attached at the rightmost attachment point of the molecule.

As used herein, "isosteres" of a chemical group are other chemical groups that exhibit the same or similar properties. For example, tetrazole is an isostere of carboxylic acid because it mimics the properties of carboxylic acid even though they both have very different molecular formulae. Tetrazole is one of many possible isosteric replacements for carboxylic acid. Other carboxylic acid isosteres contemplated include —SO$_3$H, —SO$_2$HNR, —PO$_2$(R)$_2$, —PO$_3$(R)$_2$, —CONHNHSO$_2$R, —COHNSO$_2$R, and —CONRCN, where R is selected from hydrogen, C$_{1-6}$ alkyl, C$_{2-6}$ alkenyl, C$_{2-6}$ alkynyl, C$_{3-7}$ carbocyclyl, C$_{6-10}$ aryl, 5-10 membered heteroaryl, and 3-10 membered heterocyclyl, as defined herein. In addition, carboxylic acid isosteres can include 5-7 membered carbocycles or heterocycles containing any combination of CH$_2$, O, S, or N in any chemically stable oxidation state, where any of the atoms of said ring structure are optionally substituted in one or more positions. The following structures are non-limiting examples of carbocyclic and heterocyclic isosteres contemplated. The atoms of said ring structure may be optionally substituted at one or more positions with R as defined above.

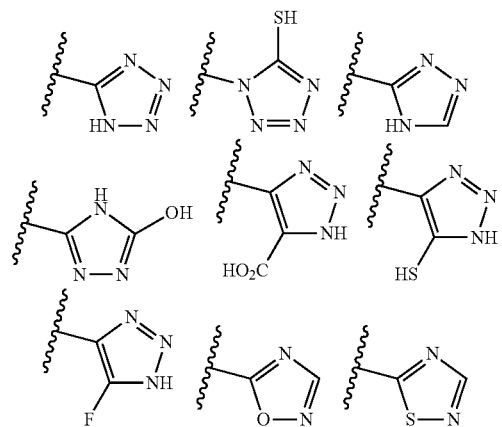

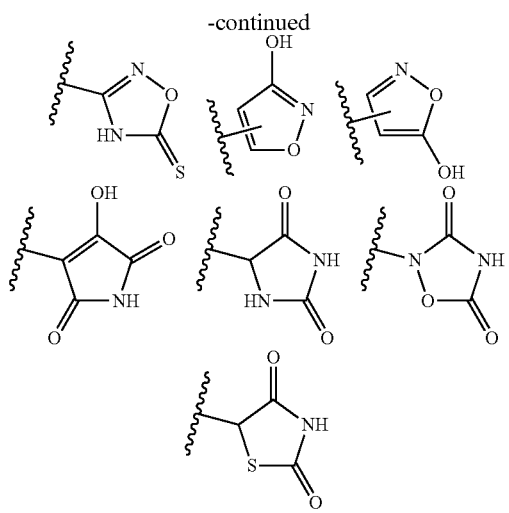

It is also contemplated that when chemical substituents are added to a carboxylic isostere, the compound retains the properties of a carboxylic isostere. It is contemplated that when a carboxylic isostere is optionally substituted with one or more moieties selected from R as defined above, then the substitution and substitution position is selected such that it does not eliminate the carboxylic acid isosteric properties of the compound. Similarly, it is also contemplated that the placement of one or more R substituents upon a carbocyclic or heterocyclic carboxylic acid isostere is not a substitution at one or more atom(s) that maintain(s) or is/are integral to the carboxylic acid isosteric properties of the compound, if such substituent(s) would destroy the carboxylic acid isosteric properties of the compound.

Other carboxylic acid isosteres not specifically exemplified in this specification are also contemplated.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

The term "mammal" is used in its usual biological sense. Thus, it specifically includes, but is not limited to, primates, including simians (chimpanzees, apes, monkeys) and humans, cattle, horses, sheep, goats, swine, rabbits, dogs, cats, rodents, rats, mice guinea pigs, or the like.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press.

A therapeutic effect relieves, to some extent, one or more of the symptoms of a disease or condition, and includes curing a disease or condition. "Curing" means that the symptoms of a disease or condition are eliminated; however, certain long-term or permanent effects may exist even after a cure is obtained (such as extensive tissue damage).

"Treat," "treatment," or "treating," as used herein refers to administering a compound or pharmaceutical composition to a subject for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject already suffering from a disease or condition.

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopes may be present in the compounds described. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. Conventional procedures for the selection and preparation of suitable prodrug derivatives are described, for example, in *Design of Prodrugs*, (ed. H. Bundgaard, Elsevier, 1985), which is hereby incorporated herein by reference in its entirety.

The term "pro-drug ester" refers to derivatives of the compounds disclosed herein formed by the addition of any of several ester-forming groups that are hydrolyzed under physiological conditions. Examples of pro-drug ester groups include pivoyloxymethyl, acetoxymethyl, phthalidyl, indanyl and methoxymethyl, as well as other such groups known in the art, including a (5-R-2-oxo-1,3-dioxolen-4-yl)methyl group. Other examples of pro-drug ester groups can be found in, for example, T. Higuchi and V. Stella, in "Prodrugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14-21 (1987) (providing examples of esters useful as prodrugs for compounds containing carboxyl groups). Each of the above-mentioned references is herein incorporated by reference in their entirety.

"Metabolites" of the compounds disclosed herein include active species that are produced upon introduction of the compounds into the biological milieu.

"Solvate" refers to the compound formed by the interaction of a solvent and a compound described herein, a metabolite, or salt thereof. Suitable solvates are pharmaceutically acceptable solvates including hydrates.

The term "pharmaceutically acceptable salt" refers to salts that retain the biological effectiveness and properties of a compound, which are not biologically or otherwise undesirable for use in a pharmaceutical. In many cases, the compounds herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety). Some examples of pharmaceutically acceptable base addition salts of the compounds disclosed herein have the structure of Formula I', Ia', Ib', Ic', Id', II', IIa', IIb', IIc' or IId':

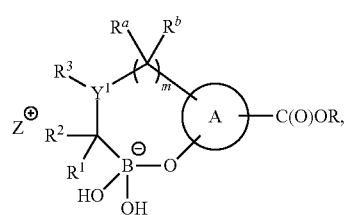
I'

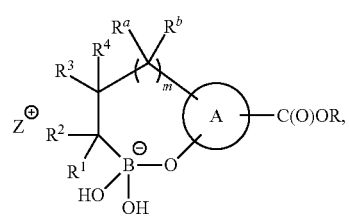
Ia'

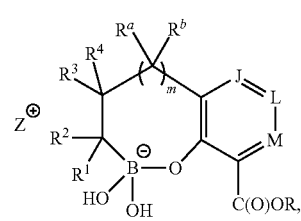
Ib'

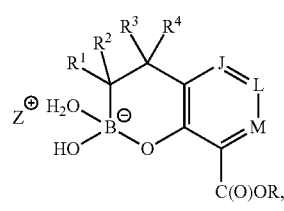
Ic'

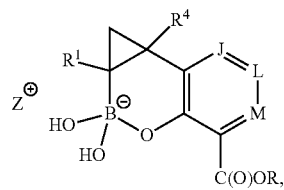
Id'

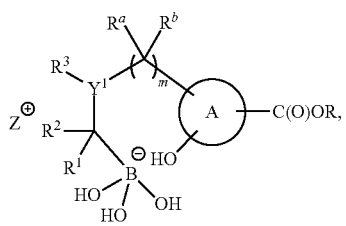
II'

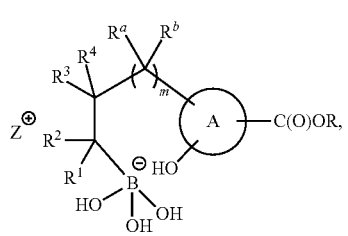
IIa'

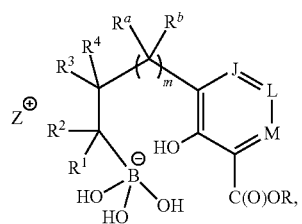

IIb′

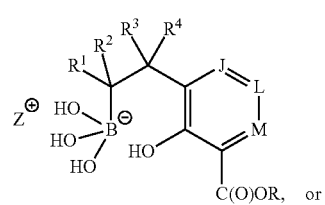

IIc′, or

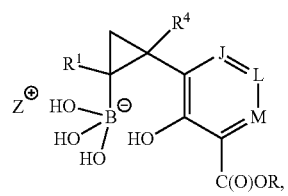

IId′, wherein each of $Z^{\oplus}$ and R may be independently selected from an alkali metal cation or an ammodium cation ($NH_4^+$).

Some other examples of pharmaceutically acceptable base addition salts of the compounds described herein have the structure of Formula III′, IIIa′, IIIb′, IV′, IVa′, or IVb′:

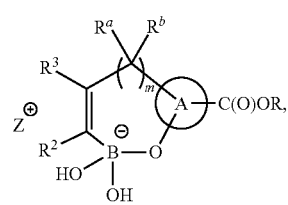

III′

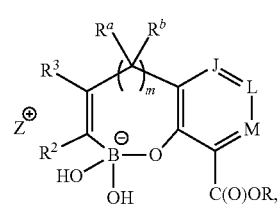

IIIa′

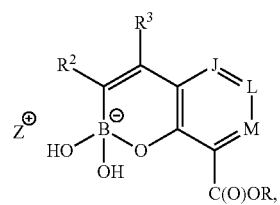

IIIb′,

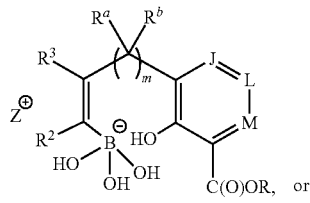

IV′

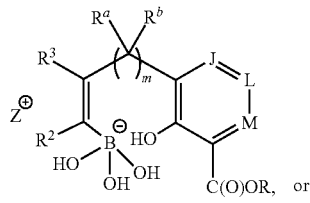

IVa′, or

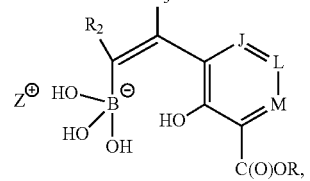

IVb′, wherein each of $Z^{61}$ and R may be independently selected from an alkali metal cation or an ammodium cation ($NH_4^+$).

Some other examples of pharmaceutically acceptable base addition salts of the compounds described herein have the structure of Formula V′, Va′, Vb′ or Vc′:

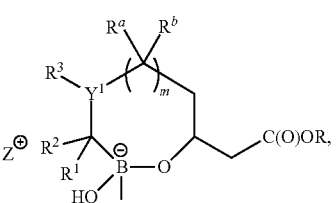

V′

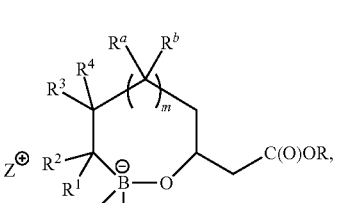

Va′

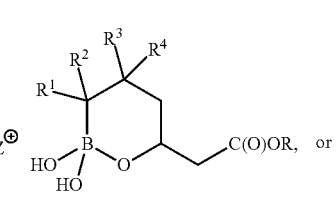

Vb′, or

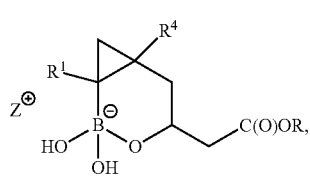

wherein each of $Z^\oplus$ and R may be independently an alkali metal cation or an ammodium cation ($NH_4^+$).

Methods of Preparation

The compounds disclosed herein may be synthesized by methods described below, or by modification of these methods. Ways of modifying the methodology include, among others, temperature, solvent, reagents etc., known to those skilled in the art. In general, during any of the processes for preparation of the compounds disclosed herein, it may be necessary and/or desirable to protect sensitive or reactive groups on any of the molecules concerned. This may be achieved by means of conventional protecting groups, such as those described in *Protective Groups in Organic Chemistry* (ed. J. F. W. McOmie, Plenum Press, 1973); and P. G. M. Green, T. W. Wutts, *Protecting Groups in Organic Synthesis* (3rd ed.) Wiley, New York (1999), which are both hereby incorporated herein by reference in their entirety. The protecting groups may be removed at a convenient subsequent stage using methods known from the art. Synthetic chemistry transformations useful in synthesizing applicable compounds are known in the art and include e.g. those described in R. Larock, *Comprehensive Organic Transformations*, VCH Publishers, 1989, or L. Paquette, ed., *Encyclopedia of Reagents for Organic Synthesis*, John Wiley and Sons, 1995, which are both hereby incorporated herein by reference in their entirety. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

In the following schemes, protecting groups for oxygen atoms are selected for their compatibility with the requisite synthetic steps as well as compatibility of the introduction and deprotection steps with the overall synthetic schemes (P. G. M. Green, T. W. Wutts, Protecting Groups in Organic Synthesis (3rd ed.) Wiley, New York (1999)). Handling of protecting and/or sterodirecting groups specific to boronic acid derivatives is described in a recent review of chemistry of boronic acids: D. G. Hall (Ed.), Boronic Acids. Preparation and Application in Organic Synthesis and Medicine, Wiley VCH (2005) and in earlier reviews: Matteson, D. S. (1988). Asymmetric synthesis with boronic esters. Accounts of Chemical Research, 21(8), 294-300, and Matteson, D. S. (1989). Tetrahedron, 45(7), 1859-1885), all of which are incorporated herein by reference in their entirety. The latter review articles also describe methodology for stereoselective insertion of halomethine functionality next to the boronate which is employed in the synthetic schemes below.

In addition to standard acid catalyzed deprotection, special methods for removal of boronic acid protecting and/or sterodirecting groups methods using fluorides (Yuen, A. K. L., & Hutton, C. A. (2005). Tetrahedron Letters, 46(46), 7899-7903, which is incorporated herein by reference in its entirety) or periodate oxidation (Coutts, S. J., et al. (1994). Tetrahedron Letters, 35(29), 5109-5112, which is incorporated herein by reference in its entirety) can also be employed in preparations of the compounds disclosed herein.

In strategies employing pinanediol or other diol-based chiral auxiliaries for stereospecific introduction of new chiral centers, the early stages of chemistry on boronic intermediates can be performed on chiral boronate esters or alternatively nonchiral borate/boronate intermediates can be used in early stages followed by transesterification with chiral diols prior to the step where stereoselection is required.

Exemplary Synthetic Schemes for the Preparation of Compounds of Formulae I, III and V The following example schemes are provided for the guidance of the reader, and collectively represent an example method for making the compounds encompassed herein. Furthermore, other methods for preparing compounds described herein will be readily apparent to the person of ordinary skill in the art in light of the following reaction schemes and examples. Unless otherwise indicated, all variables are as defined above.

Compounds of formula IX (embodiments of the compound of Formula I) where R is H can be prepared as depicted in Schemes 1-4 from key intermediates I-3, II-5, III-3 and IV-1, which may be assembled by known reactions (Boronic Acids: Preparations and Applications in Organic Synthesis, Medicine and Materials, D. G. Hall, ed., Wiley-VCH, Weinheim, 2011, which is incorporated herein by reference in its entirety).

Scheme 1

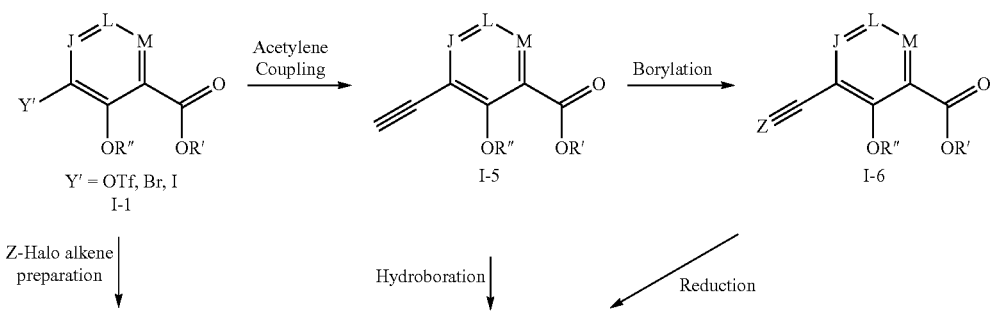

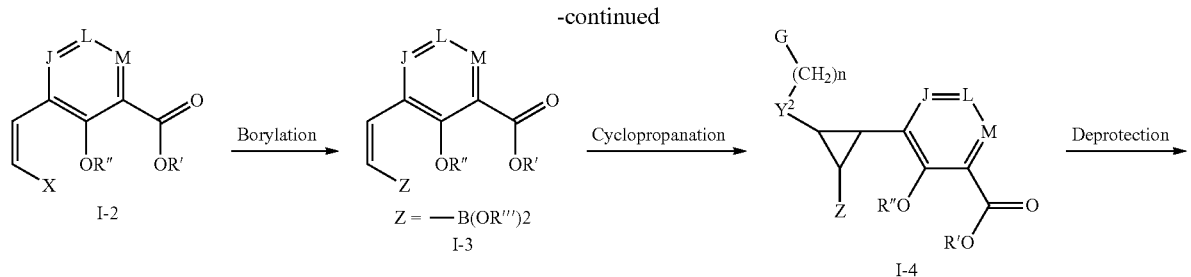

Formula IX

Compounds of formula IX can be made starting from protected aryl or heteroaryl precursors of formula I-1 via Z-vinyl boronate (I-3) followed by cyclopropanation and deprotection. The compounds of formula I-3 may be attained from I-2 (where X is halogen), which may be made by means of known methods of Z-haloalkene formation (*Tetrahedron Lett.*, 2001, 42, 3893-3896) with conventional protecting groups for R', R", and R'", such as those described in *Protective Groups in Organic Chemistry* (ed. J. F. W. McOmie, Plenum, 1973, which is incorporated herein by reference in its entirety); and *Protecting Groups in Organic Synthesis* P. G. M. Wutts, T. W. Green, Wiley, New York, 1999, which is incorporated herein by reference in its entirety). Aryl compounds of formula I-2 upon borylation by well-known available methods (*Chem. Rev.* 2010, 110, 890-931, which is incorporated herein by reference in its entirety) and boronate ester formation with desired chiral auxiliary give intermediates of formula I-3. Alternatively vinyl boronate derivative I-3 can also be made via acetylene derivative of formula I-5, which can be made from compounds of formula I-1 by acetylene coupling such as in Sonogoshira reaction. Phenyl acetylene derivatives of formula I-5 can be transformed into Z-vinylboronates (I-3) by ruthenium hydride pincer complex catalysed addition of pinacolborane to terminal alkynes. (*J. Am. Chem. Soc.*, 2012, 134, 14349-14352). A Cu-catalysed Z-selective hydroboration of alkynes with 1,8-diaminonaphthaleneborane may also be utilized to make compounds of formula I-3 from terminal alkynes (I-5) (*Org. Lett.*, 2016, 18, 1390-1393). Terminal acetylenes of formula I-5 can be selectively transformed under silver catalyzed hydroboration conditions to compounds of formula I-6 (*Tetrahedron*, 2014, 70, 5815-5819). Such alkynyl boronates of formula I-6 can be reduced stereoselectively to the cis-alkenyl pinacolboronates (I-3) via hydroboration with dicyclohexylborane (*J. Org. Chem.*, 2008, 73, 6841-6844).

Cyclopropanation of compounds of formula I-3 to I-4 may be attained by palladium or Zn mediated carbene additions (*J. Am. Chem. Soc.*, 2015, 137, 13176-13182). Such transformations can also be done to give compounds of I-4 in high enantioselectivity (*Tetrahedron*, 2008, 64, 7041-7095; *Eur. J. Org. Chem.* 2000, 2557-2562). Alternatively, dimethyloxosulfonium methylide also reacts with enones to undergo 1,4-addition followed by ring closure to give a cyclopropane derivatives (*Tetrahedron Lett.*, 2003, 44, 3629-3630). A phosphate carbenoid $(RO)_2P(O)OZnCH_2I$ (*J. Org. Chem.*, 2010, 75, 1244-1250; *Org. Process Res. Dev.*, 2016, 20, 786-798) that can be stored may be utilized in such cyclopropanations from I-3 to 1-4. Iodonium ylides derived from malonate methyl ester may also be utilized for higher reactivity in the Rh catalyzed cyclopropanation (*Org. Lett.*, 2012, 14, 317-3173).

Simultaneous deprotection of pinane ester and salicylic acid protective groups of compounds of formula I-4 can be achieved by treating with dilute HCl or trifluoroacetic acid, affording the desired compounds of structure IX. This transformation may also be achieved by treatment with $BCl_3$ or $BBr_3$ as disclosed in WO 2009/064414, which is incorporated herein by reference in its entirety. Alternatively, the deprotection may be attained via trans-esterification with isobutyl boronic acid in presence of dilute acid (as disclosed in WO 2009/064413, which is incorporated herein by reference in its entirety) or via other known methods (*J. Org. Chem.* (2010), 75, 468-471, which is incorporated herein by reference in its entirety). A two-step procedure for deprotection of alkylpinacolylboronate esters is also known via transesterification with diethanolamine followed by hydrolysis (*J. Org. Chem.*, 2011, 76, 3571-3575). Compounds of formula I-4 where Z is DAN (1,8-diaminonaphthalene) protected boramide may be deprotected utilizing mild acidic conditions (*J. Am. Chem. Soc.* 2007, 129, 758-759)

Scheme 2

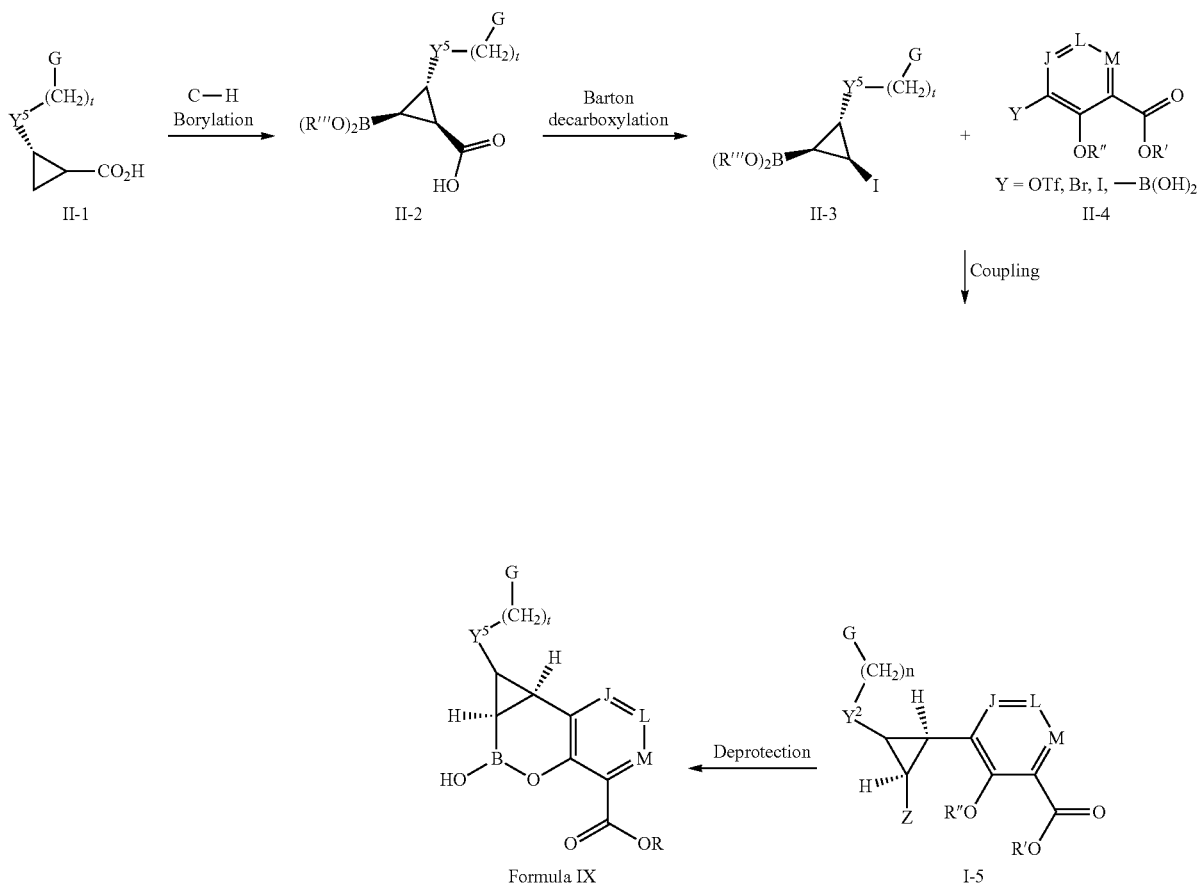

In an alternative sequence, compounds of formula IX can be made via a convergent approach from intermediates II-3 and II-4 as shown in Scheme 2. Salicylic acid derivatives of formula II-4 where Y is a leaving group undergo coupling reaction with Reformatsky reagent of II-3 in Negishi conditions to give intermediates of formula II-5 (*Tetrahedron*, 2014, 1508-1515; *J. Org. Chem.*, 2013, 78, 8250-8266, each of which is incorporated herein by reference in its entirety). Intermediates of formula II-4 where Y is —B(OH)$_2$ undergo palladium mediated Suzuki type cross-coupling with II-3 (*J. Org. Chem.*, 1996, 61, 8718-8719) to give compounds of formula II-5. Intermediates of II-3 can be made by decarboxylation of II-2 (the preparation of which is disclosed in WO 2011154953), which in turn may be made from corresponding carboxylic acid via C—H insertion (*Angew. Chem. Int. Ed.*, 2016, 55, 785-789), or via Simmons-Smith reaction of cis-vinyl boronate precursors (*Eur. J. Org. Chem.* 2000, 2557-2562). Intermediates of formula II-5 can be further transformed to compound of formula IX under the conditions described in scheme 1.

Scheme 3

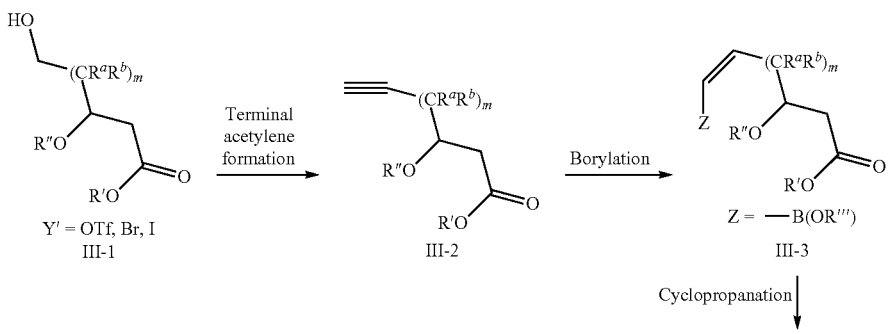

-continued

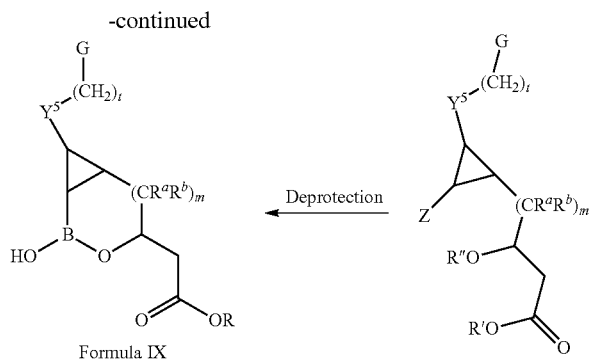

Formula IX

In another example, compounds of formula XI (embodiments of the compound of Formula V) can be made via borylation followed by cyclopropanation from acetylene intermediate III-2 as shown in Scheme 3. Alcohols of formula III-1 can be made by a variety of ways known in literature in both chiral forms. Such protected alcohols of III-1 may be made by selective reduction of diketones to give 3,5-dihydroxypentanoate (m=1) (*J. Org. Chem.*, 2000, 65, 7792-7799) or 3,6-dihydroxypentanoate (m=2) (*Org. Biomol. Chem.*, 2011, 9, 4823-4830) intermediates. Acetylene intermediates of formula III-2 can be made from oxidation of intermediates of III-1 followed by Corey-Fuchs method (*Org. Synth.* 2005, 81, 1). Alternatively, aldehydes of III-1 can also be transformed to III-2 by treating with dimethy-1-(1-diazo-2-oxopropyl)phosphonate (*J. Am. Chem. Soc.*, 2003, 125, 3714-3715). Such acetylene intermediates of III-2 can be further converted to compounds of XI via borylation, cyclopropanation and deprotection sequence as described above in Scheme 1.

Compounds of formula IV-2 (embodiments of compounds of Formula III), IV-4 (embodiments of compounds of Formula I), and IV-6 (embodiments of compounds of Formula I), may be prepared from appropriately protected vinyl boronate intermediates of formula IV-1 (prepared in Scheme 1) as shown in Scheme 4. Derivatives of formula IV-1 can be directly transformed to vinyl boronates of IV-2 by deprotection in the conditions described above in scheme 1. Intermediates of formula IV-1 may be treated with diazoacetates (*Tetrahedron*, 2008, 64, 7041-7095) to undergo cyclopropanation followed by selective ester deprotection to carboxylic acid intermediates of formula IV-3. Such carboxylic acids undergo amide formation followed by deprotection to give amide analogs of formula IV-4 (*Org. Process Res. Dev.*, 2016, 20, 140-177). The carboxylic acids of IV-3 may be converted to carbamates (IV-5) via Curtius rearrangement (*Chem. Rev.* 1988, 88, 297-368; *Org. Lett.*, 2005, 4107-4110; *Eur. J. Org. Chem.* 2009, 5998-6008 which is incorporated herein by reference in its entirety). Intermediates of IV-5 upon selective hydrolysis of carbamate followed by appropriate amide formation give compounds of formula IV-6. Compounds of formula IV-5 may also be transformed to compounds of formula IX where $Y^5$ is —NHC(O)—O— by hydrolysis.

Scheme 4

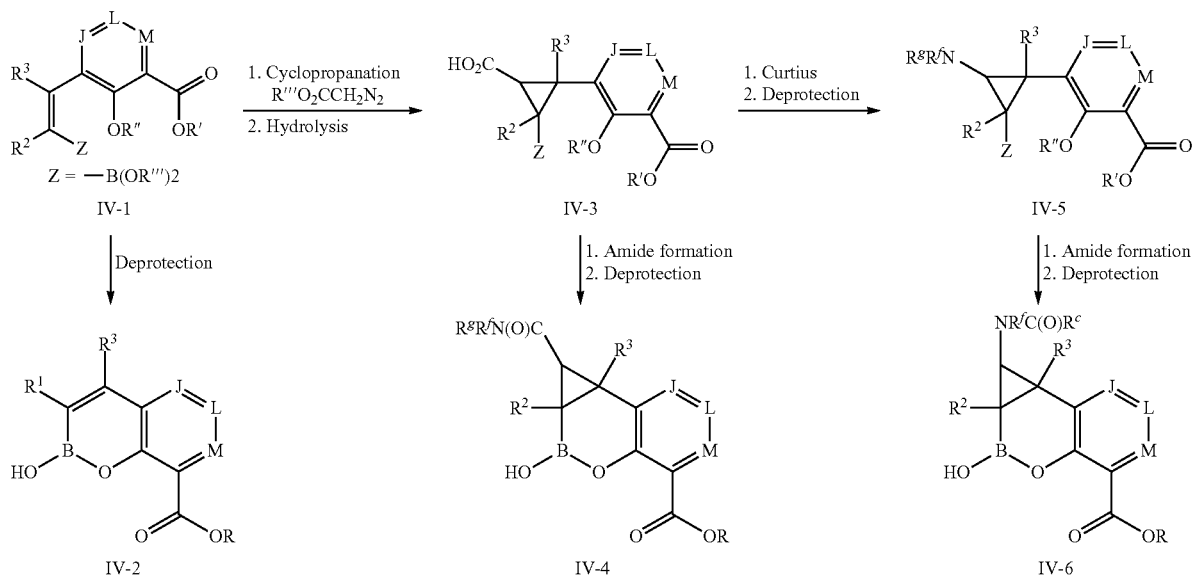

Scheme 5.

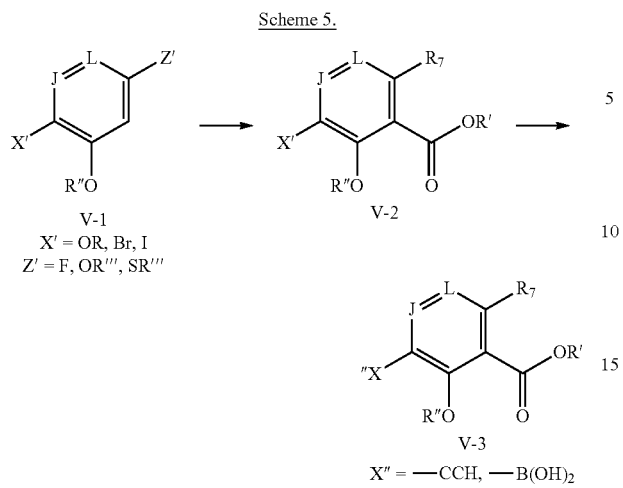

V-1
X' = OR, Br, I
Z' = F, OR''', SR'''

V-2

V-3
X'' = —CCH, —B(OH)$_2$

Intermediates of formula V-3 may be prepared as shown in Scheme 5. V-3 may be used in the preparation of compound of formula IX. Such intermediates of formula V-3 can be synthesized from V-2 where X' is a triflate or bromo or iodo group. Synthesis of boronates of V-3 may be achieved via Miyaura borylation reaction by cross-coupling of bis(pinacolato)diboron (B$_2$pin$_2$) with aryl halides (*J. Org. Chem.*, 1995, 60, 7508-7510). The coupling of aryl halides with terminal acetylenes catalyzed by palladium and other transition metals may be achieved via Sonogashira cross-coupling reaction to give acetylenes of formula V-3 (*Chem. Soc. Rev.*, 2011, 40, 5084-5121). Compounds where X' is substituted with bromo or iodo groups can be attained from appropriately protected commercial 2,5-hydroxy-benzoic acid derivatives (*J. Med. Chem.*, 2003, 46, 3437-3440, which is incorporated herein by reference in its entirety). Intermediates of V-2 can also be prepared via carboxylation of derivatives of formula V-1 where Z' is a fluoro or OR' or SR' by the method described in WO 2012/106995, which is incorporated herein by reference in its entirety.

Synthesis of Prodrugs

Compounds of formula IX where the R is a prodrug moiety may be synthesized by a variety of known methods of different carboxylic acid prodrugs (*Prodrugs: Challenges and Rewards*, V. J. Stella, et al., ed., Springer, New York, 2007, which is incorporated herein by reference in its entirety). These prodrugs include but are not limited to substituted or non-substituted alkyl esters, (acyloxy)alkyl (*Synthesis* 2012, 44, 207, which is incorporated herein by reference in its entirety), [(alkoxycarbonyl)oxy]methyl esters (WO10097675, which is incorporated herein by reference in its entirety), or (oxodioxolyl)methyl esters (*J. Med. Chem.* 1996, 39, 323-338, which is incorporated herein by reference in its entirety). Such prodrugs can be made from compounds of formula VI-1 where R=H by treatment with acid or in neutral conditions (e.g., carbodiimide coupling) in the presence of alcohols (ROH) or via base promoted esterification with RX where X is a leaving group in the presence of an appropriate base.

Scheme 6

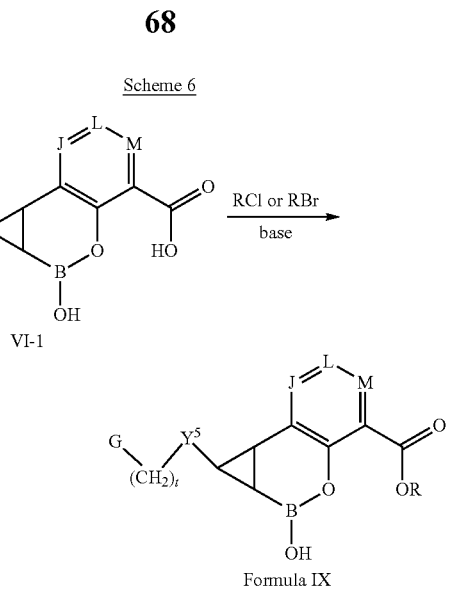

One exemplary but non-limiting general synthetic scheme for preparing prodrugs is shown in Scheme 6. The boronic acid of formula VI-1 where R is hydrogen can react with a chloro/bromo-substituted prodrug moiety to form a prodrug of formula IX where R is a prodrug moiety. Examples of the prodrug moiety R can be —C$_{1-9}$alkyl, —CR$^{10}$R$^{11}$OC(O)C$_{1-9}$alkyl, —CR$^{10}$R$^{11}$OC(O)OC)OC$_{1-9}$alkyl, and Scheme 7

Alternatively, boronate derivatives of formula VII-1 where Z is a boronate ester of pinacol or pinanediol or boramide of 1,8-diaminonaphthalene (*J. Am. Chem. Soc.*, 2007, 129, 758) or corresponding tetrafluoroborates (*Chem. Rev.* 2008, 108, 288-325), which is incorporated herein by reference in its entirety) may be also utilized for introduction of prodrugs and convert them to final prodrugs as shown in Scheme 7. Such carboxylic acids (VII-1) can be made from compounds of formula I-4 by selective deprotection of OR'. The prodrug group may also be introduced earlier in the sequence in compounds of formula I-1 where R' is R. Such sequence where prodrug is introduced in earlier intermediates is only feasible when the ester is stable under the final deprotection conditions to remove the phenol protective group and boronate ester group.

Administration and Pharmaceutical Compositions

The compounds are administered at a therapeutically effective dosage. While human dosage levels have yet to be optimized for the compounds described herein, generally, a daily dose may be from about 0.25 mg/kg to about 120 mg/kg or more of body weight, from about 0.5 mg/kg or less to about 70 mg/kg, from about 1.0 mg/kg to about 50 mg/kg of body weight, or from about 1.5 mg/kg to about 10 mg/kg of body weight. Thus, for administration to a 70 kg person, the dosage range would be from about 17 mg per day to about 8000 mg per day, from about 35 mg per day or less to about 7000 mg per day or more, from about 70 mg per day to about 6000 mg per day, from about 100 mg per day to about 5000 mg per day, or from about 200 mg to about 3000 mg per day. The amount of active compound administered will, of course, be dependent on the subject and disease state being treated, the severity of the affliction, the manner and schedule of administration and the judgment of the prescribing physician.

Administration of the compounds disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, or intraocularly. Oral and parenteral administrations are customary in treating the indications that are the subject of the preferred embodiments.

The compounds useful as described above can be formulated into pharmaceutical compositions for use in treatment of these conditions. Standard pharmaceutical formulation techniques are used, such as those disclosed in *Remington's The Science and Practice of Pharmacy*, 21st Ed., Lippincott Williams & Wilkins (2005), incorporated by reference in its entirety. Accordingly, some embodiments include pharmaceutical compositions comprising: (a) a safe and therapeutically effective amount of a compound described herein (including enantiomers, diastereoisomers, tautomers, polymorphs, and solvates thereof), or pharmaceutically acceptable salts thereof; and (b) a pharmaceutically acceptable carrier, diluent, excipient or combination thereof.

In addition to the selected compound useful as described above, come embodiments include compositions containing a pharmaceutically-acceptable carrier. The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

The compositions described herein are preferably provided in unit dosage form. As used herein, a "unit dosage form" is a composition containing an amount of a compound that is suitable for administration to an animal, preferably mammal subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, though a single administration is not specifically excluded. The skilled artisan will recognize that the formulation does not specifically contemplate the entire course of therapy and such decisions are left for those skilled in the art of treatment rather than formulation.

The compositions useful as described above may be in any of a variety of suitable forms for a variety of routes for administration, for example, for oral, nasal, rectal, topical (including transdermal), ocular, intracerebral, intracranial, intrathecal, intra-arterial, intravenous, intramuscular, or other parental routes of administration. The skilled artisan will appreciate that oral and nasal compositions comprise compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutically-active materials may be included, which do not substantially interfere with the inhibitory activity of the compound. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules, granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

In a similar vein, an ophthalmically acceptable antioxidant includes, but is not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium, although other chelating agents may also be used in place or in conjunction with it.

For topical use, creams, ointments, gels, solutions or suspensions, etc., containing the compound disclosed herein are employed. Topical formulations may generally be comprised of a pharmaceutical carrier, co-solvent, emulsifier, penetration enhancer, preservative system, and emollient.

For intravenous administration, the compounds and compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA J Pharm Sci and Tech* 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided to caregivers in the form of one more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

The actual dose of the active compounds described herein depends on the specific compound, and on the condition to be treated; the selection of the appropriate dose is well within the knowledge of the skilled artisan.

Methods of Treatment

Some embodiments of the present invention include methods of treating bacterial infections with the compounds and compositions comprising the compounds described herein. Some methods include administering a compound, composition, pharmaceutical composition described herein to a subject in need thereof. In some embodiments, a subject can be an animal, e.g., a mammal (including a human). In some embodiments, the bacterial infection comprises a bacteria described herein. As will be appreciated from the foregoing, methods of treating a bacterial infection include methods for preventing bacterial infection in a subject at risk thereof.

In some embodiments, the subject is a human.

Further embodiments include administering a combination of compounds to a subject in need thereof. A combination can include a compound, composition, pharmaceutical composition described herein with an additional medicament.

Some embodiments include co-administering a compound, composition, and/or pharmaceutical composition described herein, with an additional medicament. By "co-administration," it is meant that the two or more agents may be found in the patient's bloodstream at the same time, regardless of when or how they are actually administered. In one embodiment, the agents are administered simultaneously. In one such embodiment, administration in combination is accomplished by combining the agents in a single dosage form. In another embodiment, the agents are administered sequentially. In one embodiment the agents are administered through the same route, such as orally. In another embodiment, the agents are administered through different routes, such as one being administered orally and another being administered intravenous (i.v.).

Examples of additional medicaments include an antibacterial agent, antifungal agent, an antiviral agent, an anti-inflammatory agent and an anti-allergic agent.

Preferred embodiments include combinations of a compound, composition or pharmaceutical composition described herein with an antibacterial agent such as a β-lactam. Examples of such β-lactams include Amoxicillin, Ampicillin (e.g., Pivampicillin, Hetacillin, Bacampicillin, Metampicillin, Talampicillin), Epicillin, Carbenicillin (Carindacillin), Ticarcillin, Temocillin, Azlocillin, Piperacillin, Mezlocillin, Mecillinam (Pivmecillinam), Sulbenicillin, Benzylpenicillin (G), Clometocillin, Benzathine benzylpenicillin, Procaine benzylpenicillin, Azidocillin, Penamecillin, Phenoxymethylpenicillin (V), Propicillin, Benzathine phenoxymethylpenicillin, Pheneticillin, Cloxacillin (e.g., Dicloxacillin, Flucloxacillin), Oxacillin, Methicillin, Nafcillin, Faropenem, Biapenem, Doripenem, Ertapenem, Imipenem, Meropenem, Panipenem, Cefazolin, Cefacetrile, Cefadroxil, Cefalexin, Cefaloglycin, Cefalonium, Cefaloridine, Cefalotin, Cefapirin, Cefatrizine, Cefazedone, Cefazaflur, Cefradine, Cefroxadine, Ceftezole, Cefaclor, Cefamandole, Cefminox, Cefonicid, Ceforanide, Cefotiam, Cefprozil, Cefbuperazone, Cefuroxime, Cefuzonam, Cefoxitin, Cefotetan, Cefmetazole, Loracarbef, Cefixime, Ceftazidime, Ceftriaxone, Cefcapene, Cefdaloxime, Cefdinir, Cefditoren, Cefetamet, Cefmenoxime, Cefodizime, Cefoperazone, Cefotaxime, Cefpimizole, Cefpiramide, Cefpodoxime, Cefsulodin, Cefteram, Ceftibuten, Ceftiolene, Ceftizoxime, Flomoxef, Latamoxef, Cefepime, Cefozopran, Cefpirome, Cefquinome, Ceftobiprole, Ceftaroline, Ceftiofur, Cefquinome, Cefovecin, Aztreonam, Tigemonam and Carumonam.

Preferred embodiments include β-lactams such as Ceftazidime, Biapenem, Doripenem, Ertapenem, Imipenem, Meropenem, Tebipenem, Tebipenem pivoxil, Apapenem, and Panipenem.

Additional preferred embodiments include β-lactams such as Aztreonam, Tigemonam, and Carumonam.

Some embodiments include a combination of the compounds, compositions and/or pharmaceutical compositions described herein with an additional agent, wherein the additional agent comprises a monobactam. Examples of monobactams include aztreonam, tigemonam, nocardicin A, carumonam, and tabtoxin. In some such embodiments, the compound, composition and/or pharmaceutical composition comprises a class A, C, or D beta-lactamase inhibitor. Some embodiments include co-administering the compound, composition or pharmaceutical composition described herein with one or more additional agents.

Some embodiments include a combination of the compounds, compositions and/or pharmaceutical compositions described herein with an additional agent, wherein the additional agent comprises a class B beta lactamase inhibitor. An example of a class B beta lactamase inhibitor includes ME1071 (Yoshikazu Ishii et al, "In Vitro Potentiation of Carbapenems with ME1071, a Novel Metallo-β-Lactamase Inhibitor, against Metallo-β-lactamase Producing *Pseudomonas aeruginosa* Clinical Isolates." Antimicrob. Agents Chemother. doi:10.1128/AAC.01397-09 (July 2010)). Some embodiments include co-administering the compound, composition or pharmaceutical composition described herein with one or more additional agents.

Some embodiments include a combination of the compounds, compositions and/or pharmaceutical compositions described herein with an additional agent, wherein the additional agent comprises one or more agents that include a class A, B, C, or D beta lactamase inhibitor. Some embodiments include co-administering the compound, composition or pharmaceutical composition described herein with the one or more additional agents.

Indications

The compounds and compositions comprising the compounds described herein can be used to treat bacterial infections. Bacterial infections that can be treated with the compounds, compositions and methods described herein can comprise a wide spectrum of bacteria. Example organisms include gram-positive bacteria, gram-negative bacteria, aerobic and anaerobic bacteria, such as *Staphylococcus, Lactobacillus, Streptococcus, Sarcina, Escherichia, Enterobacter, Klebsiella, Pseudomonas, Acinetobacter, Mycobacterium, Proteus, Campylobacter, Citrobacter, Nisseria, Baccillus, Bacteroides, Peptococcus, Clostridium, Salmonella, Shigella, Serratia, Haemophilus, Brucella* and other organisms.

More examples of bacterial infections include *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis,* or *Staphylococcus saccharolyticus.*

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples. The following examples will further describe the present invention, and are used for the purposes of illustration only, and should not be considered as limiting.

EXAMPLES

General Procedures

Materials used in preparing the cyclic boronic acid ester derivatives described herein may be made by known methods or are commercially available. It will be apparent to the skilled artisan that methods for preparing precursors and functionality related to the compounds claimed herein are generally described in the literature including, for example, procedures described in U.S. Pat. No. 7,271,186 and WO2009064414, each of which is incorporated by reference in its entirety. In these reactions, it is also possible to make use of variants which are themselves known to those of ordinary skill in this art, but are not mentioned in greater detail. The skilled artisan given the literature and this disclosure is well equipped to prepare any of the compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as March Advanced Organic Chemistry (Wiley), Carey and Sundberg, Advanced Organic Chemistry (incorporated herein by reference in their entirety) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts Protecting Groups in Organic Synthesis, 4th Ed., John Wiley & Sons (2007), incorporated herein by reference in its entirety.

The following example schemes are provided for the guidance of the reader, and represent preferred methods for making the compounds exemplified herein. These methods are not limiting, and it will be apparent that other routes may be employed to prepare these compounds. Such methods specifically include solid phase based chemistries, including combinatorial chemistry. The skilled artisan is thoroughly equipped to prepare these compounds by those methods given the literature and this disclosure. The compound numberings used in the synthetic schemes depicted below are meant for those specific schemes only, and should not be construed as or confused with same numberings in other sections of the application.

Trademarks used herein are examples only and reflect illustrative materials used at the time of the invention. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the invention.

Example 1

Disodium salt of 2-Hydroxy-5-methoxy-a,7b-dihydro-1H-cyclopropa[c][1,2]benzoxaborinine-4-carboxylic acid (Compound 1')

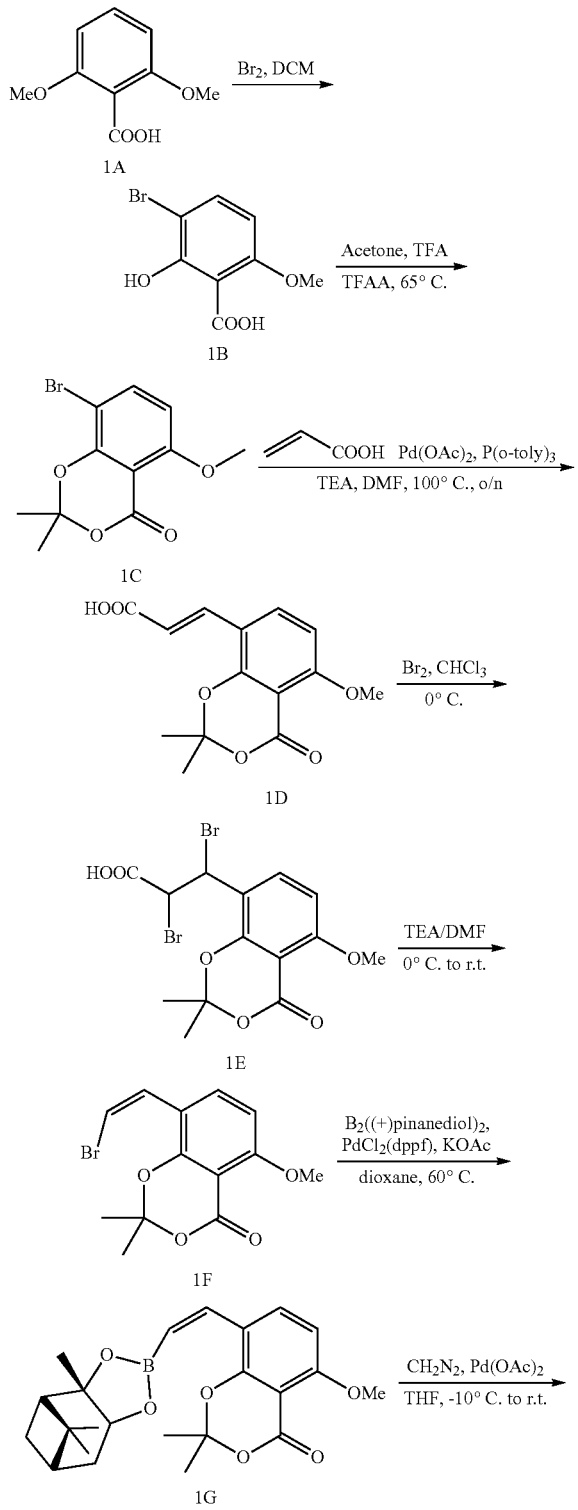

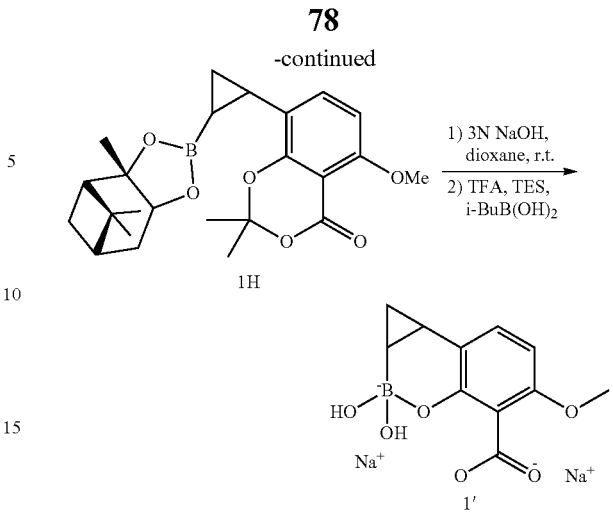

Step 1: Synthesis of 1B

A solution of bromine (14.06 mL, 274 mmol, 1 eq.) in $CH_2Cl_2$ (20 mL) was added slowly over 8 h to a suspension of 2,6-dimethoxybenzoic acid (1A) (50 g, 274 mmol) in $CH_2C_{12}$ (200 mL). After stirring at rt overnight, the light orange slurry was heated and a portion of the solvent (methyl bromide, hydrogen bromide and $CH_2Cl_2$) was removed by distillation at atmospheric pressure (total volume distilled 100 mL). Ethanol (150 mL) was added and the remaining $CH_2C_{12}$ was distilled off at atmospheric pressure, slowly increasing the bath temperature to 90° C. Upon completion of the distillation (1 h), the heterogeneous mixture was cooled to rt. After stirring 1 h at rt, the slurry was cooled to 0° C. After stirring at 0° C. for 2 h, the solids were collected by filtration. The filtrate was recirculated to rinse the flask and stir bar. The solids were rinsed with ethanol at 0° C. (2×50 mL), air dried, then dried under high vacuum to give 1B as fine white needles (58.23 g, 85.9%).

Step 2: Synthesis of 1C

A 10-mL syringe filled with trifluoroacetic anhydride (11.25 mL, 81 mmol, 2 eq) and a 20-mL syringe filled with acetone (17 mL, 232 mmol, 5.7 eq) were added simultaneously via syringe pump over 24 hours to a clear solution of 1B (10 g, 40 mmol) in TFA (10 mL) at 70° C. After 1 hour, the starting material began to crystallize out. TFA (5 mL) was added, affording a clear solution. After another hour at 70° C. the solution became slightly heterogeneous. Upon completion of the addition, HPLC showed 89:11 product to starting material. After stirring at 70° C. overnight, the ratio was 92:8. The reaction mixture was cooled to rt, diluted with ethyl acetate (15 mL), filtered over celite, and the pad and flask were rinsed with ethyl acetate (2×10 mL). The clear black filtrate was concentrated to dryness. The solids were taken up in ethyl acetate (50 mL) and $CH_2Cl_2$ (10 mL, to improve solubility of the product) and washed twice with a saturated solution of $NaHCO_3$ (50 and 30 mL). The brown/black solution was concentrated to dryness. The residue was taken up in ethyl acetate (10 mL) and the mixture was heated to reflux. Heptane (3×10 mL) was added and the mixture was brought to reflux (after the last addition of heptane, the product started crystallizing). The heterogeneous mixture was refluxed for 15 min and was allowed to cool to rt. After stirring at rt for 2 hours and 0° C. for 2 hours, the solids were collected by filtration. The filtrate was recirculated to rinse the flask. The solids were rinsed with 3:1 heptane/ethyl acetate at 0° C. (2×10 mL), air dried, then dried under high vacuum to give 1C as a light tan powder (8.83 g, 76%).

Step 3: Synthesis of Compound 1D

To the solution of compound 1C (8.61 g, 30 mmol, 1.0 eq) in DMF (30 mL) was added acrylic acid (3.1 mL, 45 mmol, 1.5 eq), TEA (12.5 mL, 90 mmol, 3 eq), Pd(OAc)$_2$ (337 mg, 1.5 mmol, 0.05 eq) and tri(o-tolyl)phosphine (913 mg, 3.0 mmol, 0.1 eq). The reaction mixture was flushed with nitrogen and stirred at 100° C. for 14 hours. The reaction mixture was concentrated to dryness and the solid was washed with 0.2N HCl and DCM to give compound 1D (5.3 g, 64%) as off-white solid, which is pure enough. $^1$H NMR (CDCl$_3$, 300 MHz): δ7.70-7.64 (m, 2H), 6.63 (d, J=9.0 Hz, 1H), 6.29 (d, J=16.2 Hz, 1H), 3.89 (s, 3H), 1.65 (s, 6H).

Step 4: Synthesis of Compound 1E

To the suspension of compound 1D (5.2 g, 18.7 mmol, 1.0 eq) in chloroform (200 mL) was added bromine liquid (1.1 mL, 21.5 mmol, 1.15 eq) dropwise in 5 minutes at 0° C. The reaction solution was stirred at 0° C. for 2 hours before it was concentrated under reduced pressure. The obtained yellow solid is crude compound 1E (8.2 g, 99%), which was used directly for next step without purification.

Step 5: Synthesis of Compound 1F

To the solution of compound 1E (8.2 g, 18.7 mmol, 1.0 eq) in DMF (24 mL) was added triethylamine (5.2 mL, 37.4 mmol, 2.0 eq) dropwise in 2 minutes at 0° C. The resulting reaction mixture was slowly warmed up to rt and stirred for 8 hours. The reaction mixture was diluted with EtOAc and washed with 0.1N HCl and water. After dried over Na$_2$SO$_4$, the organic layer was concentrated and chromatography (hexanes/EtOAc=3/1 to 1/1) to give compound 1F (3.2 g) as off-white solid. $^1$H NMR (CDCl$_3$, 300 MHz): δ8.23 (d, J=9.3 Hz, 1H), 7.09 (d, J=8.4 Hz, 1H), 6.69 (d, J=9.0 Hz, 1H), 6.44 (d, J=8.4 Hz, 1H), 3.99 (s, 3H), 1.72 (s, 6H).

Step 6: Synthesis of Compound 1G

The mixture of compound 1F (626 mg, 2.0 mmol, 1.0 eq), bis((+)pinanediolato)diboron (1.1 g, 3.0 mmol, 1.5 eq), PdCl$_2$(dppf) (163 mg, 0.2 mmol, 0.1 eq) and KOAc (400 mg, 4.0 mmol, 2.0 eq) in dioxane (15 mL) was stirred at 60° C. for 2 hours under nitrogen atmosphere. The reaction mixture was diluted with EtOAc and washed with 0.1N HCl and water. After dried over Na$_2$SO$_4$, the organic layer was concentrated and purified by column chromatography (hexanes/EtOAc=3/1 to 1/1) to give compound 1G (605 mg, 73%) as yellow solid. ESI-MS: [M+H]$^+$: 413

Step 7: Synthesis of Compound 1H

To the solution of compound 1G (98 mg, 0.24 mmol, 1.0 eq) and Pd(OAc)$_2$ (2.7 mg, 0.012 mmol, 0.05 eq) in THF (3 mL) was slowly added diazomethane (5 mL, freshly made, about 0.2 to 0.3 M in ether) at −10° C. in 15 minutes. The solution was slowly warmed up to rt and stirred for 2 hours before it was concentrated to dryness. The obtained residue was and purified by column chromatography (hexanes/ EtOAc=3/1 to 1/1) to give compound 1H (70 mg, 70%) as yellow oil. ESI-MS: [M+H]$^+$: 427

Step 8: Synthesis of Compound 1'

The mixture of compound 1H (95 mg, 0.22 mmol, 1.0 eq) in dioxane (1.5 mL) and 3N NaOH (1.5 mL) was stirred at rt for 1 hour, LCMS indicating the disappearance of starting material. The reaction mixture was cooled to 0° C. and TES (200 mg), TFA (5 mL) and i-BuB(OH)$_2$ (80 mg) was added in sequence. The resulting yellow clear solution was stirred at rt for 2 hours before it was concentrated to dryness. The residue was dissolved in water/MeCN and purified by prep-HPLC (C18, acetonitrile and water as mobile phases, 0.1% HCOOH). The obtained solid (26 mg) was dissolved in MeCN/water and adjusted to pH=9.5 with 1N NaOH (0.22 mL). After lyophilization, the obtained crude sodium salt of Compound 1 was dissolved in 0.6 mL water and was added acetone (1.1 mL) dropwise. The resulting suspension was stirred at rt for 3 hours. The mixture was filtered and the solid was washed with 10% water in acetone twice to give sodium salt of Compound 1 (24 mg) as a white solid. $^1$H NMR (D$_2$O, 300 MHz): δ6.83 (d, J=8.4 Hz, 1H), 6.15 (d, J=8.4 Hz, 1H), 3.50 (s, 3H), 1.60-1.48 (m, 1H), 0.60-0.46 (m, 1H), 0.06-0.10 (m, 2H). ESI-MS: [M−H$_2$O+H]$^+$: 217

Example 2

Disodium salt of (1 aS,7bR)-2-hydroxy-5-methoxy-1a,7b-dihydro-1H-cyclopropa[c][1,2] benzoxaborinine-4-carboxylic acid (Compound 2')

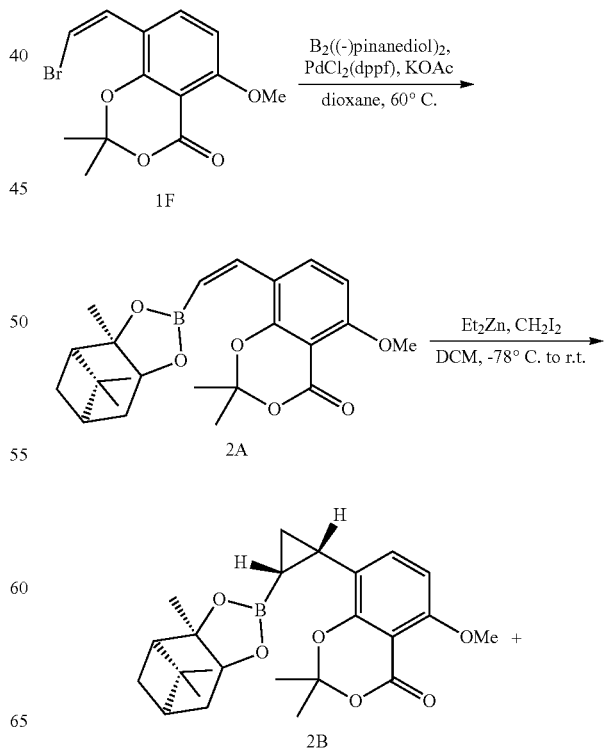

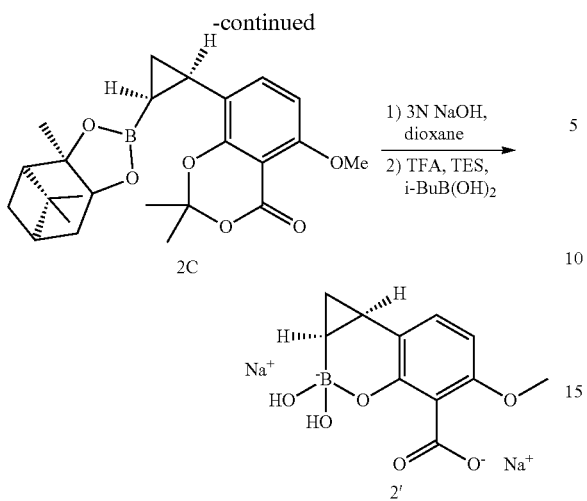

Step 1: Synthesis of Compound 2A

The mixture of compound 1F (940 mg, 3.0 mmol, 1.0 eq), bis((−)-pinanediolato)diboron (1.4 g, 3.9 mmol, 1.3 eq), $PdCl_2(dppf)$ (245 mg, 0.3 mmol, 0.1 eq) and KOAc (600 mg, 6.0 mmol, 2.0 eq) in dioxane (15 mL) was stirred at 60° C. for 2 hours under nitrogen atmosphere. The reaction mixture was diluted with EtOAc and washed with 0.1N HCl and water. After dried over $Na_2SO_4$, the organic layer was concentrated and purified by column chromatography (hexanes/EtOAc=3/1 to 1/1) to give compound 2A (560 mg, 45%) as a yellow solid. ESI-MS: [M+H]$^+$: 413

Step 2: Synthesis of Compound 2C

To the solution of $Et_2Zn$ (11.0 mL, 1M in hexanes, 11.0 mmol, 8.0 eq) in DCM (8 mL) was added diiodomethane (1.44 mL, 16.0 mmol, 12 eq) dropwise in 3 minutes at −78° C. under nitrogen atmosphere. The resulting white mixture was stirred at −78° C. for 10 minutes before compound 2A (560 mg, 1.36 mmol, 1.0 eq) in DCM (6 mL) was added dropwise in 5 minutes. The solution was slowly warmed up to rt in 6 hours and stirred for 30 hours. The reaction mixture was quenched with saturated aqueous ammonium chloride solution was extracted with EtOAc (2×). The combined organic layer was dried over $Na_2SO_4$ and then concentrated to dryness. The residue was briefly purified by column chromatography (hexanes/EtOAc=3/1 to 1/1) to give a mixture of two isomers (2B and 2C) (510 mg, NMR/HPLC showed ~1:3 ratio of two isomers) as yellow oil. The mixture was further purified by prep-HPLC (C18, acetonitrile and water as mobile phases, 0.1% HCOOH) to give 3C as a white solid (154 mg). ESI-MS: [M+H]$^+$: 427.

Step 3: Synthesis of Compound 2'

The mixture of compound 2C (217 mg, 0.51 mmol, 1.0 eq) in dioxane (3.0 mL) and 3N NaOH (3.0 mL) was stirred at rt for 2 hours, LCMS indicating the disappearance of starting material. The reaction mixture was cooled to 0° C. and TES (300 mg), TFA (5 mL) and i-BuB(OH)$_2$ (150 mg) was added in sequence. The resulting yellow clear solution was stirred at rt for 2 hours before it was concentrated to dryness. The residue was dissolved in water/MeCN and purified by prep-HPLC (C18, acetonitrile and water as mobile phases, 0.1% HCOOH) to give free acid of Compound 2 (74 mg) as a white solid. The obtained solid (74 mg) was dissolved in MeCN/water and adjusted to pH=9.5 with 1N NaOH (0.58 mL). After lyophilization, the obtained crude sodium salt of Compound 2 was dissolved in 1.5 mL water and was added acetone (4.5 mL) dropwise. The resulting suspension was stirred at rt for 3 hours. The mixture was filtered and the solid was washed with 10% water in acetone twice to give Compound 2' (82 mg) as a white solid. $^1$H NMR (D$_2$O, 300 MHz): δ6.85 (d, J=8.4 Hz, 1H), 6.19 (d, J=8.4 Hz, 1H), 3.53 (s, 3H), 1.62-1.55 (m, 1H), 0.64-0.55 (m, 1H), 0.12-0.050 (m, 2H). ESI-MS: [M−H$_2$O+H]$^+$: 217.

Example 3

Disodium Salt of (1aR,7bS)-2-hydroxy-5-methoxy-1a,7b-dihydro-1H-cyclopropa[c][1,2] benzoxaborinine-4-carboxylic acid (Compound 3')

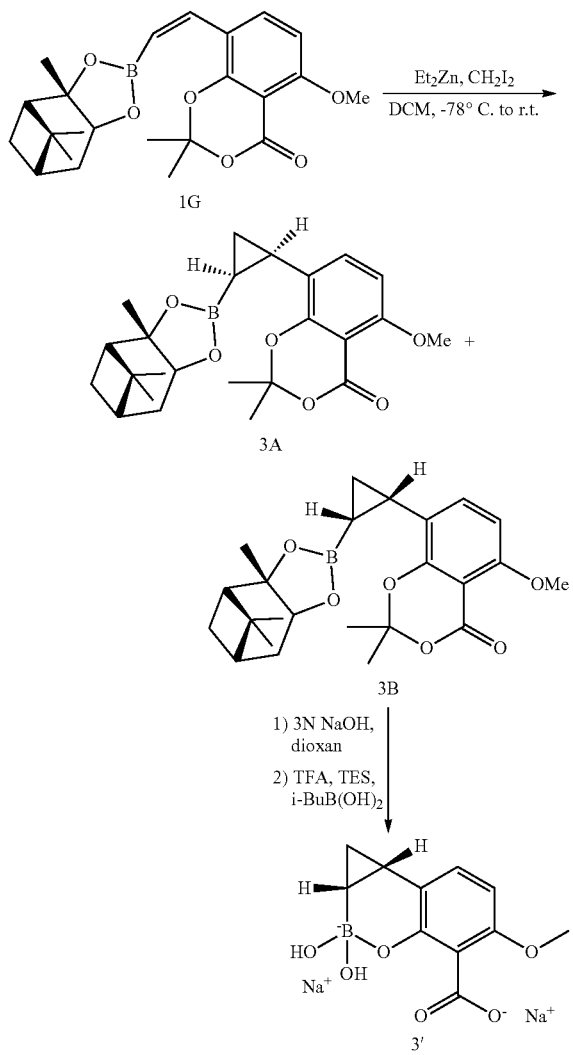

Step 1: Synthesis of Compound 3B

To the solution of $Et_2Zn$ (13.6 mL, 1M in hexanes, 13.6 mmol, 8.0 eq) in DCM (8 mL) was added diiodomethane (1.69 mL, 21 mmol, 12 eq) dropwise in 3 minutes at −78° C. under nitrogen atmosphere. The resulting white mixture was stirred at −78° C. for 10 minutes before compound 1G (700 mg, 1.7 mmol, 1.0 eq) in DCM (8 mL) was added dropwise in 5 minutes. The solution was slowly warmed up to rt in 6 hours and stirred for 30 hours. The reaction mixture was quenched with saturated aqueous ammonium chloride solution was extracted with EtOAc (2×). The combined organic layer was dried over $Na_2SO_4$ and then concentrated to dryness. The residue was briefly purified by column chromatography (hexanes/EtOAc=3/1 to 1/1) to give a mixture of two isomers of compound 3A and 3B (670 mg, NMR/HPLC showed ~1:3 ratio of two isomers) as yellow oil. The mixture was further purified by prep-HPLC (C18, acetonitrile and water as mobile phases, 0.1% HCOOH) to give 330 mg pure 3B as a white solid. ESI-MS: $[M+H]^+$: 427. Absolute configuration of 3B was defined by Single Crystal X-ray Analysis.

Step 2: Synthesis of Compound 3'

The mixture of compound 3B (245 mg, 0.58 mmol, 1.0 eq) in dioxane (4.0 mL) and 3N NaOH (4.0 mL) was stirred at rt for 2 hours, LCMS indicating the disappearance of starting material. The reaction mixture was cooled to 0° C. and TES (300 mg), TFA (5 mL) and i-BuB(OH)$_2$ (180 mg) was added in sequence. The resulting yellow clear solution was stirred at rt for 2 hours before it was concentrated to dryness. The residue was dissolved in water/MeCN and purified by prep-HPLC (C18, acetonitrile and water as mobile phases, 0.1% HCOOH) to give free acid Compound 3 (80 mg) as a white solid. The obtained solid (80 mg) was dissolved in MeCN/water and adjusted to pH=9.5 with 1N NaOH (0.62 mL). After lyophilization, the obtained crude sodium salt of Compound 3 was dissolved in 1.5 mL water and was added acetone (4.5 mL) dropwise. The resulting suspension was stirred at rt for 3 hours. The mixture was filtered and the solid was washed with 10% water in acetone twice to give Compound 3' (84 mg) as a white solid. $^1$H NMR ($D_2O$, 300 MHz): δ6.86 (d, J=8.4 Hz, 1H), 6.20 (d, J=8.1 Hz, 1H), 3.53 (s, 3H), 1.64-1.55 (m, 1H), 0.64-0.55 (m, 1H), 0.13-0.05 (m, 2H). ESI-MS: $[M-H_2O+H]^+$: 217.

Example 4

Disodium Salt of 5-Fluoro-2-hydroxy-1a,7b-dihydro-1H-cyclopropa[c][1,2]benzoxaborinine-4-carboxylic acid (Compound 4')

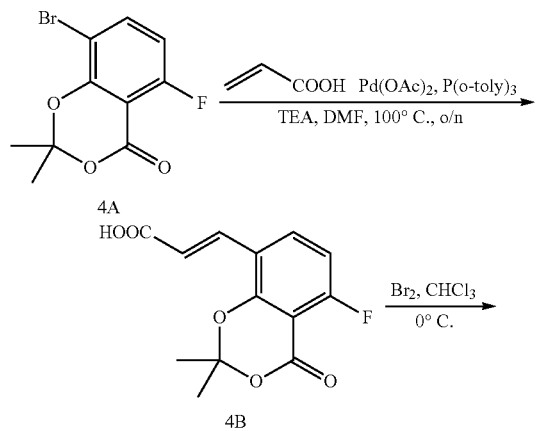

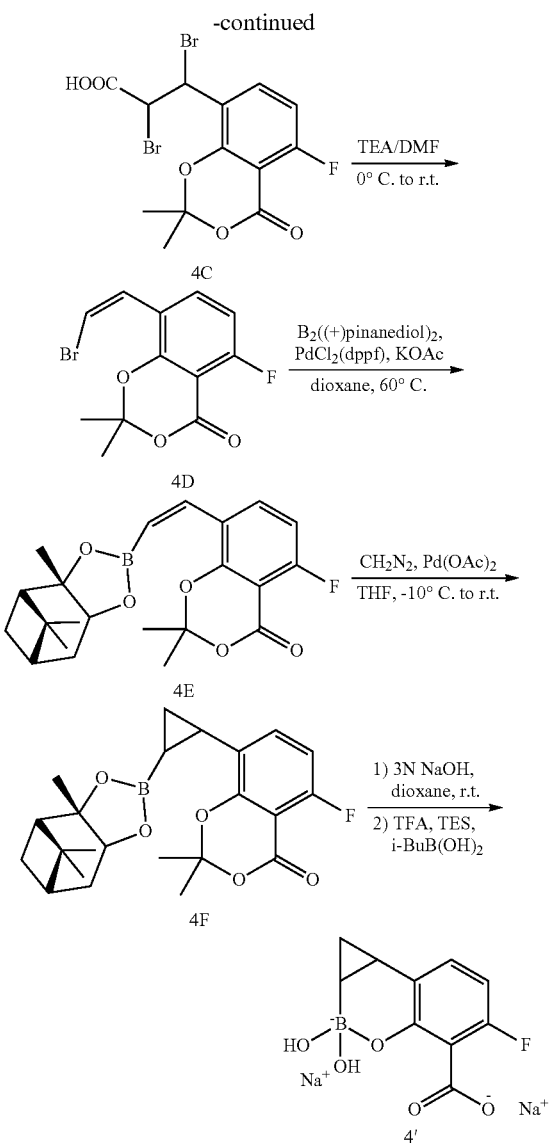

Step 1: Synthesis of Compound 4A

Compound 4A was prepared from Boc-t-Butyl ester intermediate (previously disclosed in WO 2015/179308) by TFA deprotection followed by isopropylidene protection as described in step 2 of Example 1.

Step 2: Synthesis of Compound 4B

To the solution of compound 4A (16.0 g, 58 mmol, 1.0 eq) in DMF (50 mL) was added acrylic acid (6.0 mL, 87 mmol, 1.5 eq), TEA (24 mL, 175 mmol, 3 eq), Pd(OAc)$_2$ (651 mg, 2.9 mmol, 0.05 eq) and tri(o-tolyl)phosphine (1.77 g, 5.8 mmol, 0.1 eq). The reaction mixture was flushed with nitrogen and stirred at 100° C. for 14 hours. The reaction mixture was concentrated to dryness and the solid was washed with 0.2N HCl and DCM to give a yellow solid. The solid was re-crystallized in EtOAc and hexanes to give compound 4B (8.2 g, 53%) as an off-white solid. $^1$H NMR (CD$_3$OD, 400 MHz): δ8.01 (dd, 1H), 7.78 (d, J=16.4 Hz, 1H), 7.00 (dd, 1H), 6.57 (d, J=16.0 Hz, 1H), 1.80 (s, 6H).

Step 3: Synthesis of Compound 4C

To the suspension of compound 4B (8.2 g, 30.8 mmol, 1.0 eq) in chloroform (300 mL) was added bromine liquid (1.8 mL, 35.4 mmol, 1.15 eq) dropwise in 5 minutes at 0° C. The reaction solution was stirred at 0° C. for 2 hours before it was concentrated under reduced pressure. The obtained yellow solid is crude compound 4C (14.7 g), which was used directly for next step without purification.

Step 4: Synthesis of Compound 4D

To the solution of compound 4C (14.7 g, 30.8 mmol, 1.0 eq) in DMF (35 mL) was added triethylamine (8.6 mL, 61.6 mmol, 2.0 eq) dropwise in 2 minutes at 0° C. The resulting reaction mixture was slowly warmed up to rt and stirred for 8 hours. The reaction mixture was diluted with EtOAc and washed with 0.1N HCl and water. After dried over $Na_2SO_4$, the organic layer was concentrated and chromatography (hexanes/EtOAc=3/1 to 1/1) to give compound 4D (5.5 g) as an off-white solid. $^1$H NMR (CDCl$_3$, 400 MHz): δ8.20 (dd, 1H), 7.08 (d, J=8.0 Hz, 1H), 6.88 (t, J=8.2 Hz, 1H), 6.55 (d, J=8.0 Hz, 1H), 1.75 (s, 6H).

Step 5: Synthesis of Compound 4E

The mixture of compound 4D (700 mg, 2.3 mmol, 1.0 eq), bis((+)pinanediolato)diboron (1.24 g, 3.5 mmol, 1.5 eq), PdCl$_2$(dppf) (188 mg, 0.23 mmol, 0.1 eq) and KOAc (450 mg, 4.6 mmol, 2.0 eq) in dioxane (15 mL) was stirred at 60° C. for 2 hours under nitrogen atmosphere. The reaction mixture was diluted with EtOAc and washed with 0.1N HCl and water. After dried over Na$_2$SO$_4$, the organic layer was concentrated and purified by column chromatography (hexanes/EtOAc=3/1 to 1/1) to give compound 4E (240 mg, 26%) as a yellow solid. ESI-MS: [M+H]$^+$: 401.

Step 6: Synthesis of Compound 4F

To the solution of compound 4E (240 mg, 0.6 mmol, 1.0 eq) and Pd(OAc)$_2$ (6.8 mg, 0.03 mmol, 0.05 eq) in THF (3 mL) was slowly added diazomethane (6 mL, freshly made, about 0.2 to 0.3 M in ether) at −10° C. in 15 minutes. The solution was slowly warmed up to rt and stirred for 2 hours before it was concentrated to dryness. The obtained residue was and purified by column chromatography (hexanes/EtOAc=3/1 to 1/1) to give compound 4F (240 mg, 99%) as yellow oil. ESI-MS: [M+H]$^+$: 415.

Step 7: Synthesis of Compound 4'

The mixture of compound 4F (140 mg, 0.34 mmol, 1.0 eq) in dioxane (1.5 mL) and 3N NaOH (1.5 mL) was stirred at rt for 1 hour, LCMS indicating the disappearance of starting material. The reaction mixture was cooled to 0° C. and TES (250 mg), TFA (5 mL) and i-BuB(OH)$_2$ (100 mg) was added in sequence. The resulting yellow clear solution was stirred at rt for 2 hours before it was concentrated to dryness. The residue was dissolved in water/MeCN and purified by prep-HPLC (C18, acetonitrile and water as mobile phases, 0.1% TFA). The obtained solid (28 mg) was dissolved in MeCN/water and adjusted to pH=9.5 with 1N NaOH (0.27 mL). After lyophilization, the crude sodium salt of Compound 4 was dissolved in 1.0 mL water and acetone (8.0 mL) was added dropwise. The resulting suspension was stirred at rt for 3 hours. The mixture was filtered and the solid was washed with 10% water in acetone twice to give Compound 4' (26 mg) as an off-white solid. $^1$H NMR (D$_2$O, 300 MHz): δ6.87 (t, J=7.2 Hz, 1H), 6.25 (d, J=8.4 Hz, 1H), 1.65-1.56 (m, 1H), 0.67-0.57 (m, 1H), 0.14-0.03 (m, 2H). F NMR (D$_2$O, 300 MHz): δ−124.9. ESI-MS: [M−H$_2$O+H]$^+$: 205.

Example 5

Disodium Salt of 1,1-Difluoro-2-hydroxy-5-methoxy-1a,7b-dihydrocyclopropa[c][1,2] benzoxaborinine-4-carboxylic acid (Compound 5')

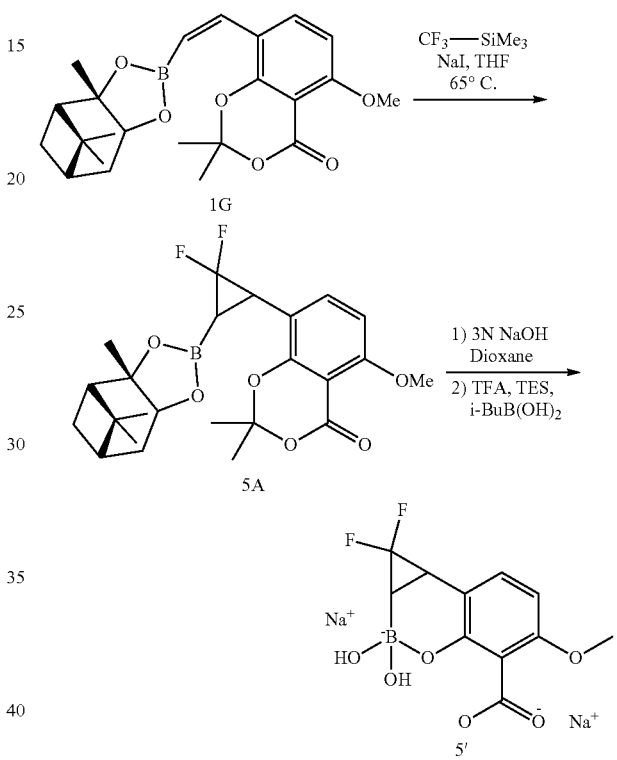

Step 1: Synthesis of Compound 5A

To the suspension of compound 1G (180 mg, 0.44 mmol, 1.0 eq) and sodium iodide (52 mg, 0.35 mmol, 0.8 eq) in THF (6 mL) was slowly added TMS-CF$_3$ (0.65 mL, 4.4 mmol, 10 eq) at 65° C. in 6 hours. After another 12 hours, the reaction mixture was cooled down and concentrated to dryness. The obtained residue was and purified by column chromatography (hexanes/EtOAc=4/1 to 1/1) to give compound 5A (40 mg, 20%) as yellow oil. ESI-MS: [M+H]$^+$: 463.

Step 2: Synthesis of Compound 5'

The mixture of compound 5A (40 mg, 0.09 mmol, 1.0 eq) in dioxane (0.7 mL) and 3N NaOH (0.7 mL) was stirred at rt for 2 hours, LCMS indicating the disappearance of starting material. The reaction mixture was cooled to 0° C. and TES (80 mg), TFA (1.5 mL) and i-BuB(OH)$_2$ (30 mg) were added in sequence. The resulting yellow clear solution was stirred at rt for 2 hours before it was concentrated to dryness. The residue was dissolved in water/MeCN and purified by prep-HPLC (C18, acetonitrile and water as mobile phases, 0.1%

HCOOH). The obtained solid (10 mg) was dissolved in MeCN/water and adjusted to pH=9.5 with 1N NaOH. After lyophilization, Compound 5' as a sodium salt (11 mg) was obtained as a yellow solid. $^1$H NMR (D$_2$O, 300 MHz): δ6.86 (d, J=8.4 Hz, 1H), 6.26 (d, J=8.4 Hz, 1H), 3.55 (s, 3H), 2.37 (t, J=10.8 Hz, 1H), 1.05-0.92 (m, 1H). ESI-MS: [M−H$_2$O+H]$^+$: 253.

Example 6

Disodium Salt of (7R,10R)-6-hydroxy-3-methoxy-6a,7,10,10a-tetrahydro-6H-7,10-methanodibenzo[c,e][1,2]oxaborinine-4-carboxylic acid (Compound 6')

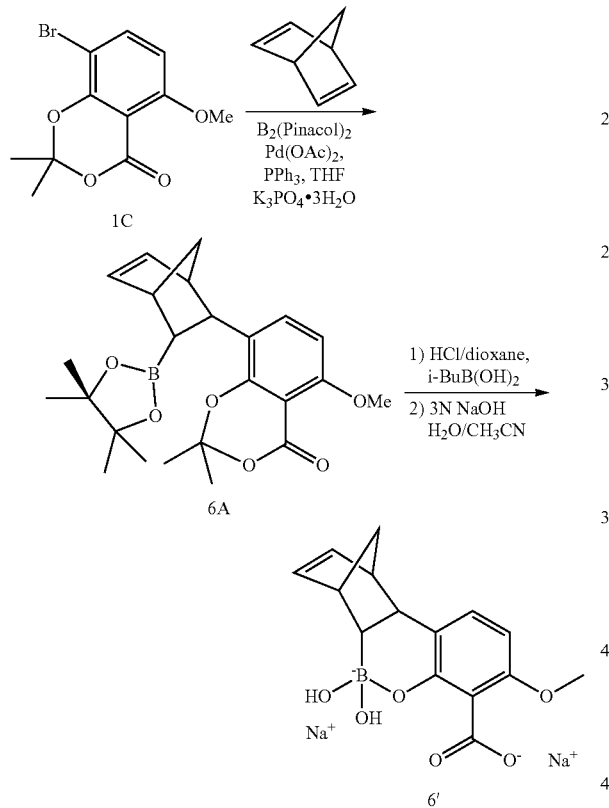

Step 1: Synthesis of Compound 6A

To a mixture of Pd(OAc)$_2$ (273 mg, 1.22 mmol, 0.1 eq) in THF (20 mL) was added PPh$_3$ (640 mg, 2.44 mmol, 0.2 eq) and K$_3$PO$_4$·3H$_2$O (8.1 g, 30.5 mmol, 2.5 eq) in a sealed tube. The reaction mixture was stirred at rt for 30 minutes under nitrogen atmosphere before compound 1C (3.5 g, 12.2 mmol, 1.0 eq), norbornadiene (2.25 g, 24.4 mmol, 2.0 eq) and bis(pinacolato)diboron (4.65 g, 18.3 mmol, 1.5 eq) were added. The mixture was then stirred at 100° C. for 16 hours before it was filtered and concentrated. The residue was purified by flash chromatography on silica (PE/EA=20:1-8:1) to give compound 6A (800 mg, 17%) as a white solid. ESI-MS: [M+H]$^+$: 427.

Step 2: Synthesis of Compound 6'

To a mixture of compound 6A (300 mg, 0.7 mmol, 1.0 eq) in dioxane (4 mL) and concentrated HCl (2 mL) was added i-BuB(OH)$_2$ (144 mg, 1.4 mmol, 2.0 eq). The mixture was stirred at rt for 1 hour before it was evaporated to dryness. The residue was dissolved in H$_2$O/CH$_3$CN (4 mL/4 mL) and was adjusted to pH=12 with 2N NaOH. The reaction was monitored by LCMS until all dimer was transferred to monomer. The mixture was purified by prep-HPLC (C18, acetonitrile and water as mobile phases, neutral condition) to give Compound 6' (13 mg, 6%) as a white solid. ESI-MS: [M+H]$^+$: 287. $^1$H NMR (400 MHz, CD$_3$OD): δ 6.95 (d, J=8.0 Hz, 1H), 6.37 (d, J=8.0 Hz, 1H), 3.82-3.74 (m, 2H), 3.67 (s, 3H), 2.62 (s, 1H), 2.20 (t, J=7.2 Hz, 2H), 1.47-1.43 (m, 1H), 1.36-1.24 (m, 1H), 0.91-0.89 (m, 1H).

Example 7

Disodium Salt of (7R,10S)-6-hydroxy-3-methoxy-6a,7,8,9,10,10a-hexahydro-6H-7,10-methanodibenzo[c,e][1,2]oxaborinine-4-carboxylic acid (Compound 7')

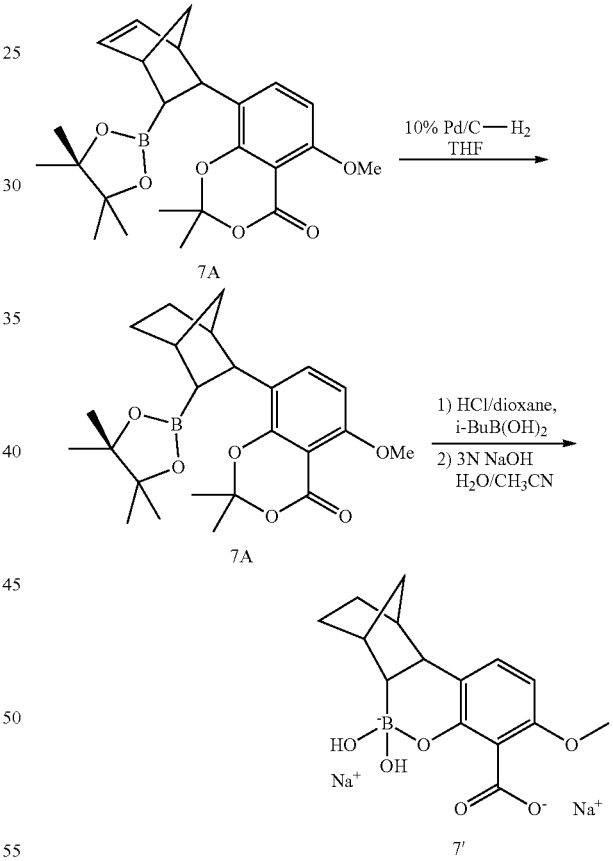

Step 1: Synthesis of Compound 7A

The mixture of compound 6A (300 mg, 0.7 mmol, 1.0 eq) and Pd/C (30 mg, 10% on carbon) in THF (10 mL) was stirred under hydrogen atmosphere (1 atm) at rt for 16 hours until LC-MS indicated the disappearance of starting material. The mixture was filtered and evaporated to dryness to give compound 7A (560 mg, 54%) as a white solid. ESI-MS: [M+H]$^+$: 429.

Step 2: Synthesis of Compound 7'

To a mixture of compound 7A (300 mg, 0.7 mmol, 1.0 eq) in dioxane (4 mL) and concentrated HCl (2 mL) was added i-BuB(OH)$_2$ (143 mg, 1.4 mmol, 2.0 eq). The mixture was stirred at rt for 1 hour before it was evaporated to dryness. The residue was dissolved in H$_2$O/CH$_3$CN (4 mL/4 mL) and was adjusted to pH=12 with 2N NaOH. The reaction was monitored by LCMS until all dimer was transferred to monomer. The mixture was purified by prep-HPLC (C18, acetonitrile and water as mobile phases, neutral condition) to give Compound 7' (32 mg, 15%) as a white solid. ESI-MS: [M+H]$^+$: 289. $^1$H NMR (400 MHz, CD$_3$OD): δ 6.80 (d, J=8.4 Hz, 1H), 6.27 (dd, J=2, 8.4 Hz, 1H), 3.71 (s, 3H), 2.71 (d, J=9.6 Hz, 1H), 2.12 (s, 1H), 1.95 (s, 1H), 1.41-1.38 (m, 2H), 1.34-1.31 (m, 1H), 1.30-1.26 (m, 2H), 0.76 (d, J=9.6 Hz, 1H), 0.68 (d, J=10.0 Hz, 1H).

Example 8

3-Fluoro-2-hydroxy-7-methoxy-1,2-benzoxaborinine-8-carboxylic acid (Compound 8)

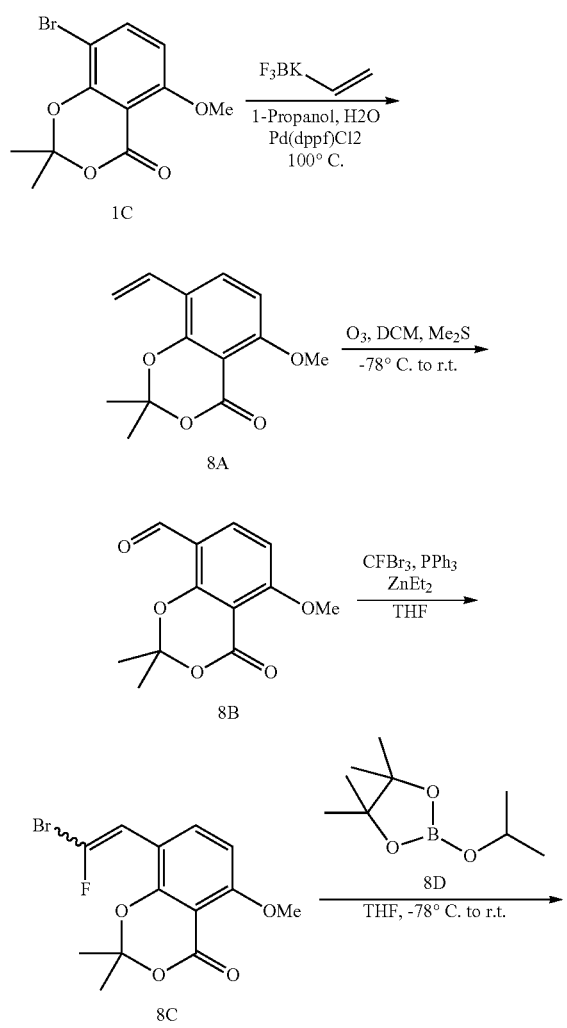

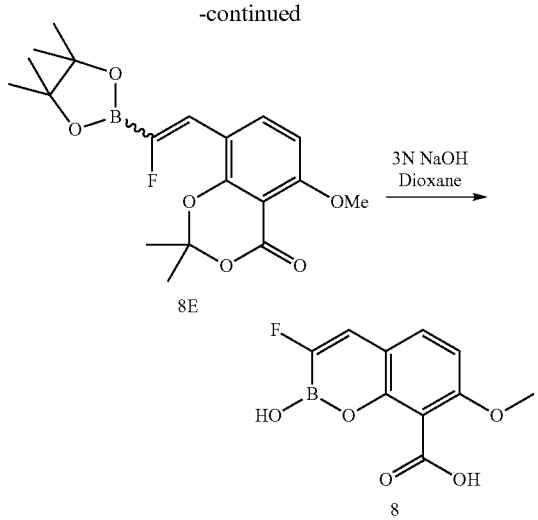

Step 1: Synthesis of 8A

A heterogeneous mixture of aryl bromide 1C (20 g, 70 mmol), vinyl trifluoroborate (11.2 g, 84 mmol, 1.2 eq) and Pd(dppf)Cl$_2$ (204 mg, 0.4 mol %) in 7/3 1-propano/water (100 mL) was degassed with argon at rt. Et$_3$N (14.6 mL, 104 mmol, 1.5 eq) was added and the reaction mixture was heated at 100° C. The orange heterogeneous reaction mixture turned light amber slightly turbid upon reaching 70° C. The orange/amber reaction mixture was cooled to 50° C. Water (60 mL) and. EA (60 mL) were added. The biphasic orange reaction mixture was cooled to rt and filtered over Celite 545 (2 g). The flask and pad were rinsed with ethyl acetate (2×10 mL). The filtrate was partitioned. The organic layer was washed with water (60 mL), then concentrated to dryness. The orange solid was taken up in 3/7 1-propanol/water (80 mL) and heated at 90° C. A biphasic solution was obtained. Propanol (6 mL) was added to get a homogeneous solution. Upon cooling, at 60° C., a biphasic mixture was obtained. Seeds were added and the mixture was allowed to cool to 50° C.; a heterogeneous mixture was obtained. After stirring for 1 h at 50° C. The slurry was allowed to cool to rt then stirred at 0° C. After stirring at 0° C. for 2 h, the solids were collected by filtration. The filtrate was recirculated to rinse the flask and the cake was rinsed with cold 7/3 propanol/water (2×20 mL), air dried then dried under high vacuum to give 8A as a grey solid (12.30 g, 75.4% yield).

Step 2: Synthesis of 8B

To a solution of compound 8A in DCM was bubbled with O3 at −78° C. until the solution turned to slightly blue. The nitrogen was bubbled in to remove the color. The colorless solution was added dimethylsulfide (3 mL) and slowly warmed up to rt in 6 hours. The solvent was removed under reduced pressure and the residue was purified by column chromatography to give compound 8B.

Step 3: Synthesis of Compound 8C

To the solution of triphenylphosphine (1.33 g, 5.06 mmol, 1.3 eq) in THF (50 mL) added fluorotribromomethane (1.37 g, 5.06 mmol, 1.3 eq) at rt. After 5 minutes, compound 8B (920 mg, 3.9 mmol, 1.0 eq) was added. To the resulting clear solution was slowly added diethylzinc solution (5.0 mL, 1.0 M in hexanes, 5 mmol, 1.3 eq) dropwise in 10 minutes. The reaction mixture was stirred at rt for 20 hours before it was quenched with methanol (10 mL). The resulting reaction mixture was diluted with EtOAc and washed with water. After dried over $Na_2SO_4$, the organic layer was concentrated and purified by column chromatography (hexanes/EtOAc=3/1 to 1/1) to give compound 8C (800 mg, 62%) as slightly yellow oil. $^1$H NMR (CDCl$_3$, 300 MHz): δ7.83 (t, 1H), 6.65-6.58 (m, 1H+1H from isomer 1), 6.15 (d, 1H from isomer 2), 3.95 (s, 3H).

Step 4: Synthesis of Compound 8E

To the solution of compound 8C (800 mg, 2.4 mmol, 1 eq) and compound 8D (0.59 mL, 2.9 mmol, 1.2 eq) in THF (20 mL) was added n-butyllithium solution (1.06 mL, 2.5 M in hexane, 2.7 mmol, 1.1 eq) dropwise over 5 minutes at −78° C. under nitrogen atmosphere. The resulting solution was slowly warmed up to rt in 3 hours before it was quenched with saturated aqueous ammonium chloride solution. The mixture was extracted with EtOAc (2×10 mL). The combined organic layer was dried over $Na_2SO_4$ and then concentrated to dryness. The residue was briefly purified by column chromatography (dichloromethane/EtOAc=5/1 to 1/1) to give a mixture of two isomers of compound 8E (520 mg, 57%) as yellow solid. ESI-MS: [M+H]$^+$: 379.

Step 5: Synthesis of Compound 8

The mixture of compound 8E (460 mg, 1.2 mmol, 1.0 eq) in dioxane (6.0 mL) and 3N NaOH (6.0 mL) was stirred at rt for 3 hours, LCMS indicating the disappearance of starting material. The mixture was adjusted to pH=3 with 1N HCl and was added MeCN to make a clear solution. The solution was purified by prep-HPLC (C18, acetonitrile and water as mobile phases, 0.1% HCOOH) to give Compound 8 free acid (28 mg) as off-white solid. $^1$H NMR (D$_2$O+CD$_3$CN, 300 MHz): δ7.70 (d, J=8.7 Hz, 1H), 7.57 (d, J=20.1 Hz, 1H), 7.17 (d, J=9.0 Hz, 1H), 4.10 (s, 3H). 19F NMR (D$_2$O+CD$_3$CN, 300 MHz): δ−135.47 (d). ESI-MS: [M−H$_2$O+H]$^+$: 221.

Example 9

2-Hydroxy-7-methoxy-1,2-benzoxaborinine-8-carboxylic acid (Compound 9)

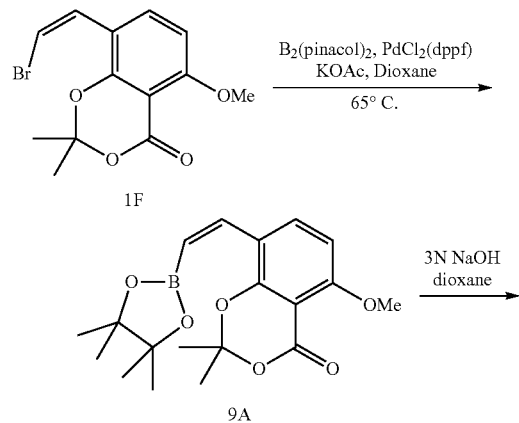

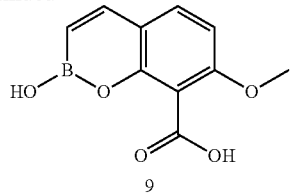

Step 1: Synthesis of Compound 9A

The mixture of compound 1F (62 mg, 0.2 mmol, 1.0 eq), bis(pinacoato)diboron (76 mg, 0.3 mmol, 1.5 eq), PdCl$_2$(dppf) (16 mg, 0.02 mmol, 0.1 eq) and KOAc (40 mg, 0.4 mmol, 2.0 eq) in dioxane (2 mL) was stirred at 65° C. for 2 hours under nitrogen atmosphere. The reaction mixture was diluted with EtOAc and washed with 0.1N HCl and water. After drying over $Na_2SO_4$, the organic layer was concentrated and purified by column chromatography (hexanes/EtOAc=3/1 to 1/1) to give compound 9A (29 mg, 40%) as a yellow solid. ESI-MS: [M+H]$^+$: 361.

Step 2: Synthesis of Compound 9

The mixture of compound 9A (29 mg, 0.08 mmol, 1.0 eq) in dioxane (0.5 mL) and 3N NaOH (0.5 mL) was stirred at rt for 2 hours, LCMS indicating the disappearance of starting material. The reaction mixture was adjusted to pH=3 and was dissolved in water/MeCN. The solution was purified by prep-HPLC (C18, acetonitrile and water as mobile phases, 0.1% HCOOH) to give Compound 9 free acid (3.6 mg) as a light yellow solid. $^1$H NMR (CD$_3$OD, 300 MHz): δ7.74 (d, J=11.7 Hz, 1H), 7.47 (d, J=9.0 Hz, 1H), 6.92 (d, J=8.4 Hz, 1H), 6.02 (d, J=11.7 Hz, 1H), 3.90 (s, 3H). ESI-MS: [M−H$_2$O+H]$^+$: 203.

Example 10

2-Hydroxy-1a,7b-dihydro-1H-cyclopropa[c][1,2]benzoxaborinine-4-carboxylic acid (Compound 10)

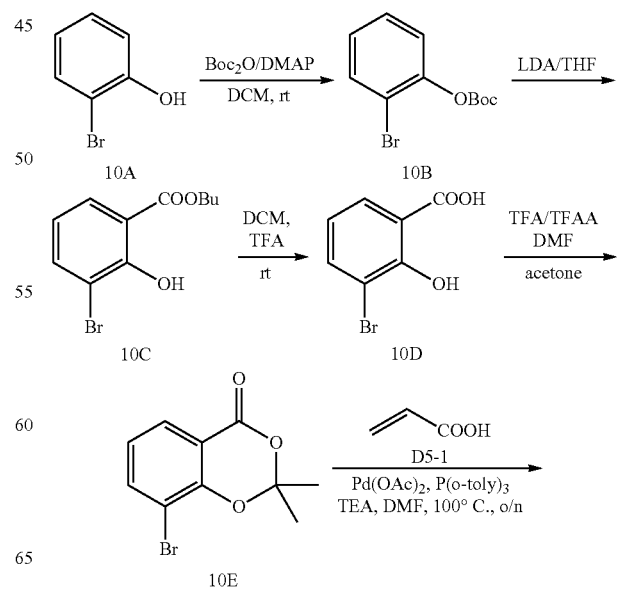

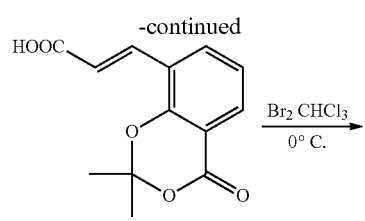

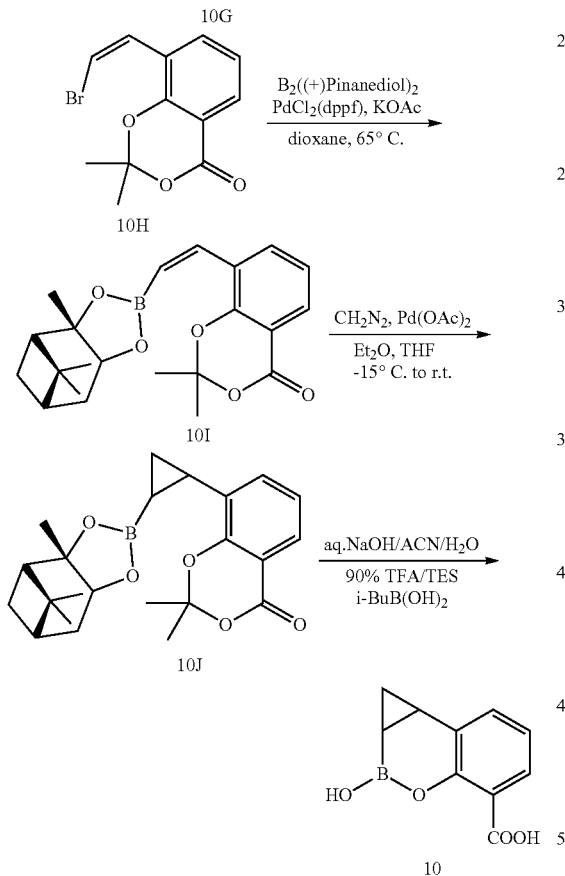

1.2 eq) dropwise at −78° C. The resulting solution was slowly warmed up to rt and stirred for 16 hours. The reaction was monitored by TLC. The mixture was concentrated under reduced pressure and the residue was purified by flash chromatography on silica (PE/EA=50:1 to 20:1) to give compound 10C (21.8 g, 64%) as light yellow oil.

Step 3: Synthesis of 10D

To the solution of compound 10C (21.8 g, 79.8 mmol, 1.0 eq) in DCM (110 mL) was added TFA (110 mL) at rt. After 16 hours at this temperature, the mixture was concentrated under reduced pressure and the residue was purified by flash chromatography on silica (PE/EA=50:1 to 10:1) to give compound 10D (13.9 g, 80%) as a white solid.

Step 4: Synthesis of 10E

To the solution of compound 10D (14.7 g, 68 mmol, 1.0 eq) in TFA (95 mL) was added DMF (65 mL) at 0° C., followed by slow addition of acetone (50.6 mL) and TFAA (65 mL) at the same time. After 16 hours at 100° C. under nitrogen atmosphere, the mixture was concentrated under reduced pressure and the residue was purified by flash chromatography on silica (PE/EA=50:1 to 10:1) to give compound 10E (7.7 g, 44%) as a yellow solid.

Step 5: Synthesis of 10F

The mixture of compound 10E (7.54 g, 29.7 mmol, 1.0 eq), accrylic acid (3.18 g, 44.2 mmol, 1.5 eq), Pd(OAc)$_2$ (662 mg, 2.95 mmol, 0.1 eq), P(o-toly)$_3$ (1.81 g, 5.9 mmol, 0.2 eq) and TEA (8.9 g, 88.4 mmol, 3.0 eq) in DMF (150 mL) was flushed with N$_2$ (3×) and then stirred at 100° C. for 16 hours. The mixture was concentrated under reduced pressure and the resuling solid was washed with 20% EA in hexanes to give crude compound 10F (4.4 g, 60%) as a brown solid which was directly used in the next step without further purification.

Step 6: Synthesis of 10G

To the mixture of compound 10F (4.4 g, 17.7 mmol, 1.0 eq) in CHCl$_3$ (200 mL) was added Br$_2$ (3.4 g, 21.3 mmol, 1.2 eq) over 10 min at 0° C. and stirred at this temperature for 2 hour before it was concentrated to dryness. The resulting crude compound 10G (7.2 g, 99%) was a brown solid which was directly used into the next step.

Step 7: Synthesis of 10H

To the solution of compound 10G (7.2 g, 17.7 mmol, 1.0 eq) in DMF (100 mL) was added TEA (3.59 g, 35.5 mmol, 2.0 eq) dropwise at 0° C. and stirred at rt for 16 hours before it was evaporated to dryness. The residue was purified by flash chromatography on silica (PE/EA=100:1 to 5:1) to give compound 10H (3.0 g, 60%) as a light yellow solid.

Step 8: Synthesis of 10I

The mixture of compound 10H (800 mg, 2.8 mmol, 1.0 eq), bis[(+)-pinanediolato]diboron (1.5 g, 4.3 mmol, 1.5 eq), PdCl$_2$(dppf) (230 mg, 0.28 mmol, 0.1 eq) and KOAc (560 mg, 5.67 mmol, 2.0 eq) in dioxane (15 mL) was flushed with N$_2$ (3×) and heated at 65° C. for 3 hours. The reaction was monitored by LCMS. The reaction mixture was filtered and evaporated to dryness. The residue was purified by flash Step 1: Synthesis of 10B A mixture of compound 10A (20 g, 116 mmol, 1.0 eq) and DMAP (4.2 g, 34 mmol, 0.3 eq) in DCM (200 mL) was added Boc$_2$O (37.8 g, 173 mmol, 1.5 eq) and stirred at rt for 1 hour. The reaction was monitored by TLC. The mixture was concentrated under reduced pressure and the residue was purified by flash chromatography on silica (PE/EA=50:1 to 20:1) to give compound 10B (31 g, 98%) as light yellow oil.

Step 2: Synthesis of 10C

To the solution of compound 10B (34 g, 125 mmol, 1.0 eq) in THF (350 mL) was added LDA (75 mL, 150 mmol, chromatography on silica (PE/EA=100:1 to 5:1) to give compound 10I (240 mg, 22%) as light yellow oil. ESI-MS: [M+H]$^+$: 383.

Step 9: Synthesis of 10J

To the mixture of compound 10I (200 mg, 0.52 mmol, 1.0 eq) and Pd(OAc)$_2$ (5.9 mg, 0.026 mmol, 0.05 eq) in THF (5 mL) was added CH$_2$N$_2$ (freshly made, in 15 mL Et$_2$O, about 6 mmol) slowly over 1 hour at −15° C. The mixture was slowly warmed up to rt and stirred for 16 hours. The mixture was filtered and evaporated to dryness to give compound 10J (200 mg, 96%) as light yellow oil. ESI-MS: [M+H]$^+$: 397.

Step 10: Synthesis of 10

To the solution of compound 10J (200 mg, 0.5 mmol, 1.0 eq) in ACN (5 mL) and water (1 mL) was added 3N NaOH (1.5 mL) at rt. After 3 hours at 30° C., the resulting mixture was added TES (2 mL), TFA (6 mL) and i-BuB(OH)$_2$ (77 mg, 0.76 mmol, 1.5 eq) and stirred at rt for one hour. The reaction was monitored by LC-MS. The mixture was concentrated in vacuo and purified by prep-HPLC (C18) to give 10 (20 mg, 19%) as white solid. $^1$H NMR (400 MHz, CD$_3$OD): δ 7.62 (dd, J=1.2, 1.6 Hz, 1H), 7.38 (d, J=8.0 Hz, 1H), 6.89 (t, J=8.0 Hz, 1H), 2.33-2.27 (m, 1H), 1.23-1.17 (m, 1H), 0.68-0.54 (m, 2H). ESI-MS: [M+MeCN+H]$^+$: 246.

Example 11

Disodium salt of 2-hydroxy-7-methoxy-spiro[3H-1,2-benzoxaborinine-4,1'-cyclopropane]-8-carboxylic acid (Compound 11')

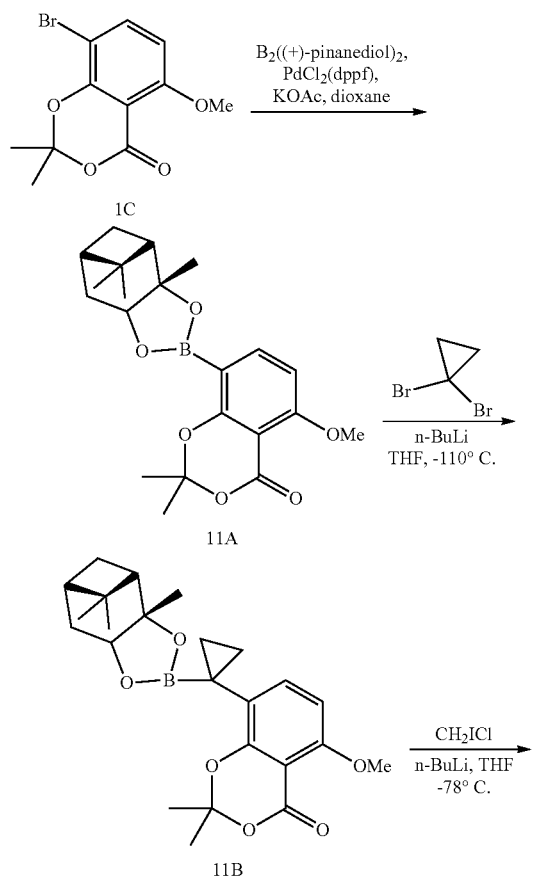

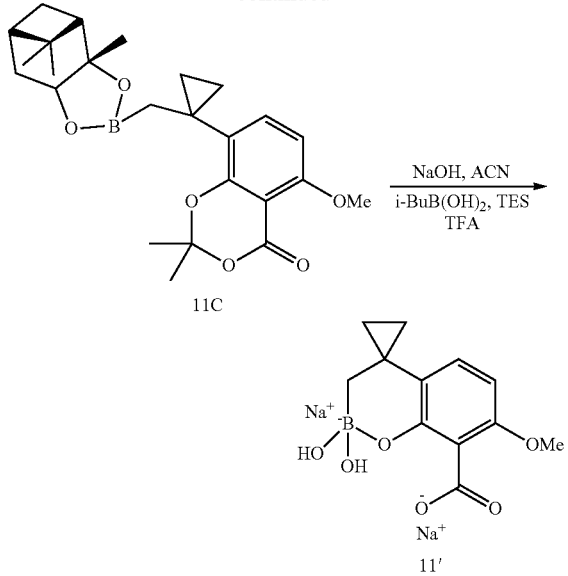

Step 1: Synthesis of 11A

A mixture of compound 1C (10.0 g, 34.8 mmol, 1.0 eq), bis[(+)-pinanediolato]diboron (18.7 g, 52.2 mmol, 1.5 eq), PdCl$_2$(dppf) (1.42 g, 1.74 mmol, 0.05 eq) and KOAc (10.2 g, 105 mmol, 3.0 eq) in dioxane (80 mL) was stirred at 85° C. for 16 h under nitrogen atmosphere. The reaction was monitored by TLC. The mixture was cooled down, filtered and concentrated under reduced pressure. The residue was purified by flash chromatography on silica (PE/EA=100:0 to 5:1) to give compound 11A (8.07 g, 60%) as a slightly yellow solid. ESI-MS: [M+H]$^+$: 387.

Step 2: Synthesis of 11B

To the solution of compound 1,1-dibromocyclopropane (4.4 g, 22.1 mmol, 2.1 eq) in THF (15 mL) was added n-BuLi (6.2 mL, 15.5 mmol, 1.5 eq) slowly over 30 min at −110° C. and stirred for one hour at this temperature. Then compound 11A (4 g, 10.36 mmol, 1.0 eq) in THF (25 mL) was added to the reaction mixture over 20 min. After 2 hours at −110° C., the reaction mixture was slowly warmed up to rt and stirred for 16 hours. The mixture was quenched with saturated aqueous NH$_4$Cl (4 mL) and was extracted with EA (3×20 mL). The combined organic layer was dried over Na$_2$SO$_4$ before it was concentrated under reduced pressure. The residue was purified by flash chromatography on silica (PE/EA=100:0 to 10:1) to give compound 11B (2.0 g, 45%) as a slightly yellow solid. ESI-MS: [M+H]$^+$: 427.

Step 3: Synthesis of 11C

To the solution of compound 11B (1 g, 2.3 mmol, 1.0 eq) and CH$_2$ICl (2.07 g, 11.8 mmol, 5.1 eq) in THF (50 mL) was added n-BuLi (1.8 mL, 4.6 mmol, 2.0 eq) at −78° C. After 2 hours at −78° C., the reaction mixture was slowly warmed up to rt and stirred for 16 hours. The mixture was quenched with saturated aqueous NH$_4$Cl (4 mL) and was extracted with EA (3×20 mL). The combined organic layer was dried over Na$_2$SO$_4$ before it was concentrated under reduced pressure. The residue was purified by flash chromatography on silica (PE/EA=100:0 to 10:1) to give compound 11C (380 mg, 37%) as a white solid. ESI-MS: [M+H]+: 441.

Step 4: Synthesis of Compound 11'

To the solution of compound 11C (190 mg, 0.432 mmol, 1.0 eq) in ACN (3 mL) was added 3N NaOH (3 mL) at rt. After two hours, the resulting mixture was added TES (2 mL), TFA (5 mL) and i-BuB(OH)$_2$ (88 mg, 0.86 mmol, 2.0 eq) and stirred at rt for 30 minutes. The reaction was monitored by LC-MS. The mixture was concentrated in vacuo, re-dissolved in MeCN/water and was adjusted to pH=12 with 3N NaOH. The resulting solution was purified by prep-HPLC (C18, neutral) to give disodium salt Compound 11' (40 mg, 37%) as a white solid. $^1$H NMR (400 MHz, CD$_3$OD): δ 6.45 (d, J=8.8 Hz, 1H), 6.19 (d, J=8.4 Hz, 1H), 3.69 (s, 3H), 0.68 (t, 2H), 0.56 (t, 2H), 0.45 (s, 2H). ESI-MS: [M+H]+: 249.

Example 12

Disodium salt of (1 aS,7bR)-5-fluoro-2-hydroxy-1a, 7b-dihydro-1H-cyclopropa[c][1,2] benzoxaborinine-4-carboxylic acid (Compound 12')

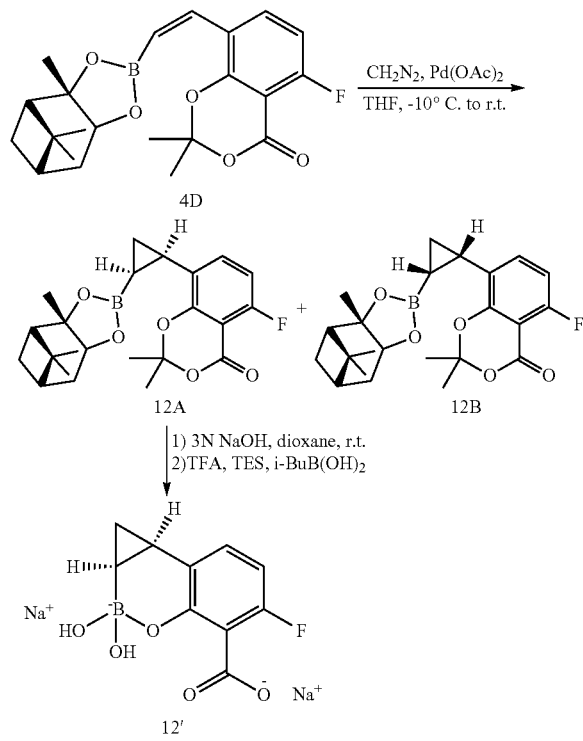

Step 1: Synthesis of 12A and 12B

To a solution of compound 4D (2.0 g, 5.0 mmol, 1.0 eq) and Pd(OAc)$_2$ (56 mg, 0.25 mmol, 0.05 eq) in THF (30 mL) was slowly added diazomethane (200 mL, freshly made, about 0.2 M in ether, 10 eq) at −20° C. in 2 hours. The solution was slowly warmed up to rt and stirred for 12 hours before it was concentrated to dryness. The obtained residue was purified by column chromatography (hexanes/EtOAc=3/1 to 1/1) to give a mixture of compound 12A and 12B (1.96 g, 99%) as yellow oil. The two isomers were further purified by prep-HPLC (C18, acetonitrile and water as mobile phases, 0.1% HCOOH) to give 12A (650 mg, 31%) and 12B (750 mg, 36%) as white solid.

$^1$H NMR (CDCl$_3$, 400 MHz) for 12A: δ 7.37-7.33 (m, 1H), 6.73 (t, J=9.2 Hz, 1H), 4.02 (dd, J=1.6, 1.6 Hz, 1H), 2.27-2.24 (m, 1H), 2.15-2.08 (m, 1H), 2.05-2.00 (m, 1H), 1.87 (t, J=5.2 Hz, 1H), 1.76 (s, 3H), 1.74 (s, 3H), 1.29-1.21 (m, 2H), 1.19 (s, 3H), 1.17-1.13 (m, 1H), 1.07 (s, 3H), 0.69 (s, 3H), 0.56-0.53 (m, 1H), 0.52-0.49 (m, 1H). ESI-MS: [M+H]+: 415.

$^1$H NMR (CDCl$_3$, 400 MHz) for 12B: δ 7.32-7.25 (m, 1H), 6.72 (t, J=9.2 Hz, 1H), 4.00 (dd, J=1.6, 1.6 Hz, 1H), 2.28-2.24 (m, 1H), 2.17-2.14 (m, 1H), 1.86-1.81 (m, 2H), 1.75 (s, 8H), 1.62 (d, J=1.2 Hz, 1H), 1.21-1.19 (m, 1H), 1.18 (s, 3H), 1.17 (s, 3H), 1.16-1.13 (m, 1H), 0.72 (s, 3H), 0.53-0.47 (m, 2H). ESI-MS: [M+H]+: 415.

Step 2: Synthesis of 12'

The mixture of compound 12A (650 mg, 1.6 mmol, 1.0 eq) in dioxane (4 mL) and 3N NaOH (1.05 mL, 2 eq) was stirred at rt for 0.5 hour, LC-MS indicating the disappearance of starting material. The reaction mixture was cooled to 0° C. and TES (1 mL), TFA (5 mL) and i-BuB(OH)$_2$ (320 mg, 3.14 mmol, 2 eq) were added in sequence. The resulting yellow clear solution was stirred at rt for 0.5 hours before it was concentrated to dryness. The residue was dissolved in water/MeCN and purified by prep-HPLC (C18, acetonitrile and water as mobile phases, 0.1% TFA) to give Compound 12 free acid (132 mg) as a white solid after lyophilizatio. It was dissolved in MeCN/water and adjusted to pH=9.5 with 1 N NaOH (1.02 mL). After lyophilization, the crude sodium salt was dissolved in 2.0 mL water and was slowly added acetone (50 mL). The resulting suspension was stirred at rt for 3 hours. The mixture was filtered and the solid was washed with acetone twice to give disodium salt Compound 12' (146 mg) as an off-white solid. $^1$H NMR (D$_2$O, 300 MHz): δ6.87 (t, J=7.2 Hz, 1H), 6.25 (d, J=8.4 Hz, 1H), 1.65-1.56 (m, 1H), 0.67-0.57 (m, 1H), 0.14 (m, 2H). $^{19}$F NMR(D$_2$O, 300 MHz): δ−124.9. ESI-MS: [M−H$_2$O+H]+: 205.

Example 13

Disodium salt of (1 aR,7bS)-5-fluoro-2-hydroxy-1a, 7b-dihydro-1H-cyclopropa[c][,21] benzoxaborinine-4-carboxylic acid (Compound 13')

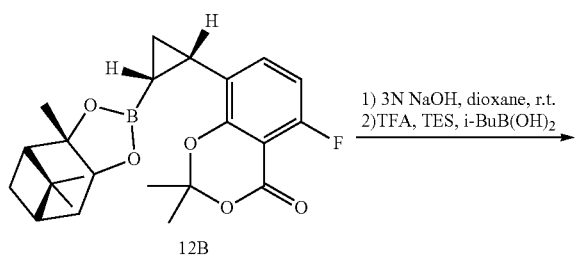

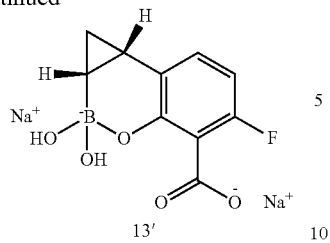

13'

The mixture of compound 12B (750 mg, 1.8 mmol, 1.0 eq) in dioxane (4 mL) and 3 N NaOH (1.2 mL, 2 eq) was stirred at rt for 0.5 hour, LCMS indicated the disappearance of starting material. The reaction mixture was cooled to 0° C., TES (1 mL), TFA (5 mL) and i-BuB(OH)$_2$ (369 mg, 3.6 mmol, 2 eq) were added in sequence. The resulting yellow clear solution was stirred at rt for 0.5 hour before it was concentrated to dryness. The residue was dissolved in water/MeCN and purified by prep-HPLC (C18, acetonitrile and water as mobile phases, 0.1% TFA) to give Compound 13 free acid (160 mg) as a white solid after lyophilization. It was dissolved in MeCN/water and adjusted to pH=9.5 with 1 N NaOH (1.38 mL). After lyophilization, the crude sodium salt was dissolved in 2.0 mL water and was slowly added acetone (50 mL). The resulting suspension was stirred at rt for 3 hours. The mixture was filtered and the solid was washed with acetone twice to give the disodium salt Compound 13' (145 mg) as an off-white solid. $^1$H NMR (D$_2$O, 300 MHz): δ6.87 (t, J=7.2 Hz, 1H), 6.25 (d, J=8.4 Hz, 1H), 1.65-1.56 (m, 1H), 0.67-0.57 (m, 1H), 0.14 (m, 2H). $^{19}$F NMR (D$_2$O, 300 MHz): δ-124.9. ESI-MS: [M−H$_2$O+H]$^+$: 205.

Alternatively, Compound 13' can be synthesized utilizing enantioselective cyclopropanation method as shown in the following scheme:

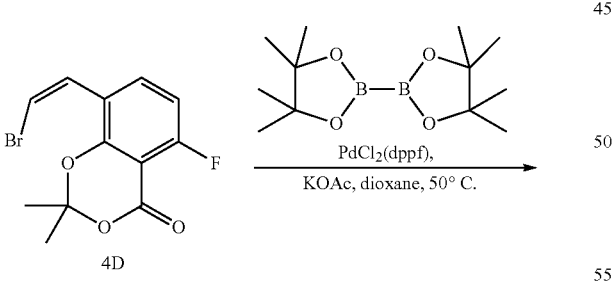

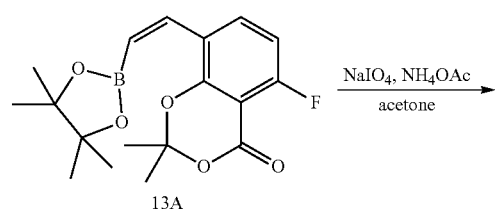

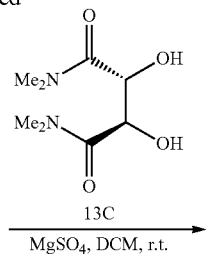

Step 1: Synthesis of 13A

Intermediate 13A was prepared from 4D using method described in step 1 of Example 9.

Step 2: Synthesis of 13B

To the solution of compound 13A (23.5 g, 67.5 mmol, 1.0 eq) in acetone (675 mL) and water (41 mL) was added ammonium acetate aqueous solution (304 mL, 1M in water, 4.5 eq), followed by sodium periodate (43.4 g, 203 mmol, 3.0 eq) at 0° C. The resulting reaction mixture was heated up to 40° C. and stirred at this temperature until NMR and LCMS showed to disappearance of 13A (normally takes 24 hours). The reaction mixture was filtered with celite and washed with acetone. The filtrate was concentrated to about 250 mL and was extracted with dichloromethane (300 mL) and ethyl acetate (300 mL). The combined organic layers were dried over Na$_2$SO$_4$ before it was concentrated under reduced pressure. The crude compound 13B (12.0 g) was obtained as yellow solid, which was used directly for next step without purification. ESI-MS: [M+H]$^+$: 267.

Step 3: Synthesis of 13D

To a solution of crude compound 13B (12.0 g, ~45 mmol, 1.0 eq) in dichloromethane (150 mL) was added 13C (11.0 g, 54 mmol, 1.2 eq) and MgSO$_4$ (12 g). The mixture was stirred at rt for 12 hours before it was filtered under nitrogen atmosphere. The filtrate was added more 13C (4.6 g, 23 mmol, 0.5 eq). The resulting solution of 13D was used directly for next step without further purification. ESI-MS: [M-S4+H]$^+$: 267.

Step 4: Synthesis of 13E

The solution of diethylzinc (360 mL, 1.0 M solution in hexanes, 8.0 eq) was added into dichloromethane (600 mL) at −78° C., followed by diiodomethane (44 mL, 12 eq) dropwise. The resulting white mixture was stirred at −78° C. for 30 minutes before the solution of 13D (~45 mmol, dichloromethane solution from previous step, pre-cooled to −78° C.) was added via cannula under nitrogen atmosphere. The resulting reaction mixture was stirred at −78° C. for 3 hours and slowly warmed up to rt over a period of 4 hours. The reaction was quenched with saturated aqueous ammonium chloride (~1 L) and extracted with dichloromethane (500 mL) and ethyl acetate (500 mL). After dried over Na$_2$SO$_4$, the organic layer was concentrated to give crude compound 13E as yellow solid, which was used directly for next step without purification. ESI-MS: [M-S4+H]$^+$: 281.

Step 5: Synthesis of 12B

To a solution of crude compound 13E (~45 mmol, 1.0 eq) in THF (~150 mL) was added (+)-pinanediol (23.0 g, 135 mmol, 3.0 eq) and MgSO$_4$ (20 g). The resulting reaction mixture was stirred at rt for 12 hours before it was filtered and concentrated to dryness. The obtained residue was purified by column chromatography (hexanes/EtOAc=5/1 to 3/1) to give compound 12B (12.1 g, ~90% purity and ~93% de) as yellow solid. The product was further purified by re-crystallization in 10% ethyl acetate in hexanes to give 6.8 g pure 12B (>99% purity and >99% de). $^1$H NMR (CDCl$_3$, 400 MHz) for 12B: δ 7.32-7.25 (m, 1H), 6.72 (t, J=9.2 Hz, 1H), 4.00 (dd, J=1.6, 1.6 Hz, 1H), 2.28-2.24 (m, 1H), 2.17-2.14 (m, 1H), 1.86-1.81 (m, 2H), 1.75 (s, 8H), 1.62 (d, J=1.2 Hz, 1H), 1.21-1.19 (m, 1H), 1.18 (s, 3H), 1.17 (s, 3H), 1.16-1.13 (m, 1H), 0.72 (s, 3H), 0.53-0.47 (m, 2H).

Step 6: Synthesis of Compound 13'

The mixture of compound 12B (830 mg, 2 mmol, 1.0 eq) in dioxane (8 mL) and 3N NaOH (4 mL, 6 eq) was stirred at rt for 3 hours, LC-MS indicating the disappearance of starting material. The reaction mixture was adjusted to pH=2 with 6 N HCl and i-BuB(OH)$_2$ (815 mg, 8 mmol, 4 eq) were added in sequence. The resulting mixture was stirred at rt for 3 hours and then was directly purified by prep-HPLC (C18, acetonitrile and water as mobile phases, 0.1% HCOOH) to give compound 13 free acid (310 mg) as white solid after lyophilization. It was dissolved in MeCN/water and adjusted to pH=9.5 with 1 N NaOH. After lyophilization, the crude sodium salt was dissolved in 0.5 mL water and acetone (25 mL) was slowly added. The resulting suspension was stirred at rt for 3 hours. The mixture was filtered and the solid was washed with acetone twice to give 13' (146 mg) as an off-white solid. $^1$H NMR (D$_2$O, 300 MHz): δ6.87 (t, J=7.2 Hz, 1H), 6.25 (d, J=8.4 Hz, 1H), 1.65-1.56 (m, 1H), 0.67-0.57 (m, 1H), 0.14 (m, 2H). $^{19}$F NMR (D$_2$O, 300 MHz): δ-124.9. ESI-MS: [M−H2O+H]$^+$: 205.

Example 14

Disodium salt of 4,4-dihydroxyspiro[5-oxa-4-boranuidabicyclo[4.4.0]deca-1 (6),7,9-triene-2,1'-cyclopropane]-7-carboxylic acid (Compound 14')

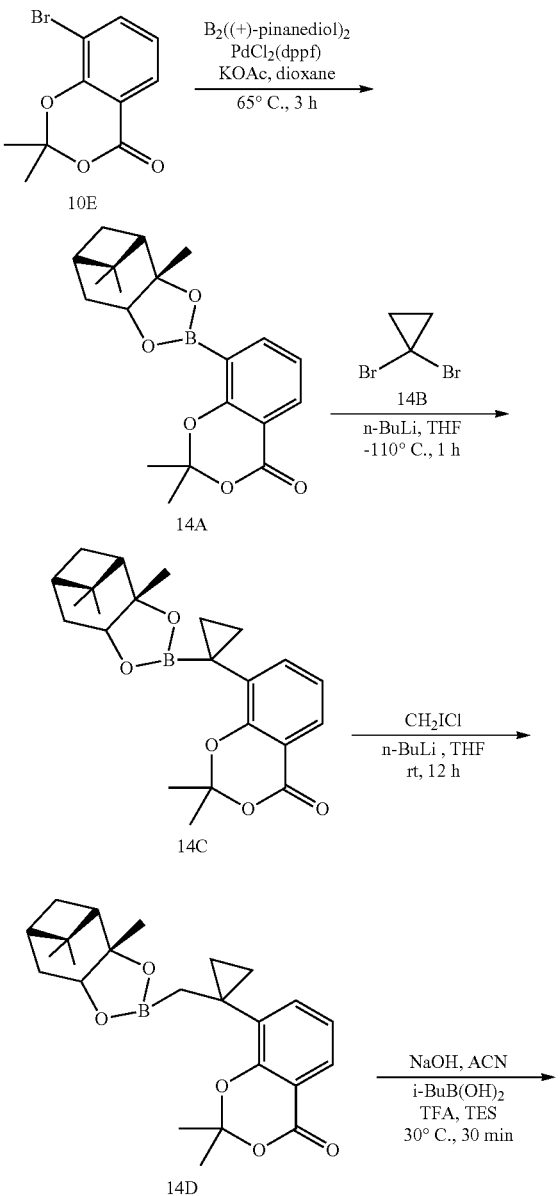

103

-continued

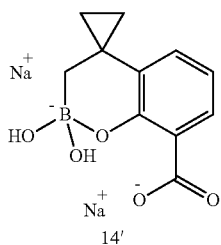

14'

Step 1: Synthesis of 14A

To a solution of compound 10E (10 g, 35.46 mmol, 1.0 eq), bis[(+)-pinanediolato]diboron (15.2 g, 42.55 mmol, 1.2 eq) and PdCl₂(dppf) (2.9 g, 3.546 mmol, 0.1 eq) in dioxane (250 mL) was added KOAc (7.0 g, 71 mmol, 2.0 eq). The mixture was stirred at 65° C. for 3 h under nitrogen atmosphere. Then the mixture was filtered and the filtrate was concentrated in vacuum. The residue was purified by column chromatography on silica gel (PE/EA, 100:1~10:1) to give compound 14A (2.9 g, 21%).

Step 2: Synthesis of 14C

A solution of compound 14B (2.8 g, 14.04 mmol, 2.0 eq) in THF (25 mL) was cooled to −110° C., then n-BuLi (4.2 mL, 10.53 mmol, 1.5 eq) was added in slowly and stirred at −110° C. for 30 min. Then a solution of compound 14A (2.5 g, 7.02 mmol, 1.0 eq) in THF (25 mL) was added in. The mixture was stirred at rt for 30 min under nitrogen atmosphere. After the reaction was complete, the mixture was poured into aq. NH₄Cl, and extracted with ethyl acetate. The organic layer was washed with brine, dried over Na₂SO₄, concentrated, and purified by column chromatography on silica gel (PE/EA, 5:1~10:1) to give compound 14C (880 mg, 35%).

Step 3: Synthesis of 14D

To a solution of compound 14C (880 mg, 2.22 mmol, 1.0 eq) in THF (15 mL) were added CH₂ICl (2.0 g, 11.11 mmol, 5.0 eq), cooled to −78° C. To the solution n-BuLi (2.7 mL, 6.66 mmol, 3.0 eq) was added in slowly and stirred at −78° C. for 30 min. The mixture was stirred at rt for 12 h under nitrogen atmosphere. After the reaction was complete, the mixture was poured into aq. NH₄Cl, extracted with DCM. The organic layer was washed with brine, dried over Na₂SO₄, concentrated, purified by column chromatography on silica gel (PE/EA, 5:1~10:1) to give compound 14D (110 mg, 25%).

Step 4: Synthesis of Compound 14'

To a mixture of compound 14D (100 mg, 0.24 mmol, 1.0 eq) in H₂O/CH₃CN (0.5 mL/3 mL) was added 2 N NaOH (0.24 mL, 0.48 mmol, 2.0 eq). The solution was stirred at rt for 1 h. To the mixture was added TFA/TES (4 mL/1 mL) and i-BuB(OH)₂ (48.9 mg, 0.48 mmol, 2.0 eq). The mixture was stirred at 30° C. for 30 min. Adjusting the solution with 1 N NaOH to pH-10. The residue was purified by prep-HPLC to give compound 14' (4 mg, 15%). LC-MS: 260[M+ACN+H]⁺. ¹H NMR (400 MHz, CD₃OD) δ 7.63 (d, J=7.6 Hz, 1H), 6.85 (d, J=7.6 Hz, 1H), 6.41-6.24 (m, 1H), 0.85-0.76 (m, 2H), 0.69-0.64 (m, 2H), 0.56-0.51 (m, 2H).

104

Example 15

Disodium salt of 8-fluoro-4,4-dihydroxy-spiro[5-oxa-4-boranuidabicyclo[4.4.0]deca-1 (6),7,9-triene-2,1'-cyclopropane]-7-carboxylic acid (Compound 15')

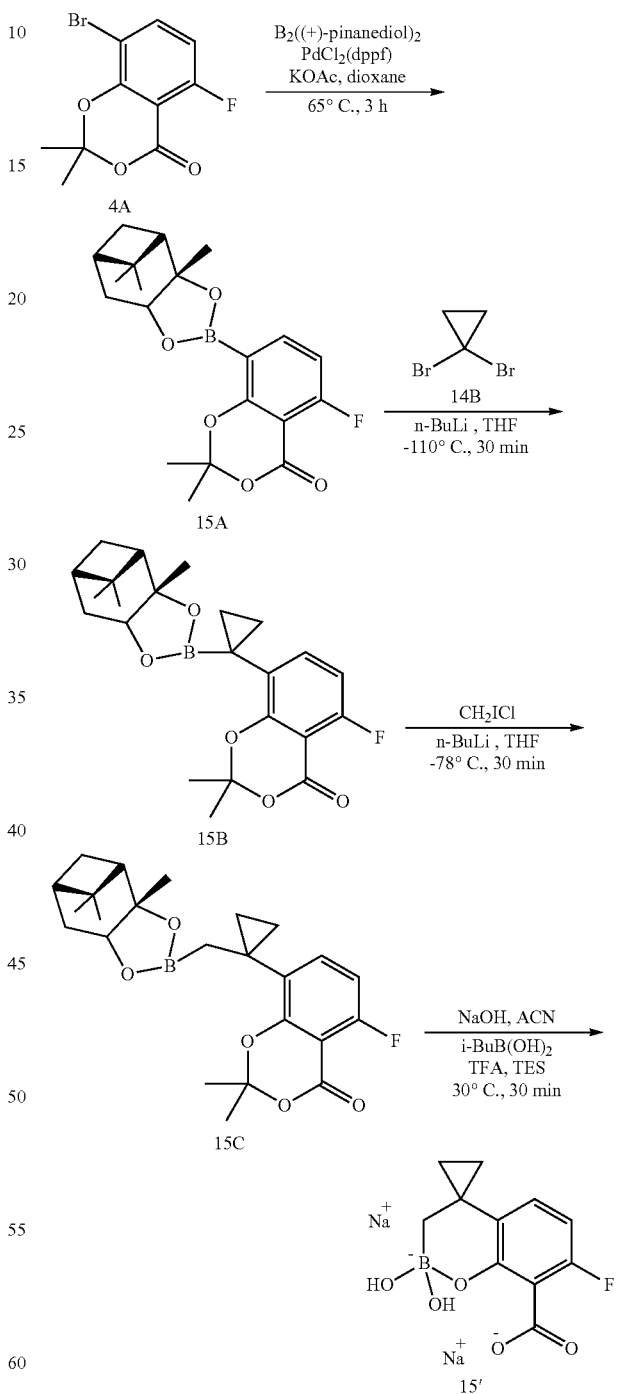

Step 1: Synthesis of Compound 15A

A mixture of compound 4A (7.0 g, 25.44 mmol, 1.0 eq), bis[(+)-pinanediolato]diboron (10.9 g, 30.52 mmol, 1.2 eq)

105 and PdCl$_2$(dppf) (2.08 g, 2.544 mmol, 0.1 eq) and KOAc (5.0 g, 50.88 mmol, 2.0 eq) in dioxane (200 mL) stirred at 65° C. for 3 h under nitrogen atmosphere. The mixture was filtered and the filtrate was concentrated in vacuum. The residue was purified by column chromatography on silica gel (PE/EA, 100:1~10:1) to give compound 15A (3.0 g, 31%).

Step 2: Synthesis of Compound 15B

To a solution of compound 15A (3.19 g, 16.02 mmol, 2.0 eq) in THF (25 mL) at −110° C. was added n-BuLi (2.5 M, 4.8 mL, 12.01 mmol, 1.5 eq) was added in slowly and stirred at −110° C. for 30 min. Then a solution of compound 14B (3.0 g, 8.01 mmol, 1.0 eq) in THF (25 mL) was added in. The mixture was stirred at rt for 30 min under nitrogen atmosphere. After the reaction was complete, the mixture was poured into aq. NH$_4$Cl, and extracted with ethyl acetate. The organic layer was washed with brine, dried over Na$_2$SO$_4$, concentrated to give compound 15B (1.0 g, 30%).

Step 3: Synthesis of Compound 15C

To a solution of compound 15B (800 mg, 1.93 mmol, 1.0 eq) and CH$_2$ICl (1.73 g, 9.65 mmol, 5.0 eq) in THF (15 mL) at −78° C. was added n-BuLi (2.3 mL, 5.79 mmol, 3.0 eq) slowly, and stirred at −78° C. for 30 min. The mixture was stirred under nitrogen atmosphere at rt for 12 h. The mixture was poured into aq. NH$_4$Cl, and extracted with DCM. The organic layer was washed with brine, dried over Na$_2$SO$_4$, concentrated to give compound 15C (100 mg, 12%).

Step 4: Synthesis of Compound 15'

To a mixture of compound 15C (100 mg, 0.23 mmol, 1.0 eq) in H$_2$O/CH$_3$CN (0.5 mL/3 mL) was added 2 N NaOH (0.23 mL, 0.46 mmol, 2.0 eq) and stirred at rt for 1 h. Then the mixture was added TFA/TES (4 mL/1 mL) and i-BuB(OH)$_2$ (46.8 mg, 0.46 mmol, 2.0 eq). The mixture was stirred at 30° C. for 30 min. T the mixture was added 1 N NaOH to adjust the mixture to pH~10, and concentrated. The residue was purified by prep-HPLC to give compound 15' (6 mg, 11%). LC-MS: 278 [M+ACN+H]$^+$. $^1$H NMR (400 MHz, CD$_3$OD) δ 6.75 (d, J=2.4 Hz, 1H), 6.41 (d, J=1.6 Hz, 1H), 0.75-0.79 (m, 2H), 0.64-0.69 (m, 2H), 0.61-0.55 (m, 2H).

Example 16

Disodium salt of (1aR,7bS)-2,2-dihydroxy-1a,7b-dihydro-1H-cyclopropa[c][1,2]benzoxaborinine-4-carboxylic acid (Compound 16')

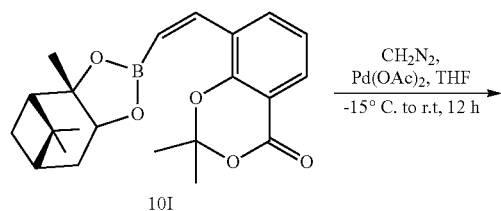

106

-continued

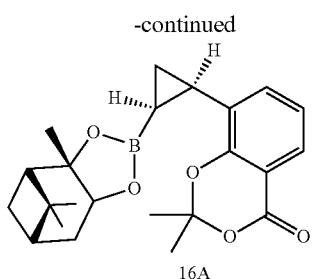

16A

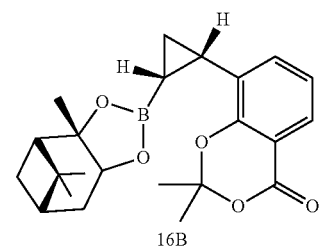

16B

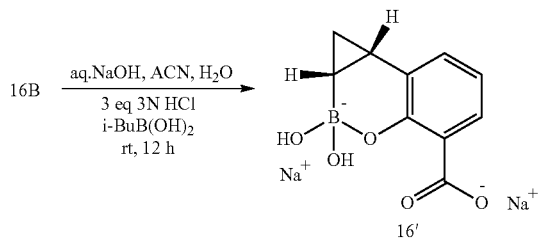

16'

Step 1: Synthesis of Compounds 16A and 16B

To a mixture of compound 10I (2.9 g, 7.59 mmol, 1.0 eq) and Pd(OAc)$_2$ (85 mg, 0.37 mmol, 0.05 eq) in THF (50 mL) at −15° C. was added diazomethane (200 mL) dropwise. After the addition, the resulting mixture was stirred at rt overnight, and then filtered and the filtrate was concentrated. The residue was purified by prep-HPLC to give compound 16A (860 mg, 28%) and compound 16B (950 mg, 31%).

Step 2: Synthesis of Compound 16

To a solution of compound 16B (950 mg, 2.3 mmol, 1.0 eq) in ACN/H$_2$O (6 mL/6 mL) was added 0.5N NaOH to adjust to pH 12. The mixture was stirred at rt for 1 h. To the mixture was added i-BuB(OH)$_2$ (480 mg, 4.6 mol, 2.0 eq) and adjust to pH-2 using 3N HCl. The mixture was purified by prep-HPLC and lyophilized to give a free acid, which was dissolved in ACN/water. The solution was adjusted to pH 9 using 0.5N NaOH. To the mixture was added acetone/water (50 mL/2 mL) and stirred at rt for 3 h. The solid was filtered and washed with water, and dried to give 16' (344 mg, 63%). LC-MS: 246 [M+ACN+H]$^+$. $^1$H NMR (400 MHz, CD$_3$OD) δ 7.23 (d, J=8 Hz, 1H), 7.06 (d, J=7.2 Hz, 1H), 6.53-6.47 (m, 1H), 1.78-1.70 (m, 1H), 0.86-0.78 (m, 1H), 0.41-0.36 (m, 1H), 0.34-0.28 (m, 1H).

Example 17

Disodium salt of 5-(2-fluoroethoxy)-2,2-dihydroxy-1a,7b-dihydro-1H-cyclopropa[c][1,2]benzoxaborinine-4-carboxylic acid (compound 17')

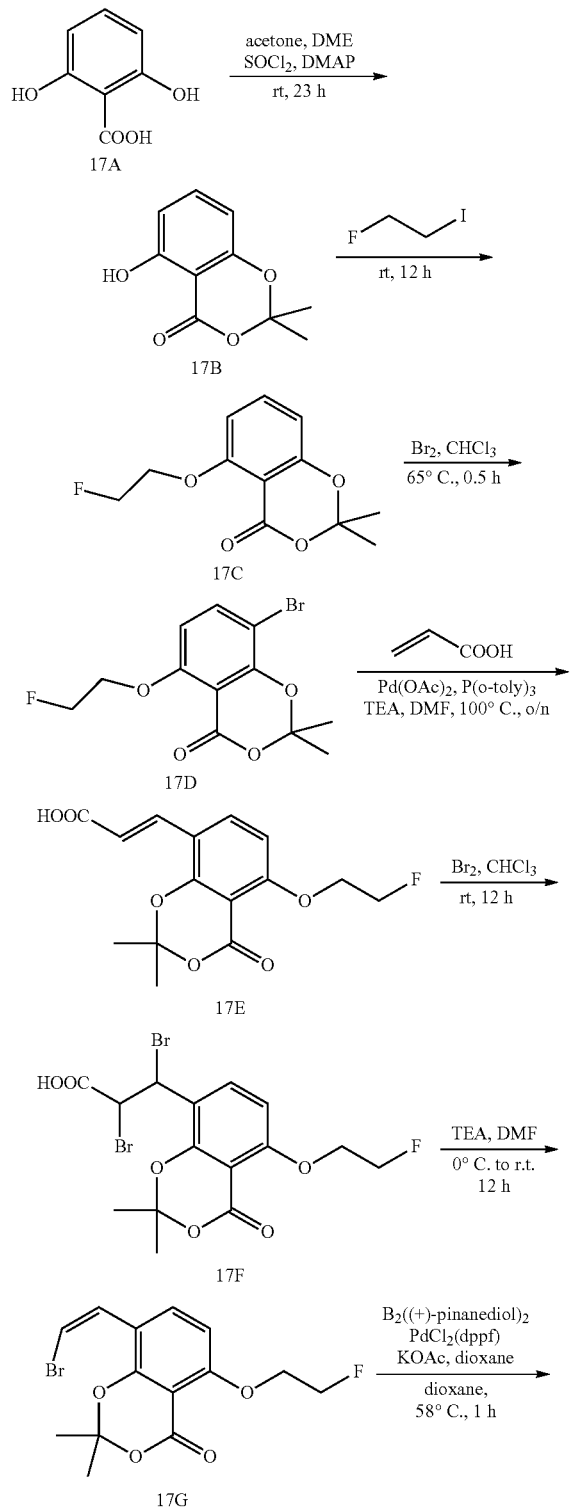

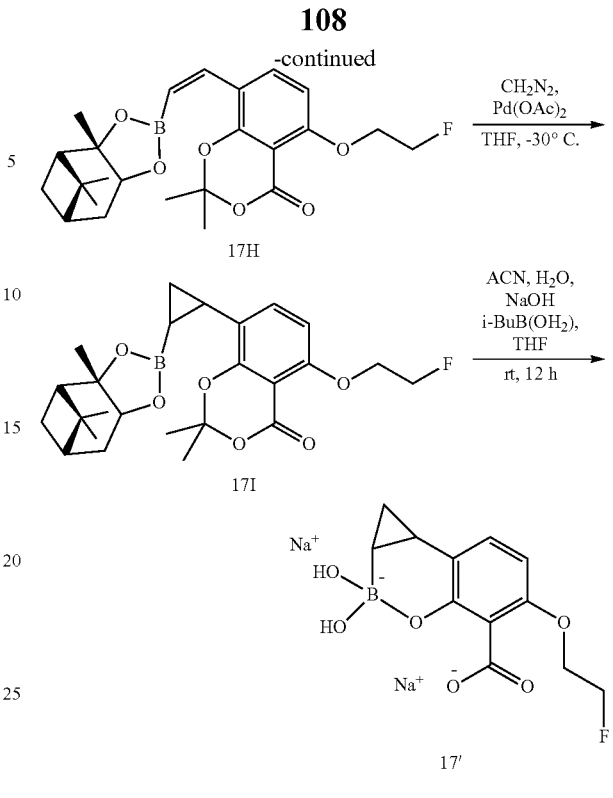

Step 1: Synthesis of Compound 17B

To a mixture of compound 17A (8.0 g, 51.9 mmol, 1.0 eq), acetone (4.9 mL, 67.47 mmol, 1.3 eq), and DMAP (316 mg, 2.595 mmol, 0.05 eq) in DME (30 mL) at 0° C. was added thionyl chloride (4.85 mL, 67.47 mmol, 1.3 eq). The reaction mixture was stirred at 0° C. for 1 h and stirred at rt for 23 h under nitrogen atmosphere. Then the mixture was quenched by aq.NaHCO$_3$ and extracted with ethyl acetate. The organic layer was washed with brine, dried over Na$_2$SO$_4$, and concentrated in vacuum. The residue was purified by column chromatography on a silica gel (PE/EA, 30:1) to give compound 17B (7.1 g, 70%).

Step 2: Synthesis of Compound 17C

A mixture of compound 17B (3.1 g, 15.97 mmol, 1.0 eq), 2-fluoro-1-iodo-ethane (2.69 g, 15.5 mmol, 1.5 eq) and K$_2$CO$_3$ (4.27 g, 31 mmol, 2.0 eq) in DMF (10 mL) was stirred at rt for 12 h under nitrogen atmosphere. Then water was added and extracted with PE:EA=2:1. The organic layer was washed with brine, dried over Na$_2$SO$_4$, and concentrated in vacuo to give the crude compound 17C (3.9 g, 100%).

Step 3: Synthesis of Compound 17D

To a solution of compound 17C (3.9 g, 16 mmol, 1.0 eq) in CHCl$_3$ (20 mL) was added bromine (0.92 mL, 17.9 mmol, 1.1 eq). The reaction was stirred at 65° C. for 0.5 h. Then the reaction was concentrated. The residue was purified by silica gel column chromatography (PE/EA, 5:1) to give compound 17D (4.6 g, 89%).

Step 4: Synthesis of Compound 17E

A solution of compound 17D (4.1 g, 11.6 mmol, 1.0 eq), acrylic acid (1.68 g, 23.3 mmol, 2.0 eq), Pd(OAc)$_2$ (285 mg, 1.16 mmol, 0.1 eq), P(O-toly)$_3$ (532 mg, 1.75 mmol, 0.15 eq) and triethylamine (4.87 mL, 3.49 mmol, 3.0 eq) in DMF (30 mL) was stirred at 100° C. for 12 h under nitrogen atmosphere. After being cooled to rt, the mixture was filtered. The filtrate was washed with DCM/MeOH (10:1), adjust to pH 4~5 using 0.2 N HCl. The mixture was filtered to collect the solid, which was dried to give compound 17E (3.1 g, 77%).

Step 5: Synthesis of Compound 17F

To a solution of compound 17E (3.0 g, 9.7 mmol, 1.0 eq) in chloroform (30 mL) was added bromine (0.54 mL, 10.6 mmol, 1.1 eq), and stirred at rt for 12 h. The reaction was concentrated to give crude compound 17F (5.0 g).

Step 6: Synthesis of Compound 17G

To a solution of compound 17F (5.0 g, 9.7 mmol, 1.0 eq) in DMF (40 mL) at 0° C. was added triethylamine (2.7 mL, 19.4 mmol, 2.0 eq). The mixture was stirred at rt for 12 h. Water was added, and the mixture was extracted with PE:EA=1:1. The organic layer was washed with brine, dried over Na$_2$SO$_4$, concentrated in vacuum. The residue was purified by column chromatography on silica gel (PE/EA, 30:1-7:1) to give compound 17G (2.36 g, 64%).

Step 7: Synthesis of Compound 17H

A mixture of compound 17G (2.46 g, 7.15 mmol, 1.0 eq) in dioxane (30 mL) was degassed with N$_2$. Then the mixture was added bis[(+)-pinanediolato]diboron (3.0 g, 8.58 mmol, 1.2 eq), PdCl$_2$(dppf) (583 mg, 0.715 mmol, 1.0 eq) and potassium acetate (2.1 g, 2.14 mmol, 3.0 eq). The resulting mixture was stirred at 58° C. for 1 h, and concentrated. The residue was purified by prep-HPLC to give compound 17H (370 mg, 12%).

Step 8: Synthesis of Compound 17I

To a solution of compound 17H (370 mg, 0.833 mmol, 1.0 eq) in dry THF (2 mL) at −30° C. was added diazomethane (10 mL, 3.332 mmol, 4.0 eq) and Pd(OAc)$_2$ (10.2 mg, 0.042 mmol, 0.05 eq). The mixture was stirred at −30° C. for 2 h, filtered. The filtrate was concentrated in vacuo. The residue was purified by silica gel column chromatography (PE/EA, 1:1) to give compound 17I (340 mg, 89%).

Step 9: Synthesis of Compound 17'

To a solution of compound 17I (340 mg, 0.74 mmol, 1.0 eq) in ACN/H$_2$O (1.5 mL/1.5 mL) was added 2 N NaOH (0.74 mL, 1.48 mmol, 2.0 eq). The mixture was stirred at rt for 3 h. To the mixture was added i-BuB(OH)$_2$ (151 mg, 1.48 mmol, 2.0 eq) and ACN/THF (2 mL/2 mL). The solution was adjusted to pH 2~3 (3 N HCl), and stirred at rt for 1 h. The mixture was concentrated in vacuum, adjusted to pH~10 (1 N NaOH). The mixture was purified by prep-HPLC (neutral conditions) to give 17' (94 mg, 47%). LC-MS: 267[M+H]$^+$. $^1$H NMR (400 MHz, CD$_3$OD) δ 7.06 (d, J=8.8 Hz, 1H), 6.35 (d, J=8 Hz, 1H), 4.75-4.55 (m, 2H), 4.22-4.13 (m, 2H), 1.85-1.76 (m, 1H), 0.91-0.80 (m, 1H), 0.37-0.28 (m, 2H).

Example 18

Disodium salt of (1aS,7bR)-2,2-dihydroxy-1a,7b-dihydro-H-cyclopropa[c][1,2]benzoxaborinine-4-carboxylic acid (Compound 18')

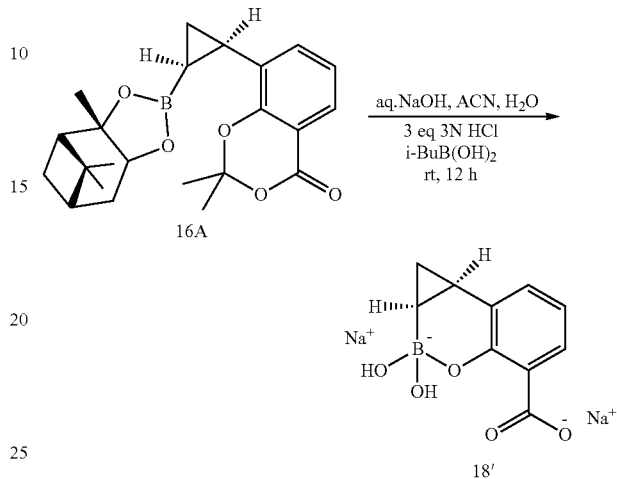

To a solution of compound 16A (860 mg, 2.1 mmol, 1.0 eq) in ACN/H$_2$O (6 mL/6 mL) was added 0.5 N NaOH to adjust to pH 12. The mixture was stirred at rt for 1 h. To the mixture was added i-BuB(OH)$_2$ (480 mg, 4.6 mol, 2.2 eq). Using 3.0 N HCl the solution was adjusted pH~2, purified by prep-HPLC and lyophilized to give a free acid. The acid was dissolved in ACN/water, and 0.5 N NaOH was added to the solution to adjust to pH 9. To the mixture was added acetone/H$_2$O (50 mL/2 mL), and stirred at rt for 3 h. The solid was collected, and dried to give compound 18' (340 mg, 69%). LC-MS: 246 [M+ACN+H]$^+$. $^1$H NMR (400 MHz, CD3OD) δ 7.22 (d, J=8 Hz, 1H), 7.05 (d, J=7.2 Hz, 1H), 6.52-6.48 (m, 1H), 1.79-1.71 (m, 1H), 0.86-0.79 (m, 1H), 0.42-0.35 (m, 1H), 0.33-0.26 (m, 1H).

Example 19

Disodium salt of 5,6-difluoro-2,2-dihydroxy-1a,7b-dihydro-1H-cyclopropa[c][1,2]benzoxaborinine-4-carboxylic acid (Compound 19')

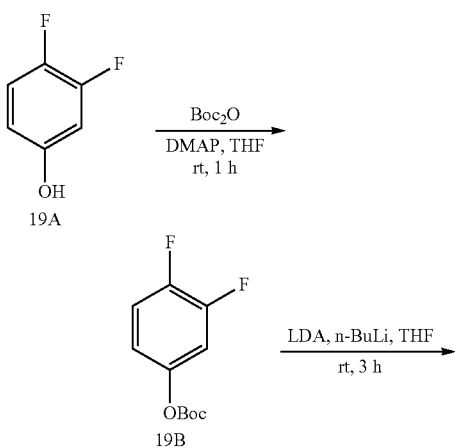

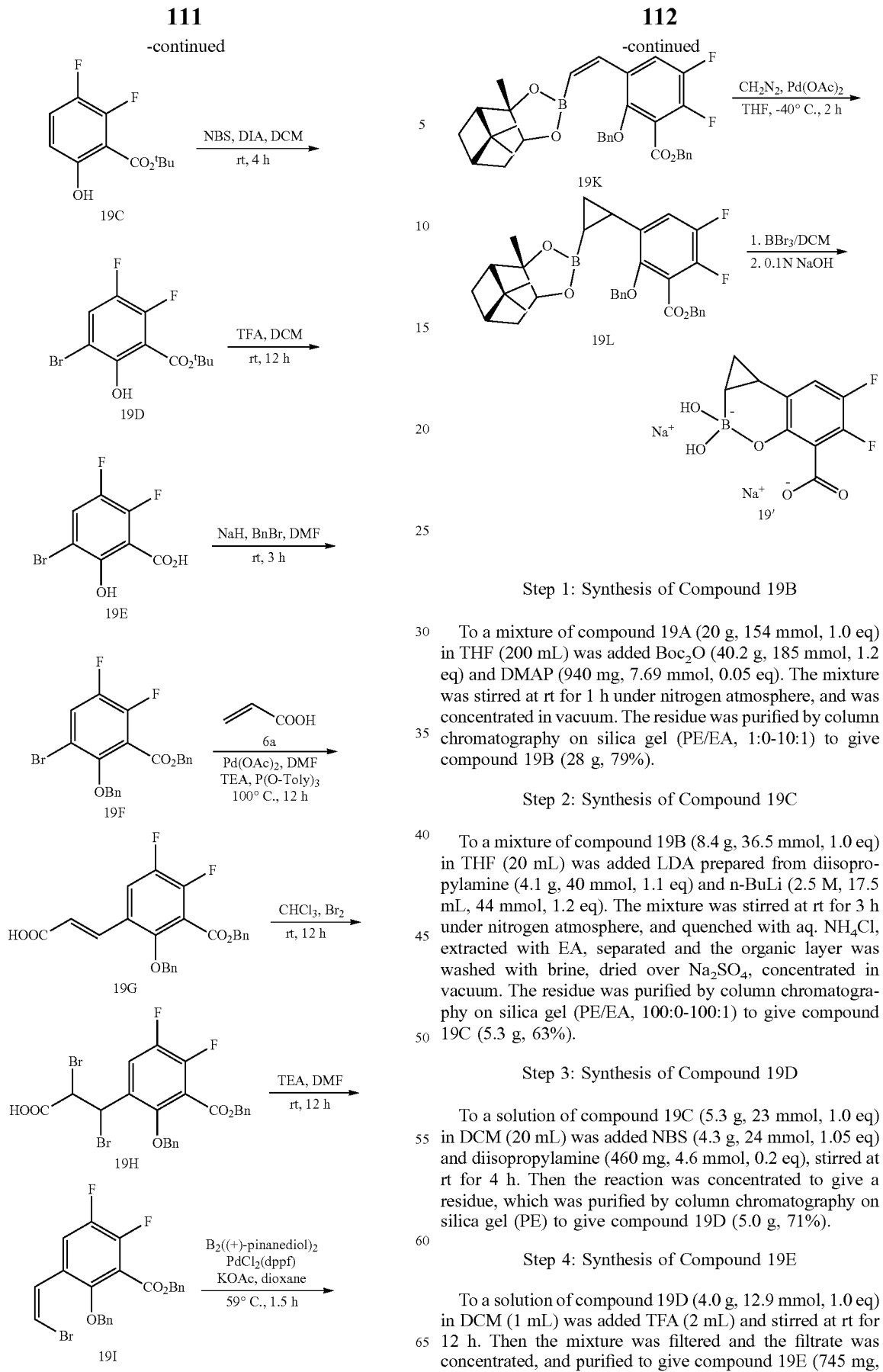

Step 1: Synthesis of Compound 19B

To a mixture of compound 19A (20 g, 154 mmol, 1.0 eq) in THF (200 mL) was added Boc$_2$O (40.2 g, 185 mmol, 1.2 eq) and DMAP (940 mg, 7.69 mmol, 0.05 eq). The mixture was stirred at rt for 1 h under nitrogen atmosphere, and was concentrated in vacuum. The residue was purified by column chromatography on silica gel (PE/EA, 1:0-10:1) to give compound 19B (28 g, 79%).

Step 2: Synthesis of Compound 19C

To a mixture of compound 19B (8.4 g, 36.5 mmol, 1.0 eq) in THF (20 mL) was added LDA prepared from diisopropylamine (4.1 g, 40 mmol, 1.1 eq) and n-BuLi (2.5 M, 17.5 mL, 44 mmol, 1.2 eq). The mixture was stirred at rt for 3 h under nitrogen atmosphere, and quenched with aq. NH$_4$Cl, extracted with EA, separated and the organic layer was washed with brine, dried over Na$_2$SO$_4$, concentrated in vacuum. The residue was purified by column chromatography on silica gel (PE/EA, 100:0-100:1) to give compound 19C (5.3 g, 63%).

Step 3: Synthesis of Compound 19D

To a solution of compound 19C (5.3 g, 23 mmol, 1.0 eq) in DCM (20 mL) was added NBS (4.3 g, 24 mmol, 1.05 eq) and diisopropylamine (460 mg, 4.6 mmol, 0.2 eq), stirred at rt for 4 h. Then the reaction was concentrated to give a residue, which was purified by column chromatography on silica gel (PE) to give compound 19D (5.0 g, 71%).

Step 4: Synthesis of Compound 19E

To a solution of compound 19D (4.0 g, 12.9 mmol, 1.0 eq) in DCM (1 mL) was added TFA (2 mL) and stirred at rt for 12 h. Then the mixture was filtered and the filtrate was concentrated, and purified to give compound 19E (745 mg, 23%).

Step 5: Synthesis of Compound 19F

To a solution of compound 19E (200 mg, 0.79 mmol, 1.0 eq) in DMF (2 mL) at 0° C. was added sodium hydride (133 mg, 60%, 1.98 mmol, 2.5 eq). The mixture was stirred at 0° C. for 15 min and then benzyl bromide (299 mg, 1.75 mmol, 2.2 eq) was added. The mixture was stirred at rt for 3 h, and quenched with ammonium chloride solution (1 mL). The mixture was extracted with PE:EA=1:1. The organic layer was washed with brine, dried over $Na_2SO_4$, concentrated in vacuum. The residue was purified by prep-TLC to give compound 19F (100 mg, 29%).

Step 6: Synthesis of Compound 19G

To a solution of compound 19F (500 mg, 1.4 mmol, 1.0 eq) in dry DMF (4 mL) was added acrylic acid (0.19 mL, 2.8 mmol, 2.0 eq), $Pd(OAc)_2$ (34.7 mg, 0.142 mmol, 0.1 eq), $P(O\text{-toly})_3$ (65 mg, 0.21 mmol, 0.15 eq) and triethylamine (0.59 mL, 4.26 mmol, 3.0 eq). The mixture was stirred at 100° C. for 12 h. The mixture was filtered, and extracted with EA. The organic layer was washed with brine, dried over $Na_2SO_4$, concentrated in vacuo to give compound 19G (369 mg, 75%).

Step 7: Synthesis of Compound 19H

A mixture of compound 19G (2.33 g, 5.49 mmol, 1.0 eq) in chloroform (20 mL) at 0° C. was added bromine (0.31 mL, 6.04 mmol, 1.1 eq). The resulting mixture was stirred at rt for 12 h, and concentrated to give crude compound 19H (2.33 g, 73%).

Step 8: Synthesis of Compound 19I

To a solution of compound 19H (2.33 g, 5.49 mmol, 1.0 eq) in DMF (15 mL) at 0° C. was added triethylamine (1.11 g, 11.0 mmol, 2.0 eq). The mixture was stirred at rt for 12 h. The mixture was concentrated in vacuum. The residue was purified by column chromatography on silica gel (PE/EA, 3:1) to give compound 19I (1.73 g, 94%).

Step 9: Synthesis of Compound 19J

A mixture of compound 19I (1.68 g, 3.67 mmol, 1.0 eq) in dioxane (20 mL) was added bis[(+)-pinanediolato]diboron (1.57 g, 4.4 mmol, 1.2 eq), $PdCl_2(dppf)$ (299 mg, 0.37 mmol, 0.1 eq) and KOAc (1.08 g, 11 mmol, 3.0 eq). The resulting mixture was stirred at 59° C. for 1.5 h, and then concentrated. The residue was purified by prep-TLC to give compound 19J (408 mg, 22%).

Step 10: Synthesis of Compound 19K

To a solution of compound 19J (408 mg, 0.731 mmol, 1.0 eq) and $Pd(OAc)_2$ (9 mg, 0.036 mmol, 0.05 eq) in dry THF (2 mL) −40° C. was added diazomethane (20 mL, 2.92 mmol, 4.0 eq) and stirred at −40° C. for 2 h, and filtered. The filtrate was concentrated in vacuo to give compound 19K (379 mg, 90%).

Step 11: Synthesis of Compound 19′

To a solution of compound 19K (375 mg, 0.66 mmol, 1.0 eq) in DCM (1 mL) was added tribromoborane solution in DCM (1 M, 6.6 mL, 6.6 mmol, 10 eq). The mixture was stirred at rt for 1 h. The mixture was concentrated, dissolve in acetonitrile and water (1 mL/1 mL), and purified by prep-HPLC to give a free acid (28.7 mg), which was treated with 0.1N NaOH (2.0 eq) in $MeCN/H_2O$ at rt for 2 h. The mixture was purified by prep-HPLC again to give 19′ (28.2 mg, 18%) as a white solid. LC-MS: 282 [M+MeCN+H]$^+$. $^1$H NMR (400 MHz, $CD_3OD$) δ 7.05-6.93 (m, 1H), 1.85-1.76 (m, 1H), 0.91-0.83 (m, 1H), 0.48-0.31 (m, 2H).

Example 20

Disodium salt of (1aS,7bR)-2-hydroxy-1a,7b-dihydro-1H-cyclopropa[6,7]oxaborinino[2,3-c]pyridine-4-carboxylic acid (Compound 20′)

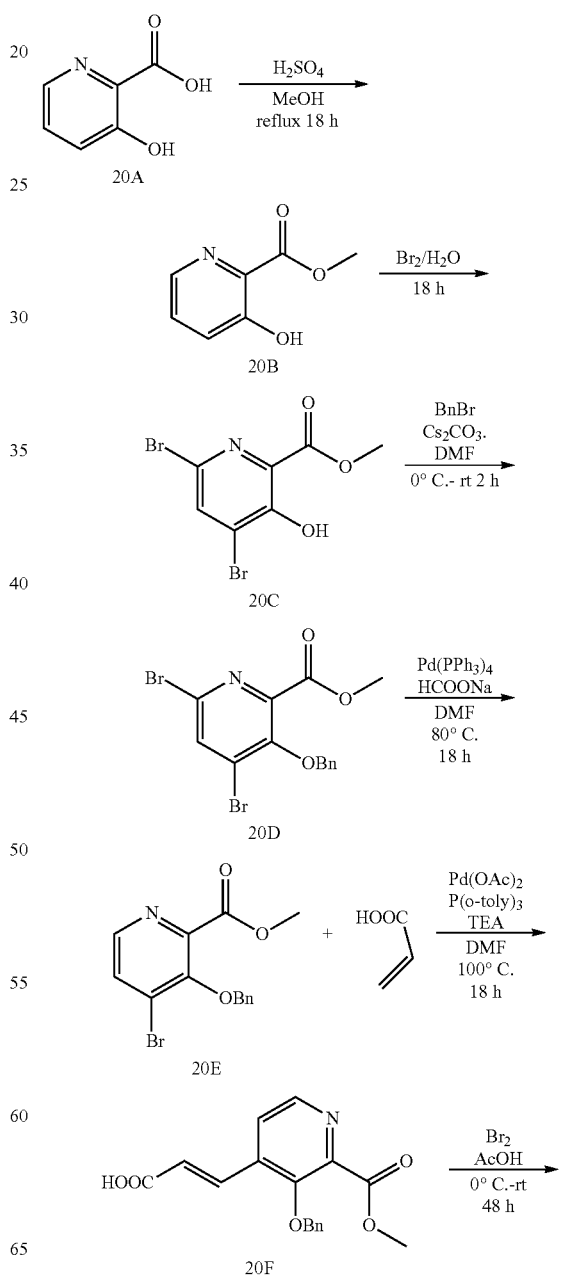

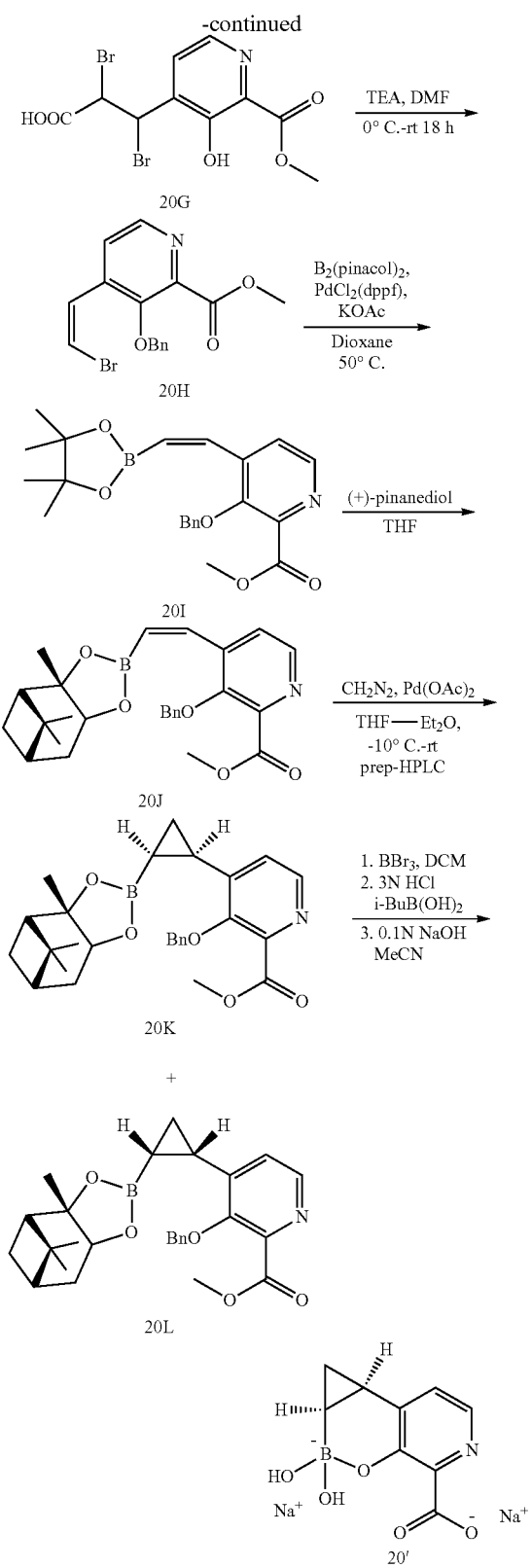

Step 1: Synthesis of Compound 20B

To a solution of compound 20A (100.0 g, 0.719 mol, 1.0 eq) in methanol (1.5 L) was added conc. sulfuric acid (120 mL, 2.157 mol, 3.0 eq) and the reaction mixture was heated to reflux (83° C.) overnight. The solvent was removed in vacuo, and the residue was diluted with water (1.5 L), and adjusted to pH 8.5 with solid $K_2CO_3$, then extracted with DCM (3×1 L). The organic phases were dried over sodium sulfate and concentrated under reduced pressure to give compound 20B (94 g, 85%) as a slightly blue solid. $^1$H NMR (400 MHz, CDCl$_3$) δ 10.61 (s, 1H), 8.28 (dd, J=4.1, 1.4 Hz, 1H), 7.42 (dd, J=8.5, 4.2 Hz, 1H), 7.37 (dd, J=8.5, 1.5 Hz, 1H), 4.05 (s, 3H)

Step 2: Synthesis of Compound 20C

To a solution of compound 20B (114 g, 0.745 mol, 1.0 eq) in water (8 L) at 10° C. was added bromine (114.6 mL, 2.235 mol, 3.0 eq). The reaction mixture was stirred at rt overnight. The reaction mixture was extracted with DCM (2×8 L). The organic phase was separated, and dried over sodium sulfate, and concentrated to give crude compound 20C (186 g, 81%) as a slightly yellow solid. $^1$H NMR (400 MHz, CDCl$_3$) δ 11.35 (s, 1H), 7.56 (s, 1H), 4.06 (s, 3H).

Step 3: Synthesis of Compound 20D

To a solution of compound 20C (186 g, 0.631 mol, 1.0 eq) and cesium carbonate (514.3 g, 1.578 mol, 2.5 eq) in DMF (2 L) at 0° C. was added benzyl bromide (89.1 mL, 0.757 mol, 1.2 eq). The reaction mixture was stirred at rt for 2 h. The reaction mixture was filtered through a pad of Celite. The filtrate was concentrated under reduced pressure to give a residue, which was purified by flash column chromatography on silica (PE/EA=20:1) to give compound 20D (199 g, 83%) as a white solid. $^1$H NMR (400 MHz, CDCl$_3$) δ 7.88 (s, 1H), 7.52-7.50 (d, J=6.1 Hz, 2H), 7.43-7.37 (d, J=7.2 Hz, 3H), 5.13 (s, 2H), 3.92 (s, 3H).

Step 4: Synthesis of Compound 20E

A solution of compound 20D (199 g, 0.499 mol, 1.0 eq), Pd(PPh$_3$)$_4$ (28.8 g, 0.025 mol, 0.05 eq) and sodium formate (37.3 g, 0.549 mol, 1.1 eq) in DMF (2 L) under nitrogen was heated at 80° C. and stirred overnight. After being filtered through a pad of Celite, the filtrate was concentrated under reduced pressure. The residue was triturated with MeOH/DCM/EA/PE (1:3:3:3, 2×2 L), the mother liquid was concentrated under reduced pressure, and the residue was purified by flash chromatography on silica (PE/EA=10:1) to give compound 20E (78 g, 49%) as a slightly yellow solid. $^1$H NMR (400 MHz, CDCl$_3$) δ 8.25-8.20 (m, 1H), 7.68-7.65 (m, 1H), 7.49 (m, 2H), 7.37-7.30 (m, 2H), 7.22-7.20 (m, 3.0 Hz, 1H), 5.16-4.99 (m, 2H), 3.89-3.88 (m, 3.0 Hz, 3H).

Step 5: Synthesis of Compound 20F

To a solution of compound 20E (78 g, 0.243 mol, 1.0 eq) in dry DMF (800 mL) was added compound acrylic acid (26.3 g, 0.364 mol, 1.5 eq), Pd(OAc)$_2$ (3.27 g, 14.6 mmol, 0.04 eq), P(o-toly)$_3$ (4.44 g, 29.2 mmol, 0.08 eq) and triethylamine (152 mL, 1.09 mol, 3.0 eq). The reaction mixture under N$_2$ was stirred at 100° C. overnight. The reaction was monitored by TLC. The mixture was filtered, and concentrated under reduced pressure. The solid was washed with PE:EA:MeOH=3:3:1 (2×), and filtered. The solid was dried to give compound 20F (60.2 g, 79%) as an off-white solid. $^1$H NMR (400 MHz, DMSO-d6) δ 8.43 (d, J=4.9 Hz, 1H), 7.96 (d, J=4.9 Hz, 1H), 7.69 (d, J=16.2 Hz, 1H), 7.40-7.37 (m, 5H), 6.77 (d, J=16.1 Hz, 1H), 4.96 (s, 2H), 3.85 (s, 3H).

Step 6: Synthesis of Compound 20G

To a solution of compound 20F (60.2 g, 0.192 mol, 1.0 eq) in acetic acid (1.0 L) at 5° C. was added bromine (19.7 mL, 0.384 mol, 2.0 eq). The reaction mixture was stirred at rt for two days. The reaction was monitored by LCMS. Then the solvent was removed under reduced pressure to give crude compound 20G (87 g), which was used directly for the next step without further purification.

Step 7: Synthesis of Compound 20H

To a solution of crude compound 20G (87 g, 0.184 mmol, 1.0 eq) in DMF (1.0 L) at 0° C. was added triethylamine (76.8 mL, 0.552 mol, 3.0 eq). The reaction mixture was stirred at rt overnight. The reaction was monitored by LC-MS. Then the mixture was filtered and the filtrate was concentrated under reduced pressure and the residue was purified by flash chromatography on silica (PE/EA=30:1-15:1-7:1) to give compound 20H (13.2 g, 19% over two steps) as brown oil. $^1$H NMR (400 MHz, CDCl$_3$) δ 8.50 (d, J=4.8 Hz, 1H), 7.96 (d, J=4.8 Hz, 1H), 7.43-7.37 (m, 5H), 7.24 (d, J=8.3 Hz, 1H), 6.71 (d, J=8.3 Hz, 1H), 5.01 (s, 2H), 3.96 (s, 3H).

Step 8: Synthesis of Compound 20I

A mixture of bromide 20H (14.8 g, 42.6 mmol, 1.0 eq), bis(pinacolato)diboron (16.3 g, 64 mmol, 1.5 eq), [1,1'-bis(diphenylphosphino)ferrocene]dichloropalladium (5.2 g, 6.4 mmol, 0.15 eq), potassium acetate (8.4 g, 85.0 mmol, 2.0 eq) in dioxane (150 mL) was degassed and filled with nitrogen three times, and heated at 50° C. overnight. The reaction mixture was cooled to rt, filtered through a pad of Celite, washed with ethyl acetate. The filtrate was concentrated and purified with flash column chromatography (ethyl acetate:hexane=1:2 to 2:1 and DCM:MeOH, 10:1) to give boronic ester 20I (14.6 g, 87%) as brown oil.

Step 9: Synthesis of Compound 20J

A mixture of 20I (4.75 g, 12.0 mmol, 1.0 eq) and (+)-pinanediol (4.08 g, 24.0 mmol, 2.0 eq) in THF (50 mL) was stirred at rt overnight. The reaction was concentrated and purified by flash column chromatography (ethyl acetate:hexane=1:3 to 1:2) to give compound 20J (4.0 g, 75%) as light yellow oil.

Step 10: Synthesis of Compounds 20K and 20 L

To a mixture of compound 20J (4.0 g, 8.95 mmol, 1.0 eq) and palladium acetate (60 mg, 0.268 mmol, 0.03 eq) in THF (50 mL) at −10° C. (ice-water salt bath) was added diazomethane solution (0.30 M in ether, 150 mL, 45 mmol, 5.0 eq) dropwise over 30 min. The brown clear solution was warmed up to rt and stirred overnight. The reaction mixture was filtered through a pad of Celite, and washed with DCM. The filtrate was concentrated and purified by flash column chromatography (ethyl acetate:hexane=1:3 to 1:2) to give cyclopropannulated isomeric mixture (3.37 g, 82%) as yellow oil. Part of the diastereoisomer mixture was purified with prep-HPLC (C18, 250×21 mm, 0.1% formic acid in both acetonitrile and water) to give isomer 20K and pure isomer 20 L.

Step 11: Synthesis of Compound 20'

To a solution of 20K (150 mg, 0.28 mmol, 1.0 eq) in dichloromethane (6 mL) at −78° C. was added boron tribromide (0.08 mL, 0.84 mmol, 3.0 eq). The reaction mixture was slowly warmed to rt and stirred for 1 h. The mixture was concentrated to give a solid residue, which was dissolved in acetonitrile (5 mL). To the solution at rt were added 3N HCl (1.5 mL) and isobutylboronic acid (114 mg, 1.12 mmol, 4.0 eq). After being stirred at rt for 4 h, the reaction mixture was purified by prep-HPLC (C18, 250×21 mm, 0.1% formic acid in both acetonitrile and water) to give the free acid compound 20 (34 mg, 94%). The acid product (34 mg, 0.16 mmol) in acetonitrile/water (1:2, 5 mL) was treated with 0.1 N NaOH (3.5 mL), and stirred for 4 h, and lyophilized to give sodium salt compound 20' (50.6 mg) as an off-white solid. LC-MS: 206 [M+1]$^+$. $^1$H NMR (300 MHz, D$_2$O) δ 7.54 (d, J=5.1 Hz, 1H), 7.17 (d, J=5.4 Hz, 1H), 1.82-1.75 (m, 1H), 0.96-0.87 (m, 1H), 0.45-0.28 (m, 2H).

Example 21

Disodium salt of (1aR,7bS)-2-hydroxy-1a,7b-dihydro-1H-cyclopropa[6,7]oxaborinino[2,3-c]pyridine-4-carboxylic acid (Compound 21')

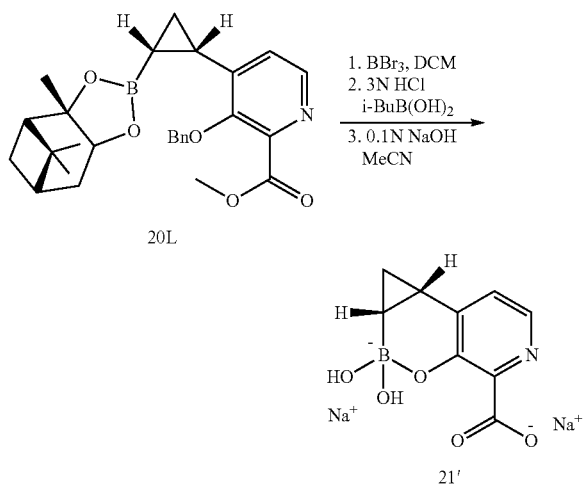

To a solution of compound 20L (420 mg, 0.91 mmol, 1.0 eq) in dichloromethane (20 mL) at −78° C. was added boron tribromide (0.264 mL, 2.74 mmol, 3.0 eq). The reaction mixture was slowly warmed to rt and stirred for 2 h. The mixture was concentrated to give a residue, which was dissolved in acetonitrile (10 mL). To the solution at rt were added 3N HCl (3 mL) and isobutylboronic acid (200 mg, 2.0 eq). After being stirred at rt for 4 h, the reaction mixture was concentrated, and dissolved in acetonitrile and water, and lyophilized to obtain the crude product as yellow brown solid. The crude product was purified by prep-HPLC (C18, 250×21 mm, 0.1% formic acid in both acetonitrile and water) to give the free acid compound 21 (175 mg, 94%). The acid product (175 mg, 0.85 mmol) in acetonitrile/water (1:2, 15 mL) was treated with 1 N NaOH (0.85 mL), and stirred for 2 h, and lyophilized to give a crude sodium salt as a light yellow solid. The yellow solid was dissolved in water (2.2 mL). To the solution was added acetone (20 mL). The acetone solution was decanted, and the solid was washed with acetone (3×). The water/acetone washing process was repeated to give the pure product sodium salt compound 21' (150 mg, 78%) after drying in vacuo. LC-MS: 206 [M+1]+. 1H NMR (300 MHz, D2O) δ 7.46 (d, J=4.8 Hz, 1H), 7.06 (d, J=5.1 Hz, 1H), 1.75-1.65 (m, 1H), 0.88-0.78 (m, 1H), 0.36-0.18 (m, 2H).

Example 22

Disodium salt of 2,2-dihydroxy-1a-(hydroxymethyl)-5-methoxy-1,7b-dihydrocyclopropa[c][1,2]benzoxaborinine-4-carboxylic acid (Compound 22')

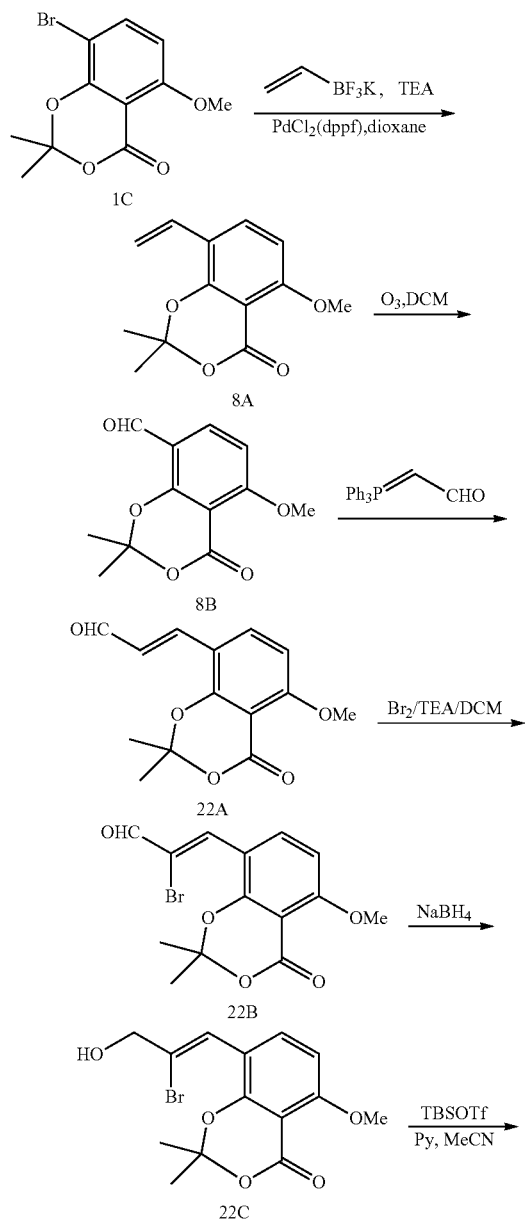

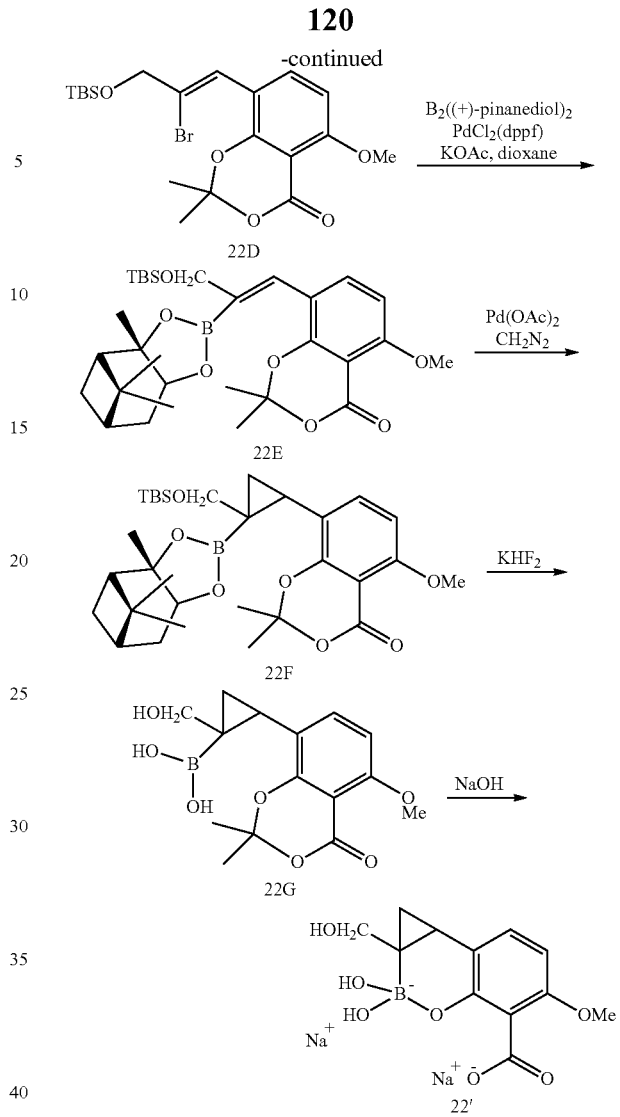

Step 1: Synthesis of Compound 8A

A mixture of compound 1C (60.0 g, 0.210 mol, 1.0 eq), potassium vinyltrifluoroborate (42.2 g, 0.315 mol, 1.5 eq), PdCl2(dppf) (17.0 g, 0.021 mol, 0.1 eq), and triethylamine (87.7 mL, 0.629 mol, 3.0 eq) in dioxane (600 mL) under nitrogen was heated to 95° C. overnight. TLC showed no 1C left. The reaction mixture was filtered through a pad of Celite. The filtrate was concentrated under reduced pressure to give a residue, which was purified by flash column chromatography on silica (PE/EA/DCM=2:1:1) to give compound 8A (43 g, 87%) as a white solid. 1H NMR (400 MHz, CDCl3) δ 7.65 (d, J=8.9 Hz, 1H), 6.80 (dd, J=17.6, 11.4 Hz, 1H), 6.64 (d, J=8.8 Hz, 1H), 5.66 (d, J=17.7 Hz, 1H), 5.41-5.11 (m, 1H), 3.96 (s, 3H), 1.71 (d, J=8.9 Hz, 6H).

Step 2: Synthesis of Compound 8B

To a solution of compound 8A (23 g, 0.098 mol, 1.0 eq) in DCM (200 mL) at −78° C. was bubbled with ozone till the color of the solution turned into blue. The reaction mixture was stirred for 16 h. TLC showed no 8A left. The reaction mixture was added PPh3 (15 g, 0.057 mol, 0.6 eq), warm to rt., stirred for 0.5 h. the reaction was monitored by TLC. The reaction mixture was concentrated under reduced pressure to give a residue, which was purified by flash column chromatography on silica (PE/EA/DCM=3:1:1) to give compound 8B (15 g, 64%) as a yellow solid. $^1$H NMR (400 MHz, CDCl$_3$) δ 10.22 (s, 1H), 8.08 (d, J=9.0 Hz, 1H), 6.76 (d, J=8.6 Hz, 1H), 4.05 (s, 3H), 1.79 (s, 6H).

Step 3: Synthesis of Compound 22A

To a solution of compound 8B (15 g, 0.064 mol, 1.0 eq) in dry THF (200 mL) was added 2-(triphenylphosphoranylidene)acetaldehyde (35 g, 0.115 mol, 1.8 eq) under nitrogen. The reaction mixture was stirred at 100° C. overnight. The reaction mixture was concentrated under reduced pressure to give a residue, which was purified by flash column chromatography on silica (DCM/MeOH=100:1) to give compound 22A (6.0 g, 36%) as a yellow solid. $^1$H NMR (400 MHz, CDCl$_3$) δ 9.73-9.61 (m, 1H), 7.83-7.72 (m, 1H), 7.64-7.54 (m, 1H), 6.78-6.62 (m, 2H), 4.09-3.96 (m, 3H), 1.86-1.72 (m, 6H).

Step 4: Synthesis of Compound 22B

To a solution of compound 22A (6.0 g, 0.023 mol, 1.0 eq) in dry DCM (120 mL) at −78° C. under nitrogen was added bromine (1.17 mL, 0.023 mol, 1.0 eq). The solution was stirred for 0.5 h. Triethylamine (3.8 mL, 0.027 mol, 1.2 eq) was added. The solution was warmed to rt, and stirred overnight. The reaction mixture was concentrated under reduced pressure to give a residue, which was purified by flash column chromatography on silica (DCM/MeOH=300:1) to give compound 22B (6.2 g, 80%) as a yellow solid. $^1$H NMR (400 MHz, CDCl$_3$) δ 9.34 (s, 1H), 8.76 (d, J=8.5 Hz, 1H), 8.06 (s, 1H), 6.79 (d, J=9.0 Hz, 1H), 4.05 (s, 3H), 1.77 (d, J=16.3 Hz, 6H).

Step 5: Synthesis of Compound 22C

To a solution of compound 22B (6.2 g, 0.018 mol, 1.0 eq) in methanol (60 mL) was added NaBH$_4$ (0.69 g, 0.018 mol, 1.0 eq) at 0° C. under nitrogen, the reaction mixture was stirred for 0.5 h, TLC showed no 22B left. The mixture was concentrated under reduced pressure to give a residue, which was purified by flash column chromatography on silica (DCM/MeOH=100:1) to give compound 22C (5.7 g, 92%) as a white foam solid. $^1$H NMR (400 MHz, CDCl$_3$) δ 8.10 (d, J=7.2 Hz, 1H), 7.02 (s, 1H), 6.68 (d, J=7.1 Hz, 1H), 4.42 (s, 2H), 3.98 (d, J=1.8 Hz, 3H), 1.72 (d, J=1.8 Hz, 6H).

Step 6: Synthesis of Compound 22D

To a solution of compound 22C (4.5 g, 0.013 mol, 1.0 eq) and pyridine (2.1 mL, 0.026 mol, 2.0 eq) in ACN (45 mL) at 0° C. was added TBSOTf (3.6 mL, 0.016 mol, 1.2 eq) under nitrogen. The reaction mixture was warm to rt and stirred overnight. TLC showed no 22C left. Then the solvent was quenched with saturated NaHCO$_3$ (20 mL), extracted with EA (3×100 mL). The organic phases were dried over sodium sulfate and concentrated under reduced pressure to give a residue, which was purified by flash column chromatography on silica (PE/EA=7:1) to give compound 22D (5.6 g, 93%) as a white solid. $^1$H NMR (400 MHz, CDCl$_3$) δ 8.14 (d, J=8.8 Hz, 1H), 7.14 (s, 1H), 6.67 (d, J=9.1 Hz, 1H), 4.39 (s, 2H), 3.98 (s, 3H), 1.71 (s, 6H), 0.96 (s, 9H), 0.14 (s, 6H).

Step 7: Synthesis of Compound 22E

A mixture of compound 22D (5.6 g, 0.012 mol, 1.0 eq), Bis[(+)-pinanediolato]diboron (6.6 g, 0.018 mol, 1.5 eq) and KOAc (3.6 g, 0.037 mol, 3.0 eq) and PdCl$_2$(dppf) (1.0 g, 0.001 mol, 0.1 eq) in dry dioxane (60 mL) under nitrogen. The reaction mixture was stirred at 60° C. overnight. TLC showed no 22D left. Then the mixture was filtered and the filtrate was extracted with EA (3×150 mL). The organic phase was dried over sodium sulfate and concentrated under reduced pressure to give a residue, which was purified by flash column chromatography on silica (PE/EA=10:1) to give compound 22E (5.5 g, 81%) as a yellow oil. $^1$H NMR (400 MHz, CDCl$_3$) δ 7.68 (d, J=8.4 Hz, 1H), 7.19 (s, 1H), 6.55 (d, J=8.8 Hz, 1H), 4.42 (s, 2H), 4.28 (d, J=7.7 Hz, 1H), 3.95 (s, 3H), 2.28 (dd, J=33.7, 22.5 Hz, 2H), 2.03 (s, 1H), 1.90 (s, 2H), 1.70 (s, 6H), 1.36 (s, 3H), 1.16 (d, J=10.4 Hz, 1H), 0.94 (s, 15H), 0.11 (s, 6H).

Step 8: Synthesis of Compound 22F

To a solution of compound 22E (200 mg, 0.360 mmol, 1.0 eq) and Pd(OAc)$_2$ (4 mg, 0.018 mmol, 0.05 eq) in dry THF (3 mL) at −20° C. under nitrogen was added CH$_2$N$_2$ (0.277 M in ether, 19.5 mL, 5.4 mmol, 15 eq). The reaction mixture was warm to rt, stirred for 4 h. The reaction was monitored by LCMS. Then the mixture was filtered and the filtrate was concentrated under reduced pressure to give a residue, which was purified by prep-TLC (PE/EA=3.5:1) to give compound 22F (90 mg, 43.9%) as a colorless oil. $^1$H NMR (400 MHz, CDCl$_3$) δ 7.30 (d, J=8.8 Hz, 1H), 7.24 (s, 1H), 4.04 (t, J=10.7 Hz, 1H), 3.92 (s, 3H), 3.89 (s, 1H), 3.59 (d, J=3.7 Hz, 1H), 2.20-2.13 (m, 1H), 2.08 (t, J=7.0 Hz, 1H), 2.01 (d, J=5.9 Hz, 1H), 1.84 (s, 1H), 1.76 (s, 1H), 1.70 (s, 6H), 1.59 (s, 1H), 1.27 (dd, J=10.9, 6.9 Hz, 3H), 1.16 (s, 1H), 1.14 (s, 1H), 0.89 (s, 12H), 0.70 (d, J=4.3 Hz, 3H), 0.50 (d, J=10.1 Hz, 1H), 0.06 (d, J=5.8 Hz, 6H).

Step 9: Synthesis of Compound 22G

To a solution of compound 22F (85 mg, 0.149 mmol, 1.0 eq) in MeOH/H$_2$O (2 mL/0.4 mL) was added KHF$_2$ (76 mg, 0.974 mmol, 7 eq), stirred at 30° C. for 5 h, then stirred at rt for 1 d. The reaction was monitored by LCMS. The reaction was purified by prep-HPLC (under netrual condition) to give compound 22G (30 mg, 62.5%) as a white solid. $^1$H NMR (400 MHz, cd$_3$od) δ 7.34 (d, J=8.8 Hz, 1H), 6.69 (t, J=9.0 Hz, 1H), 3.87 (s, 3H), 3.73 (d, J=10.8 Hz, 1H), 3.38 (d, J=10.9 Hz, 1H), 1.82 (t, J=7.0 Hz, 1H), 1.72 (s, 6H), 1.33 (t, J=5.0 Hz, 1H), 0.88 (dd, J=8.1, 4.3 Hz, 1H).

Step 10: Synthesis of Compound 22'

To a mixture of compound 22G (30 mg, 0.093 mmol, 1.0 eq) in ACN/H$_2$O (0.5 mL/0.5 mL) was added 3 M NaOH (0.06 mL, 0.186 mmol, 2.0 eq), stirred for 2 h. The reaction was monitored by LCMS. The reaction was purified by prep-HPLC (under netrual conditions) to give compound 22' (9.5 mg, 39%) as a white solid. $^1$H NMR (400 MHz, CD$_3$OD) δ 6.88 (d, J=8.2 Hz, 1H), 6.23 (d, J=8.2 Hz, 1H), 3.95 (d, J=10.2 Hz, 1H), 3.70 (s, 3H), 3.07 (d, J=10.2 Hz, 1H), 1.48 (dd, J=7.7, 3.9 Hz, 1H), 0.53 (d, J=8.9 Hz, 2H).

Example 23

Disodium salt of (3aS,9bS)-4,4-dihydroxy-7-methoxy-1,3,3a,9b-tetrahydrofuro[3,4-c][1,2]benzoxaborinine-6-carboxylic acid (Compound 23')

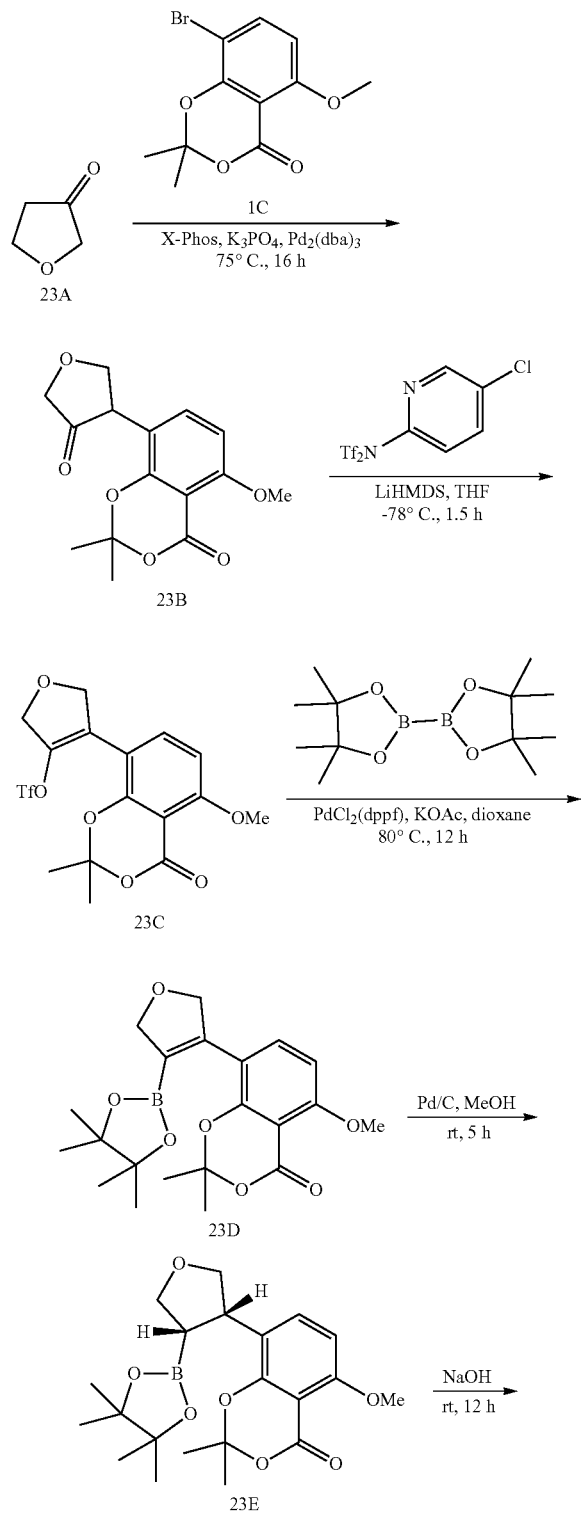

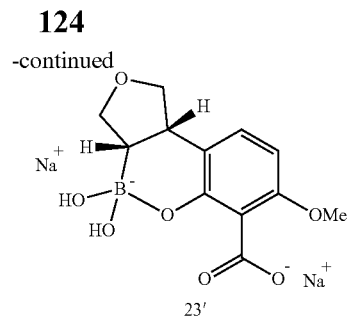

23'

Step 1: Synthesis of Compound 23B

A mixture of compound 23A (15.0 g, 174.8 mmol, 10.0 eq), 1C (5.0 g, 17.5 mmol, 1.0 eq), X-Phos (5.0 g, 10.49 mmol, 0.6 eq), $K_3PO_4$ (18.5 g, 87.4 mmol, 5.0 eq) and $Pd_2(dba)_3$ (3.2 g, 3.50 mmol, 0.2 eq) in THF (150 mL) was heated at 75° C. for 16 h under nitrogen atmosphere. The mixture was cooled to rt, filtered and the filtrate was concentrated in vacuum. The residue was purified by column chromatography on a silica gel (PE/EA, 5:1) to give compound 23B (1.1 g, 22%).

Step 2: Synthesis of Compound 23C

To a solution of compound 23B (440 mg, 1.5 mmol, 1.0 eq) in dry THF (15 mL) at −78° C., was LiHMDS (1.8 mL, 1.8 mmol, 1.2 eq) was added dropwise. The solution was stirred −78° C. for 30 min. To the mixture was added compound N-(5-Chloro-2-pyridyl)bis(trifluoromethanesulfonimide) (650 mg, 1.66 mmol, 1.1 eq) in dry THF (5 mL) and stirred at −78° C. for 1.5 h. After the reaction was complete, the mixture was poured into water, and extracted with ethyl acetate. The organic layer was washed with brine, dried over $Na_2SO_4$, concentrated. The residue was purified by column chromatography on a silica gel (PE/EA, 1:1) to give compound 22C (367 mg, 57%).

Step 3: Synthesis of Compound 23D

To a solution of compound 23C (400 mg, 1.06 mmol, 1.0 eq) in dioxane (20 mL) was added compound bis(pinacolato)diboron (323 mg, 1.27 mmol, 1.2 eq), $PdCl_2(dppf)$ (26 mg, 0.032 mmol, 0.03 eq) and KOAc (312 mg, 3.18 mmol, 3.0 eq). The mixture was stirred at 80° C. overnight. To the reaction was added water and extracted with ethyl acetate. The organic layer was washed with brine, dried over $Na_2SO_4$, concentrated. The residue was purified by column chromatography on silica gel (PE/EA, 1:1) to give compound 23D (310 mg, 81%).

Step 4: Synthesis of Compound 23E

To a solution of compound 23D (90 mg, 0.22 mmol, 1.0 eq) in methanol (10 mL) was added Pd/C (9 mg, 10% w/w). The mixture was stirred at rt for 5 h, then filtered and the filtrate was concentrated to give crude compound 23E (90 mg).

Step 5: Synthesis of Compound 23'

To a mixture of compound 23E (90 mg, 0.22 mmol, 1.0 eq) in $CH_3CN/H_2O$ (1 mL/1 mL) was added 3.0 N NaOH to adjust the solution to pH 9~10. The mixture was stirred at rt for 12 h, purified by prep-HPLC to give compound 23' (17.1 mg, 29%). LC-MS: 265 [M+H]⁺. ¹H NMR (400 MHz, CD₃OD) δ 6.83 (d, J=8.4 Hz, 1H), 6.35 (d, J=8.4 Hz, 1H), 4.01-3.94 (m, 3H), 3.73 (s, 3H), 3.61-3.52 (m, 1H), 3.41-3.28 (m, 1H), 1.55-1.42 (m, 1H).

Example 24

Disodium salt 4,4-dihydroxy-7-methoxy-1,3-dihydrofuro[3,4-c][1,2]benzoxaborinine-6-carboxylic acid (Compound 24')

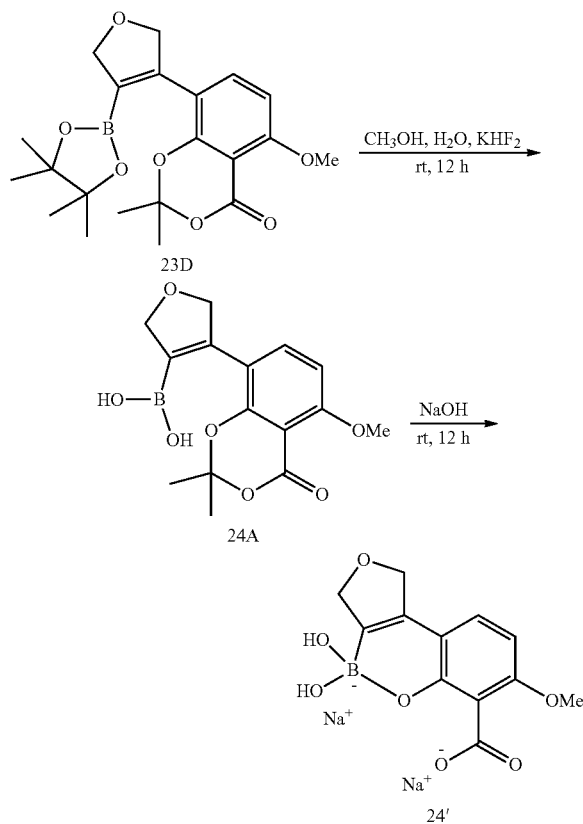

Step 1: Synthesis of Compound 24A

To a solution of compound 23D (150 mg, 0.373 mmol, 1.0 eq) in CH₃OH/H₂O (1.5 mL/0.3 mL) was added KHF₂ (203 mg, 2.61 mol, 7.0 eq). The mixture was stirred at rt for 12 h. purified by prep-HPLC to give compound 24A (25 mg, 21%).

Step 2: Synthesis of Compound 24'

To a mixture of compound 24A (47 mg, 0.14 mmol, 1.0 eq) in CH₃CN/H₂O (1 mL/1 mL) was added 3.0 N NaOH to adjust the mixture to pH 10. The mixture was stirred at rt for 12 h, purified by prep-HPLC to give compound 24' (20 mg, 52%). LC-MS: 263[M+H]⁺. ¹H NMR (400 MHz, CD3OD): δ 6.69 (d, J=8.8 Hz, 1H), 6.33 (d, J=8.4 Hz, 1H), 4.98-4.92 (m, 2H), 4.86-4.81 (m, 2H), 3.75 (s, 3H).

Example 25

General Procedures for the Preparation of Chloromethylcarbonate Prodrug Precursors

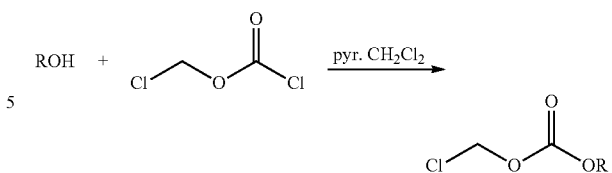

To a stirred solution of chloromethyl chloroformate (5.0 mmol) and pyridine (5.1 mmol) in anhydrous dichloromethane (30 mL) at 0° C. (ice-bath) slowly added an alcohol (5.0 mmol). The reaction was warmed to rt and monitored by TLC plate. After the starting material was completely consumed, the solvents were removed to give a residue, which was purified by silica-gel flash chromatography to afford corresponding chloride prodrug precursor.

The following prodrug precursors were synthesized using the general procedure described above.

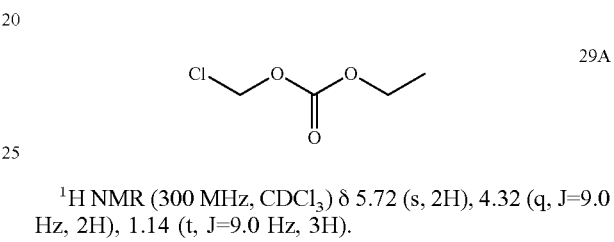

¹H NMR (300 MHz, CDCl₃) δ 5.72 (s, 2H), 4.32 (q, J=9.0 Hz, 2H), 1.14 (t, J=9.0 Hz, 3H).

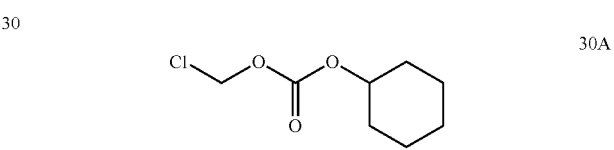

¹H NMR (300 MHz, CDCl₃) δ 5.72 (s, 2H), 4.74-4.62 (m, 1H), 1.98-1.92 (m, 2H), 1.81-1.69 (m, 2H), 1.42-1.25 (m, 5H).

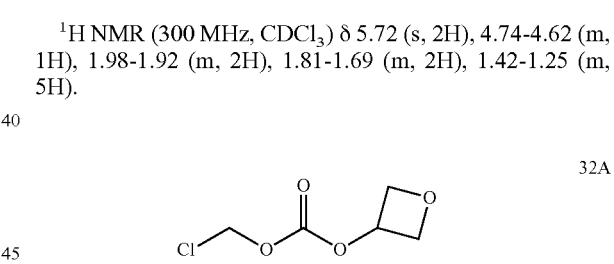

¹H NMR (300 MHz, CDCl₃) δ 5.73 (s, 2H), 5.21-4.92 (m, 1H), 4.92-4.88 (m, 2H), 4.73-4.69 (m, 2H).

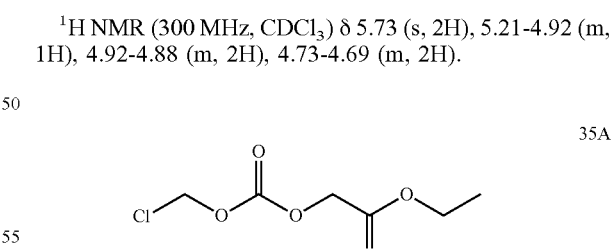

¹H NMR (300 MHz, CDCl₃) δ 5.76 (s, 2H), 4.69 (s, 2H), 4.26 (dd, J=15.0, and 6.0 Hz, 2H), 1.30 (t, J=9.0 Hz, 3H).

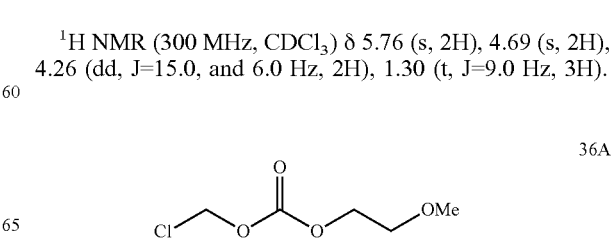

¹H NMR (300 MHz, CDCl₃) δ 5.73 (s, 2H), 4.37 (t, J=6.0 Hz, 2H), 3.64 (t, J=6.0 Hz, 2H), 3.39 (s, 3H).

37A

¹H NMR (300 MHz, CDCl₃) δ 5.73 (s, 2H), 4.90-4.81 (m, 2H), 3.97-3.90 (m, 2H), 2.04-1.98 (m, 2H), 1.80-1.74 (m, 2H).

40A

¹H NMR (300 MHz, CDCl₃) δ 5.74 (s, 2H), 4.43 (t, J=6.0 Hz, 2H), 4.31 (t, J=6.0 Hz, 2H), 2.09 (s, 3H).

41A

¹H NMR (300 MHz, CDCl₃) δ 5.77 (s, 2H), 4.81 (s, 2H), 3.02 (s, 3H), 2.98 (s, 3H).

General Procedures for the Preparation of Chloromethyl-acyloxy esters Prodrug Precursors To a well stirred solution an acid (5.0 mmol) and potassium hydroxide (5.1 mmol) tetrabutylammonium hydrogen sulfate (0.5 mmol) and potassium bicarbonate (50 mmol) in water (2 mL) and DCM (4 mL) was chloromethanesulfonyl chloride (5.0 mmol). The mixture was monitored by TLC plate. When the starting material was completely consumed, the mixture was extracted with DCM for 3 times. The combined DCM solution was dried over sodium sulfate. The solution was concentrated and the residue was purified by silica gel flash chromatography with eluent of 10% DCM in ethyl acetate to give the product.

The following prodrug precursors were synthesized using the general procedure described above.

38A

¹H NMR (300 MHz, CDCl₃) δ 5.71 (s, 2H), 4.47-4.41 (m, 1H), 3.68-3.60 (m, 2H), 2.25-2.21 (m, 2H), 2.10 (s, 3H).

39A

¹H NMR (300 MHz, CDCl₃) δ 5.71 (s, 2H), 4.01-3.91 (m, 1H), 3.46-3.38 (m, 2H), 3.38-3.25 (m, 2H), 1.95-1.71 (m, 4H).

42A

¹H NMR (300 MHz, CDCl₃) δ 5.75 (s, 2H), 4.67 (s, 2H), 2.12 (s, 3H).

43A

¹H NMR (300 MHz, CDCl₃) δ 5.77 (s, 2H), 4.11 (s, 2H), 3.47 (s, 3H);

General Procedures for the Preparation of Compound 13 Prodrugs

-continued

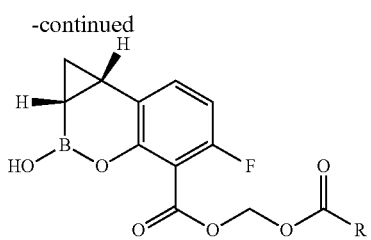

A 10 mL-flask was flame-dried under vacuum, back-filled with nitrogen and cooled to rt. The flask was charged with compound 13 (100 mg, 0.45 mmol, 1 eq.), potassium carbonate (186 mg, 1.35 mmol, 3 eq.), and potassium iodide (224 mg, 1.35 mmol, 3 eq.). The reaction flask was placed under vacuum and back-filled with nitrogen three times. Anhydrous DMF (2 mL, 0.25 M) followed by freshly prepared chloride (0.90 mmol, 2 eq.) were added via syringe under nitrogen. The resulting mixture was stirred at 50° C. for 12 hrs under a nitrogen balloon. The reaction was monitored by LCMS and HPLC. After the starting material was consumed, the mixture cooled to rt. Acetonitrile (1 mL) and water (2 mL) were added, and the clear solution was purified preparative-HPLC to afford the desired product after lyophilization.

The following prodrugs were synthesized using the general procedure described above.

Isopropoxycarbonyloxymethyl (1 aR,7bS)-5-fluoro-2-hydroxy-1a,7b-dihydro-1H-cyclopropa[c][1,2]benzoxaborinine-4-carboxylate (Compound 25)

25

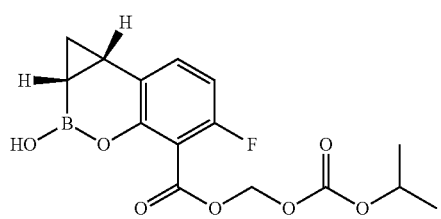 [SMILES: CC(C)OC(=O)OCOC(=O)c1c(F)ccc2c1OB(O)[C@@H]1C[C@H]21]

LCMS: 676.0 [2M+1]$^+$; $^1$H NMR (300 MHz, CDCl$_3$) δ 7.34 (dd, J=8.4 and 6.3 Hz, 1H), 6.74 (t, J=9.0 Hz, 1H), 5.99 (d, J=5.4 Hz, 1H), 5.86 (d, J=5.7 Hz, 1H), 4.98-4.92 (m, 1H), 2.28-2.21 (m, 1H), 1.37-1.30 (m, 8H), 0.69-0.61 (m, 1H), 0.48-0.43 (m, 1H); $^{19}$F NMR (282 MHz, CDCl$_3$) δ –117.4.

Butanoyloxymethyl (1 aR,7bS)-5-fluoro-2-hydroxy-1a,7b-dihydro-1H-cyclopropa[c][1,2]benzoxaborinine-4-carboxylate (Compound 26)

26

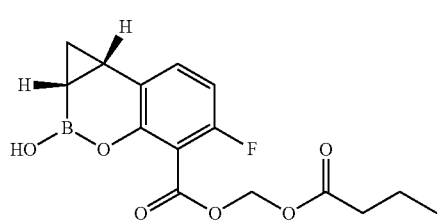 [SMILES: CCCC(=O)OCOC(=O)c1c(F)ccc2c1OB(O)[C@@H]1C[C@H]21]

LCMS: 340.0 [M+H$_2$O]$^+$; $^1$H NMR (300 MHz, CDCl$_3$) δ 7.27 (t, J=6.0 Hz, 1H), 6.67 (t, J=9.0 Hz, 1H), 5.94 (d, J=3.0 Hz, 1H), 5.87 (d, J=3.0 Hz, 1H), 2.41-2.36 (m, 2H), 2.30-2.17 (m, 1H), 1.73-1.61 (m, 2H), 1.30-1.25 (m, 1H), 0.94 (t, J=7.5 Hz, 3H), 0.67-0.57 (m, 1H), 0.46-0.38 (m, 1H); $^{19}$F (CDCl$_3$, 282 MHz) δ –117.6.

Cyclopropoxycarbonyloxymethyl (1 aR,7bS)-5-fluoro-2-hydroxy-1a,7b-dihydro-1H-cyclopropa[c][1,2]benzoxaborinine-4-carboxylate (Compound 27)

27

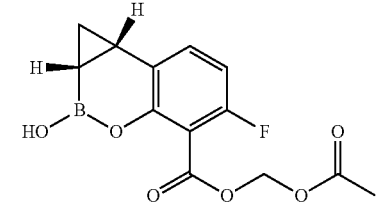 [SMILES: CC(=O)OCOC(=O)c1c(F)ccc2c1OB(O)[C@@H]1C[C@H]21]

LCMS: 338.0 [M+H$_2$O]; $^1$H NMR (300 MHz, CDCl$_3$) δ 7.14 (t, J=6.0 Hz, 1H), 6.53 (t, J=9.0 Hz, 1H), 5.79 (d, J=3.0 Hz, 1H), 5.69 (d, J=3.0 Hz, 1H), 2.30-2.17 (m, 1H), 1.78-1.60 (m, 1H), 1.16-1.00 (m, 2H), 1.00-0.85 (m, 2H), 0.58-0.60 (m, 1H), 0.48-0.42 (m, 1H); $^{19}$F (CDCl$_3$, 282 MHz) δ –117.6.

Acetoxymethyl (1 aR,7bS)-5-fluoro-2-hydroxy-1a,7b-dihydro-1H-cyclopropa[c][1,2]benzoxaborinine-4-carboxylate (Compound 28)

28

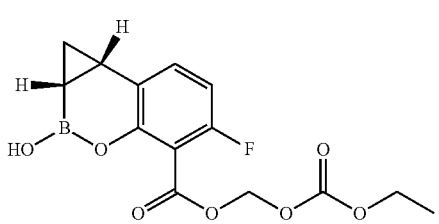 [SMILES: CCOC(=O)OCOC(=O)c1c(F)ccc2c1OB(O)[C@@H]1C[C@H]21]

LCMS: 317.0 [M+Na]$^+$; $^1$H NMR (300 MHz, CDCl$_3$) δ 7.14 (t, J=6.0 Hz, 1H), 6.53 (t, J=9.0 Hz, 1H), 5.79 (d, J=3.0 Hz, 1H), 5.69 (d, J=3.0 Hz, 1H), 2.30-2.17 (m, 1H), 2.17 (s, 3H), 1.30-1.25 (m, 1H), 0.58-0.60 (m, 1H), 0.48-0.42 (m, 1H); $^{19}$NMR (CDCl$_3$, 282 MHz) δ –117.4.

Ethoxycarbonyloxymethyl (1 aR,7bS)-5-fluoro-2-hydroxy-1a,7b-dihydro-1H-cyclopropa[c][1,2]benzoxaborinine-4-carboxylate (Compound 29)

29

LCMS: 646.7 [2M−H]⁻; ¹H NMR (300 MHz, CDCl₃) δ 7.14 (t, J=6.0 Hz, 1H), 6.53 (t, J=9.0 Hz, 1H), 5.79 (d, J=3.0 Hz, 1H), 5.69 (d, J=3.0 Hz, 1H), 4.08 (q, J=6.0 Hz, 1H), 2.04-1.98 (m, 1H), 1.41 (t, J=3.0 Hz, 3H), 1.20-1.12 (m, 1H), 0.51-0.41 (m, 1H), 0.27-0.21 (m, 1H); ¹⁹F NMR (CDCl₃, 282 MHz) δ −117.2.

Cyclohexoxycarbonyloxymethyl (1aR,7bS)-5-fluoro-2-hydroxy-1a,7b-dihydro-1H-cyclopropa[c][1,2]benzoxaborinine-4-carboxylate (Compound 30)

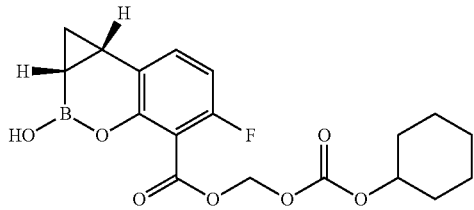 [SMILES: O=C(OCOC(=O)c1c(F)ccc2c1OB(O)[C@@H]1C[C@H]21)OC1CCCCC1]

30

LCMS: 754.7 [2M−H]⁻; ¹H NMR (300 MHz, CDCl₃) δ 7.33 (dd, J₁=15.0 Hz, J₂=8.7 Hz, 1H), 6.72 (t, J=8.4 Hz, 1H), 5.98 (d, J=6.0 Hz, 1H), 5.87 (d, J=6.0 Hz, 1H), 4.72-4.65 (m, 1H), 2.25-2.19 (m, 2H), 1.76-1.73 (m, 2H), 1.56-1.45 (m, 3H), 1.42-1.20 (m, 4H), 0.67-0.61 (m, 1H), 0.48-0.43 (m, 1H); ¹⁹F NMR (CDCl₃, 282 MHz) δ −117.6.

[2-(dimethylamino)-2-oxo-ethyl](1aR,7bS)-5-fluoro-2-hydroxy-1a,7b-dihydro-1H-cyclopropa[c][1,2]benzoxaborinine-4-carboxylate (Compound 31)

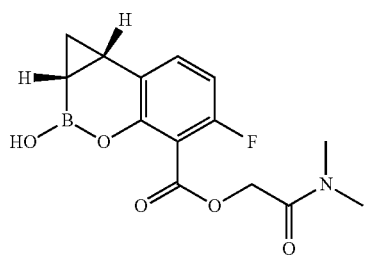 [SMILES: CN(C)C(=O)COC(=O)c1c(F)ccc2c1OB(O)[C@@H]1C[C@H]21]

31

LCMS: 308.0 [M+H]⁺; ¹H NMR (300 MHz, CDCl₃) δ 7.34 (dd, J=8.4 and 6.5 Hz, 1H), 6.71 (t, J=9.0 Hz, 1H), 4.39 (d, J=13.8 Hz, 1H), 4.24 (d, J=13.8 Hz, 1H), 3.10 (s, 3H), 3.01 (s, 3H), 2.21-2.15 (m, 1H), 1.37-1.30 (m, 1H), 0.69-0.61 (m, 1H), 0.48-0.43 (m, 1H); ¹⁹F NMR (282 MHz, CDCl₃) δ −117.4.

Oxetan-3-yloxycarbonyloxymethyl (1aR,7bS)-5-fluoro-2-hydroxy-1a,7b-dihydro-1H-cyclopropa[c][1,2]benzoxaborinine-4-carboxylate (Compound 32)

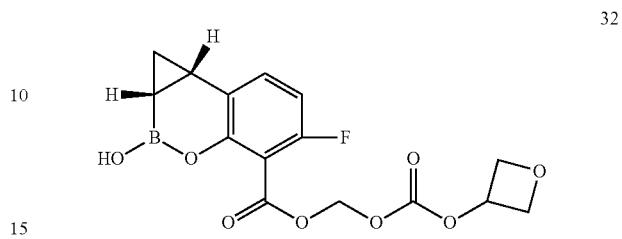

32

LCMS: 351.0 [M−H₂O]⁻; ¹H NMR (300 MHz, CDCl₃) δ 7.36 (dd, J₁=15.0 Hz, J₂=8.7 Hz, 1H), 6.74 (t, J=8.4 Hz, 1H), 6.00 (d, J=6.0 Hz, 1H), 5.90 (d, J=6.0 Hz, 1H), 5.51-5.44 (m, 1H), 4.94-4.89 (m, 1H), 4.79-4.70 (m, 1H), 2.04-1.98 (m, 1H), 1.41 (t, J=3.0 Hz, 3H), 1.20-1.12 (m, 1H), 0.51-0.41 (m, 1H), 0.27-0.21 (m, 1H); ¹⁹F NMR (CDCl₃, 282 MHz) δ −117.6.

(5-Methyl-2-oxo-1,3-dioxol-4-yl)methyl (1aR,7bS)-5-fluoro-2-hydroxy-1a,7b-dihydro-1H-cyclopropa[c][1,2]benzoxaborinine-4-carboxylate (Compound 33)

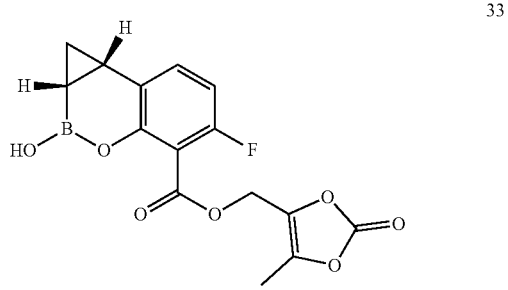

33

LCMS: 352.0 [M+H₂O]⁺; ¹H NMR (300 MHz, CDCl₃) δ 7.34 (t, J=6.0 Hz, 1H), 6.73 (t, J=9.0 Hz, 1H), 5.08 (s, 2H), 2.22 (s, 3H), 2.30-2.17 (m, 1H), 1.41-1.31 (m, 1H), 0.67-0.58 (m, 1H), 0.46-0.38 (m, 1H); ¹⁹F NMR (CDCl₃, 282 MHz) δ −117.5.

1-Ethoxycarbonyloxyethyl (1aR,7bS)-5-fluoro-2-hydroxy-1a,7b-dihydro-1H-cyclopropa[c][1,2]benzoxaborinine-4-carboxylate (Compound 34)

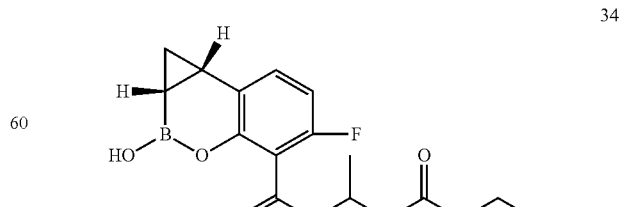

34

LCMS: 356.0 [M+H₂O]; ¹H NMR (300 MHz, CDCl₃) δ 7.34-7.27 (m, 1H), 6.73-6.68 (m, 1H), 6.12-5.96 (m, 1H), 4.27-4.23 (m, 2H), 2.22-2.17 (m, 1H), 1.36 (t, J=6.0 Hz, 3H), 1.41-1.31 (m, 1H), 0.67-0.58 (m, 1H), 0.46-0.38 (m, 1H); $^{19}$F NMR (CDCl$_3$, 282 MHz) δ −117.6, −117.8.

(2-Ethoxy-2-oxo-ethoxy)carbonyloxymethyl (1aR, 7bS)-5-fluoro-2-hydroxy-1a,7b-dihydro-1H-cyclopropa[c][1,2]benzoxaborinine-4-carboxylate (Compound 35)

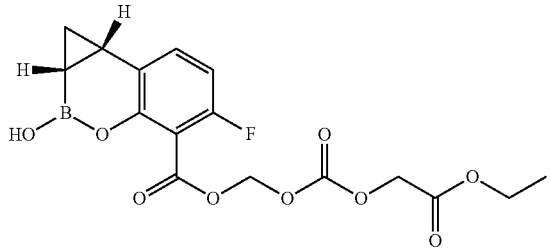

LC-MS: 382.8 [M+H]$^+$; $^1$H NMR (300 MHz, CDCl$_3$) δ 7.33 (dd, J$_1$=6.0, J$_2$=3.0 Hz, 1H), 6.73 (t, J=9.0 Hz, 1H), 5.59 (d, J=3.0 Hz, 1H), 5.53 (d, J=3.0 Hz, 1H), 4.41 (s, 2H), 4.29-4.22 (m, 2H), 2.26-2.21 (m, 1H), 1.38-1.33 (m, 1H), 1.30 (t, J=3.0 Hz, 3H), 0.68-0.63 (m, 1H), 0.49-0.45 (m, 1H); $^{19}$F NMR (CDCl$_3$, 282 MHz) δ −117.8.

2-Methoxyethoxycarbonyloxymethyl (1aR,7bS)-5-fluoro-2-hydroxy-1a,7b-dihydro-1H-cyclopropa[c][1,2]benzoxaborinine-4-carboxylate (Compound 36)

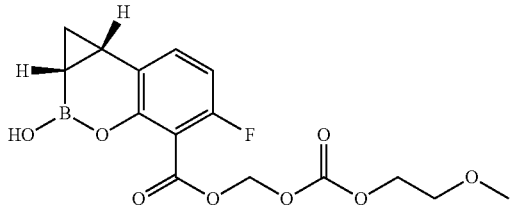 [SMILES: COCCOC(=O)OCOC(=O)c1c(F)ccc2c1OB(O)[C@@H]1C[C@H]21]

LCMS: 355.0 [M+H]$^+$; $^1$H NMR (300 MHz, CDCl$_3$) δ 7.34 (dd, J$_1$=6.0, J$_2$=3.0 Hz, 1H), 6.73 (t, J=9.3 Hz, 1H), 5.99 (d, J=6.0 Hz, 1H), 5.89 (d, J=6.0 Hz, 1H), 4.39-4.36 (m, 2H), 3.66-3.64 (m, 2H), 3.39 (s, 3H), 2.03-1.97 (m, 1H), 1.40-1.33 (m, 1H), 0.66-0.60 (m, 1H), 0.47-0.43 (m, 1H); $^{19}$F NMR (CDCl$_3$, 282 MHz) δ −116.6.

Tetrahydropyran-4-yloxycarbonyloxymethyl (1aR, 7bS)-5-fluoro-2-hydroxy-1a,7b-dihydro-1H-cyclopropa[c][1,2]benzoxaborinine-4-carboxylate (Compound 37)

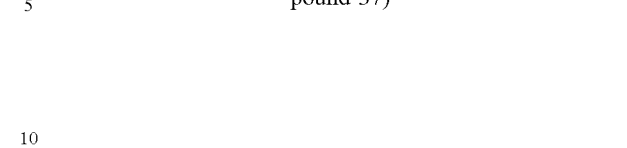

LCMS: 759.7 [2M+H]$^+$; $^1$H NMR (300 MHz, CDCl$_3$) δ 7.34 (dd, J$_1$=15.0 Hz, J$_2$=8.7 Hz, 1H), 6.73 (t, J=8.4 Hz, 1H), 5.99 (d, J=6.0 Hz, 1H), 5.89 (d, J=6.0 Hz, 1H), 4.91-4.86 (m, 1H), 3.98-3.89 (m, 2H), 3.58-3.51 (m, 2H), 2.25-2.19 (m, 1H), 2.03-1.97 (m, 2H), 1.83-1.71 (m, 2H), 1.40-1.33 (m, 1H), 0.68-0.62 (m, 1H), 0.47-0.44 (m, 1H); $^{19}$F NMR (CDCl$_3$, 282 MHz) δ −117.6.

[(1aR,7bS)-5-Fluoro-2-hydroxy-1a,7b-dihydro-1H-cyclopropa[c][1,2]benzoxaborinine-4-carbonyl]oxymethyl (2R)-1-acetylpyrrolidine-2-carboxylate (Compound 38)

LCMS: 392.1 [M+H]$^+$; $^1$H NMR (300 MHz, CDCl$_3$) δ 7.14 (t, J=6.0 Hz, 1H), 6.53 (t, J=9.0 Hz, 1H), 5.79 (d, J=3.0 Hz, 1H), 5.69 (d, J=3.0 Hz, 1H), 4.53-4.49 (m, 1H), 3.70-3.60 (m, 1H), 3.58-3.54 (m, 1H), 2.30-2.32 (m, 1H), 2.21-2.01 (m, 4H), 2.12 (s, 3H), 1.30-1.25 (m, 1H), 0.58-0.60 (m, 1H), 0.48-0.42 (m, 1H); $^{19}$F NMR (CDCl$_3$, 282 MHz) δ −119.3.

Tetrahydropyran-4-carbonyloxymethyl (1aR,7bS)-5-fluoro-2-hydroxy-1a,7b-dihydro-1H-cyclopropa[c][1,2]benzoxaborinine-4-carboxylate (Compound 39)

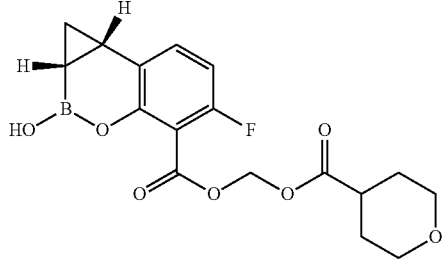 [SMILES: O=C(OCOC(=O)C1CCOCC1)c1c(F)ccc2c1OB(O)[C@@H]1C[C@H]21]

LCMS: 728.0 [2M+H]⁺; ¹H NMR (300 MHz, CDCl₃) δ 7.33 (dd, J₁=6.0, J₂=3.0 Hz, 1H), 6.73 (t, J=Hz, 1H), 5.59 (d, J=6.0 Hz, 1H), 5.53 (d, J=6.0 Hz, 1H), 3.95-3.91 (m, 2H), 3.46-3.37 (m, 2H), 2.64-2.59 (m, 1H), 2.26-2.21 (m, 1H), 1.72-1.60 (m, 4H), 1.38-1.33 (m, 1H), 0.67-0.58 (m, 1H), 0.46-0.38 (m, 1H); ¹⁹F NMR (CDCl₃, 282 MHz) δ −114.6.

2-Acetoxyethoxycarbonyloxymethyl (1 aR,7bS)-5-fluoro-2-hydroxy-1a,7b-dihydro-1H-cyclopropa[c][1,2]benzoxaborinine-4-carboxylate (Compound 40)

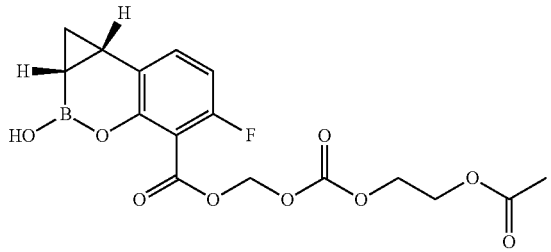

LCMS: 763.90[2M+H]⁺; ¹H NMR (300 MHz, CDCl₃) δ 7.14 (t, J=6.0 Hz, 1H), 6.53 (t, J=9.0 Hz, 1H), 5.79 (d, J=3.0 Hz, 1H), 5.69 (d, J=3.0 Hz, 1H), 4.41 (t, J=3.9 Hz, 1H), 4.32 (t, J=3.9 Hz, 1H), 2.30-2.17 (m, 1H), 1.30-1.25 (m, 1H), 0.58-0.60 (m, 1H), 0.48-0.42 (m, 1H); ¹⁹F NMR (CDCl₃, 282 MHz) δ −116.9.

[2-(Dimethylamino)-2-oxo-ethoxy]carbonyloxymethyl (1 aR,7bS)-5-fluoro-2-hydroxy-1a,7b-dihydro-1H-cyclopropa[c][1,2]benzoxaborinine-4-carboxylate (Compound 41)

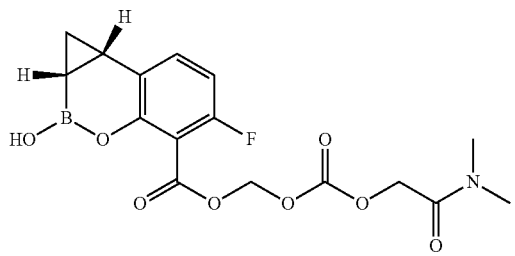

LCMS: 399.05 [M+H₂O]⁺; ¹H NMR (300 MHz, CDCl₃) δ 7.31 (dd, J₁=6.0, J₂=3.0 Hz, 1H), 6.71 (t, J=9.3 Hz, 1H), 6.03 (d, J=12.0 Hz, 1H), 5.94 (d, J=12.0 Hz, 1H), 4.81 (s, 2H), 3.02 (s, 3H), 2.98 (s, 3H), 2.23-2.17 (m, 1H), 1.40-1.33 (m, 1H), 0.66-0.60 (m, 1H), 0.47-0.43 (m, 1H); ¹⁹F NMR (CDCl₃, 282 MHz) δ −118.2.

(2-Acetoxyacetyl)oxymethyl (1 aR,7bS)-5-fluoro-2-hydroxy-1a,7b-dihydro-1H-cyclopropa[c][1,2]benzoxaborinine-4-carboxylate (Compound 42)

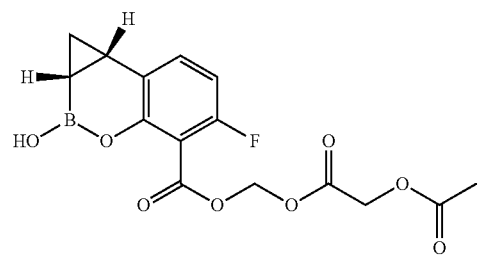 [SMILES: CC(=O)OCC(=O)OCOC(=O)c1c(F)ccc2c1OB(O)[C@@H]1C[C@H]21]

LCMS: 703.90 [2M+H]⁺; ¹H NMR (300 MHz, CDCl₃) δ 7.33 (t, J=6.0 Hz, 1H), 6.72 (t, J=9.0 Hz, 1H), 6.01 (d, J=3.0 Hz, 1H), 5.94 (d, J=3.0 Hz, 1H), 4.70 (s, 1H), 2.21 (s, 3H), 2.23-2.19 (m, 1H), 1.41-1.31 (m, 1H), 0.67-0.58 (m, 1H), 0.46-0.38 (m, 1H). ¹⁹F NMR (CDCl₃, 282 MHz) δ −117.8.

(2-Methoxyacetyl)oxymethyl (1aR,7bS)-5-fluoro-2-hydroxy-1a,7b-dihydro-1H-cyclopropa[c][1,2]benzoxaborinine-4-carboxylate (Compound 43)

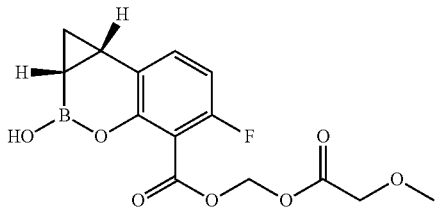 [SMILES: COCC(=O)OCOC(=O)c1c(F)ccc2c1OB(O)[C@@H]1C[C@H]21]

LCMS: 647.7 [2M+H]⁺; ¹H NMR (300 MHz, CDCl₃) δ 7.33 (t, J=6.0 Hz, 1H), 6.72 (t, J=9.0 Hz, 1H), 6.04 (d, J=3.0

Hz, 1H), 6.01 (d, J=3.0 Hz, 1H), 4.11 (s, 3H), 3.47 (s, 2H), 2.30-2.17 (m, 1H), 1.35-1.34 (m, 2H), 0.67-0.58 (m, 1H), 0.46-0.38 (m, 1H); $^{19}$F NMR (CDCl$_3$, 282 MHz) δ −116.9.

Example 26. Potentiation of Aztreonam

The potency and spectrum of β-lactamase inhibitors (BLIs) was determined by assessing their aztreonam potentiation activity in a dose titration potentiation assay using strains of various bacteria that are resistant to aztreonam due to expression of various β-lactamases. Aztreonam is a monobactam antibiotic and is hydrolyzed by the majority of beta-lactamases that belong to class A or C (but not class B or D). The potentiation effect was observed as the ability of BLI compounds to inhibit growth in the presence of sub-inhibitory concentration of aztreonam. MICs of test strains varied from 64 µg/mL to ≥128 µg/mL. Aztreonam was present in the test medium at 4 µg/mL. Compounds were tested at concentrations up to 40 µg/mL. In this assay, potency of compounds was reported as the minimum concentration of BLI required to inhibit growth of bacteria in the presence of 4 µg/mL of aztreonam (MPC$_{@4}$). Table 2 summarizes the BLI potency of aztreonam potentiation (MPC$_{@4}$) for various strains overexpressing class A (ESBL and KPC), and class C beta-lactamases. Aztreonam MIC for each strain is also shown.

TABLE 2

Table 2. Activity of BLIs to potentiate aztreonam against strains expressing class A and class C enzymes.

| | Aztreonam MIC (µg/mL) | | | | | | | |
|---|---|---|---|---|---|---|---|---|
| Compound | >128 AZT MPC4 CTX-M-14 KP1005 | >128 AZT MPC4 CTX-M-15 KP1009 | >128 AZT MPC4 SHV-5 ec308 | 64 AZT MPC4 SHV-12 KP1010 | 128 AZT MPC4 TEM-10 ec302 | >128 AZT MPC4 KPC-2 KP1004 | 64 AZT MPC4 ECL1002 | >128 AZT MPC4 CMY-6 EC1010 |
| 1 | X | X | X | X | X | X | X | X |
| 2 | X | X | X | X | X | X | X | X |
| 3 | X | X | X | X | X | X | X | X |
| 4 | X | X | X | X | X | X | X | X |
| 5 | X | X | X | X | X | X | Y | X |
| 6 | Z | Z | Z | Z | Z | Z | Z | Z |
| 7 | Z | Z | Z | Z | Z | Y | Z | Z |
| 8 | X | X | X | X | X | X | X | X |
| 9 | Y | Y | Y | X | Y | X | Y | X |
| 10 | X | X | X | X | X | X | X | X |
| 11 | X | X | X | X | X | X | X | X |
| 12 | X | X | X | X | X | X | X | X |
| 13 | X | X | X | X | X | X | X | X |
| 14 | Z | Y | Y | X | Y | X | Y | X |
| 15 | X | X | X | X | X | X | X | X |
| 16 | X | X | X | X | X | X | X | X |
| 17 | X | X | X | X | X | X | X | X |
| 18 | X | X | X | X | X | X | Y | X |
| 19 | X | X | X | X | X | X | X | X |
| 20 | Y | Y | Y | X | X | X | Y | Y |
| 21 | X | X | X | X | X | X | X | X |
| 22 | Y | Y | Y | X | X | X | X | X |
| 23 | X | X | X | X | X | X | X | X |
| 24 | Y | X | X | X | X | X | X | X |
| Tazobactam | Y | Y | Y | X | X | Z | Z | Y |
| Clavulanic Acid | X | X | X | X | X | Z | Z | Z |

X = MPC$_{@4}$ ≤5 µg/mL
Y = 5 µg/mL < MPC$_{@4}$ ≤ 20 µg/mL
Z = MPC$_{@4}$ >20 µg/mL

Example 27. Potentiation of Tigemonam

Selected β-lactamase inhibitors were also tested for their ability to potentiate the monobactam tigemonam. The potentiation effect was observed as the ability of BLI compounds to inhibit growth in the presence of sub-inhibitory concentration of tigemonam. MICs of test strains varied from 16 µg/mL to >64 µg/mL. Tigemonam was present in the test medium at 4 µg/mL. Compounds were tested at concentrations up to 40 µg/mL. In this assay potency of compounds was reported as the minimum concentration of BLI required to inhibit growth of bacteria in the presence of 4 µg/mL of aztreonam (MPC$_{@4}$). Table 3 summarizes the BLI potency of tigemonam potentiation (MPC$_{@4}$) for various strains overexpressing class A (ESBL) and class C beta-lactamases. Tigemonam MIC for each strain is also shown.

TABLE 3

Table 3. Activity of BLIs to potentiate tigemonam against strains expressing class A and class C enzymes.

| | Tigemonam MIC (µg/mL) | | | | | | |
|---|---|---|---|---|---|---|---|
| Compound | >64 TIG MPC$_4$ CTX-M-14 KP1005 | >64 TIG MPC$_4$ CTX-M-15 KP1009 | >64 TIG MPC$_4$ SHV-5 ec308 | >64 TIG MPC$_4$ SHV-12 KP1010 | >64 TIG MPC$_4$ TEM-10 ec302 | 32 TIG MPC4 ECL1002 | 16 TIG MPC4 CMY-6 EC1010 |
| 1 | X | X | X | X | X | X | X |
| 2 | X | X | X | X | X | X | X |
| 3 | X | X | X | X | X | X | X |
| 4 | X | X | X | X | X | X | X |
| 5 | X | X | X | X | X | X | X |
| 6 | Z | Z | Z | Z | Z | Y | Z |
| 7 | Z | Z | Z | Z | Z | Z | Z |
| 8 | Y | X | X | X | Y | X | X |
| 9 | Z | Z | Z | Y | Z | X | X |
| 10 | Y | X | X | X | X | X | X |
| 11 | Y | X | X | X | Y | X | X |
| 12 | X | X | X | X | X | X | X |
| 13 | X | X | X | X | X | X | X |
| 14 | Z | Z | Z | Y | Z | X | X |
| 15 | X | X | X | X | Y | X | X |
| 16 | X | X | X | X | X | X | X |
| 17 | Y | X | X | X | X | X | X |
| 18 | Y | Y | Y | X | Y | X | X |
| 19 | X | X | X | X | X | X | X |
| 20 | Z | Z | Z | Y | Z | X | X |
| 21 | X | X | X | X | X | X | X |
| 22 | Y | Y | Y | Y | Y | X | X |
| 23 | Y | X | Y | X | Z | X | X |
| 24 | Y | X | X | X | Y | X | X |
| Tazobactam | Y | Y | X | X | X | Y | X |
| Clavulanic Acid | X | X | X | X | X | Z | Z |

X = MPC$_{@4}$ ≤ 5 µg/mL
Y = 5 µg/mL < MPC$_{@4}$ ≤ 20 µg/mL
Z = MPC$_{@4}$ > 20 µg/mL

Example 28. Potentiation of Biapenem

β-lactamase inhibitors were also tested for their ability to potentiate the carbapenem biapenem against strains producing class A (KPC) and class D (OXA-48) carbapenemases. The potentiation effect was observed as the ability of BLI compounds to inhibit growth in the presence of a sub-inhibitory concentration of biapenem. Biapenem MIC of test strains were 16-32 µg/mL. Biapenem was present in the test medium at 1 µg/mL. Compounds were tested at concentrations up to 40 µg/mL. In this assay potency of compounds was reported as the minimum concentration of BLI required to inhibit growth of bacteria in the presence of 1 µg/mL of biapenem (MPC$_{@1}$). Table 4 summarizes the BLI potency of biapenem potentiation (MPC$_{@1}$) for two strains overexpressing class A (KPC) and class D (OXA-48) carbapenemases. Biapenem MIC for each strain is also shown.

TABLE 4

Table 4. Activity of BLIs to potentiate biapenem against strains expressing class A (KPC) or class D (OXA-48) carbapenemases.

| | Biapenem MIC (µg/mL) | | | |
|---|---|---|---|---|
| Compound | 32 BPM MPC$_1$ KP1004 KPC-2 | 16 BPM MPC$_1$ OXA-48 KP1086 | 16 BPM MPC$_1$ KP1081 NDM-1 | 16 BPM MPC$_1$ KP1054 VIM-1 |
| 1 | X | X | X | X |
| 2 | X | X | X | Y |
| 3 | X | X | X | X |
| 4 | X | X | X | X |
| 5 | X | X | X | Y |
| 6 | Y | Z | Z | Z |
| 7 | X | Z | Y | Y |
| 8 | X | X | X | X |
| 9 | X | X | Z | Z |
| 10 | X | X | X | X |
| 11 | X | X | X | Y |
| 12 | X | X | X | Z |
| 13 | X | X | X | X |
| 14 | X | X | X | Y |
| 15 | X | X | X | Z |
| 16 | X | X | X | X |
| 17 | X | X | X | X |
| 18 | X | X | X | Y |

TABLE 4-continued

Table 4. Activity of BLIs to potentiate biapenem against strains expressing class A (KPC) or class D (OXA-48) carbapenemases.

| | Biapenem MIC (µg/mL) | | | |
|---|---|---|---|---|
| Compound | 32 BPM MPC$_1$ KP1004 KPC-2 | 16 BPM MPC$_1$ OXA-48 KP1086 | 16 BPM MPC$_1$ KP1081 NDM-1 | 16 BPM MPC$_1$ KP1054 VIM-1 |
| 19 | X | X | X | X |
| 20 | X | X | Y | Y |
| 21 | X | X | X | X |
| 22 | X | X | X | X |
| 23 | X | Y | X | X |
| 24 | X | X | Y | Y |
| Tazobactam | Z | Y | Z | Z |
| Clavulanic Acid | Y | Z | Z | Z |

X = MPC$_{@1}$ ≤ 5 µg/mL
Y = 5 µg/mL < MPC$_{@1}$ ≤ 20 µg/mL
Z = MPC$_{@1}$ > 20 µg/mL

Example 29. Potentiation of Meropenem

β-lactamase inhibitors were also tested for their ability to potentiate the carbapenem meropenem against strains of *Acinetobacter baumannii* producing class D (OXA-23 and OXA-72) carbapenemases. The potentiation effect was observed as the ability of BLI compounds to inhibit growth in the presence of a sub-inhibitory concentration of meropenem. Meropenem MIC of test strains were 32 to >64 µg/mL. Meropenem was present in the test medium at 8 µg/mL. Compounds were tested at concentrations up to 20 µg/mL. In this assay potency of compounds was reported as the minimum concentration of BLI required to inhibit growth of bacteria in the presence of 8 µg/mL of meropenem (MPC$_{@8}$). Table 5 summarizes the BLI potency of meropenem potentiation (MPC$_{@8}$) for two strains overexpressing OXA-72 and OXA-23 carbapenemases. Meropenem MIC for each strain is also shown.

TABLE 5

Table 5. Activity of BLIs to potentiate meropenem against strains expressing class D carbapenemases from *Acinetobacter baumannii*

| | Meropenem MIC (µg/mL) | |
|---|---|---|
| Compound | >64 MPM MPC$_8$ AB1053 OXA-72 | 32 MPM MPC$_8$ AB1054 OXA-23 |
| 1 | X | X |
| 2 | X | X |
| 3 | X | X |
| 4 | X | X |
| 5 | X | Y |
| 6 | Z | Z |
| 7 | Z | Z |
| 8 | X | X |
| 9 | Y | Z |
| 10 | Y | X |
| 11 | X | X |
| 12 | X | Y |
| 13 | X | X |
| 14 | Z | X |
| 15 | Z | X |
| 16 | Y | X |
| 17 | Y | X |
| 18 | Z | X |
| 19 | Y | X |
| 20 | Z | Y |
| 21 | Z | X |
| 22 | X | X |
| 23 | Z | X |
| 24 | Y | Y |
| Tazobactam | ND | ND |
| Clavulanic Acid | ND | ND |

X = MPC$_{@1}$ ≤ 5 µg/mL
Y = 5 µg/mL < MPC$_{@1}$ ≤ 20 µg/mL
Z = MPC$_{@1}$ > 20 µg/mL
ND = Not determined.

Example 30. Inhibitory Activity $K_i$ values of inhibition of purified class A, C and D enzymes were determined spectrophotometrically using nitrocefin as reporter substrate. Purified enzymes were mixed with various concentrations of inhibitors in reaction buffer and incubated for 10 min at room temperature. Nitrocefin was added and substrate cleavage profiles were recorded at 490 nm every 10 sec for 10 min. The results of these experiments are presented in Table 6. These experiments confirmed that the described compounds are inhibitors with a broad-spectrum of activity towards various β-lactamases.

TABLE 6

Table 6. Activity of BLIs (Ki, uM) to inhibit cleavage of nitrocefin by purified class A, C and D enzymes

| Compd. | Ki (CTX-M-14, NCF), uM | Ki (SHV-12, NCF), uM | Ki (TEM-10, NCF), uM | Ki (KPC-2, NCF), uM | Ki (P99, NCF), uM | Ki (Pa-AmpC, NCF), uM | Ki (OXA-48, NCF), uM | Ki (OXA-23, NCF), uM | Ki (VIM-1, NCF), uM |
|---|---|---|---|---|---|---|---|---|---|
| 1 | X | ND | X | X | X | X | X | X | X |
| 2 | X | ND | X | X | X | X | X | X | Y |
| 3 | X | ND | X | X | X | X | X | X | X |
| 4 | X | ND | X | X | X | X | X | X | Y |
| 5 | X | ND | X | X | Y | Z | X | X | Z |
| 6 | Z | Y | Y | X | X | X | X | Y | Y |
| 7 | X | Y | Y | X | X | X | X | X | X |
| 8 | X | ND | X | X | X | X | X | X | Y |
| 9 | ND | ND | X | X | X | Y | X | X | Z |
| 10 | X | X | X | X | X | X | X | X | X |
| 11 | X | X | X | X | X | X | X | X | Y |
| 12 | X | X | X | X | X | Y | X | X | Z |
| 13 | X | X | X | X | X | X | X | X | X |
| 14 | X | ND | X | X | X | X | X | X | Z |
| 15 | X | ND | X | X | X | X | X | X | Z |
| 16 | X | ND | X | X | X | X | X | X | X |
| 17 | X | ND | X | X | X | X | X | X | X |
| 18 | X | ND | X | X | Y | Y | X | Y | Y |
| 19 | X | ND | X | X | X | X | X | X | X |
| 20 | X | ND | X | Y | Z | Z | X | Y | Z |
| 21 | X | ND | X | Y | Y | Z | X | X | Y |
| 22 | X | ND | X | X | X | X | X | Z | X |
| 23 | X | ND | X | X | X | Y | X | X | Y |
| 24 | X | ND | X | X | X | X | X | X | Z |
| Tazobactam | X | X | X | Z | Z | Y | Y | Y | Z |
| Clavulanic Acid | X | X | X | Z | Z | Z | Z | Z | Z |

X = $K_i \leq 0.1$ μM
Y = $0.1$ μM $< K_i \leq 1$ μM
Z = $K_i > 1$ μM
ND = not determined $K_i$ values of inhibition of purified class B enzymes NDM-1 and IMP-1 were determined spectrophotometrically using imipenem as reporter substrate. Purified enzymes were mixed with various concentrations of inhibitors in reaction buffer and incubated for 10 min at room temperature. Imipenem was added and substrate cleavage profiles were recorded at 294 nm every 30 seconds for 30 minutes at 37° C. The results of these experiments are presented in Table 7. These experiments further confirmed that the described compounds have the ability to inhibit carbapenemase activity of metallo-beta-lactamases.

TABLE 7

Table 7. Activity of BLIs (Ki, uM) to inhibit cleavage of imipenem by purified class B NDM-1 and IMP-1 enzymes

| Compd. | Ki (NDM-1, IMI), uM | Ki (IMP-1, IMI), uM |
|---|---|---|
| 1 | X | X |
| 2 | Y | Z |
| 3 | X | X |
| 4 | Y | Z |
| 5 | Y | Z |
| 6 | Z | Z |
| 7 | X | X |
| 8 | ND | Z |
| 9 | Z | Z |
| 10 | X | Y |
| 11 | X | Y |
| 12 | Y | Z |
| 13 | X | Y |
| 14 | X | Z |
| 15 | Y | Z |
| 16 | X | X |
| 17 | X | X |
| 18 | X | Z |
| 19 | Y | Z |
| 20 | Z | ND |
| 21 | Y | ND |
| 22 | X | X |
| 23 | X | Z |
| 24 | Y | Z |
| Tazobactam | Z | Z |
| Clavulanic Acid | Z | Z |

X = $K_i \leq 0.1$ μM
Y = $0.1$ μM $< K_i \leq 1$ μM
Z = $K_i > 1$ μM

Example 31. Mexab-Oprm Dependent Efflux of BLIs

Efflux of BLIs from *Pseudomonas aeruginosa* by the MexAB-OprM efflux pump was also evaluated. The plasmid expressing the gene encoding KPC-2 was introduced into two strains of *P. aeruginosa*, PAM1032 and PAM1154 that overexpressed or lacked MexAB-OprM, respectively. Due to expression of KPC-2 both strains became resistant to biapenem. Biapenem is not affected by efflux in *P. aeruginosa* and both strains had the same biapenem MIC of 32

µg/ml. Potency of BLIs to potentiate biapenem in these strains was determined. Potency was defined as the ability of BLI to decrease MIC of biapenem 64-fold, from 32 µg/ml to 0.5 µg/ml, or MPC$_{64}$. The ratio of MPC$_{64}$ values for each BLI in PAM1032/KPC-2 (efflux proficient) and PAM1154/KPC-2 (efflux deficient) was determined to generate the Efflux Index (EI) as shown in Table 8.

TABLE 8

Table 8. MexAB-OprM Dependent Efflux of BLIs from *P. aeruginosa*

| Compound | PAM1032/<br>KPC-2<br>Biapenem<br>MPC64 | PAM1154/<br>KPC-2<br>Biapenem<br>MPC64 | EI |
| --- | --- | --- | --- |
| 1 | 2.5 | 1.25 | 2 |
| 2 | 2.5 | 1.25 | 2 |
| 3 | 5 | 2.5 | 2 |
| 4 | 2.5 | 2.5 | 1 |
| 5 | 20 | 10 | 2 |
| 6 | ND | ND | ND |
| 7 | ND | ND | ND |
| 8 | 2.5 | 2.5 | 1 |
| 9 | >10 | 1.25 | >8 |
| 10 | ND | ND | ND |
| 11 | ND | ND | ND |
| 12 | 2.5 | 1.25 | 2 |
| 13 | 2.5 | 2.5 | 1 |
| 14 | 40 | 1.25 | 32 |
| 15 | 5 | 1.25 | 4 |
| 16 | 1.25 | 0.3 | 4 |
| 17 | 20 | 5 | 4 |
| 18 | 5 | 0.3 | 16 |
| 19 | 5 | 1.25 | 4 |
| 20 | 5 | 5 | 1 |
| 21 | 1.25 | 1.25 | 1 |
| 22 | 20 | 10 | 2 |
| 23 | 20 | 20 | 1 |
| 24 | ND | ND | ND |

ND = not determined

These experiments demonstrated that the described compounds are effected by the MexAB-OprM efflux pump from *P. aeruginosa* to various degrees and that it was possible to overcome the MexAB-OprM mediated efflux.

Example 32: Stability of Compound 13 Prodrugs in Human Serum

The rate of hydrolysis for several prodrugs of 13 was evaluated in vitro by measuring their stability in human serum and human liver microsomes.

All serum stability experiments were conducted by aliquoting 10 µL of test compound at 500 µg/mL (10× final concentration) in 95:5 water:acetonitrile v/v into 1.5 mL Eppendorf tubes. Each tube was assigned to a specific timepoint: 0, 5, 10 or 30 minutes. The tubes were then warmed to 37° C. in a water bath along with human serum (Bioreclamations) in a separate tube. Serum esterase activity for each lot of serum used was established by assaying an unrelated ester prodrug as a control. To initiate the reaction, 90 µL of serum was added to tubes for all timepoints using a repeating-tip pipette, thereby bringing the final concentration of test compound to 50 µg/mL and the final concentration of acetonitrile to 0.5% v/v. At each timepoint, the reaction was halted and serum proteins precipitated through the addition of an equal volume of cold acetonitrile containing 25 µg/mL diclofenac as an internal standard. The mixture was vortexed then centrifuged for 5 minutes at 15,000 rpm. 50 µL of supernatant was then combined with 100 µL of water in an amber-glass HPLC vial containing a glass insert, and 10.0 µL of this mixture was injected on HPLC.

Sample analysis for serum stability experiments was conducted using an Agilent 1100 binary pump HPLC equipped with a diode array detector set to monitor absorbance at 286 nm (8 nm bandwidth). Separation was achieved on a Waters XBridge BEH Shield 2.1×50 mm column with 5 am particles and a Phenomenex Gemini guard column, using a flow rate of 400 µL/min with 0.1% trifluoroacetic acid in water for mobile phase A and 0.1% trifluoroacetic acid in methanol for mobile phase B. Initial conditions were 80% mobile phase A, 20% mobile phase B with a 6% per minute gradient to 80% B at 10 minutes, followed by re-equilibration at initial conditions. The samples were analyzed together with appropriate blanks in order to ensure specificity.

Chromatograms were checked for the appearance of active drug (compound 13) to ensure the test compound was converted to active. The rate of activation was determined by monitoring the concentration of test compound as follows. The peak area for the analyte was divided by the peak area for the internal standard to give an area ratio. The area ratio for each timepoint was divided by the area ratio for timepoint 0 to give the percent remaining at each timepoint. The natural logarithm of the percent remaining versus time was plotted using Microsoft Excel and fitted to a linear trendline. The half-life for each test compound was estimated by dividing the natural logarithm of 2 by the slope of the trendline. The percent remaining for each test compound and the calculated half-life is presented in Table 9 below.

TABLE 9

Table 9. Rate of activation of compound 13 prodrugs in human serum at a prodrug concentration of 50.0 µg/mL

| Compound # | % of initial area ratio at t = 0 min | % of initial area ratio at t = 5 min | % of initial area ratio at t = 10 min | % of initial area ratio at t = 30 min | Estimated half-life (minutes) (rounded to nearest integer value) |
| --- | --- | --- | --- | --- | --- |
| 32 | 100 | 86.8 | 77.2 | 38.7 | 21 |
| 33 | 100 | 48.4 | 15.4 | 0 | 4 |
| 39 | 100 | 69.3 | 59.4 | 41.1 | 26 |
| 42 | 100 | 29.1 | 8.1 | 0 | 3 |
| 43 | 100 | 58.6 | 34.5 | 2.9 | 6 |

Example 33: Stability of Compound 13 Prodrugs in Human Liver Microsomes (HLM)

All microsome stability experiments were conducted by diluting test compound to 2.00 µM (2× final concentration) in 50 mM pH 7.4 potassium phosphate buffer containing 3.3 mM MgCl$_2$. 50 µL of this solution was then aliquoted into 1.5 mL Eppendorf tubes, two per timepoint for four specific timepoints: 0, 5, 10 and 30 minutes. In the meantime, a 20.0 mg/mL solution of human liver microsomes (XenoTech, LLC) was diluted to 1.00 mg/mL (2× final concentration). Esterase activity for each lot of microsomes used was established by assaying an unrelated ester prodrug as a control. Both the Eppendorfs for each timepoint and the diluted liver microsomes were then warmed to 37° C. in a water bath. No cofactors (e.g. NADPH) were added to ensure that only hydrolytic reactions as opposed to reactions mediated by other cofactor-dependent enzymes (e.g. CYP450 enzymes) would take place.

To initiate the reaction, 50 μL of diluted human liver microsomes was added to tubes for all timepoints using a repeating-tip pipette, thereby bringing the final concentration of test compound to 1.00 μM and the final concentration of human liver microsomes to 0.500 mg/mL. At each timepoint, the reaction was halted and proteins precipitated through the addition of 200 μL of 10:45:45 water:methanol:acetonitrile v/v/v containing an unrelated ester prodrug at 250 ng/mL as an internal standard. The resulting mixture was vortexed and centrifuged for 5 minutes at 15,000 rpm, then 100 μL of supernatant was transferred to a 96-well plate and combined with 500 μL of water preparatory to analysis on LC-MS.

Sample analysis for microsome stability experiments was conducted using a 20.0 μL injection on a LEAP PAL autosampler with Agilent 1100 binary pump HPLC coupled to an AB Sciex 3200 QTrap mass spectrometer. Separation was achieved on a Waters XBridge BEH Shield 2.1×50 mm column with 5 am particles and a Phenomenex Gemini guard column, using a flow rate of 400 μL/min with 0.1% formic acid in water for mobile phase A and 0.1% formic acid in acetonitrile for mobile phase B. The gradient was adjusted as needed to give the desired resolution and run time. Detection was in positive mode; source parameters and parent-daughter ion selection criteria were chosen as needed for each compound to achieve an appropriate limit of detection and signal-to-noise ratio. The samples were analyzed together with appropriate blanks in order to ensure specificity.

The rate of hydrolysis for each prodrug was determined by monitoring the concentration of test compound as follows. The peak area for the analyte was divided by the peak area for the internal standard to give an area ratio. The area ratio for each of the two replicates at each timepoint was divided by the area ratio for timepoint 0 to give the percent remaining at each timepoint. The natural logarithm of the percent remaining versus time for all replicates was plotted using Microsoft Excel and fitted to a linear trendline. The half-life for each test compound was estimated by dividing the natural logarithm of 2 by the slope of the trendline. The percent remaining for each test compound and the calculated half-life is presented in Table 10 below.

TABLE 10

Table 10. Rate of activation of compound 13 prodrugs in 0.500 mg/mL human liver microsomes at a prodrug concentration of 1.00 μM

| Compound # | Average % of initial area ratio at t = 0 min | Average % of initial area ratio at t = 5 min | Average % of initial area ratio at t = 10 min | Average % of initial area ratio at t = 30 min | Estimated half-life (minutes) (rounded to nearest integer value) |
|---|---|---|---|---|---|
| 26 | 100 | 73.4 | 55.9 | 11.9 | 10 |
| 27 | 100 | 91.4 | 80.4 | 25.0 | 14 |
| 28 | 100 | 50.8 | 23.3 | 19.6 | 15 |
| 42 | 100 | 27.1 | 10.3 | 0.4 | 4 |
| 43 | 100 | 64.4 | 44.6 | 0.6 | 4 |

What is claimed is:

1. A compound having the structure

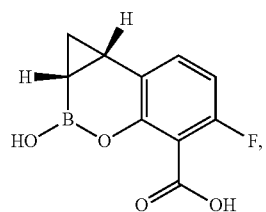 [SMILES: O=C(O)c1c(F)ccc2c1OB(O)[C@@H]1C[C@H]21]

or a pharmaceutically acceptable salt thereof.

2. The compound claim 1, wherein the pharmaceutically acceptable salt is an alkaline metal salt or an ammonium salt.

3. The compound of claim 2, wherein the pharmaceutically acceptable salt is a sodium salt.

4. A pharmaceutical composition comprising a compound of claim 1 or a pharmaceutically acceptable salt thereof, and a pharmaceutically acceptable excipient.

5. The pharmaceutical composition of claim 4, further comprising an additional medicament.

6. The pharmaceutical composition of claim 5, wherein the additional medicament is a β-lactam antibacterial agent.

7. The pharmaceutical composition of claim 6, wherein the β-lactam antibacterial agent is Meropenem, or a pharmaceutically acceptable salt thereof.

8. The pharmaceutical composition of claim 6, wherein the β-lactam antibacterial agent is Ceftibuten, or a pharmaceutically acceptable salt thereof.

9. A method of treating a bacterial infection caused by β-lactam antibacterial agent-resistant enterobacteriaceae, comprising administering a therapeutically effective amount of a compound of claim 1, or a pharmaceutically acceptable salt thereof to a subject in need thereof.

10. The method of claim 9, further comprising administering a β-lactam antibacterial agent to the subject.

11. The method of claim 10, wherein the β-lactam antibacterial agent is Meropenem or Ceftibuten, or pharmaceutically acceptable salts thereof.

12. The method of claim 10, wherein the β-lactam antibacterial agent is administered separately from the compound or pharmaceutically acceptable salt thereof.

13. The method of claim 10, wherein the β-lactam antibacterial agent and the compound or pharmaceutically acceptable salt thereof are in a single dosage form.

14. A method of treating a bacterial infection caused by β-lactam antibacterial agent-resistant enterobacteriaceae, comprising administering a pharmaceutical composition comprising therapeutically effective amounts of a compound of the structure

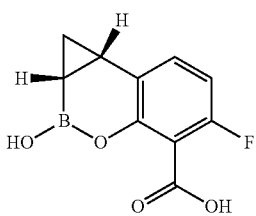 [SMILES: O=C(O)c1c(F)ccc2c1OB(O)[C@@H]1C[C@H]21]

and Meropenem, or pharmaceutically acceptable salts thereof to a subject in need thereof.

15. The method of claim 14, wherein the pharmaceutical composition is administered intravenously.

16. A method of treating a bacterial infection caused by β-lactam antibacterial agent-resistant enterobacteriaceae, comprising administering a pharmaceutical composition comprising therapeutically effective amounts of a compound of the structure

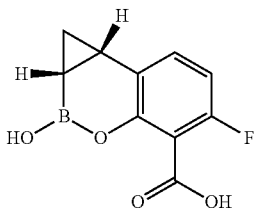 [SMILES: O=C(O)c1c(F)ccc2c1OB(O)[C@@H]1C[C@H]21]

and Ceftibuten, or pharmaceutically acceptable salts thereof to a subject in need thereof.

17. The method of claim 16, wherein the pharmaceutical composition is administered orally.

18. The method of claim 9, wherein the bacterial infection is caused by Carbapenem-resistant enterobacteriaceae.

19. The method of claim 9, wherein the bacterial infection is caused by *Klebsiella, Pseudomonas, Escherichia, Enterobacter* or *Acinetobacter.*

20. The method of claim 9, wherein the bacterial infection is caused by *Klebsiella pneumoniae, Pseudomonas aeruginosa, Escherichia coli, Enterobacter cloacae,* or *Acinetobacter baumannii.*

21. The method of claim 14, wherein the bacterial infection is caused by Carbapenem-resistant enterobacteriaceae.

22. The method of claim 14, wherein the bacterial infection is caused by *Klebsiella, Pseudomonas, Escherichia, Enterobacter* or *Acinetobacter.*

23. The method of claim 14, wherein the bacterial infection is caused by *Klebsiella pneumoniae, Pseudomonas aeruginosa, Escherichia coli, Enterobacter cloacae,* or *Acinetobacter baumannii.*

24. The method of claim 16, wherein the bacterial infection is caused by Carbapenem-resistant enterobacteriaceae.

25. The method of claim 16, wherein the bacterial infection is caused by *Klebsiella, Pseudomonas, Escherichia, Enterobacter* or *Acinetobacter.*

26. The method of claim 16, wherein the bacterial infection is caused by *Klebsiella pneumoniae, Pseudomonas aeruginosa, Escherichia coli, Enterobacter cloacae,* or *Acinetobacter baumannii.*

\* \* \* \* \*

UNITED STATES PATENT AND TRADEMARK OFFICE
CERTIFICATE OF CORRECTION

PATENT NO. : 10,570,159 B2
APPLICATION NO. : 16/378323
DATED : February 25, 2020
INVENTOR(S) : Scott J. Hecker et al.

Page 1 of 4

It is certified that error appears in the above-identified patent and that said Letters Patent is hereby corrected as shown below:

In the Specification

In Column 5, Line 21, delete "—$C(O)(CH_2)_{0-4}SR^c$" and insert -- —$C(O)(CH_2)_{0-3}SR^c$--.

In Column 8, Line 6, delete "—$C(O)(CH_2)_{0-4}SR^c$" and insert -- —$C(O)(CH_2)_{0-3}SR^c$--.

In Column 8, Lines 33-34, delete "—$C(O)(CH_2)_{0-4}SR^c$" and insert -- —$C(O)(CH_2)_{0-3}SR^c$--.

In Column 8, Line 67, delete "—$C(O)(CH_2)_{0-4}SR^c$" and insert -- —$C(O)(CH_2)_{0-3}SR^c$--.

In Column 9, Line 45, delete "$C_2$-8" and insert --$C_{2-8}$--.

In Column 10, Line 27, delete "—$NR'S(O)_2NR^fR^g$" and insert --$NR^fS(O)_2NR^fR^g$--.

In Column 11, Line 26, delete "Y" and insert --$Y^1$--.

In Column 15, Line 27, delete "$C_{6-10}$-aryl" and insert --$C_{6-10}$ aryl--.

In Column 16, Line 21, delete "$C_{6-10}$-aryl" and insert --$C_{6-10}$ aryl--.

In Column 44, Line 51, delete "Ca to Cb" and insert --$C_a$ to $C_b$--.

In Column 44, Line 51, delete "Ca-b" and insert --$C_{a-b}$--.

In Column 47, Line 36, delete "isoquinlinyl," and insert --isoquinolinyl,--.

In Column 47, Line 43, delete "isoxazollylalkyl," and insert --isoxazolylalkyl,--.

In Column 50, Line 12, delete "a$C_{6-10}$ ryl," and insert --$C_{6-10}$ aryl,--.

Signed and Sealed this
Twenty-sixth Day of January, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,570,159 B2

In Column 51, Line 65, delete "carbocylyl," and insert --carbocyclyl,--.

In Column 52, Line 10, delete "carbocylyl" and insert --carbocyclyl--.

In Column 55, Line 5, delete "pivoyloxymethyl," and insert --pivaloyloxymethyl,--.

In Column 57, Line 32, delete "ammodium" and insert --ammonium--.

In Column 58, Line 31, delete "$Z^{61}$" and insert --$Z^{\oplus}$--.

In Column 58, Line 32, delete "ammodium" and insert --ammonium--.

In Column 59, Line 11, delete "ammodium" and insert --ammonium--.

In Column 60, Line 1, delete "sterodirecting" and insert --stereodirecting--.

In Column 60, Line 15, delete "sterodirecting" and insert --stereodirecting--.

In Column 61, Line 53, delete "Sonogoshira" and insert --Sonogashira--.

In Column 68, Line 29, delete "OC(O)OC)OC$_{1-9}$alkyl," and insert --OC(O)OC$_{1-9}$alkyl,--.

In Column 71, Line 25, delete "croscarmelose;" and insert --croscarmellose;--.

In Column 77, Line 4, delete "2-Hydroxy-5-methoxy-a," and insert --2-Hydroxy-5-methoxy-1a,--.

In Column 78, Line 27 (Approx.), delete "CH$_2$C$_{12}$" and insert --CH$_2$Cl$_2$--.

In Column 78, Line 32, delete "CH$_2$C$_{12}$" and insert --CH$_2$Cl$_2$--.

In Column 80, Line 32, delete "(1 aS," and insert --(1aS,--.

In Column 90, Line 55, delete "03" and insert --O$_3$--.

In Column 92, Line 15, delete "pinacoato)" and insert --pinacolato)--.

In Column 94, Line 31, delete "accrylic" and insert --acrylic--.

In Column 94, Line 36, delete "resuling" and insert --resulting--.

In Column 97, Line 21 (Approx.), delete "(1 aS," and insert --(1aS,--.

In Column 98, Line 34, delete "lyophilizatio." and insert --lyophilization.--.

In Column 98, Line 50, delete "1 aR," and insert --1aR,--.

CERTIFICATE OF CORRECTION (continued)
U.S. Pat. No. 10,570,159 B2

In Column 98, Line 51, delete "[,21]" and insert --[1,2]--.

In Column 109, Line 41 (Approx.), delete "Compound 171" and insert --Compound 17I--.

In Column 110, Line 4, delete "dihydro-H" and insert --dihydro-1H--.

In Column 113, Line 34 (Approx.), delete "Compound 191" and insert --Compound 19I--.

In Column 117, Line 55, delete "20 L" and insert --20L--.

In Column 118, Line 3, delete "20 L." and insert --20L.--.

In Column 122, Line 46 (Approx.), delete "netrual" and insert --neutral--.

In Column 122, Line 62, delete "netrual" and insert --neutral--.

In Column 129, Line 29 (Approx.), delete "1 aR," and insert --1aR,--.

In Column 129, Line 52 (Approx.), delete "1 aR," and insert --1aR,--.

In Column 130, Line 7 (Approx.), delete "1 aR," and insert --1aR,--.

In Column 130, Line 24, delete "[M+H$_2$O];" and insert --[M+H$_2$O]$^+$;--.

In Column 130, Line 31 (Approx.), delete "1 aR," and insert --1aR,--.

In Column 130, Line 52 (Approx.), delete "1 aR," and insert --1aR,--.

In Column 131, Line 11 (Approx.), delete "1 aR," and insert --1aR,--.

In Column 131, Line 39 (Approx.), delete "1 aR," and insert --1aR,--.

In Column 132, Line 66, delete "[M+H$_2$O];" and insert --[M+H$_2$O]$^+$;--.

In Column 135, Line 35 (Approx.), delete "1 aR," and insert --1aR,--.

In Column 136, Line 2 (Approx.), delete "1 aR," and insert --1aR,--.

In Column 136, Line 27 (Approx.), delete "1 aR," and insert --1aR,--.

In Column 138, Line 4, delete "≥ 28 μg/mL" and insert --> 128 μg/mL--.

In Column 142, Line 67 (Approx.), delete "3-lactamases" and insert --β-lactamases- --.

In Column 146, Line 10, delete "am" and insert --μm--.

CERTIFICATE OF CORRECTION (continued)
U.S. Pat. No. 10,570,159 B2

In Column 147, Line 25, delete "am" and insert --μm--.

In the Claims

In Column 148, Line 30, Claim 2, delete "compound" and insert --compound of--.